(12) United States Patent
Lewis et al.

(10) Patent No.: US 10,091,963 B2
(45) Date of Patent: *Oct. 9, 2018

(54) TOBACCO INBRED AND HYBRID PLANTS AND USES THEREOF

(71) Applicant: North Carolina State University, Raleigh, NC (US)

(72) Inventors: Ramsey S. Lewis, Apex, NC (US); Ralph E. Dewey, Apex, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/420,799

(22) Filed: Jan. 31, 2017

(65) Prior Publication Data

US 2017/0164574 A1 Jun. 15, 2017

Related U.S. Application Data

(63) Continuation of application No. 14/194,362, filed on Feb. 28, 2014, now Pat. No. 9,560,830.

(60) Provisional application No. 61/772,786, filed on Mar. 5, 2013, provisional application No. 61/772,788, filed on Mar. 5, 2013, provisional application No. 61/772,792, filed on Mar. 5, 2013, provisional application No. 61/772,797, filed on Mar. 5, 2013, provisional application No. 61/915,951, filed on Dec. 13, 2013, provisional application No. 61/915,964, filed on Dec. 13, 2013, provisional application No. 61/915,970, filed on Dec. 13, 2013, provisional application No. 61/915,976, filed on Dec. 13, 2013.

(51) Int. Cl.
*A01H 5/12* (2018.01)
*A24B 15/10* (2006.01)
*A01H 6/82* (2018.01)

(52) U.S. Cl.
CPC .............. *A01H 5/12* (2013.01); *A01H 6/823* (2018.05); *A24B 15/10* (2013.01)

(58) Field of Classification Search
CPC ..................................................... A01H 5/12
See application file for complete search history.

(56) References Cited

U.S. PATENT DOCUMENTS

| | | | |
|---|---|---|---|
| 4,693,976 A | 9/1987 | Schilperoort et al. |
| 4,732,856 A | 3/1988 | Federoff |
| 4,762,785 A | 8/1988 | Comai |
| 4,801,540 A | 1/1989 | Hiatt et al. |
| 4,940,838 A | 7/1990 | Schilperoort et al. |
| 4,945,050 A | 7/1990 | Sanford et al. |
| 5,004,863 A | 4/1991 | Umbeck |
| 5,013,658 A | 5/1991 | Dooner et al. |
| 5,034,323 A | 7/1991 | Jorgensen et al. |
| 5,104,310 A | 4/1992 | Saltin |
| 5,107,065 A | 4/1992 | Shewmaker et al. |
| 5,141,131 A | 8/1992 | Miller, Jr. et al. |
| 5,149,645 A | 9/1992 | Hoekema et al. |
| 5,159,135 A | 10/1992 | Umbeck |
| 5,177,010 A | 1/1993 | Goldman et al. |
| 5,231,019 A | 4/1994 | Q |
| 5,302,523 A | 4/1994 | Coffee et al. |
| 5,352,605 A | 10/1994 | Fraley et al. |
| 5,378,619 A | 1/1995 | Rogers |
| 5,384,253 A | 1/1995 | Krzyzek et al. |
| 5,463,174 A | 10/1995 | Moloney et al. |
| 5,464,763 A | 11/1995 | Schilperoort et al. |
| 5,464,765 A | 11/1995 | Coffee et al. |
| 5,469,976 A | 11/1995 | Burchell |
| 5,472,869 A | 12/1995 | Krzyzek et al. |
| 5,583,021 A | 12/1996 | Dougherty et al. |
| 5,595,733 A | 1/1997 | Carswell et al. |
| 5,614,399 A | 3/1997 | Quail et al. |
| 5,641,664 A | 6/1997 | D'Halluin et al. |
| 5,668,295 A | 9/1997 | Wahab et al. |
| 5,679,558 A | 10/1997 | Gobel et al. |
| 5,684,241 A | 11/1997 | Nakatani |
| 5,712,135 A | 1/1998 | D'Halluin et al. |
| 5,713,376 A | 2/1998 | Berger |
| 5,766,900 A | 6/1998 | Shillito |
| 5,929,304 A | 7/1999 | Radin et al. |
| 6,002,070 A | 12/1999 | D'Halluin et al. |
| 6,074,877 A | 6/2000 | D'Halluin et al. |
| 6,907,887 B2 | 6/2005 | Conkling |
| 6,953,040 B2 | 10/2005 | Atchley et al. |

(Continued)

FOREIGN PATENT DOCUMENTS

| | | |
|---|---|---|
| EP | 0120516 | 10/1984 |
| EP | 0267159 | 5/1988 |
| EP | 0292435 | 11/1988 |
| EP | 0320500 | 6/1989 |
| EP | 0116718 | 5/1990 |

(Continued)

OTHER PUBLICATIONS

Lewis, R.S. et al. Phytochemistry, 2010, vol. 71; pp. 1988-1998.*
Adams et al., "Genes duplicated by polyploidy show unequal contributions to the transcriptome and organ-specific reciprocal silencing," PNAS, 100(8):4649-4654 (2003).

(Continued)

*Primary Examiner* — Russell Kallis
(74) *Attorney, Agent, or Firm* — Myers Bigel, P.A.

(57) ABSTRACT

The present disclosure provides tobacco inbred plants TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, and CMS TN86 SRC, and hybrids KY14×L8 SRC, NC7 SRC, and NCBH129 SRC. The present disclosure also provides parts of such plants and products made from those parts. The present disclosure also includes progeny of the provided plants including hybrids.

14 Claims, 10 Drawing Sheets
Specification includes a Sequence Listing.

(56) References Cited

U.S. PATENT DOCUMENTS

| | | |
|---|---|---|
| 6,965,062 B2 | 11/2005 | Rufty |
| 7,032,601 B2 | 4/2006 | Atchley et al. |
| 7,700,834 B2 | 4/2010 | Xu et al. |
| 7,700,851 B2 | 4/2010 | Xu |
| 7,812,227 B2 | 10/2010 | Xu |
| 7,855,318 B2 | 12/2010 | Xu |
| 7,884,263 B2 | 2/2011 | Dewey et al. |
| 8,058,504 B2 | 11/2011 | Xu |
| 8,124,851 B2 | 2/2012 | Dewey et al. |
| 8,319,011 B2 | 11/2012 | Xu et al. |
| 2002/0042934 A1 | 4/2002 | Staub et al. |
| 2004/0103449 A1 | 5/2004 | Xu |
| 2004/0111759 A1 | 6/2004 | Xu |
| 2004/0117869 A1 | 6/2004 | Xu |
| 2004/0162420 A1 | 8/2004 | Xu |
| 2005/0132444 A1 | 6/2005 | Xu |
| 2005/0160493 A9 | 7/2005 | Ratcliffe et al. |
| 2005/0178398 A1 | 8/2005 | Breslin et al. |
| 2005/0223442 A1 | 10/2005 | Xu |
| 2005/0244521 A1 | 11/2005 | Strickland et al. |
| 2006/0037096 A1 | 2/2006 | Xu |
| 2006/0037623 A1 | 2/2006 | Lawrence, Jr. |
| 2006/0041949 A1 | 2/2006 | Xu et al. |
| 2006/0157072 A1 | 7/2006 | Albino et al. |
| 2006/0185686 A1 | 8/2006 | Lawrence, Jr. |
| 2006/0191548 A1 | 8/2006 | Strickland et al. |
| 2007/0149408 A1 | 6/2007 | Thomas et al. |
| 2007/0199097 A1 | 8/2007 | Xu |
| 2007/0292871 A1 | 12/2007 | Xu |
| 2008/0076126 A1 | 3/2008 | Xu |
| 2008/0202541 A1 | 8/2008 | Dewey |
| 2008/0245377 A1 | 10/2008 | Marshall et al. |
| 2009/0119788 A1 | 5/2009 | Mallmann et al. |
| 2009/0205072 A1 | 8/2009 | Dewey et al. |
| 2010/0218270 A1 | 8/2010 | Xu et al. |
| 2010/0235938 A1 | 9/2010 | Xu et al. |
| 2010/0235945 A1 | 9/2010 | Xu et al. |
| 2010/0235952 A1 | 9/2010 | Xu et al. |
| 2011/0048437 A1 | 3/2011 | Xu |
| 2011/0078817 A1 | 3/2011 | Xu |
| 2011/0174322 A1 | 7/2011 | Dewey et al. |
| 2011/0263328 A1 | 10/2011 | Yamashita et al. |
| 2012/0117933 A1 | 5/2012 | Dewey et al. |
| 2012/0118308 A1 | 5/2012 | Dewey et al. |
| 2012/0216822 A1 | 8/2012 | Lewis et al. |
| 2012/0222689 A1 | 9/2012 | Xu et al. |
| 2014/0196730 A1 | 7/2014 | Lewis et al. |
| 2014/0251353 A1 | 9/2014 | Lewis et al. |

FOREIGN PATENT DOCUMENTS

| | | |
|---|---|---|
| EP | 0159418 | 5/1990 |
| EP | 0176112 | 5/1990 |
| EP | 131624 | 9/1992 |
| EP | 0627752 | 7/1997 |
| EP | 1033405 | 9/2000 |
| EP | 0290799 | 11/2003 |
| WO | WO87/06614 | 11/1987 |
| WO | WO92/09696 | 6/1992 |
| WO | WO93/21335 | 10/1993 |
| WO | WO94/01930 | 1/1994 |
| WO | WO00/67558 | 11/2000 |
| WO | WO02/072758 | 9/2002 |
| WO | WO02/100199 | 12/2002 |
| WO | WO03/078577 | 9/2003 |
| WO | WO2004/035745 | 4/2004 |
| WO | WO2005/038018 | 4/2005 |
| WO | WO2005/038033 | 4/2005 |
| WO | WO2005/046363 | 5/2005 |
| WO | WO2005/111217 | 11/2005 |
| WO | WO2005/116199 | 12/2005 |
| WO | WO2006/022784 | 3/2006 |
| WO | WO2006/091194 | 8/2006 |
| WO | WO2006/120570 | 11/2006 |
| WO | WO2008/070274 | 6/2008 |
| WO | WO2008/076802 | 6/2008 |
| WO | WO2009/064771 | 5/2009 |
| WO | WO2011/088180 | 7/2011 |
| WO | WO2012/118779 | 9/2012 |
| WO | WO2014/110363 | 7/2014 |

OTHER PUBLICATIONS

Allen et al., "RNAi-mediated replacement of morphine with the nonnarcotic alkaloid reticuline in opium poppy," Nature Biotecnnology, 22(12):1559-1566 (2004).

Alonso et al., "A Hox gene mutation that triggers nonsense-mediated RNA decay and affects alternative splicing during Drosophila development," Nucleic Acids Research, 31(14):3873-3880 (2003).

Arciga-Reyes et al., "UPF1 is required for nonsense-mediated mRNA decay (NMD) and RNAi in Arabidopsis" The Plant Journal, 47:480-489 (2006).

Arndt et al., "Colocalization of antisense RNAs and ribozymes with their target mRNAs." Genome, 40:785-797 (1997).

ARS-GRIN: PI 543792, "Nicotiana tabacum—TN 90" http://www.ars-grin.gov/cgi-bin/npgs/acc/display.pl?1438728, Retrieved Date: Sep. 2013 (2 pp).

ARS-GRIN PI 551280 "Nicotiana tabacum," http://www.ars-grin.gov/cgi-bin/npgs/acc/display.pl?1446216, accessed Feb. 2009).

Bak et al., "Transgenic Tobacco and Arabidopis Plans Expressing the Two Multifunctional Sorghum Cytochrome P450 Enzymes, CYP79A1 and CYP71E1, Are Cyanogenic and Accumulate Metabolites Derived from Intermediates in Dhurnin Biosynthesis," Plant Physiol., 123: 1437-1448 (2000).

Bartoszewski et al., "Cloning of a Wound Inducible Lycopersicon esculentum Cytochrome P450 Gene and Lack of Regeneration of Transgenic Plants with Sense of Antisense Constructs," J. Am Soc. Hort. Sci.; 124(4):535-539 (2002).

Baseggio et al., "Size and genomic location of the pMGA multigene family of Mycoplasma gallisepticum," Microbiology, 142:1429-1435 (1996).

Batard et al., "Increasing Expression of P450 and P4500-Reductase Proteins from Monocots in Heterologous Systems," Arch. Biochem. Biophys., 379:161-169 (2000).

Baulcombe, "Test Forward Genetics Based on Virus-Induced Gene Silencing,"Current Opinion in Plant Biology, 2:109-113(1999).

Bindler et al., "CORESTA Task Force Genetically Modified Tobacco: Detection Methods," 1999, 41 pages.

Bolitno et at., "Antisense applc ACC-oxidase RNA reduces ethylene production in transgenic tomato fruit," Plant Science, 122:91-99 (1997).

Bosher et al., "RNA interference: genetic wand and genetic watchdog," Nat. Cell Biol., 2:E31-E36 (2000).

Bosi et al., "The role of noise and positive feedback in the onset of autosomal dominant diseases," BMC Systems Biology, 4:1-15 (2010).

Boyette et al., "Results of year 2000 TSNA sampling program in flue-cured tobacco," Recent Advances in Tobacco Science, 27:17-22 (2001).

Branch, "A good antisense molecule is hard to t1nd," TIES, 23: 45-50 (1998).

Brignetti at al., "Viral pathogenicity determinants are suppressors of trangene silencing in Nicotiana benthamlana," EMBO J., 17(22)6739-6746 (1998).

Burns et al, "Large-scale analysis of gene expression, protein localization, and gene disruption in Saccharomyces corevisiae," Genes Dev., 8:1087-1105(1994).

Burton et al., "Changes in Chemical Composition on Burley Tobacco during Senescence and Curing. 2, Acylated Pyridine Alkaloids," J. Argic. Food Chem., 38(3):579-584 (1998).

Burton et al., "Distribution of Tobacco Constituents in Tobacco Leaf Tissue. 1. Tobacco-Specific Nitrosamines, Nitrate, Nitrite, and Alkaloids," J. Agric. Food Chem., 40:1050-1055(1992).

Burton et al., Changes in Chemical Composition of Burley Tobacco During Senescence and Curing. 2. Acylayed Pyridine Alkaloids, American Chemical Society, pp. 579-583 (1998).

(56) References Cited

OTHER PUBLICATIONS

Bush et al., "Formation of tobacco-specific nitrosamines in air-cured tobacco," Rec. Adv. Tob. Sci,, 27:23-46 (2001).
Byers et al., "Killing the messenger: new insights into nonsense-mediated mRNA decay" The Journal of Clinical Investigation, 109(1):3-6 (2002).
Byzova et al., "Transforming petals into sepaiold organs in *Arabidopsis* and oilseed rape: implementation of the hairpin RNA-mediated gene silencing technology in an organ-specific manner," Planta, 218:379-387 (2004).
Callis et al., "Introns increase gene expression in cultured maize cells," Genes and Dev., 1:1183-1200 (1987).
Carron et al., "Genetic modification of condensed tannin biosynthesis in Lotus comiculatus. 1. Heterologous antisense dihydroflavonol reductase down-regulates tannin accumulation in "hairy roof" cultures," Theoretical and Applied Genetics, 87(8): 1006-1015 (1994).
Caruthers, "Chapter 1: New Methods for Chemically Synthesizing Deoxyoligonuoleotides," Methods of DNA and RNA Sequencing, Weissman (ed.), Praeger Publishers, New York, pp. 1-22 (1983).
Chai et al., "Reducing the maize amylopectin content through RNA interference manipulation," Zhi Wu Sheng Li Yu Fen Zi Sheng Wu Xue Xue Buo, 31:625-630 (2005) (English Abstract only).
Chakrabarti et al,. "CYP82E4-mediated nicotine to nomicotine conversion in tobacco is regulated by a senescence-specific signaling pathway," Plant Mol. Biol., 66: 415-427 (2008).
Chakrabarti et al., "Inactivation of the cytochrome P450 gene CYP62E2 by degenerative mutations was a key event in the evolution of the alkaloid profile of modem tobacco," New Phytologist. 175:565-574 (2007).
Chang et al., "Predicting and Testing Physical Locations of Genetically Mapped Loci on Tomato Pachytene Chromosome," Genetics, 176:2131-2138 (2007).
Chao et al., "A silent mutation induces exon skipping in the phenylalanine hydroxylase gene in phenyiketonuria," Hum. Genet., 108:14-19(2001).
Chappell, "Biochemistry and Molecular Biology of the Isoprenoid Biosynthetic Pathway in Plants," Annu. Rev. Plant Physiol. Plant Mol. Biol., 46:521-547 (1995).
Chapple, "Molecular-Genetic Analysis of Plant Cytochrome P450-Dependent Monocxygenases," Annu. Rev. Plant Physiol. Plant Mol. Biol., 49:311-343(1998).
Chelvarajan et al., Study of Nicotine Demethylation in Nicotiana otophora, J. Agric. Food Chem., 41:858-862 (1993).
Chen et al., "Toxicological analysis of low-nicotine and nicotine-free cigarettes," Toxicology, vol. 249, No. 2-3, Jul. 30, 2008, 19 pages.
Cheung et al., "A Floral Transmitting Tissue-Specific Glycoprotein Attracts Pollen Tubes and Stimulates Their Growth," Cell: 82:383-393 (1995).
Chintapakorn, et al., "Antisense-Mediated Down-Regulation of Putrescine N-Methyltransferase Activity in Transgenic *Nicotiana tabacum* L. can Lead to Elevated Levels of Anatabine at the Expense of Nicotine," Plant Molecular Biology, 53:87-105 (2003).
Cho et al., "Transcriptome Analysis and Physical Mapping of Barley Genes in Wheat-Barley Chromosome Addition Lines," Genetics, 172:1277-1285 (2006).
Chou et al., "Chromosome Rearrangements in *Arabidopsis thaliana* Generated Through Cre-lox Site Specific Recombination," Plant and Animal Genome VII Conference, Abstract No. P133, 1 page (1999).
Chuang at al., "Specific and heritable genetic interference by double-stranded Rna in *Arabidopsis thaliana*," PNAS, 97 (9):4985-4990 (2000).
Cogoni et al., "Post-transcriptional gene silencing across kingdoms," Curr. Opin. Genet. Dev., 10:638-643 (2000).
Colbert et al., "High-throughput screening for induced point mutations," Plant Physiology, 126:480-484 (2001).
Collier at al., "A Method for Specific Amplification and P C R Sequencing of Individual Members of Multigene Families: Application to the Study of Steriod 21-Hydrozxylase Deficiency," PCR Methods and Applications, 1:181-186 (1992).
Colliver at al., "Differential modification of flavonoid and isofiavonoid biosynthesis with an antisense chalcone synthase construct in transgenic Lotus comiculatus," Plant Mol. Biol., 35(4):509-522 (1997).
Crookshanks et al., "The potato tuber transcriptome: analysis of 6077 expressed sequence tags," FEBS Lett., 506:123-126 (2001).
D'Souze et al., "Missense and silet tau gene mutations cause frontotemporal dementia with parkinsonism-chromosome 17 type, by affecting multiple alternative RNA splicing regulatory elements" PNAS, 96:5598-5603 (1999).
Davuluri et al., "Fruit-specific RNAi-mediated suppression of DET1 enhances carotenoid and favonoid content in tomatoes," Nat. Biotech nol., 23:890-895(2005).
Dekeyser al., Transient Gene Expression in Intact and Organized Rice Tissues, Plant Cell, 2:591-602 (1990).
Dewey et al., Meeting Abstract dated Sep. 27, 2005, 1 page.
Dewey et al., Power point presentation titled "Functional characterization of the nicotine N-Demethylase gene of tobacco," Philip Morris USA, 21 pages, 2006.
Donato et al., "Fluorescence-Based Assays in intact Cells Expressing Individual Activities for Screening Nine Cytochrome P450 (P450) Human P450 Enzymes," Drug Metab. Dispos., 32(7):699-706 (2004).
EBI Accession AV557806, dated Jun. 16, 2000, 2 pages.
Einset, "Differential expression of antisense in regenerated tobacco plants transformed with an antisense version of a tomato ACC oxidase gene," Plant Cell Tissue and Organ Culture. 46(2): 137-141 (1996).
Elkind at al., "Abnormal plant development and down-regulation of phenylpropenoid biosynthesis in transgenic tobacco containing a heterologus phenylalanine ammonia-lyase gene," PNAS, 87(22):9057-61 (1990).
EMBL Database Report for Accession No. EU182719, dated Dec. 2, 2007.
Escobar et al., "RNAi-mediated oncogene silencing confers resistance to crown gall tumorigenesis," PNAS, 98:13437-13442 (2001).
European Search Report completed on Feb. 10, 2010, in European Application No. EP 07 86 5628, 4 pages.
European Search Report completed on Mar. 31, 2011, in European Application No. EP 10 01 5540, 8 pages.
Falcon-Perez et al., "Functional Domain Analysis of the Yeast ABC Transporter Ycflp by Site-directed Mutagenesis," J. Biol. Chem., 274(33):23584-23590 (1999).
Fang et al., "Multiple cis regulatory elements for maximal expression of the cauliflower mosaic virus 35S promoter in transgenic plants," Plant Cell, 1:141-150(1989).
Fannin et al., "Nicotine demethylation in Nicotiana," Med. Sci. Res., 20:807-808(1992).
Faske et al., "Transgenic Tobacco Plants Expressing Pea Chloroplast Nmdh eDNA in Sense and Antisense Orientation," Plant Physiol, 115(2): 705-715 (1997).
Fedoroff et al., "Cloning of the bronze locus in maize by a simple and generalizable procedure using the transposable controlling element Activator (Ac)," PNAS, 81:3825-3829 (1984).
Fire et al., "Potent and specific genetic interference by double-stranded RNA in Caenorhabditis elegans," Nature, 391:806-811 (1998).
Force et al., "Preservation of Duplicate Genes by Complementary, Degenerative Mutations," Genetics, 151:1531-1545 (1999).
Forsthoefel et al., "T-DNA Insertion Mutagenesis in *Arabidopsis*: Prospects and Perspectives," Aust. J. Plant Physiol., 19:353-366 (1992).
Frank et al., "Cloning of Woud-Induced Cytochrome P450 Monoxygenases Expressed in Pea," Plant Physiol., 110:1035-1046 (1996).
Freeman et al., "Quantitative RT-PCR: Pitfalls and Potential," BioTechniques, 26:112-125 (1999).
Fromm et al., "An octopine synthase enhancer element directs tissue-specific expression and binds ASF-1, a factor from tobacco nuclear extracts," Plant Cell, 1:977-984 (1989).

(56) References Cited

OTHER PUBLICATIONS

Gavilano et al., "Funcational Analysis of Nicotine Demethylase Genes Reveals Insights into the Evolution of Modern Tobacco," J. Biol. Chem., 282:249-256 (2007).
Gavilano et al., "Genetic Engineering of Nicotiana tabacum for Reduced Nornicotine Content" J. Agric. Food Chem., 54:9071-9078 (2006).
Gavilano et al., "Isolation and Characterization of the Cytochrome P450 Gene CYP82E5v2 that Mediates Nicotine to Nornicotine Conversion in the Green Leaves of Tobacco," Plant Cell Physiol., 48(11):1567-1574 (2007).
Gavilano, "Isolation, Cloning and Characterization of Novel Tobacco Cytochrome P450 Genes Involved in Secondary Metabolism," Plant Biology Meeting, American Society of Plant Biologists, Abstract No. 992, 1 page (2004).
Gen Bank Accession No. AAK62343, dated Feb. 11, 2002, 2 pages.
GenBank Accession No. DQ350355, dated Dec. 31, 2006, 2 pages.
GenBank Accession No. 0Q350341, dated Dec. 31, 2006, 2 pages.
GenBank Accession No. AAK62342, Sep. 20, 2005, 2 pages.
GenBank Accession No. AAK62346, dated Feb. 11, 2002, 2 pages.
GenBank33 Accession No. AAK62347, dated Jun. 14, 2001, 2 pages.
GenBank Accession No. ABA07804, dated Oct. 13, 2005, 2 pages.
GenBank Accession No. ABA07805, dated Oct. 13, 2005, 2 pages.
GenBank Accession No. ABA07806, dated Mar. 7, 2007, 2 pages.
GenBank Accession No. ABA07807, dated Oct. 13, 2005, 2 pages.
GenBank Accession No. AEK08729 dated Feb. 23, 2005, 2 pages.
GenBank Accession No. BAA35080, dated Sep. 26, 2000, 2 pages.
GenBank Accession No. CAA64635, dated Sep. 12, 1996, 2 pages.
GenBank Accession No. D0219352, dated Oct. 1, 2006, 2 pages.
GenBank Accession No. D0350337, dated Dec. 31, 2006, 2 pages.
GenBank Accession No. DQ131885, dated Oct. 13, 2005, 2 pages.
GenBank Accession No. DQ131886, dated Oct. 13, 2005, 2 pages.
GenBank Accession No. DQ131887, dated Mar. 7, 2007, 2 pages.
GenBank Accession No. DQ131888, dated Oct. 13, 2005, 2 pages.
GenBank Accession No. DQ205656, dated Jan. 18, 2007, 2 pages.
GenBank Accession No. DQ219341, dated Oct. 1, 2006, 2 pages.
GenBank Accession No. DQ219342, dated Oct. 1, 2006, 2 pages.
GenBank Accession No. DQ219343, dated Oct. 1, 2006, 2 pages.
GenBank Accession No. DQ219344, dated Oct. 1, 2006, 2 pages.
GenBank Accession No. DQ219345, dated Oct. 1, 2006, 2 pages.
GenBank Accession No. DQ219346, dated Oct. 1, 2006, 2 pages.
GenBank Accession No. DQ219347, dated Oct. 1, 2006, 2 pages.
GenBank Accession No. DQ219348, dated Oct. 1, 2006, 2 pages.
GenBank Accession No. DQ219349, dated Oct. 1, 2006, 2 pages.
GenBank Accession No. DQ219350, dated Oct. 1, 2006, 2 pages.
GenBank Accession No. DQ219351, dated Oct. 1, 2006, 2 pages.
GenBank Accession No. DQ350312, dated Dec. 31, 2006, 2 pages.
GenBank Accession No. DQ350313, dated Dec. 31, 2006, 2 pages.
GenBank Accession No. DQ350314, dated Dec. 31, 2006, 2 pages.
GenBank Accession No. DQ350315, dated Dec. 31, 2006, 2 pages.
GenBank Accession No. DQ350316, dated Dec. 31, 2006, 2 pages.
GenBank Accession No. DQ350317, dated Dec. 31, 2006, 2 pages.
GenBank Accession No. DQ350318, dated Dec. 31, 2006, 2 pages.
GenBank Accession No. DQ350319, dated Dec. 31, 2006, 2 pages.
GenBark Accession No. DQ350320, dated Dec. 31, 2006, 2 pages.
GenBank Accession No. DQ350321, dated Dec. 31, 2006, 2 pages.
GenBank Accession No. DQ350322, dated Dec. 31, 2006, 2 pages.
GenBank Accession No. DQ350323, dated Dec. 31, 2006, 2 pages.
GenBank Accession No. DQ350324, dated Dec. 31, 2006, 2 pages.
GenBank Accession No. DQ350325, dated Dec. 31, 2006, 2 pages.
GenBank Accession No. DQ350326, dated Dec. 31, 2006, 2 pages.
GenBank Accession No. DQ350327, dated Dec. 31, 2006, 2 pages.
GenBank Accession No. DQ350328, dated Dec. 31, 2006, 2 pages.
GenBank Accession No. DQ350329, dated Dec. 31, 2006, 2 pages.
GenBank Accession No. DQ350330, dated Dec. 31, 2006, 2 pages.
GenBank Accession No. DQ350331, dated Dec. 31, 2006, 2 pages.
GenBank Accession No. DQ350332, dated Dec. 31, 2006, 2 pages.
GenBank Accession No. DQ350333, dated Dec. 31, 2006, 2 pages.
GenBank Accession No. DQ350334, dated Dec. 31, 2006, 2 pages.
GenBank Accession No. DQ350335, dated Dec. 31, 2006, 2 pages.
GenBank Accession No. DQ350336, dated Dec. 31, 2006, 2 pages.
GenBank Accession No. DQ350338, dated Dec. 31, 2006, 2 pages.
GenBank Accession No. DQ350339, dated Dec. 31, 2006, 2 pages.
GenBank Accession No. DQ350340, dated Dec. 31, 2006, 2 pages.
GenBank Accession No. DQ350342, dated Dec. 31, 2006, 2 pages.
GenBank Accession No. DQ350343, dated Dec. 31, 2006, 2 pages.
GenBank Accession No. DQ350344, dated Dec. 31, 2006, 2 pages.
GenBank Accession No. DQ350345, dated Dec. 31, 2006, 2 pages.
GenBank Accession No. DQ350346, dated Dec. 31, 2006, 2 pages.
GenBank Accession No. DQ350347, dated Dec. 31, 2006, 2 pages.
GenBank Accession No. DQ350348, dated Dec. 31, 2006, 2 pages.
GenBank Accession No. DQ350349, dated Dec. 31, 2006, 2 pages.
GenBank Accession No. DQ350350, dated Dec. 31, 2006, 2 pages.
GenBank Accession No. DQ350351, dated Dec. 31, 2006, 2 pages.
GenBank Accession No. DQ350352, dated Dec. 31, 2006, 2 pages.
GenBank Accession No. DQ350353, dated Dec. 31, 2006, 2 pages.
GenBank Accession No. DQ350354, dated Dec. 31, 2006, 2 pages.
GenBank Accession No. DQ350356, dated Dec. 31, 2 006, 2 pages.
GenBank Accession No. DQ350357, dated Dec. 31, 2006, 2 pages.
GenBank Accession No. DQ350358, dated Dec. 31, 2006, 2 pages.
GenBank Accession No. DQ350359, dated Dec. 31, 2006, 2 pages.
GenBank Accession No. DQ350360, dated Dec. 31, 2006, 2 pages.
GenBank Accession No. DQ350361, dated Dec. 31, 2006, 2 pages.
GenBank Accession No. DQ350362, dated Dec. 31, 2006, 2 pages.
GenBank Accession No. DQ350363, dated Dec. 31, 2006, 2 pages.
Ghosh, "Polyamines and plant alkaloids," Indian J. Exp. Biol., 38:1086-1091 (2000).
Goldrick et al., "Molecular Genetic Analysis of the User Group Associated with Two Mouse Light Chain Genetic Markers," J. Exp. Med. 162:713-728 (1985).
Graham-Lorence et al., "P450s: Structural similarities and functional differences," FASEB J. 10:206-214 (1996).
Guo et al., "Protean Tolerance to Random Amino Acid Change," PNAS, 101(25):9205-9210 (2004).
Hao et al., "Evidence in Favour of an Oxidative N-Demethylation of Nicotine to Nemicotine in Tobacco Cell Cultures," Journal Plant Physiology, 152:420-426 (1998).
Hao et al., "Mechanism of Nicotine N-Demethylation in Tobacco Cell Suspension Cuitures," Phytochemistry, 41(2):477-482 (1995).
Hoe et al., "Nicotine N-Demethylase in Cell-Free Preparations from Tobacco Cell Cultures," Phytochemistry, 42(2):325-329 (1996).
Haseloff et al., "Simple RNA enzymes with new and highly specific endoribonuclease activities," Nature, 334:585-591 (1998).
Hayes et al., "Blotting techniques for the study of DNA, RNA, and proteins," BMJ, 299(14):965-968 (1989).
Hecht el al., "The relevance of tobacco-specific nitrosamines to human cancer," Cancer Surveys, 8(2):273-294 (1989).
Hecht, "Biochemistry, Biology, and Carcinogenicity of Tobacco-Specific N-Nitrosamines," Chemical Research in Toxicology, 11(6):559-603 (1998).
Helene et al., "Control of Gene Expression by Triple Helix-Forming Oligonucleotides," Ann. NY. Acad. Sci., 660:27-36 (1992).
Helene, "The anti-gene strategy: control of gene expression by triplex-fanning-oligonucleotides," Anti-Cancer Drug Des., 6:569-584 (1991).
Helliwell et al., "High-throughput vectors for effcient gene silencing in plants," Funct. Plant Biol., 29:1217-1225 (2002).
Henikoff et al., "Single-Nucleotide Mutations for Plant Functional Genomics," Annu. Rev. Plant Biol., 54:375-401 (2003).
Herbik et at., "Isolation, characterization and c DNA cloning of nicotianamine synthase from barley," Eur J Biochem., 265(1):231-9 (1989).
Hibino et al., "Increase of Cinnamaldehyde Groups in Lignin of Transgenic Tobacco Plants Carrying an Antisense Gene for Cinnamyl Alcohol Dehydrogenase," Biosci. Biotec. Biochem, 59:929-931 (1995).
Hildering et at., "Chimeric Structure of the Tomato Plant After Seed Treatment with EMS and X-Rays," The Use of Induced Mutations in Plant Breeding, Pergamon Press, pp. 317-320 (1965).
Hill et al., "Functional analysis of conserved histidines in ADP-glucose pyrophosphorylase from *Escerichia coli*," Biochem. Biophys. Res. Commun., 244:573-577 (1998) (Abstract only).

(56) References Cited

OTHER PUBLICATIONS

Hoekema et al., "A binary plant vector strategy based on separation of the vir- and T-region of the Agrobacterium tumefaciens Ti-plasmid," Nature, 303: 179-180(1983).
Hoffmann et al., "Tobacco-specific N-nitrosamines and Areca-derived N-nitrosamines: chemistry, biochemistry, carcinogenicity, and relevance to humans," Journal of Toxicology and Environmental Health, 41:1-52(1994).
Horlow et al., "Transfer of cytoplamic male sterility by spontaneous androgenesis in tobacco (Nicotiana tabacum L.)" Euphytica 66:45-53 (1993).
Huang et et al., "Insights into Reguiation and Function of the Major Stress-h1duced hsp70 Molecular Chaperone In Vivo: Analysis of Mice with Targeted Gene Disruption of the hsp70. 1 or hsp70.3 Gene," Mol Cell Biol, 21(24):8575-8591 (2001).
Ingelbrecht et al., "Posttranscriptional silencing of reporter transgenes in tobacco correlates with DNA methylation," PNAS, 91:10502-10509 (1994).
International Preliminary Report on Patentability corresponding to International Application No. PCT/US2014/019381; dated Sep. 8, 2015.
International Preliminary Report on Patentability in PCT/US07/087386 dated Jun. 25, 2009, 6 pages.
International Search Report and the Written Opinion of the International Searching Authonty, or the Declaration dated Jul. 4, 2012, in International Application No. PCT/US2012/026795 (15 pages).
International Search Report and the Written Opinion of the International Searching Authority, or the Declaration dated May 4, 2012, in International Application No. PCT/US2012/026864 (13 pages).
International Search Report and Written Opinion Corresponding to International Application No. PCT/US2014/019381; dated Aug. 28, 2014.
Invitation to Pay Additional Fees, PCT/U52014/19381, dated Jun. 23, 2014, 8 pages.
Invitation to Pay Additional Fees, PCT/US2014/019381, dated Jun. 23, 2014, 8 pages.
Invitation to Pay Additional Fees, PCT/US2015/018387, dated Jun. 1, 2015, 8 pages.
Invitation to Pay Additional Fees, PCT/US2015/018408, dated May 18, 2015, 8 pages.
Isshiki et al., "Nonsense-mediated decay of mutant waxy mRNA in rice," Plant Phsiology, 125:1388-1395 (2001).
Jack et al., "Relative Stability of Nicotine to Nornicotine Conversion in Three Burley Cultivars," 18 pages, 36 slides (basis for Jack et al., published in COREST Congress Abstract AP2, Kyoto (2004) Agro Phyto Groups; 32 pages (unpaginated, abstract appearing on p. 11)).
Jack et al., "Relative stability of nicotine to nornicotine conversion in three burley cultivars," Coresta Congress, Kyoto, Agro-Phyto groups, Abstract AP2 (2004).
Johnston et al., "Dosage-sensitive function of retinoblastoma related and convergent epigenetic control are required during the Arabidopsis life cycle," PLoS Genet, 6(6):e1000988 (2010).
Jorgensen et al., "Chalcone synthase cosuppression phenotypes in petunia flowers: comparison of sense vs. antisense constructs and single-copy vs. complex T-DNA sequences," Plant Mol. Biol., 31:957-973 (1996).
Julio et al. Targeted Mutation Breeding as a tool for tobacco crop improvement, presentation made in Oct. 2008.
Julio et al., "Reducing the content of nornicotine in tobacco via targeted mutation breeding," Mol. Breeding (2008) 21:369-381.
Kafri et al., "The regulatory utilization of genetic redundancy through responsive backup circuits," PNAS, 103(31):11653-11658 (2006).
Kempin et al., "Targeted disruption in Arabidopsis," Nature, 389:802-803 (1997).
Keskin et al., "A new, structurally nonredundant, diverse data set of protein-protein interfaces and its implications," Protein Science, 13:1043-1055 (2004).

Kim et al., "Arabidopsis CYP35A2, a Cytochrome P450, Mediates the Baeyer-Villiger Oxidation of Castasterone to Brassinoilde in Brassinosteroid Biosynthesis," Plant Cell, 17:2397-2412 (2005).
Klahre et al., "High molecular weight RNAs and small interfering RNAs Induce systemic posttranscriptional gene silencing in plants," PNAS, 99:11981-11986 (2002).
Klink et al., The Efficacy of RNAi in the Study of the Plant Cytoskeleton. J Plant Growth Regul., 19:371-384 (2000).
Koornneff, "Chapter 1: Classical mutagenesis in higher plants," Molecular Plant Biology, Gilmartin and Bowler, ed., Oxford University Press, pp. 1-11 (2002).
Koshinsky et al., "Cre-lox site-specific recombination between Arabidopsis and tobacco chromosomes," Plant J. 23 (6):715-722 (2000).
Kusaba et al., "Low glutelin content: A Dominant Mutation That Suppresses the Glutelin Mutigene Family via RNA Silencing in Rice," Plant Cell, 15:1455-1467 (2003).
Kynast et al., "Dissecting the maize genome by using chromosome addition and radiation hybrid lines," PNAS, 101 (26):9921-9926 (2004).
Lazar al., "Transforming Growth Factor Mutation of Aspartic Acid 47 and Leucine 48 Results in Different Biological Activities," Mol. Cell. Biol., 8(3):1247-1252 (1988).
Levin et al., "Methods of double-stranded RNA mediated gene inactivation in Arabidopsis and their use to define an essential gene in methionine biosynthesis," Plant Mel. Biol., 44:759-775 (2000).
Lewis et al., "Three nicotine demethylase genes mediate nornicotine biosynthesis in Nicotiana tabacum L.: Functional characterization of the CYP82E10 gene," Phytochemistry (2010) 71:1988-1998.
Lewis, et al., "RNA interference (RNAi)-induced suppression of nicotine demethylase activity reduces levels of a key carcinogen in cured tobacco leaves." Plant Biotechnology Journal, 6:1-9 (2008).
Lewis, R. S. et al. Phytochemistry (2010): vol. 71, pp. 1988-1998.
Liu et al. "Genetic and transformation studies reveal negative regulation of E R S 1 ethylene receptor signaling in Arabidopsis," BMC Plant Biol, 10:60-73 (2010).
Liu et al., "High-Stearic and High-Oleic Cottonseed Oils Produced by Hairpin RNA-Mediated Post-Transcriptional Gene Silencing," Plant Physiol., 129:1732-1743 (2002).
Liu et al., "Indentification and characterization of HTD2: a novel gene negatively regulating tiller bud outgrowth in rice," Planta, 230(4):649-658 (2009).
Maher, "DNA Triple-Helix Formation: An Approach to Artificial Gene Repressors?" BioEssays, 14(12):807-815 (1992).
Maniatis et al., "Regulation of inducible and tissue-specific gene expression," Science, 236:1237-1245 (1987).
Mann et al., "Inheritance of the Conversion if Nicotine to Nornicotine in Varieties of Nicotiana tabacum L. and Related Amphiploids," Crop. Sci., 4:349-53 (1964).
Mansoor et al. "Engineering novel traits in plants through RNA interference," Trends in Plant Science, 11(11):1-7 (2006).
Maquat, "Nonsense-mediated mRNA decay," Curr. Biol., 12(6):R196-R197 (2002).
Matthew, "RNAi for plant functional genomics," Comparative and Functional Genomics, 5:240-244 (2004).
McDougall et al., "Detection of Viral DNA and RNA by in Situ Hybridization," J. Histochem. Cytochem., 34:33-38 (1986).
McKinney et al., "Sequence-based identification of T-DNA insertion mutations in Arabidopsis: actin mutants act2-1 and act4-1," PlantJ., 8(4):613-622 (1995).
Mesnard et al., "Evidence for the involvement of tetrahydrofolate in the demethylation by Nicotiana plumbaginifolia cell-suspension cultures," Planta, 214:911-919 (2002).
Mette et al., "Transcriptional silencing and promoter methylation triggered by double-stranded RNA," EMBO J. 19(19):5194-5201 (2000).
Mol et al., "Regulation of plant gene expression by antisense RNA," FEBS Lett., 268(2):427-430 (1990).
Napoli et al., "Introduction of a Chimeric Chalcone Synthase Gene into Petunia Results in Reversible Co-Suppression of Homologous Genes in trans," Plant Cell, 2:279-289 (1990).

(56) References Cited

OTHER PUBLICATIONS

Nawrath et al., "Salicylic Acid Induction-Deficient Mutants of *Arabidopsis* Express PR-2 and PR-5 and Accumulate High Levels of Camalexin after Pathogen Inoculation," Plant Cell, 11:1393-1404 (1999).
NCSU Office of the Dean, Electronic Administrative Briefings, Jun. 2008, 11 pages.
Needleman et al., "A General Method Applicable to the Search for Similarities in the Amino Acid Sequence of Two Proteins," J. Mol. Biol. 48:443-453 (1970).
Nelson et al., "Comparative Genomics of Rice and *Arabidopsis*. Analysis of 727 Cytochrome P450 Genes and Pseudogenes from a Monocot and a Dicot," Plant Physiol., 135:756-772 (2004).
Nelson et al., "Comparison of cytochrome P450 (CYP) genes from the mouse and human genomes, including nomenclature recommendations for genes, pseudogenes and alternative-splice variants," Phannacogenetics, 14:1-18 (2004).
Ng et al., "Specific Detection and Confirmation of Campylobacterjejuni by DNA Hybridization and PCR," Appl. Environ. Microbiol. 63(11):4558-4563 (1997).
Nikova, V. et al. Euphytica (1997), vol. 94, pp. 375-378.
Nishihara et al., "Flavanoid components and flower color change in transgenic tobacco plants by suppression of chalcone isomerase gene," FEBS Lett, 579:6074-6078 (2005).
Notification Concerning Transmittal of International Preliminary Report on Patentability in corresponding PCT Application No. PCT/US20112/026864 dated Sep. 12, 2013, 8 pages.
Notification of Transmittal of the International Preliminary Report on Patentability and the Written Opinion of the International Searching Authority, PCT/US2014/011035, dated Jul. 23, 2015, 8 pages.
Notification of Transmittal of the International Search Report and the Written Opinion of the International Searching Authority, or the Declaration in correspondence PCT Application No. PCT/US2012/026864 dated May 4, 2012 (13 pages).
Notification of Transmittal of the International Search Report and The Written Opinion of The International Searching Authority, of The Declaration, PCT/U52014/011035, dated Apr. 23, 2014, 11 pages.
Notification of Transmittal of the International Search Report and the Written Opinion of the International Searching Authority, or the Declaration, PCT/US2014/011035, dated Apr. 23, 2014, 11 pages.
Notification of Transmittal of the International Search Report and the Written Opinion of the International Searching Authority, or the Declaration, PCT/US2015/018393, dated Jun. 2, 2015, 11 pages.
Notification of Transmittal of the International Search Report and the Written Opnion of the International Searching Authority, or the Declaration, PCT/US2015/018408, dated Jul. 6, 2015, 11 pages.
Odell et al., "Identification of DNA sequences required for activity of the cauliflower mosaic virus 35S promoter," Nature, 313:810-612 (1985).
Office Action dated Jun. 12, 2007, in U.S. Appl. No. 10/934,944.
Office Action dated May 4, 2007, in U.S. Appl. No. 10/943,507.
Office Action dated Nov. 14, 2006, in U.S. Appl. No. 10/340,861.
Office Action dated Nov. 14, 2006, in U.S. Appl. No. 10/387,346.
Office Action dated Oct. 18, 2006, in U.S. Appl. No. 10/293,252.
Office Action dated Oct. 30, 2006, in U.S. Appl. No. 10/686,947.
Ogita et al., "Application of RNAi to confirm theobromine as the major intermediate for caffeine biosynthesis in coffee plants with potential for construction of decaffeinated varieties," Plant Mol. Biol., 54:931-941(2004).
Ohshima et al., "Nucleotide sequence of the PR-1 gene of Nicotiana tabacum," FEBS Letters, 225:243-246 (1987).
Oliver et al., "Inhibition of tobacco NADH-hydroxypyruvate reductase by expression of a heterologous antisense RNA derived from a cucumber cDNA: Implications for the mechanism of action of antisense RNAs," Mol. Gen Genet, 239(3):425-34 (1993).
Pearson et al., "Improved tools for biological sequence comparison," PNAS, 85:2444-2448 (1988).

Peele et al., "Formation of Tobacco-specific Nitrosamines in Flue-cured Tobacco," CORESTA Meeting, Agro-Phyto Groups, Suzhou, China (1999),
Pickett et al., "Seeing Double: Appreciating Genetic Redundancy," Plant Cell, 7:1347-1356 (1995).
Plant Variety Protection Office (USDA-AMS, Beltsville, MD, http://www.ars-grin.gov/cgi-bin/npgs/htmllpvp.pl?Tobbaco, accessed Feb. 2009).
Puchta et al., "Two different but related mechanisms are used in plants for the repair of genomic double-strand breaks by homologous recombination," PNAS, 93:5055-5060 (1996).
Qin et al., "Cre recombinase-mediated site-specific recombination between plant chromosomes," PNAS, 91:1706-1710 (1994).
Qiu et al. "A computational study of off-target effects of RNA interference," Nucleic Acids Research, 33(6)1834-1847 (2005).
Ralston et al., "Cloning, Heterologous Aristolochene-1,3-Dihydroxylase from Expression, and Functional Characterization of 5-epi-Tobacco (*Nicotiana tabacum*)," Arch. Biochem. Biophys., 393(2):222-235 (2001).
Reid at al., "Studies on the Fermentation of Tobacco 1, The Microflora of Cured and Fermenting Cigar-leaf Tobacco," Bulletin 356, Pennsylvania Agricultural Experiment Station, State College, PA, 18 pages (1938).
Rodermel et al., "Nuclear-Organelle Interactions: Nuclear Antisense Gene Inhibits Ribulose Biphosehate Carboxylase Enzyme Levels in Transformed Tobacco Plants," Cell, 55:673-681(1986).
Rohr et al., "Tandem inverted repeat system for selection of effective transgenic RNAi strains of Chlamydomonas," Plant J. 40:611-621 (2004).
Ruiz et al., "Nicotine-free and salt-tolerant tobacco plants obtained by grafting to salinity-resistant rootstocks of tomato," Physiologia Plantarum, vol. 124, No. 4; Aug. 1, 2005, pp. 465-475.
Salehuzzaman et al., "Isolation and characterization of a cDNA encoding granule-bound starch synthase in cassava (Afanihot esculenta Crantz) and its antisense expression in potato," Plant Mol. Biol, 23(5).947-62 (1993).
Saunders et al., "The Use of AFLP Techniques for DNA Fingerprinting in Plants," CEQ 2000XL, Beckman Coulter, 2001, 8 pages.
Schenk et al., "Coordinated plant defense responses *Arabidopsis* revealed by microarray analysis," PNAS, 97(21):11656-11660 (2000).
Schnable et al., "Genetic recombination in plants," Curr. Opin. Plant Biol., 1:123-129 (1998).
Schopfer et al., "Identification of elicitor-induced cytochrome P450s of soybean (*Glycine max* L.) using differential display of mRNA," Mol. Gen. Genet. 258:315-322 (1998).
Seal et al., "Isolation of a Pseudomonas solanacearum-Specific DNA Probe by Subtraction Hybridization and Construction of Species-Specific Oligonucleotide Primers for Sensitive Detection by the Polymerase Chain Reaction," Appl. Environ. Microbiol., 58(2) 3751-3758 (1992).
Sequence 6912f1 obtained from the Internet at http://mrg.pscsiken.go.ip/nicotiana/menu/069.html on Dec. 6, 2007, 1 page.
Shah et al., "Expression of Silent Mutations in Disease Phenotype," Abstract for presentation at 11th International Congress of Human Genetics, 1 page, (2006).
Shen et al., "Resistance Gene Candidates Idenified by PCR with Degenerate Oligonucleotide Primers Map to Clusters of Resistance Genes in Lettuce," Molecular Plant-Microbe interactions. 11(8):815-823 (1998).
Shew et al. (Eds.), "Compendium of Tobacco Diseases," published by American Phytopathology Society, 99 pages (1991).
Siminszky et al., "Conversion of nicotine to nomicotine in Nicotiana tabacum is mediated by CYP82E4, a cytochrome P450 monooxygenase," PNAS, 102(41):14919-14924 (2005).
Sinvany-Vilialcbo et al., "Expression in Multigene Families. Analysis of Chloroplast and Mitochondrial Proteases," Plant Physiol, 135:1336-1345 (2004).
Skarnes, "Entrapment Vectors: A New Tool for Mammailan Genetics," Bio/Technology, 8:827-831 (1990).
Slater et al,. Plant biotechnology; the genetic manipulation of plants 39 (Oxford University Press 2008) Chapter 2, pp. 37-53, 2.sup.nd ed.

(56) References Cited

OTHER PUBLICATIONS

Smith et al., "Comparison of Biosequences," Adv. Appl. Math., 2:482-489 (1981).
Smith et al., "Total silencing by intron-spliced hairpin RNAs," Nature. 407:319-320 (2000).
Spradling et al., "Gene disruptions using P transposable elements: An integral compnent of the *Drosophila* genome project," PNAS, 92:10824-10830 (1995).
Stalberg et al., "Deletion analysis of a 2S seed storage protein promoter of *Brassica napus* in transgenic tobacco," Plant Mol. Biol., 23:671-683 (1993).
Sunclaresan et el., "Patterns of gene action in plant development revealed by enhancer trap and gene trap transposable elements," Genes Dev., 9:1797-1810 (1995).
Sureka et al., "Positive Feedback and Noise Activate the Stringent Response Regulator Rel in Mycobacteria," PLoS One, 3(3):d 771 (2008).
T. David Reed, "Curing Tobacco," 2008 Flue-cured Tobacco Production Guide, pp. 61-64.
Takeda et al. "Differentiation between Wild and Vaccine-Derived Strains of Poliovirus by Stringent Microplate Hybridization of PCR Products," J Clin. Microbiol., 32:202-204 (1994).
Takemoto et al., "Molecular Cloning of a Defense-Response-Related Cytochrome P450 Gene from Tobacco," Plant Cell Physiol., 40(12):1232-1242 (1999).
Takken et al. "A functional cloning strategy, based on a binary PYX-expression vector, to isolate HR-inducing cDNAs of Plant pathogens." The Plant Journal, 24(2); 275-283 (2000).
Tang et al., "Using RNAi to improve plant nutritional value: from mechanism to application," TRENDS in Biotechnology, 22(9):463-469 (2004).
Tavernarakis et al., "Heritable and inducible genetic interference by double-stranded RNA encoded by transgenes," Nat. Genet., 24:180-183 (2000).
Temple et al., "Modulation of glutamine synthetase gene expression in tobacco by the introduction of an alfalfa glutamine syhthetase gene in sense and antisense orientation: molecular and biochen1ical analysis," Mol Gen Genet. 236(2-3):315-25 (1993).
Thomas et al. "Size constraints for targeting post-transcriptional gene silencing and for RNA directed methylation in Nicotiana benthamiana using a potato virus X vector," PlantJ., 25(4):417-425 (2001).
Thornton et al., "From structure to function: Approaches and limitations," Nature Structural Biology, StructuralGenomics Supplement, pp. 991-994 (2000).
Till et al., "Discovery of induced point mutations in maize genes by TILLING," BMC Plant Biology, 4:12 (2004).
Toscano et al., "A silent mutation (2939G>A, exon 6; CYP2D6*59) leading to impaired expression and function of CYP2D6," Pharmacogenet. Genomics, 16(10):767-770 (2006).
Travella, et al., "RNA Interference-Based Gene Silencing as an Efficient Tool for Functional Genomics in Hexaploid Bread Wheat," Plant Physiology, 142:6-20 (2006).
Trevanion et al., "NADP-Malate Dehydrogenase in the C4 Plant Flaveria bidentis," Plant Physiol, 113(4):1153-1165 (1997).
Turner et al., "Post-transcriptional gene-silencing and RNA interference: genetic immunity, mechanisms and applications," J.Chem. Technol. Biotechnol., 75:869-882 (2000).
U.S. Appl. No. 14/636,565, filed Mar. 3, 2015.
U.S. Appl. No. 14/636,576, filed Mar. 3, 2015.
U.S. Appl. No. 14/636,894, filed Mar. 3, 2015.
U.S. Appl. No. 60/337,684, filed Nov. 13, 2001, Xu.
U.S. Appl. No. 60/347,444, filed Jan. 11, 2002, Xu.
U.S. Appl. No. 60/353,684, filed Mar. 12, 2002, Xu.
U.S. Appl. No. 60/418,933, filed Oct. 16, 2002, Xu.
U.S. Appl. No. 60/485,368, filed Jul. 8, 2003, Xu.
U.S. Appl. No. 60/503,989, filed Sep. 13, 2003, Xu.
U.S. Appl. No. 60/566,235, filed Apr. 29, 2004, Xu.
U.S. Appl. No. 60/607,357, filed Sep. 3, 2004, Xu.
U.S. Appl. No. 60/646,764, filed Jan. 25, 2005, Xu.
U.S. Appl. No. 60/665,097, filed Mar. 24, 2005, Xu.
U.S. Appl. No. 60/665,451, filed Mar. 24, 2005, Xu.
United States, "Tobacco in the United States," Miscellaneous Publication No. 867, U.S. Dept. of Agriculture, Agricultural Marketing Service, 27 pages (1979).
UT Extension Publications (1999) SP277S-May/1999 (Rev) Black Root Rot of Tobacco; University of Tennessee (AES), Knoxville; 5 pp. 1-5.
Vaistij et al., "Spreading of RNA Targeting and DNA Methylation in RNA Silencing Requires Transcription of the Target Gene and a Putative RNA-Dependent RNA Polymerase," Plant Cell. 14 857-867 (2002).
Van der Krol et al., "An anti-sense chalcone synthase gene in transgenic plants inhibits flower pigmentation" Nature, 333:866-869 (1968).
Van der Krol et al., "Antisense genes in plant: an overview," Gene, 72:45-50 (1988).
Vaucheret et al., "Post-transcriptional gene sliencing in plants," J. Cell Sci., 114:3083-3091 (2001).
Veena et al., "Glyoxalase I from Brassica juncea: molecular cloning, regulation and its overexpression confer tolerance in transgenic tobacco under stress," Plant Journal, 17(4):385-395 (1999).
Verdaguer et al., "Functional organization of the cassava vein mosaic virus (CsVMV) promoter," Plant Mol. Biol., 37(6):1055-1067 (1998).
Verkerk, "Chimersim of the tomato plant after seed irradiation with fast neutrons,"Neth. J. Agric, Sci., 19:197-203 (1971).
Voss et al., "The role of enhancers in the regulation of cell-type-specific transcriptional control," Trends Biochem. Sci., 11(7):287-289 (1986).
Wang et al., "Elucidation of the functions of genes central to diterpene metabolism in tobacco trichomes using post-transcriptional gene silcencing," Planta, 216:686-691 (2003).
Wang et al., "Isolation and characterization of the CYP71DI6 trichome-specific promoter from *Nicotania tabacum* L.," J. Exp. Botany, 53(376):1891-1897 (2002).
Wang et al., "Suppression of a P450 hydroxylase gene in plant trichome glands enhances natural product-based aphid resistance," Nat. Bioteohnol., 19:371-374 (2001).
Waterhouse et al., "Virus resistance and gene silencing in plants can be induced by simultaneous expression of sense and antisense RNA," PNAS, 95:13959-13964 (1998).
Weigel et al., "A development switch sufficient for flower initiation in diverse plants," Nature, 377:495-500 (1995).
Weising et al., "Foreign Genes in Plants: Transfer, Structure, Expression, and Applications," Ann. Rev. Genetics, 22:421-477 (1988).
Werck-Reichhart et al., "Cytochromes P450," The Arabidopsis Bock, American Society of Plant Biologists, 28 pages (2002).
Werck-Reichart et al., "Cytochromes P450: a success dry," Genome Biology, 1(6) reviews3003.1-3003.9 (2000).
Wernsman at al., "Chapter Seventeen: Tobacco," Cultivar Development Crop Species., W. H. Fehr (ed.) MacMillan Publishing Go., Inc., New York, N.Y., pp. 669-698 (1987).
Wernsman et al., "Relative Stability of Alleles at the Nicotine Conversion Locus of Tobacco," Tobacco Science14:34-36 (1970).
Wernsman et al., "Time and site of nicotine conversion in tobacco," Tobacco Science, 167(22):226-228 (1968).
Wesley et al., "Construct design for efficient, effeective and high-throughout gene silencing in plants," The Plant Journal, 27(6):581-590 (2001).
Wetmur, "DNA Probes: Applications ofthe Principles ofNucleic Acid Hybridization" Critical Reviews in Bio, And Mol. Biol. 26:227-259, (1991).
Whitbread et al., "Molecular Characterization of CYP73A9 and CYP82A1 P450 Genes involved in Plant Defense in Pea," Plant Physiol., 124:47-58 (2000).
Wu et al., "Herbivory Rapidly Activates MAPK Signalling in Attacked and Unattacked Leaf Region but Not between Leaves of Nicotiana attenuata." The Plant Cell, 19:1096-1122 (2007).
Xiong et al., "Difference effects on ACC oxidase gene silencing triggered by RNA interference in trangenic tomato," Plant Cell, 23:639-646 (2004).

(56) References Cited

OTHER PUBLICATIONS

Xu et al. "Computational Estimation and Experimental Verification of Off-Target Silencing during Posttranscriptional Gene Silencing in Plants," Plant Physiology, 142:429-440 (2006).

Xu et al., "Biochemical and molecular characterizations of nicotine demethylase in tobacco," Physiologia Plantarum, 129(2):307-319 (2007).

Zwart et al., "Rapid Screening for Freshwater Bacterial Groups by Using Reverse Line Blot Hybridization," Appl. Environ. Microbiol., 69(10):5875-5883 (2003).

\* cited by examiner

| Treatments | Burley% | | Bright% | Oriental% | RL% |
| --- | --- | --- | --- | --- | --- |
| | TN90 LC | TN90 SRC | | | |
| Control | 23 | 0 | | | |
| 33% Experimental | 15 | 8 | | | |
| 67% Experimental | 8 | 15 | 35 | 15 | 27 |
| 100% Experimental | 0 | 23 | | | |

FIG. 9A

TOBACCO INBRED AND HYBRID PLANTS AND USES THEREOF

STATEMENT OF PRIORITY

This application is a continuation application of U.S. patent application Ser. No. 14/194,362, filed Feb. 28, 2014, now U.S. Pat. No. 9,560,830, which claims the benefit, under 35 U.S.C. § 119 (e), of U.S. Provisional Patent Application No. 61/772,786, filed on Mar. 5, 2013; U.S. Provisional Patent Application No. 61/772,788, filed on Mar. 5, 2013; U.S. Provisional Patent Application No. 61/772,792, filed on Mar. 5, 2013; U.S. Provisional Patent Application No. 61/772,797, filed on Mar. 5, 2013; U.S. Provisional Patent Application No. 61/915,951, filed on Dec. 13, 2013; U.S. Provisional Patent Application No. 61/915,964, filed on Dec. 13, 2013; U.S. Provisional Patent Application No. 61/915,970, filed on Dec. 13, 2013; and U.S. Provisional Patent Application No. 61/915,976, filed on Dec. 13, 2013 in the United States Patent and Trademark Office. Each of the foregoing applications is incorporated by reference in their entireties.

INCORPORATION OF SEQUENCE LISTING

The Sequence Listing is hereby incorporated by reference in its entirety, including the file named P34050US02.txt, which is 38,238 bytes in size and was created on Feb. 20, 2014, which is likewise herein incorporated by reference in its entirety.

FIELD

The present disclosure provides tobacco inbred plants TN90 SRC and CMS TN90 SRC. The present disclosure also provides tobacco inbred plants KY14 SRC, CMS KY14 SRC, L8 SRC, and hybrid cultivar KY14×L8 SRC. The present disclosure further provides tobacco inbred plants NC775 SRC, CMS NC775 SRC, NC645 SRC, and hybrid cultivar NC7 SRC. The present disclosure further provides tobacco inbred plants NC638 SRC, CMS NC638 SRC, TN86 SRC, CMS TN86 SRC, and hybrid cultivar NCBH129 SRC. The present disclosure also provides parts of such plants and products made from those parts. The present disclosure also includes progeny of the provided plants including hybrids.

BACKGROUND

Tobacco (*Nicotiana tabacum* L.) is an important commercial crop in the United States as well as in other countries. In tobacco plants, N-demethylation of nicotine results in nomicotine, a secondary alkaloid known to be a precursor for formation of N-Nitrosonornicotine ("NNN") in cured leaves. NNN is an undesired component of cured leaves.

The predominant alkaloid found in commercial tobacco varieties is nicotine, typically accounting for 90-95% of the total alkaloid pool. The remaining alkaloid fraction is comprised primarily of three additional pyridine alkaloids: nomicotine, anabasine, and anatabine. Nomicotine is generated directly from nicotine through the activity of the enzyme nicotine N-demethylase. Nomicotine usually represents less than 5% of the total pyridine alkaloid pool, but through a process termed "conversion," tobacco plants that initially produce very low amounts of nomicotine give rise to progeny that metabolically "convert" a large percentage of leaf nicotine to nomicotine. In tobacco plants that have genetically converted (termed "converters"), the great majority of nomicotine production occurs during the senescence and curing of the mature leaf (Wernsman and Matzinger (1968), *Tob. Sci.*, 12:226-228). Burley tobaccos are particularly prone to genetic conversion, with rates as high as 20% per generation observed in some cultivars.

During the curing and processing of the tobacco leaf, a portion of the nomicotine is metabolized to the compound NNN, a tobacco-specific nitrosamine (TSNA) that has been asserted to be carcinogenic in laboratory animals (Hecht and Hoffmann (1990), *Cancer Surveys*. 8:273-294; Hoffmann et al. (1994), *J. Toxicol. Environ. Health*, 41:1-52; Hecht (1998), *Chem. Res. Toxicol.*, 11:559-603). In flue-cured tobaccos, TSNAs are found to be predominantly formed through the reaction of alkaloids with the minute amounts of nitrogen oxides present in combustion gases formed by the direct-fired heating systems found in traditional curing barns (Peele and Gentry (1999), "Formation of Tobacco-specific Nitrosamines in Flue-cured Tobacco," CORESTA Meeting, Agro-Phyto Groups, Suzhou, China). Retrofitting these curing barns with heat-exchangers virtually eliminated the mixing of combustion gases with the curing air and dramatically reduced the formation of TSNAs in tobaccos cured in this manner (Boyette and Hamm (2001), *Rec. Adv. Tob. Sci.*, 27:17-22.). In contrast, in the air-cured Burley tobaccos, TSNA formation proceeds primarily through reaction of tobacco alkaloids with nitrite, a process catalyzed by leaf-borne microbes (Bush et al. (2001), *Rec. Adv. Tob. Sci.*, 27:23-46). Thus far, attempts to reduce TSNAs through modification of curing conditions while maintaining acceptable quality standards have not proven to be successful for the air-cured tobaccos.

SUMMARY

In an aspect, the present disclosure includes a seed of tobacco cultivar TN90 SRC, a representative sample seed of the cultivar having been deposited with the American Type Culture Collection (ATCC) under ATCC Accession No. PTA-13567.

In another aspect, the present disclosure includes a tobacco plant, or part thereof, produced by growing the seed of tobacco cultivar TN90 SRC, a representative sample seed of the cultivar having been deposited with the ATCC under ATCC Accession No. PTA-13567.

In a further aspect, the present disclosure includes a harvested leaf, or part thereof, of a tobacco plant, or part thereof, produced by growing the seed of tobacco cultivar TN90 SRC, a representative sample seed of the cultivar having been deposited with the ATCC under ATCC Accession No. PTA-13567.

In an aspect, the present disclosure includes a harvested leaf, or part thereof, of a tobacco plant, produced by growing the seed of tobacco cultivar TN90 SRC, a representative sample seed of the cultivar having been deposited with the ATCC under ATCC Accession No. PTA-13567, where the leaf has a reduced amount of nomicotine and/or N'-nitrosonornicotine (NNN).

In an aspect, the present disclosure includes a harvested leaf, or part thereof, produced by growing the seed of tobacco cultivar TN90 SRC, a representative sample seed of the cultivar having been deposited with the ATCC under ATCC Accession No. PTA-13567, where the leaf has a reduced amount of nomicotine and/or N'-nitrosonornicotine (NNN), where the reduced amount of nomicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar TN90 SRC, a representative sample seed of the cultivar having been deposited with the ATCC under ATCC Accession No. PTA-13567, where the product is selected from the group consisting of pipe tobacco, cigar tobacco, cigarette tobacco, chewing tobacco, leaf tobacco, shredded tobacco, cut tobacco and any combination thereof.

In an aspect, the present disclosure includes a tobacco product, prepared from a tobacco plant, or part thereof, produced by growing the seed of tobacco cultivar TN90 SRC, a representative sample seed of the cultivar having been deposited with the ATCC under ATCC Accession No. PTA-13567, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar TN90 SRC, a representative sample seed of the cultivar having been deposited with the ATCC under ATCC Accession No. PTA-13567, where the product is selected from the group consisting of a cigarillo, a non-ventilated recess filter cigarette, a vented recess filter cigarette, a cigar, snuff, and chewing tobacco, and where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar TN90 SRC, a representative sample seed of the cultivar having been deposited with the ATCC under ATCC Accession No. PTA-13567, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and second product comprises a reduced amount of nornicotine and/or N'-nitrosonornicotine (NNN).

In an aspect, the present disclosure includes a part of a tobacco plant, produced by growing the seed of tobacco cultivar TN90 SRC, a representative sample seed of the cultivar having been deposited with the ATCC under ATCC Accession No. PTA-13567, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar TN90 SRC, a representative sample seed of the cultivar having been deposited with the ATCC under ATCC Accession No. PTA-13567, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar TN90 SRC, a representative sample seed of the cultivar having been deposited with the ATCC under ATCC Accession No. PTA-13567, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar TN90 SRC.

In an aspect, the present disclosure includes an $F_1$ progeny plant of tobacco cultivar TN90 SRC, a representative sample seed of the cultivar having been deposited with the ATCC under ATCC Accession No. PTA-13567.

In another aspect, the present disclosure includes an $F_1$ progeny plant of tobacco cultivar TN90 SRC, a representative sample seed of the cultivar having been deposited with the ATCC under ATCC Accession No. PTA-13567, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is a tobacco plant produced by growing the seed of tobacco cultivar TN90 SRC, a representative sample seed of the cultivar having been deposited with the ATCC under ATCC Accession No. PTA-13567, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar TN90 SRC, a representative sample seed of the cultivar having been deposited with the ATCC under ATCC Accession No. PTA-13567.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar TN90 SRC, a representative sample seed of the cultivar having been deposited with the ATCC under ATCC Accession No. PTA-13567, where the plant of tobacco cultivar TN90 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar TN90 SRC, a representative sample seed of the cultivar having been deposited with the ATCC under ATCC Accession No. PTA-13567, where the plant of tobacco cultivar TN90 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar TN90 SRC, a representative sample seed of the cultivar having been deposited with the ATCC under ATCC Accession No. PTA-13567, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar TN90 SRC, a representative sample seed of the cultivar having been deposited with the ATCC under ATCC Accession No. PTA-13567, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar TN90 SRC, a representative sample seed of the cultivar having been deposited with the ATCC under ATCC Accession No. PTA-13567, and where at least one tobacco plant is cytoplasmic male sterile (CMS).

In an aspect, the present disclosure also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar TN90 SRC, a representative sample seed of the cultivar having been deposited with the ATCC under ATCC Accession No. PTA-13567, where at least one tobacco plant is cytoplasmic male sterile (CMS).

In another aspect, the present disclosure further includes a harvested leaf of an $F_1$ progeny plant having a reduced amount of nomicotine and/or N'-nitrosonomicotine (NNN) produced by growing a seed produced by a method of comprising crossing two tobacco plants and harvesting the resultant tobacco seed, where at least one tobacco plant is a tobacco plant produced by growing the seed of tobacco cultivar TN90 SRC, a representative sample seed of the cultivar having been deposited with the ATCC under ATCC Accession No. PTA-13567, where at least one tobacco plant is cytoplasmic male sterile (CMS).

In an aspect, the present disclosure also includes a harvested leaf of an $F_1$ progeny plant having a reduced amount of nomicotine and/or N'-nitrosonomicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar TN90 SRC, a representative sample seed of the cultivar having been deposited with the ATCC under ATCC Accession No. PTA-13567, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar TN90 SRC, a representative sample seed of the cultivar having been deposited with the ATCC under ATCC Accession No. PTA-13567, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar TN90 SRC, a representative sample seed of the cultivar having been deposited with the ATCC under ATCC Accession No. PTA-13567, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In another aspect, the present disclosure includes a seed of tobacco cultivar CMS TN90 SRC, a representative sample seed of the cultivar having been deposited with the ATCC under ATCC Accession No. PTA-13573.

In an aspect, the present disclosure includes a tobacco plant, or part thereof, produced by growing the seed of tobacco cultivar CMS TN90 SRC, a representative sample seed of the cultivar having been deposited with the ATCC under ATCC Accession No. PTA-13573.

In another aspect, the present disclosure includes a harvested leaf, or part thereof, of a tobacco plant, or part thereof, produced by growing the seed of tobacco cultivar CMS TN90 SRC, a representative sample seed of the cultivar having been deposited with the ATCC under ATCC Accession No. PTA-13573.

In an aspect, the present disclosure includes a harvested leaf, or part thereof, of a tobacco plant, produced by growing the seed of tobacco cultivar CMS TN90 SRC, a representative sample seed of the cultivar having been deposited with the ATCC under ATCC Accession No. PTA-13573, where the leaf has a reduced amount of nomicotine and/or N'-nitrosonomicotine (NNN).

In another aspect, the present disclosure includes a harvested leaf, or part thereof, produced by growing the seed of tobacco cultivar CMS TN90 SRC, a representative sample seed of the cultivar having been deposited with the ATCC under ATCC Accession No. PTA-13573, where the leaf has a reduced amount of nornicotine and/or N'-nitrosonomicotine (NNN), where the reduced amount of nomicotine and/or N'-nitrosonomicotine (NNN) is reduced in a smoke stream produced from the leaf.

In a further aspect, the present disclosure includes a tobacco product, prepared from a tobacco plant, or part thereof, produced by growing the seed of tobacco cultivar CMS TN90 SRC, a representative sample seed of the cultivar having been deposited with the ATCC under ATCC Accession No. PTA-13573, where the product is selected from the group consisting of pipe tobacco, cigar tobacco, cigarette tobacco, chewing tobacco, leaf tobacco, shredded tobacco, cut tobacco and any combination thereof.

In an aspect, the present disclosure includes a tobacco product, prepared from a tobacco plant, or part thereof, produced by growing the seed of tobacco cultivar CMS TN90 SRC, a representative sample seed of the cultivar having been deposited with the ATCC under ATCC Accession No. PTA-13573, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar CMS TN90 SRC, a representative sample seed of the cultivar having been deposited with the ATCC under ATCC Accession No. PTA-13573, where the product is selected from the group consisting of a cigarillo, a non-ventilated recess filter cigarette, a vented recess filter cigarette, a cigar, snuff, and chewing tobacco where the product has a reduced amount of nomicotine and/or N'-nitrosonomicotine (NNN).

In a further aspect, the present disclosure includes a second tobacco product prepared or produced from a first tobacco product prepared from a tobacco plant, or part thereof, produced by growing the seed of tobacco cultivar CMS TN90 SRC, a representative sample seed of the cultivar having been deposited with the ATCC under ATCC Accession No. PTA-13573, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or the second product comprises a reduced amount of nornicotine and/or N'-nitrosonornicotine (NNN).

In an aspect, the present disclosure includes a part of a tobacco plant, produced by growing the seed of tobacco cultivar CMS TN90 SRC, a representative sample seed of the cultivar having been deposited with the ATCC under ATCC Accession No. PTA-13573, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar CMS TN90 SRC, a representative sample seed of the cultivar having been deposited with the ATCC under ATCC Accession No. PTA-13573, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar CMS TN90 SRC, a representative sample seed of the cultivar having been deposited with the ATCC under ATCC Accession No. PTA-13573, where the cell or protoplast of the tissue culture can be produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar CMS TN90 SRC.

In an aspect, the present disclosure includes an $F_1$ progeny plant of tobacco cultivar CMS TN90 SRC, a representative sample seed of the cultivar having been deposited with the ATCC under ATCC Accession No. PTA-13573.

In another aspect, the present disclosure includes an $F_1$ progeny plant of tobacco cultivar CMS TN90 SRC, a representative sample seed of the cultivar having been deposited with the ATCC under ATCC Accession No. PTA-13573, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is cytoplasmic male sterile (CMS), where the cytoplasmic male sterile plant is a plant of tobacco cultivar CMS TN90 SRC, a representative sample seed of the cultivar having been deposited with the ATCC under ATCC Accession No. PTA-13573.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS TN90 SRC, a representative sample seed of the cultivar having been deposited with the ATCC under ATCC Accession No. PTA-13573.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS TN90 SRC, a representative sample seed of the cultivar having been deposited with the ATCC under ATCC Accession No. PTA-13573, where the plant of tobacco cultivar CMS TN90 SRC is the female parent.

In another aspect, the present disclosure includes a method for producing a tobacco seed comprising crossing two tobacco plants and harvesting the resultant tobacco seed, where at least one tobacco plant is cytoplasmic male sterile (CMS), where the cytoplasmic male sterile plant is a plant of tobacco cultivar CMS TN90 SRC, a representative sample seed of the cultivar having been deposited with the ATCC under ATCC Accession No. PTA-13573.

In an aspect, the present disclosure also includes a container of $F_1$ progeny seeds produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN90 SRC, a representative sample seed of the cultivar having been deposited with the ATCC under ATCC Accession No. PTA-13573.

In an aspect, the present disclosure includes an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN90 SRC, a representative sample seed of the cultivar having been deposited with the ATCC under ATCC Accession No. PTA-13573.

In an aspect, the present disclosure also includes a harvested leaf of an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN90 SRC, a representative sample seed of the cultivar having been deposited with the ATCC under ATCC Accession No. PTA-13573.

In another aspect, the present disclosure further includes a harvested leaf of an $F_1$ progeny plant having a reduced amount of nomicotine and/or N'-nitrosonomicotine (NNN) produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN90 SRC, a representative sample seed of the cultivar having been deposited with the ATCC under ATCC Accession No. PTA-13573.

In an aspect, the present disclosure also includes a harvested leaf of an $F_1$ progeny plant having a reduced amount of nomicotine and/or N'-nitrosonomicotine (NNN) in a smoke stream produced from the leaf, where the plant is produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN90 SRC, a representative sample seed of the cultivar having been deposited with the ATCC under ATCC Accession No. PTA-13573.

In an aspect, the present disclosure includes a tobacco product prepared from an $F_1$ progeny tobacco plant, or part thereof, where the plant or part thereof is produced by growing a $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN90 SRC, a representative sample seed of the cultivar having been deposited with the ATCC under ATCC Accession No. PTA-13573, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present disclosure further includes a tobacco product prepared from an $F_1$ progeny tobacco plant, or part thereof, where the plant or part thereof is produced by growing a $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN90 SRC, a representative sample seed of the cultivar having been deposited with the ATCC under ATCC Accession No. PTA-13573, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing a $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN90 SRC, a representative sample seed of the cultivar having been deposited with the ATCC under ATCC Accession No. PTA-13573, and where the tobacco product is selected from the group consisting of a cigarillo, a non-ventilated recess filter cigarette, a vented recess filter cigarette, a cigar, snuff, and chewing tobacco, and further where the product has a reduced amount of nomicotine and/or N'-nitrosonomicotine (NNN).

In an aspect, the present disclosure includes a method for producing a tobacco seed comprising crossing two tobacco plants and harvesting the resultant tobacco seed, where at least one tobacco plant is cytoplasmic male sterile, where the cytoplasmic male sterile plant is a plant of tobacco cultivar CMS TN90 SRC, a representative sample seed of the cultivar having been deposited with the ATCC under ATCC Accession No. PTA-13573.

In an aspect, the present disclosure includes a method of vegetatively propagating a plant of a tobacco cultivar comprising the steps of (a) collecting tissue capable of being propagated from a plant of a tobacco cultivar TN90 SRC, a representative sample seed of the cultivar having been deposited with the ATCC under ATCC Accession No. PTA-13567 or a plant of a tobacco cultivar CMS TN90 SRC, a representative sample seed of the cultivar having been deposited with the ATCC under ATCC Accession No. PTA-13573: (b) cultivating the tissue to obtain a proliferated shoot; and (c) rooting the proliferated shoots to obtain a rooted plantlet.

In an aspect, the present disclosure includes a method of vegetatively propagating a plant of a tobacco cultivar comprising the steps of (a) collecting tissue capable of being propagated from a plant of a tobacco cultivar TN90 SRC, a representative sample seed of the cultivar having been deposited with the ATCC under ATCC Accession No. PTA-13567 or a plant of a tobacco cultivar CMS TN90 SRC, a representative sample seed of the cultivar having been deposited with the ATCC under ATCC Accession No. PTA-13573; (b) cultivating the tissue to obtain a proliferated shoot; (c) rooting the proliferated shoots to obtain a rooted plantlet; and (d) growing a plant from the rooted plantlet.

In an aspect, the present disclosure includes a method of introducing a desired trait into a tobacco cultivar comprising: (a) crossing a plant of a first tobacco cultivar TN90 SRC, a representative sample seed of the cultivar having been deposited with the ATCC under ATCC Accession No. PTA-13567 or a plant of a tobacco cultivar CMS TN90 SRC, a representative sample seed of the cultivar having been deposited with the ATCC under ATCC Accession No. PTA-13573, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of said first tobacco cultivar, TN90 SRC or CMS TN90 SRC; and (e) repeating steps (c) and (d) three or more times (e.g., 3, 4, 5, 6, 7, 8, 9, 10, and the like) in succession to produce selected fourth or higher backcross progeny that comprise the desired trait. In additional aspects, steps (c) and (d) can be repeated one or more times (e.g., 1, 2, 3, 4, 5, 6, 7, 8, 9, 10, and the like) in succession to produce second or higher backcross progeny comprising the desired trait.

In an aspect, the present disclosure includes a method of introducing a desired trait into a tobacco cultivar comprising: (a) crossing a plant of a first tobacco cultivar TN90 SRC, a representative sample seed of the cultivar having been deposited with the ATCC under ATCC Accession No. PTA-13567, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar TN90 SRC, a representative sample seed of the cultivar having been deposited with the ATCC under ATCC Accession No. PTA-13567 to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar, TN90 SRC; and (e) repeating steps (c) and (d) three or more times in succession to produce selected fourth or higher backcross progeny that comprise the desired trait, where the trait is cytoplasmic male sterility (CMS). In additional aspects, steps (c) and (d) can be repeated one or more times in succession to produce second or higher backcross progeny comprising the desired trait, where the trait is CMS.

In an aspect, the present disclosure includes a method of introducing a desired trait into a tobacco cultivar comprising: (a) crossing a plant of a first tobacco cultivar TN90

SRC, a representative sample seed of the cultivar having been deposited with the ATCC under ATCC Accession No. PTA-13567, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar TN90 SRC, a representative sample seed of the cultivar having been deposited with the ATCC under ATCC Accession No. PTA-13567 to produce a backcross $BC_1F_1$ progeny seed; (d) growing the $BC_1F_1$ progeny seed and selecting a backcross $BC_1F_1$ progeny plant comprising the desired trait and the physiological and essentially all of morphological characteristics of the first tobacco cultivar TN90 SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens* or *Nicotiana glauca*. In additional aspects, steps (c) and (d) can be repeated one or more times in succession to produce second or higher backcross progeny comprising the desired trait, where the trait is CMS and the CMS trait is obtained from the cytoplasm of *Nicotiana suaveolens* or *Nicotiana glauca*.

In an aspect, the present disclosure includes a method of introducing a desired trait into a tobacco cultivar comprising: (a) crossing a plant of a first tobacco cultivar TN90 SRC, a representative sample seed of the cultivar having been deposited with the ATCC under ATCC Accession No. PTA-13567 with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar, TN90 SRC to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of tobacco cultivar TN90 SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens*, and where the second tobacco plant is CMS TN90 SRC. In additional aspects, steps (c) and (d) can be repeated one or more times in succession to produce second or higher backcross progeny comprising the desired trait, where the trait is CMS and the CMS trait is obtained from the cytoplasm of *Nicotiana suaveolens*.

In an aspect, the present disclosure includes a tobacco plant produced by a method comprising introducing a desired trait into a tobacco cultivar comprising: (a) crossing a plant of a first tobacco cultivar TN90 SRC, a representative sample seed of the cultivar having been deposited with the ATCC under ATCC Accession No. PTA-13567 or CMS TN90 SRC, a representative sample seed of the cultivar having been deposited with the ATCC under ATCC Accession No. PTA-13573, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of the first tobacco cultivar TN90 SRC or CMS TN90 SRC to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar TN90 SRC or CMS TN90 SRC; and (e) repeating steps (c) and (d) three or more times in succession to produce selected fourth or higher backcross progeny that comprise the desired trait. In additional aspects, steps (c) and (d) can be repeated one or more times in succession to produce second or higher backcross progeny that comprise the desired trait.

In another aspect, the present disclosure includes a method of introducing a desired trait into a tobacco cultivar comprising: (a) crossing a plant of a first tobacco cultivar, TN90 SRC, a representative sample seed of the cultivar having been deposited with the ATCC under ATCC Accession No. PTA-13567 or CMS TN90 SRC, a representative sample seed of the cultivar having been deposited with the ATCC under ATCC Accession No. PTA-13573, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of the first tobacco cultivar, TN90 SRC, a representative sample seed of the cultivar having been deposited with the ATCC under ATCC Accession No. PTA-13567 or CMS TN90 SRC, a representative sample seed of the cultivar having been deposited with the ATCC under ATCC Accession No. PTA-13573, to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, TN90 SRC or CMS TN90 SRC, respectively; and (e) repeating steps (c) and (d) one or more times in succession to produce a selected second, third, fourth or higher backcross progeny plant that comprises the desired trait and essentially all of the physiological and morphological characteristics of the first tobacco cultivar, TN90 SRC or CMS TN90 SRC.

In another aspect, the present disclosure includes a method of introducing a desired trait into a tobacco cultivar comprising: (a) crossing a plant of a first tobacco cultivar, TN90 SRC, a representative sample seed of the cultivar having been deposited with the ATCC under ATCC Accession No. PTA-13567 or CMS TN90 SRC, a representative sample seed of the cultivar having been deposited with the ATCC under ATCC Accession No. PTA-13573, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected F₁ progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, TN90 SRC or CMS TN90 SRC, respectively; and (e) repeating steps (c) and (d) one or more times in succession to produce a selected second, third, fourth or higher backcross progeny plant that comprises the desired trait and essentially all of the physiological and morphological characteristics of the first tobacco cultivar, TN90 SRC or CMS TN90 SRC.

In another aspect, the present disclosure includes a method of introducing a desired trait into a tobacco cultivar comprising: (a) crossing a plant of a first tobacco cultivar, TN90 SRC, a representative sample seed of the cultivar having been deposited with the ATCC under ATCC Accession No. PTA-13567 or CMS TN90 SRC, a representative sample seed of the cultivar having been deposited with the ATCC under ATCC Accession No. PTA-13573, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an F₁ progeny seed; (b) growing the F₁ progeny seed into an F₁ progeny plant and selecting the F₁ progeny plant having the desired trait; (c) crossing the selected F₁ progeny plant with a plant of the first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, TN90 SRC or CMS TN90 SRC, respectively; and (e) repeating steps (c) and (d) one or more times in succession to produce a selected second, third, fourth or higher backcross progeny plant that comprises the desired trait and essentially all of the physiological and morphological characteristics of the first tobacco cultivar, TN90 SRC or CMS TN90 SRC, respectively, where the plant has a desired trait of disease resistance.

In another aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an F₁ seed; crossing a plant grown from the F₁ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an F₁ seed; crossing a plant grown from the F₁ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the second tobacco plant comprises a nucleotide sequence selected from the group consisting of the nucleotide sequence of SEQ ID NO: 1, SEQ ID NO: 2, SEQ ID NO: 11, and any combination thereof.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an F₁ seed; crossing a plant grown from the F₁ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the second tobacco plant does not have the nucleotide sequence selected from the group consisting of the nucleotide sequence of SEQ ID NO: 1, SEQ ID NO: 2, SEQ ID NO: 11, and any combination thereof, and the third tobacco plant is a tobacco plant comprising a nucleotide sequence selected from the group consisting of the nucleotide sequence of SEQ ID NO: 1, SEQ ID NO: 2, SEQ ID NO: 11, and any combination thereof.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an F₁ seed; crossing a plant grown from the F₁ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the first tobacco plant comprises the sequence set forth in SEQ ID NO: 1 or SEQ ID NO: 2.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an F₁ seed; crossing a plant grown from the F₁ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the third tobacco plant is a tobacco plant comprising a nucleotide sequence selected from the group consisting of the nucleotide sequence of SEQ ID NO: 1, SEQ ID NO: 2, SEQ ID NO: 11, and any combination thereof.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the first tobacco plant is a plant of tobacco cultivar TN90 SRC, a representative sample seed of the cultivar having been deposited with the ATCC under ATCC Accession No. PTA-13567, or a plant of tobacco cultivar CMS TN90 SRC, a representative sample seed of the cultivar having been deposited with the ATCC under ATCC Accession No. PTA-13573.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the third tobacco plant is a plant of tobacco cultivar TN90 SRC, a representative sample seed of the cultivar having been deposited with the ATCC under ATCC Accession No. PTA-13567, or a plant of tobacco cultivar CMS TN90 SRC, a representative sample seed of the cultivar having been deposited with the ATCC under ATCC Accession No. PTA-13573.

In another aspect, the present disclosure includes a method of producing a plant of a tobacco cultivar TN90 SRC, a representative sample seed of the cultivar having been deposited with the ATCC under ATCC Accession No. PTA-13567 or tobacco cultivar CMS TN90 SRC, a representative sample seed of the cultivar having been deposited with the ATCC under ATCC Accession No. PTA-13573 comprising at least one (e.g., 1, 2, 3, 4, 5, 6, 7, 8, and the like) additional desired trait comprising the steps of: (a) collecting tissue capable of being propagated from a plant of a tobacco cultivar TN90 SRC, a representative sample seed of the cultivar having been deposited with the ATCC under ATCC Accession No. PTA-13567 or a plant of a tobacco cultivar CMS TN90 SRC, a representative sample seed of the cultivar having been deposited with the ATCC under ATCC Accession No. PTA-13573; and (b) introducing a at least one transgene (nucleic acid construct) conferring at least one desired trait into the tissue.

In another aspect, the present disclosure includes a method of producing an herbicide resistant tobacco plant comprising transforming a tobacco plant, or part thereof, produced by growing a seed of tobacco cultivar TN90 SRC, a representative sample seed of the cultivar having been deposited with the ATCC under ATCC Accession No. PTA-13567 or a seed of tobacco cultivar CMS TN90 SRC, a representative sample seed of the cultivar having been deposited with the ATCC under ATCC Accession No. PTA-13573 with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes an herbicide resistant tobacco plant produced by a method comprising transforming a tobacco plant, or part thereof, produced by growing a seed of a tobacco cultivar TN90 SRC, a representative sample seed of the cultivar having been deposited with the ATCC under ATCC Accession No. PTA-13567 or a seed of a tobacco cultivar CMS TN90 SRC, a representative sample seed of the cultivar having been deposited with the ATCC under ATCC Accession No. PTA-13573 with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes a method of producing a pest and/or insect resistant tobacco plant where the method comprises transforming a tobacco plant produced by growing a seed of tobacco cultivar TN90 SRC, a representative sample seed of the cultivar having been deposited with the ATCC under ATCC Accession No. PTA-13567 or a seed of tobacco cultivar CMS TN90 SRC, a representative sample seed of the cultivar having been deposited with the ATCC under ATCC Accession No. PTA-13573, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of tobacco cultivar TN90 SRC, a representative sample seed of the cultivar having been deposited with the ATCC under ATCC Accession No. PTA-13567 or a seed of tobacco cultivar CMS TN90 SRC, a representative sample seed of the cultivar having been deposited with the ATCC under ATCC Accession No. PTA-13573, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of tobacco cultivar TN90 SRC, a representative sample seed of the cultivar having been deposited with the ATCC under ATCC Accession No. PTA-13567 or a seed of tobacco cultivar CMS TN90 SRC, a representative sample seed of the cultivar having been deposited with the ATCC under ATCC Accession No. PTA-13573, with at least one transgene (nucleic acid construct) that confers pest and/or insect resistance, where the transgene (nucleic acid construct) encodes a *Bacillus thuringiensis* (BT) endotoxin.

In another aspect, the present disclosure includes a method of producing a disease resistant tobacco plant, the method comprising transforming a tobacco plant produced by growing a seed of tobacco cultivar TN90 SRC, a representative sample seed of the cultivar having been deposited with the ATCC under ATCC Accession No. PTA-13567 or a seed of tobacco cultivar CMS TN90 SRC, a representative sample seed of the cultivar having been deposited with the ATCC under ATCC Accession No. PTA-13573 with at least one transgene (nucleic acid construct) that confers disease resistance.

In a further aspect, the present disclosure includes a disease resistant tobacco plant produced by transforming a tobacco plant produced by growing a seed of tobacco cultivar TN90 SRC, a representative sample seed of the cultivar having been deposited with the ATCC under ATCC Accession No. PTA-13567 or a seed of tobacco cultivar CMS TN90 SRC, a representative sample seed of the cultivar having been deposited with the ATCC under ATCC Accession No. PTA-13573 with at least one transgene (nucleic acid construct) that confers disease resistance.

In an aspect, the present disclosure includes a seed of tobacco cultivar KY14 SRC, a representative sample seed of the cultivar having been deposited with the American Type Culture Collection (ATCC) under ATCC Accession No. PTA-120311.

In another aspect, the present disclosure includes a tobacco plant, or part thereof, produced by growing the seed of tobacco cultivar KY14 SRC, a representative sample seed of the cultivar having been deposited with the ATCC under ATCC Accession No. PTA-120311.

In a further aspect, the present disclosure includes a harvested leaf, or part thereof, of a tobacco plant, or part thereof, produced by growing the seed of tobacco cultivar KY14 SRC, a representative sample seed of the cultivar having been deposited with the ATCC under ATCC Accession No. PTA-120311.

In an aspect, the present disclosure includes a harvested leaf, or part thereof, of a tobacco plant, produced by growing the seed of tobacco cultivar KY14 SRC, a representative sample seed of the cultivar having been deposited with the ATCC under ATCC Accession No. PTA-120311, where the leaf has a reduced amount of nomicotine and/or N'-nitrosonomicotine (NNN).

In an aspect, the present disclosure includes a harvested leaf, or part thereof, produced by growing the seed of tobacco cultivar KY14 SRC, a representative sample seed of the cultivar having been deposited with the ATCC under ATCC Accession No. PTA-120311, where the leaf has a reduced amount of nomicotine and/or N'-nitrosonomicotine (NNN), where the reduced amount of nornicotine and/or N'-nitrosonomicotine (NNN) is reduced in a smoke stream produced from the leaf.

In a further aspect, the present disclosure includes a tobacco product, prepared from a tobacco plant, or part thereof, produced by growing the seed of tobacco cultivar KY14 SRC, a representative sample seed of the cultivar having been deposited with the ATCC under ATCC Accession No. PTA-120311, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar KY14 SRC, a representative sample seed of the cultivar having been deposited with the ATCC under ATCC Accession No. PTA-120311, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar KY14 SRC, a representative sample seed of the cultivar having been deposited with the ATCC under ATCC Accession No. PTA-120311, where the product is selected from the group consisting of a cigarillo, a non-ventilated recess filter cigarette, a vented recess filter cigarette, a cigar, snuff, and chewing tobacco, and where the product has a reduced amount of nomicotine and/or N'-nitrosonomicotine (NNN).

In a further aspect, the present disclosure includes a second tobacco product prepared or produced from a first tobacco product prepared from a tobacco plant, or part thereof, produced by growing the seed of tobacco cultivar KY14 SRC, a representative sample seed of the cultivar having been deposited with the ATCC under ATCC Accession No. PTA-120311, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or second product comprises a reduced amount of nomicotine and/or N'-nitrosonornicotine (NNN).

In an aspect, the present disclosure includes a part of a tobacco plant, produced by growing the seed of tobacco cultivar KY14 SRC, a representative sample seed of the cultivar having been deposited with the ATCC under ATCC Accession No. PTA-120311, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar KY14 SRC, a representative sample seed of the cultivar having been deposited with the ATCC under ATCC Accession No. PTA-120311, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar KY14 SRC, a representative sample seed of the cultivar having been deposited with the ATCC under ATCC Accession No. PTA-120311, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar KY14 SRC.

In an aspect, the present disclosure includes an $F_1$ progeny plant of tobacco cultivar KY14 SRC, a representative sample seed of the cultivar having been deposited with the ATCC under ATCC Accession No. PTA-120311.

In another aspect, the present disclosure includes an $F_1$ progeny plant of tobacco cultivar KY14 SRC, a representative sample seed of the cultivar having been deposited with the ATCC under ATCC Accession No. PTA-120311, where the $F_1$ plant is cytoplasmic male sterile (CMS).

In another aspect, the present disclosure includes an $F_1$ progeny seed produced crossing two tobacco plants and harvesting the resultant tobacco seed, where at least one tobacco plant is a tobacco plant produced by growing the seed of tobacco cultivar KY14 SRC, a representative sample seed of the cultivar having been deposited with the ATCC under ATCC Accession No. PTA-120311, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar KY14 SRC, a representative sample seed of the cultivar having been deposited with the ATCC under ATCC Accession No. PTA-120311.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar KY14 SRC, a representative sample seed of the cultivar having been deposited with the ATCC under ATCC Accession No. PTA-120311, where the plant of tobacco cultivar KY14 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar KY14 SRC, a representative sample seed of the cultivar having been deposited with the ATCC under ATCC Accession No. PTA-120311, where the plant of tobacco cultivar KY14 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar KY14 SRC, a representative sample seed of the cultivar having been deposited with the ATCC under ATCC Accession No. PTA-120311, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar KY14 SRC, a representative sample seed of the cultivar having been deposited with the ATCC under ATCC Accession No. PTA-120311, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar KY14 SRC, a representative sample seed of the cultivar having been deposited with the ATCC under ATCC Accession No. PTA-120311, and where at least one tobacco plant is cytoplasmic male sterile (CMS).

In an aspect, the present disclosure also includes a harvested leaf of an $F_1$ progeny plant produced by growing a seed produced by a method of comprising crossing two tobacco plants and harvesting the resultant tobacco seed, where at least one tobacco plant is a tobacco plant produced by growing the seed of tobacco cultivar KY14 SRC, a representative sample seed of the cultivar having been deposited with the ATCC under ATCC Accession No. PTA-120311, where at least one tobacco plant is cytoplasmic male sterile (CMS).

In another aspect, the present disclosure further includes a harvested leaf of an $F_1$ progeny plant having a reduced amount of nomicotine and/or N'-nitrosonomicotine (NNN) produced by growing a seed produced by a method of comprising crossing two tobacco plants and harvesting the resultant tobacco seed, where at least one tobacco plant is a tobacco plant produced by growing the seed of tobacco cultivar KY14 SRC, a representative sample seed of the cultivar having been deposited with the ATCC under ATCC Accession No. PTA-120311, where at least one tobacco plant is cytoplasmic male sterile (CMS).

In an aspect, the present disclosure also includes a harvested leaf of an $F_1$ progeny plant having a reduced amount of nomicotine and/or N'-nitrosonomicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar KY14 SRC, a representative sample seed of the cultivar having been deposited with the ATCC under ATCC Accession No. PTA-120311, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar KY14 SRC, a representative sample seed of the cultivar having been deposited with the ATCC under ATCC Accession No. PTA-120311, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar KY14 SRC, a representative sample seed of the cultivar having been deposited with the ATCC under ATCC Accession No. PTA-120311, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar KY14 SRC, a representative sample seed of the cultivar having been deposited with the ATCC under ATCC Accession No. PTA-120311, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco, and further where the product has a reduced amount of nornicotine and/or N'-nitrosonornicotine (NNN).

In another aspect, the present disclosure includes a seed of tobacco cultivar CMS KY14 SRC, a representative sample seed of the cultivar having been deposited with the ATCC under ATCC Accession No. PTA-13571.

In an aspect, the present disclosure includes a tobacco plant, or part thereof, produced by growing the seed of tobacco cultivar CMS KY14 SRC, a representative sample seed of the cultivar having been deposited with the ATCC under ATCC Accession No. PTA-13571.

In another aspect, the present disclosure includes a harvested leaf, or part thereof, of a tobacco plant, or part thereof, produced by growing the seed of tobacco cultivar CMS KY14 SRC, a representative sample seed of the cultivar having been deposited with the ATCC under ATCC Accession No. PTA-13571.

In an aspect, the present disclosure includes a harvested leaf, or part thereof, of a tobacco plant, produced by growing the seed of tobacco cultivar CMS KY14 SRC, a representative sample seed of the cultivar having been deposited with the ATCC under ATCC Accession No. PTA-13571, where the leaf has a reduced amount of nornicotine and/or N'-nitrosonornicotine (NNN).

In another aspect, the present disclosure includes a harvested leaf, or part thereof, produced by growing the seed of tobacco cultivar CMS KY14 SRC, a representative sample seed of the cultivar having been deposited with the ATCC under ATCC Accession No. PTA-13571, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar CMS KY14 SRC, a representative sample seed of the cultivar having been deposited with the ATCC under ATCC Accession No. PTA-13571, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar CMS KY14 SRC, a representative sample seed of the cultivar having been deposited with the ATCC under ATCC Accession No. PTA-13571, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar CMS KY14 SRC, a representative sample seed of the cultivar having been deposited with the ATCC under ATCC Accession No. PTA-13571, where the product is selected from the group consisting of a cigarillo, a non-ventilated recess filter cigarette, a vented recess filter cigarette, a cigar, snuff, and chewing tobacco where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar CMS KY14 SRC, a representative sample seed of the cultivar having been deposited with the ATCC under ATCC Accession No. PTA-13571, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or second product comprises a reduced amount of nornicotine and/or N'-nitrosonornicotine (NNN).

In an aspect, the present disclosure includes a part of a tobacco plant, produced by growing the seed of tobacco cultivar CMS KY14 SRC, a representative sample seed of the cultivar having been deposited with the ATCC under ATCC Accession No. PTA-13571, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar CMS KY14 SRC, a representative sample seed of the cultivar having been deposited with the ATCC under ATCC Accession No. PTA-13571, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar CMS KY14 SRC, a representative sample seed of the cultivar having been deposited with the ATCC under ATCC Accession No. PTA-13571, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole where the regenerated plant has all, or essentially all of the morphological and physiological characteristics of cultivar CMS KY14 SRC.

In an aspect, the present disclosure includes an $F_1$ progeny plant of tobacco cultivar CMS KY14 SRC, a representative sample seed of the cultivar having been deposited with the ATCC under ATCC Accession No. PTA-13571.

In another aspect, the present disclosure includes an $F_1$ progeny plant of tobacco cultivar CMS KY14 SRC, a representative sample seed of the cultivar having been deposited with the ATCC under ATCC Accession No. PTA-13571, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is cytoplasmic male sterile (CMS), where the cytoplasmic male sterile plant is a plant of tobacco cultivar CMS KY14 SRC, a representative sample seed of the cultivar having been deposited with the ATCC under ATCC Accession No. PTA-13571.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS KY14 SRC, a representative sample seed of the cultivar having been deposited with the ATCC under ATCC Accession No. PTA-13571.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS KY14 SRC, a representative sample seed of the cultivar having been deposited with the ATCC under ATCC Accession No. PTA-13571, where the plant of tobacco cultivar CMS KY14 SRC is the female parent.

In another aspect, the present disclosure includes a method for producing a tobacco seed comprising crossing two tobacco plants and harvesting the resultant tobacco seed, where at least one tobacco plant is cytoplasmic male sterile (CMS), where the cytoplasmic male sterile plant is a plant of tobacco cultivar CMS KY14 SRC, a representative sample seed of the cultivar having been deposited with the ATCC under ATCC Accession No. PTA-13571.

In an aspect, the present disclosure also includes a container of $F_1$ progeny seeds produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS KY14 SRC, a representative sample seed of the cultivar having been deposited with the ATCC under ATCC Accession No. PTA-13571.

In an aspect, the present disclosure includes an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS KY14 SRC, a representative sample seed of the cultivar having been deposited with the ATCC under ATCC Accession No. PTA-13571.

In an aspect, the present disclosure also includes a harvested leaf of an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS KY14 SRC, a representative sample seed of the cultivar having been deposited with the ATCC under ATCC Accession No. PTA-13571.

In another aspect, the present disclosure further includes a harvested leaf of an $F_1$ progeny plant having a reduced amount of nornicotine and/or N'-nitrosonornicotine (NNN) produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS KY14 SRC, a representative sample seed of the cultivar having been deposited with the ATCC under ATCC Accession No. PTA-13571.

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by a method of comprising crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS KY14 SRC, a representative sample seed of the cultivar having been deposited with the ATCC under ATCC Accession No. PTA-13571.

In an aspect, the present disclosure includes a tobacco product prepared from an $F_1$ progeny tobacco plant, or part thereof, where the plant or part thereof is produced by growing a $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS KY14 SRC, a representative sample seed of the cultivar having been deposited with the ATCC under ATCC Accession No. PTA-13571, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing a $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS KY14 SRC, a representative sample seed of the cultivar having been deposited with the ATCC under ATCC Accession No. PTA-13571, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing a $F_1$ progeny seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS KY14 SRC, a representative sample seed of the cultivar having been deposited with the ATCC under ATCC Accession No. PTA-13571, and where the tobacco product is selected from the group consisting of a cigarillo, a non-ventilated recess filter cigarette, a vented recess filter cigarette, a cigar, snuff, and chewing tobacco, and further where the product has a reduced amount of nornicotine and/or N'-nitrosonornicotine (NNN).

In an aspect, the present disclosure includes a method for producing a tobacco seed comprising crossing two tobacco plants and harvesting the resultant tobacco seed, where at least one tobacco plant is cytoplasmic male sterile, where the cytoplasmic male sterile plant is a plant of tobacco cultivar CMS KY14 SRC, a representative sample seed of the cultivar having been deposited with the ATCC under ATCC Accession No. PTA-13571.

In another aspect, the present disclosure includes a seed of tobacco cultivar L8 SRC, a representative sample seed of the cultivar having been deposited with the ATCC under ATCC Accession No. PTA-13572.

In an aspect, the present disclosure includes a tobacco plant, or part thereof, produced by growing the seed of tobacco cultivar L8 SRC, a representative sample seed of the cultivar having been deposited with the ATCC under ATCC Accession No. PTA-13572.

In another aspect, the present disclosure includes a harvested leaf, or part thereof, of a tobacco plant, or part thereof, produced by growing the seed of tobacco cultivar L8 SRC, a representative sample seed of the cultivar having been deposited with the ATCC under ATCC Accession No. PTA-13572.

In an aspect, the present disclosure includes a harvested leaf, or part thereof, of a tobacco plant, produced by growing the seed of tobacco cultivar L8 SRC, a representative sample seed of the cultivar having been deposited with the ATCC under ATCC Accession No. PTA-13572, where the leaf has a reduced amount of nornicotine and/or N'-nitrosonornicotine (NNN).

In another aspect, the present disclosure includes a harvested leaf, or part thereof, produced by growing the seed of tobacco cultivar L8 SRC, a representative sample seed of the cultivar having been deposited with the ATCC under ATCC Accession No. PTA-13572, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar L8 SRC, a representative sample seed of the cultivar having been deposited with the ATCC under ATCC Accession No. PTA-13572, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar L8 SRC, a representative sample seed of the cultivar having been deposited with the ATCC under ATCC Accession No. PTA-13572, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar L8 SRC, a representative sample seed of the cultivar having been deposited with the ATCC under ATCC Accession No. PTA-13572, where the product is selected from the group consisting of a cigarillo, a non-ventilated recess filter cigarette, a vented recess filter cigarette, a cigar, snuff, and chewing tobacco where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar L8 SRC, a representative sample seed of the cultivar having been deposited with the ATCC under ATCC Accession No. PTA-13572, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or second product comprises a reduced amount of nornicotine and/or N'-nitrosonornicotine (NNN).

In an aspect, the present disclosure includes a part of a tobacco plant, produced by growing the seed of tobacco cultivar L8 SRC, a representative sample seed of the cultivar having been deposited with the ATCC under ATCC Accession No. PTA-13572, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar L8 SRC, a representative sample seed of the cultivar having been deposited with the ATCC under ATCC Accession No. PTA-13572, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar L8 SRC, a representative sample seed of the cultivar having been deposited with the ATCC under ATCC Accession No. PTA-13572, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole, where the regenerated plant has all, or essentially all of the morphological and physiological characteristics of cultivar L8 SRC.

In an aspect, the present disclosure includes an $F_1$ progeny plant of tobacco cultivar L8 SRC, a representative sample seed of the cultivar having been deposited with the ATCC under ATCC Accession No. PTA-13572.

In another aspect, the present disclosure includes an $F_1$ progeny plant of tobacco cultivar L8 SRC, a representative sample seed of the cultivar having been deposited with the ATCC under ATCC Accession No. PTA-13572, where the $F_1$ plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar L8 SRC, a representative sample seed of the cultivar having been deposited with the ATCC under ATCC Accession No. PTA-13572.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar L8 SRC, a representative sample seed of the cultivar having been deposited with the ATCC under ATCC Accession No. PTA-13572, where the plant of tobacco cultivar L8 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar L8 SRC, a representative sample seed of the cultivar having been deposited with the ATCC under ATCC Accession No. PTA-13572, where the plant of tobacco cultivar L8 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar L8 SRC, a representative sample seed of the cultivar having been deposited with the ATCC under ATCC Accession No. PTA-13572, where at least one tobacco plant is cytoplasmic male sterile (CMS).

In another aspect, the present disclosure includes an $F_1$ progeny seed produced by crossing two tobacco plants and harvesting the resultant tobacco seed, where at least one tobacco plant is a tobacco plant produced by growing the seed of tobacco cultivar L8 SRC, a representative sample seed of the cultivar having been deposited with the ATCC under ATCC Accession No. PTA-13572, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar L8 SRC, a representative sample seed of the cultivar having been deposited with the ATCC under ATCC Accession No. PTA-13572, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar L8 SRC, a representative sample seed of the cultivar having been deposited with the ATCC under ATCC Accession No. PTA-13572, and where at least one tobacco plant is cytoplasmic male sterile (CMS).

In an aspect, the present disclosure also includes a harvested leaf of an $F_1$ progeny plant produced by growing a seed produced by a method of comprising crossing two tobacco plants and harvesting the resultant tobacco seed, where at least one tobacco plant is a tobacco plant produced by growing the seed of tobacco cultivar L8 SRC, a representative sample seed of the cultivar having been deposited with the ATCC under ATCC Accession No. PTA-13572, where at least one tobacco plant is cytoplasmic male sterile (CMS).

In another aspect, the present disclosure further includes a harvested leaf of an $F_1$ progeny plant having a reduced amount of nornicotine and/or N'-nitrosonornicotine (NNN) produced by growing a seed produced by a method of comprising crossing two tobacco plants and harvesting the resultant tobacco seed, where at least one tobacco plant is a tobacco plant produced by growing the seed of tobacco cultivar L8 SRC, a representative sample seed of the cultivar having been deposited with the ATCC under ATCC Accession No. PTA-13572, where at least one tobacco plant is cytoplasmic male sterile (CMS).

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar L8 SRC, a representative sample seed of the cultivar having been deposited with the ATCC under ATCC Accession No. PTA-13572, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar L8 SRC, a representative sample seed of the cultivar having been deposited with the ATCC under ATCC Accession No. PTA-13572, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar L8 SRC, a representative sample seed of the cultivar having been deposited with the ATCC under ATCC Accession No. PTA-13572, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar L8 SRC, a representative sample seed of the cultivar having been deposited with the ATCC under ATCC Accession No. PTA-13572, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco, and further where the product has a reduced amount of nornicotine and/or N'-nitrosonornicotine (NNN).

In another aspect, the present disclosure includes a seed of hybrid tobacco cultivar KY14×L8 SRC (ATCC Accession No. PTA-13569). Seeds of hybrid cultivar KY14×L8 SRC are obtainable by crossing plants of cultivars L8 SRC and CMS KY14 SRC and collecting the seeds.

In an aspect, the present disclosure includes a tobacco plant, or part thereof, produced by growing a seed of hybrid tobacco cultivar KY14×L8 SRC.

In a further aspect, the present disclosure includes a harvested leaf, or part thereof, of a tobacco plant produced by growing the seed of hybrid tobacco cultivar KY14×L8 SRC.

In another aspect, the present disclosure includes a harvested leaf, or part thereof, of a tobacco plant, produced by growing the seed of hybrid tobacco cultivar KY14×L8 SRC, where the leaf has a reduced amount of nornicotine and/or N'-nitrosonornicotine (NNN).

In an aspect, the present disclosure includes a harvested leaf, or part thereof, produced by growing the seed of hybrid tobacco cultivar KY14×L8 SRC, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of hybrid tobacco cultivar KY14×L8 SRC, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of hybrid tobacco cultivar KY14×L8 SRC, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of hybrid tobacco cultivar KY14×L8 SRC, where the product is selected from the group consisting of a cigarillo, a non-ventilated recess filter cigarette, a vented recess filter cigarette, a cigar, snuff, and chewing tobacco where the product has a reduced amount of nomicotine and/or N'-nitrosonomicotine (NNN).

In a further aspect, the present disclosure includes a second tobacco product prepared or produced from a first tobacco product prepared from a tobacco plant, or part thereof, produced by growing the seed of tobacco cultivar KY14×L8 SRC, where the first tobacco product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or second product comprises a reduced amount of nomicotine and/or N'-nitrosonomicotine (NNN).

In an aspect, the present disclosure includes a part of a tobacco plant, produced by growing a seed of hybrid tobacco cultivar KY14×L8 SRC, where the part is selected from the group consisting of leaf, pollen, ovule, embryo, cotyledon, hypocotyl, meristematic cell, protoplast, root, root tip, pistil, anther, flower, shoot, stem, pod, and petiole.

In a further aspect, the present disclosure includes a tissue culture produced from a protoplast or cell from a tobacco plant, or part thereof, produced by growing the seed of hybrid tobacco cultivar KY14×L8 SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of hybrid tobacco cultivar KY14×L8 SRC, where the cell or protoplast of the tissue culture can be produced from a plant part selected from the group consisting of a leaf, pollen, embryo, cotyledon, hypocotyl, meristematic cell, root, root tip, pistil, anther, flower, shoot, stem, pod, and petiole, where the regenerated plant has all, or essentially all, of the morphological and physiological characteristics of hybrid cultivar KY14×L8 SRC.

In an aspect, the present disclosure includes an $F_1$ progeny plant of hybrid tobacco cultivar KY14×L8 SRC.

In an aspect, the present disclosure includes an $F_1$ progeny plant of hybrid tobacco cultivar KY14×L8 SRC, where the plant of tobacco cultivar KY14×L8 SRC is the female parent.

In another aspect, the present disclosure includes an $F_1$ progeny plant of hybrid tobacco cultivar KY14×L8 SRC where the $F_1$ plant is cytoplasmic male sterile (CMS).

In another aspect, the present disclosure includes a method for producing a tobacco seed of KY14×L8 SRC comprising crossing two tobacco plants and harvesting the resultant tobacco seed, where one tobacco plant is a tobacco plant produced by growing the seed of tobacco cultivar CMS KY14 SRC, a representative sample seed of the cultivar having been deposited with the ATCC under ATCC Accession No. PTA-13571.

In another aspect, the present disclosure includes a method for producing a tobacco seed of KY14×L8 SRC comprising crossing two tobacco plants and harvesting the resultant tobacco seed, where one tobacco plant is a tobacco plant produced by growing the seed of tobacco cultivar L8 SRC, a representative sample seed of the cultivar having been deposited with the ATCC under ATCC Accession No. PTA-13572.

In another aspect, the present disclosure includes a method for producing a tobacco seed of KY14×L8 SRC comprising crossing two tobacco plants and harvesting the resultant tobacco seed, where one tobacco plant is a tobacco plant produced by growing the seed of tobacco cultivar CMS KY14 SRC, a representative sample seed of the cultivar having been deposited with the ATCC under ATCC Accession No. PTA-13571 and a second tobacco plant is a tobacco plant produced by growing the seed of tobacco cultivar L8 SRC, a representative sample seed of the cultivar having been deposited with the ATCC under ATCC Accession No. PTA-13572.

In an aspect, the present disclosure includes a method of vegetatively propagating a plant of a tobacco cultivar comprising the steps of (a) collecting tissue capable of being propagated from a plant of a tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571, L8 SRC, a representative sample seed of the cultivar having been deposited with the ATCC under ATCC Accession No. PTA-13572, and hybrid cultivar KY14×L8 SRC; (b) cultivating the tissue to obtain a proliferated shoot; and (c) rooting the proliferated shoots to obtain a rooted plantlet.

In an aspect, the present disclosure includes a method of vegetatively propagating a plant of a tobacco cultivar comprising the steps of (a) collecting tissue capable of being propagated from a plant of a tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571. L8 SRC, a representative sample seed of the cultivar having been deposited with the ATCC under ATCC Accession No. PTA-13572, and hybrid cultivar KY14×L8 SRC; (b) cultivating the tissue to obtain a proliferated shoot; (c) rooting the proliferated shoots to obtain a rooted plantlet; and (d) growing a plant from the rooted plantlet.

In an aspect, the present disclosure includes a method of introducing a desired trait into a tobacco cultivar comprising: (a) crossing a plant of a first tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571, and L8 SRC, a representative sample seed of the cultivar having been deposited with the ATCC under ATCC Accession No. PTA-13572, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of said first tobacco cultivar, KY14 SRC, CMS KY14 SRC, or L8 SRC, respectively; and e) repeating steps (c) and (d) three or more times (e.g., 3, 4, 5, 6, 7, 8, 9, 10, and the like) in succession to produce selected fourth or higher backcross progeny that comprise the desired trait. In additional aspects, steps (c) and (d) can be repeated one or more times (e.g., 1, 2, 3, 4, 5, 6, 7, 8, 9, 10, and the like) in succession to produce second or higher backcross progeny comprising the desired trait.

In an aspect, the present disclosure includes a method of introducing a desired trait into a tobacco cultivar comprising: (a) crossing a plant of a first tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571, and L8 SRC, a representative sample seed of the cultivar having been deposited with the ATCC under ATCC Accession No. PTA-13572, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar, KY14 SRC, CMS KY14 SRC, or L8 SRC, respectively; and (e) repeating steps (c) and (d) three or more times in succession to produce selected fourth or higher backcross progeny that comprise the desired trait, where the trait is cytoplasmic male sterility (CMS). In additional aspects, steps (c) and (d) can be repeated one or more times in succession to produce second or higher backcross progeny comprising the desired trait, where the trait is CMS.

In an aspect, the present disclosure includes a method of introducing a desired trait into a tobacco cultivar comprising: (a) crossing a plant of a first tobacco cultivar selected from the group consisting of KY14 SRC, a representative sample seed of the cultivar having been deposited with the ATCC under ATCC Accession No. PTA-120311 and L8 SRC, a representative sample seed of the cultivar having been deposited with the ATCC under ATCC Accession No. PTA-13572, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar; (d) growing the $BC_1F_1$ progeny seed and selecting a backcross $BC_1F_1$ progeny plant comprising the desired trait and the physiological and essentially all of morphological characteristics of the first tobacco cultivar KY14 SRC or L8 SRC, respectively; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of Nicotiana suaveolens or Nicotiana glauca. In additional aspects, steps (c) and (d) can be repeated one or more times in succession to produce second or higher backcross progeny comprising the desired trait, where the trait is CMS and the CMS trait is obtained from the cytoplasm of Nicotiana suaveolens or Nicotiana glauca.

In an aspect, the present disclosure includes a method of introducing a desired trait into a tobacco cultivar comprising: (a) crossing a plant of a first tobacco cultivar selected from the group consisting of KY14 SRC, a representative sample seed of the cultivar having been deposited with the ATCC under ATCC Accession No. PTA-120311 and L8 SRC, a representative sample seed of the cultivar having been deposited with the ATCC under ATCC Accession No. PTA-13572 with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar KY14 SRC or L8 SRC; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of Nicotiana suaveolens, and where the second tobacco plant is selected from the group consisting of CMS KY14 SRC or CMS L8 SRC. In additional aspects, steps (c) and (d) can be repeated one or more times in succession to produce second or higher backcross progeny comprising the CMS trait obtained from the cytoplasm of Nicotiana suaveolens, and where the second tobacco plant is selected from the group consisting of CMS KY14 SRC or CMS L8 SRC.

In an aspect, the present disclosure includes a tobacco plant produced by a method comprising introducing a desired trait into a tobacco cultivar comprising: (a) crossing a plant of a first tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571, and L8 SRC, a representative sample seed of the cultivar having been deposited with the ATCC under ATCC Accession No. PTA-13572, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar KY14 SRC, CMS KY14 SRC, or L8 SRC, respectively; and (e) repeating steps (c) and (d) three or more times in succession to produce selected fourth or higher backcross progeny that comprise the desired trait. In additional aspects, steps (c) and (d) can be repeated one or more times in succession to produce second or higher backcross progeny comprising the desired trait.

In another aspect, the present disclosure includes a method of introducing a desired trait into a tobacco cultivar comprising: (a) crossing a plant of a first tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571, and L8 SRC, a representative sample seed of the cultivar having been deposited with the ATCC under ATCC Accession No. PTA-13572, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of said first tobacco cultivar, to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, KY14 SRC, CMS KY14 SRC, or L8 SRC, respectively; and (e) repeating steps (c) and (d) one or more times in succession to produce a selected second, third, fourth or higher backcross progeny plant that comprises the desired trait and essentially all of the physiological and morphological characteristics of the first tobacco cultivar, KY14 SRC, CMS KY14 SRC, or L8 SRC, respectively.

In another aspect, the present disclosure includes a method of introducing a desired trait into a tobacco cultivar comprising: (a) crossing a plant of a first tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571, and L8 SRC, a representative sample seed of the cultivar having been deposited with the ATCC under ATCC Accession No. PTA-13572, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of said first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, KY14 SRC, CMS KY14 SRC, or L8 SRC, respectively; and (e) repeating steps (c) and (d) one or more times in succession to produce a selected second, third, fourth or higher backcross progeny plant that comprises the desired trait and essentially all of the physiological and morphological characteristics of said first tobacco cultivar, KY14 SRC, CMS KY14 SRC, or L8 SRC, respectively, where the desired trait is disease resistance.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the first tobacco plant is a plant of a tobacco cultivar KY14 SRC, a representative sample seed of the cultivar having been deposited with the ATCC under ATCC Accession No. PTA-120311, a plant of tobacco cultivar CMS KY14 SRC, a representative sample seed of the cultivar having been deposited with the ATCC under ATCC Accession No. PTA-13571, or a plant of tobacco cultivar L8 SRC, a representative sample seed of the cultivar having been deposited with the ATCC under ATCC Accession No. PTA-13572, and hybrid cultivar KY14×L8 SRC.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the third tobacco plant is a plant of tobacco cultivar KY14 SRC, a representative sample seed of the cultivar having been deposited with the ATCC under ATCC Accession No. PTA-120311, a plant of tobacco cultivar CMS KY14 SRC, a representative sample seed of the cultivar having been deposited with the ATCC under ATCC Accession No. PTA-13571, a plant of tobacco cultivar L8 SRC, a representative sample seed of the cultivar having been deposited with the ATCC under ATCC Accession No. PTA-13572, or hybrid cultivar KY14×L8 SRC.

In another aspect, the present disclosure includes a method of producing a plant of a tobacco cultivar selected from the group consisting of tobacco cultivar KY14 SRC, a representative sample seed of the cultivar having been deposited with the ATCC under ATCC Accession No. PTA-120311, tobacco cultivar CMS KY14 SRC, a representative sample seed of the cultivar having been deposited with the ATCC under ATCC Accession No. PTA-13571, tobacco cultivar L8 SRC, a representative sample seed of the cultivar having been deposited with the ATCC under ATCC Accession No. PTA-13572, and hybrid cultivar KY14×L8 SRC comprising at least one (e.g., 1, 2, 3, 4, 5, 6, 7, 8, and the like) additional desired trait comprising the steps of: (a) collecting tissue capable of being propagated from a plant of a tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571, L8 SRC, a representative sample seed of the cultivar having been deposited with the ATCC under ATCC Accession No. PTA-13572, and hybrid cultivar KY14×L8 SRC; and (b) introducing a transgene (nucleic acid construct) conferring at least one desired trait into the tissue.

In another aspect, the present disclosure includes a method of producing an herbicide resistant tobacco plant comprising transforming a tobacco plant, or part thereof, produced by growing a seed of a tobacco cultivar selected from the group consisting of tobacco cultivar KY14 SRC, a representative sample seed of the cultivar having been deposited with the ATCC under ATCC Accession No. PTA-120311, tobacco cultivar CMS KY14 SRC, a representative sample seed of the cultivar having been deposited with the ATCC under ATCC Accession No. PTA-13571, tobacco cultivar L8 SRC, a representative sample seed of the cultivar having been deposited with the ATCC under ATCC Accession No. PTA-13572, and hybrid cultivar KY14×L8 SRC with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile and any combination thereof.

In another aspect, the present disclosure includes an herbicide resistant tobacco plant produced by a method comprising transforming a tobacco plant, or part thereof, produced by growing a seed of a tobacco cultivar selected from the group consisting of tobacco cultivar KY14 SRC, a representative sample seed of the cultivar having been deposited with the ATCC under ATCC Accession No. PTA-120311, tobacco cultivar CMS KY14 SRC, a representative sample seed of the cultivar having been deposited with the ATCC under ATCC Accession No. PTA-13571, tobacco cultivar L8 SRC, a representative sample seed of the cultivar having been deposited with the ATCC under ATCC Accession No. PTA-13572, and hybrid cultivar KY14×L8 SRC, with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes a method of producing a pest and/or insect resistant tobacco plant where the method comprises transforming a tobacco plant produced by growing a seed of a tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571, L8 SRC, a representative sample seed of the cultivar having been deposited with the ATCC under ATCC Accession No. PTA-13572, and hybrid cultivar KY14×L8 SRC, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of a tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571, L8 SRC, a representative sample seed of the cultivar having been deposited with the ATCC under ATCC Accession No. PTA-13572, and hybrid cultivar KY14×L8 SRC with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of a tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571, L8 SRC, a representative sample seed of the cultivar having been deposited with the ATCC under ATCC Accession No. PTA-13572, and hybrid cultivar KY14×L8 SRC, with at least one transgene (nucleic acid construct) that confers pest and/or insect resistance, where the transgene (nucleic acid construct) encodes a *Bacillus thuringiensis* (BT) endotoxin.

In another aspect, the present disclosure includes a method of producing a disease resistant tobacco plant, the method comprising transforming a tobacco plant produced by growing a seed of a tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571, L8 SRC, a representative sample seed of the cultivar having been deposited with the ATCC under ATCC Accession No. PTA-13572, and hybrid cultivar KY14×L8 SRC with at least one transgene (nucleic acid construct) that confers disease resistance.

In a further aspect, the present disclosure includes a disease resistant tobacco plant produced by transforming a tobacco plant produced by growing a seed of a tobacco cultivar selected from the group consisting of KY14 SRC, a representative sample seed of the cultivar having been deposited with the ATCC under ATCC Accession No. PTA-120311, CMS KY14 SRC, a representative sample seed of the cultivar having been deposited with the ATCC under ATCC Accession No. PTA-13571, L8 SRC, a representative sample seed of the cultivar having been deposited with the ATCC under ATCC Accession No. PTA-13572, and hybrid cultivar KY14×L8 SRC with at least one transgene (nucleic acid construct) that confers disease resistance.

In an aspect, the present disclosure includes a seed of tobacco cultivar NC775 SRC, a representative sample seed of the cultivar having been deposited with the American Type Culture Collection (ATCC) under ATCC Accession No. PTA-120312.

In another aspect, the present disclosure includes a tobacco plant, or part thereof, produced by growing the seed of tobacco cultivar NC775 SRC, a representative sample seed of the cultivar having been deposited with the ATCC under ATCC Accession No. PTA-120312.

In a further aspect, the present disclosure includes a harvested leaf, or part thereof, of a tobacco plant, or part thereof, produced by growing the seed of tobacco cultivar NC775 SRC, a representative sample seed of the cultivar having been deposited with the ATCC under ATCC Accession No. PTA-120312.

In an aspect, the present disclosure includes a harvested leaf, or part thereof, of a tobacco plant, produced by growing the seed of tobacco cultivar NC775 SRC, a representative sample seed of the cultivar having been deposited with the ATCC under ATCC Accession No. PTA-120312, where the leaf has a reduced amount of nomicotine and/or N'-nitrosonomicotine (NNN).

In an aspect, the present disclosure includes a harvested leaf, or part thereof, produced by growing the seed of tobacco cultivar NC775 SRC, a representative sample seed of the cultivar having been deposited with the ATCC under ATCC Accession No. PTA-120312, where the leaf has a reduced amount of nomicotine and/or N'-nitrosonomicotine (NNN), where the reduced amount of nomicotine and/or N'-nitrosonomicotine (NNN) is reduced in a smoke stream produced from the leaf.

In a further aspect, the present disclosure includes a tobacco product, prepared from a tobacco plant, or part thereof, produced by growing the seed of tobacco cultivar NC775 SRC, a representative sample seed of the cultivar having been deposited with the ATCC under ATCC Accession No. PTA-120312, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar NC775 SRC, a representative sample seed of the cultivar having been deposited with the ATCC under ATCC Accession No. PTA-120312, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar NC775 SRC, a representative sample seed of the cultivar having been deposited with the ATCC under ATCC Accession No. PTA-120312, where the product is selected from the group consisting of a cigarillo, a non-ventilated recess filter cigarette, a vented recess filter cigarette, a cigar, snuff, and chewing tobacco, and where the product has a reduced amount of nomicotine and/or N'-nitrosonomicotine (NNN).

In a further aspect, the present disclosure includes a second tobacco product prepared or produced from a first tobacco product prepared from a tobacco plant, or part thereof, produced by growing the seed of tobacco cultivar NC775 SRC, a representative sample seed of the cultivar having been deposited with the ATCC under ATCC Accession No. PTA-120312, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or second product comprises a reduced amount of nomicotine and/or N'-nitrosonomicotine (NNN).

In an aspect, the present disclosure includes a part of a tobacco plant, produced by growing the seed of tobacco cultivar NC775 SRC, a representative sample seed of the cultivar having been deposited with the ATCC under ATCC Accession No. PTA-120312, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar NC775 SRC, a representative sample seed of the cultivar having been deposited with the ATCC under ATCC Accession No. PTA-120312, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar NC775 SRC, a representative sample seed of the cultivar having been deposited with the ATCC under ATCC Accession No. PTA-120312, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole, where the regenerated plant has all or essentially all of the morphological and physiological characteristics of cultivar NC775 SRC.

In an aspect, the present disclosure includes an $F_1$ progeny plant of tobacco cultivar NC775 SRC, a representative sample seed of the cultivar having been deposited with the ATCC under ATCC Accession No. PTA-120312.

In another aspect, the present disclosure includes an $F_1$ progeny plant of tobacco cultivar NC775 SRC, a representative sample seed of the cultivar having been deposited with the ATCC under ATCC Accession No. PTA-120312, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is a tobacco plant produced by growing the seed of tobacco cultivar NC775 SRC, a representative sample seed of the cultivar having been deposited with the ATCC under ATCC Accession No. PTA-120312, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC775 SRC, a representative sample seed of the cultivar having been deposited with the ATCC under ATCC Accession No. PTA-120312.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC775 SRC, a representative sample seed of the cultivar having been deposited with the ATCC under ATCC Accession No. PTA-120312, where the plant of tobacco cultivar NC775 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC775 SRC, a representative sample seed of the cultivar having been deposited with the ATCC under ATCC Accession No. PTA-120312, where the plant of tobacco cultivar NC775 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC775 SRC, a representative sample seed of the cultivar having been deposited with the ATCC under ATCC Accession No. PTA-120312, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar NC775 SRC, a representative sample seed of the cultivar having been deposited with the ATCC under ATCC Accession No. PTA-120312, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar NC775 SRC, a representative sample seed of the cultivar having been deposited with the ATCC under ATCC Accession No. PTA-120312, and where at least one tobacco plant is cytoplasmic male sterile (CMS).

In an aspect, the present disclosure also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar NC775 SRC, a representative sample seed of the cultivar having been deposited with the ATCC under ATCC Accession No. PTA-120312, where at least one tobacco plant is cytoplasmic male sterile (CMS).

In another aspect, the present disclosure further includes a harvested leaf of an $F_1$ progeny plant having a reduced amount of nomicotine and/or N'-nitrosonomicotine (NNN) produced by growing a seed produced by crossing two tobacco plants and harvesting the resultant tobacco seed, where at least one tobacco plant is a tobacco plant produced by growing the seed of tobacco cultivar NC775 SRC, a representative sample seed of the cultivar having been deposited with the ATCC under ATCC Accession No. PTA-120312, where at least one tobacco plant is cytoplasmic male sterile (CMS).

In an aspect, the present disclosure also includes a harvested leaf of an $F_1$ progeny plant having a reduced amount of nomicotine and/or N'-nitrosonomicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar NC775 SRC, a representative sample seed of the cultivar having been deposited with the ATCC under ATCC Accession No. PTA-120312, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar NC775 SRC, a representative sample seed of the cultivar having been deposited with the ATCC under ATCC Accession No. PTA-120312, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar NC775 SRC, a representative sample seed of the cultivar having been deposited with the ATCC under ATCC Accession No. PTA-120312, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar NC775 SRC, a representative sample seed of the cultivar having been deposited with the ATCC under ATCC Accession No. PTA-120312, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco, and further where the product has a reduced amount of nomicotine and/or N'-nitrosonornicotine (NNN).

In another aspect, the present disclosure includes a seed of tobacco cultivar CMS NC775 SRC, a representative sample seed of the cultivar having been deposited with the ATCC under ATCC Accession No. PTA-13563.

In an aspect, the present disclosure includes a tobacco plant, or part thereof, produced by growing the seed of tobacco cultivar CMS NC775 SRC, a representative sample seed of the cultivar having been deposited with the ATCC under ATCC Accession No. PTA-13563.

In another aspect, the present disclosure includes a harvested leaf, or part thereof, of a tobacco plant produced by growing the seed of tobacco cultivar CMS NC775 SRC, a representative sample seed of the cultivar having been deposited with the ATCC under ATCC Accession No. PTA-13563.

In an aspect, the present disclosure includes a harvested leaf, or part thereof, of a tobacco plant, produced by growing the seed of tobacco cultivar CMS NC775 SRC, a representative sample seed of the cultivar having been deposited with the ATCC under ATCC Accession No. PTA-13563, where the leaf has a reduced amount of nornicotine and/or N'-nitrosonomicotine (NNN).

In another aspect, the present disclosure includes a harvested leaf, or part thereof, produced by growing the seed of tobacco cultivar CMS NC775 SRC, a representative sample seed of the cultivar having been deposited with the ATCC under ATCC Accession No. PTA-13563, where the leaf has a reduced amount of nomicotine and/or N'-nitrosonomicotine (NNN), where the reduced amount of nomicotine and/or N'-nitrosonomicotine (NNN) is reduced in a smoke stream produced from the leaf.

In a further aspect, the present disclosure includes a tobacco product, prepared from a tobacco plant, or part thereof, produced by growing the seed of tobacco cultivar CMS NC775 SRC, a representative sample seed of the cultivar having been deposited with the ATCC under ATCC Accession No. PTA-13563, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar CMS NC775 SRC, a representative sample seed of the cultivar having been deposited with the ATCC under ATCC Accession No. PTA-13563, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar CMS NC775 SRC, a representative sample seed of the cultivar having been deposited with the ATCC under ATCC Accession No. PTA-13563, where the product is selected from the group consisting of a cigarillo, a non-ventilated recess filter cigarette, a vented recess filter cigarette, a cigar, snuff, and chewing tobacco where the product has a reduced amount of nomicotine and/or N'-nitrosonomicotine (NNN).

In a further aspect, the present disclosure includes a second tobacco product prepared or produced from a first tobacco product prepared from a tobacco plant, or part thereof, produced by growing the seed of tobacco cultivar CMS NC775 SRC, a representative sample seed of the cultivar having been deposited with the ATCC under ATCC Accession No. PTA-13563, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or second product comprises a reduced amount of nomicotine and/or N'-nitrosonornicotine (NNN).

In an aspect, the present disclosure includes a part of a tobacco plant, produced by growing the seed of tobacco cultivar CMS NC775 SRC, a representative sample seed of the cultivar having been deposited with the ATCC under ATCC Accession No. PTA-13563, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar CMS NC775 SRC, a representative sample seed of the cultivar having been deposited with the ATCC under ATCC Accession No. PTA-13563, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar CMS NC775 SRC, a representative sample seed of the cultivar having been deposited with the ATCC under ATCC Accession No. PTA-13563, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole, where the regenerated plant has all or essentially all of the morphological and physiological characteristics of cultivar CMS NC775 SRC.

In an aspect, the present disclosure includes an $F_1$ progeny plant of tobacco cultivar CMS NC775 SRC, a representative sample seed of the cultivar having been deposited with the ATCC under ATCC Accession No. PTA-13563.

In another aspect, the present disclosure includes an $F_1$ progeny plant of tobacco cultivar CMS NC775 SRC, a representative sample seed of the cultivar having been deposited with the ATCC under ATCC Accession No. PTA-13563, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is cytoplasmic male sterile (CMS), where the cytoplasmic male sterile plant is a plant of tobacco cultivar CMS NC775 SRC, a representative sample seed of the cultivar having been deposited with the ATCC under ATCC Accession No. PTA-13563.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS NC775 SRC, a representative sample seed of the cultivar having been deposited with the ATCC under ATCC Accession No. PTA-13563.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS NC775 SRC, a representative sample seed of the cultivar having been deposited with the ATCC under ATCC Accession No. PTA-13563, where the plant of tobacco cultivar CMS NC775 SRC is the female parent.

In another aspect, the present disclosure includes a method for producing a tobacco seed comprising crossing two tobacco plants and harvesting the resultant tobacco seed, where at least one tobacco plant is cytoplasmic male sterile (CMS), where the cytoplasmic male sterile plant is a plant of tobacco cultivar CMS NC775 SRC, a representative sample seed of the cultivar having been deposited with the ATCC under ATCC Accession No. PTA-13563.

In an aspect, the present disclosure also includes a container of $F_1$ progeny seeds produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC775 SRC, a representative sample seed of the cultivar having been deposited with the ATCC under ATCC Accession No. PTA-13563.

In an aspect, the present disclosure includes an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC775 SRC, a representative sample seed of the cultivar having been deposited with the ATCC under ATCC Accession No. PTA-13563.

In an aspect, the present disclosure also includes a harvested leaf of an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC775 SRC, a representative sample seed of the cultivar having been deposited with the ATCC under ATCC Accession No. PTA-13563.

In another aspect, the present disclosure further includes a harvested leaf of an $F_1$ progeny plant having a reduced amount of nornicotine and/or N'-nitrosonornicotine (NNN) produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC775 SRC, a representative sample seed of the cultivar having been deposited with the ATCC under ATCC Accession No. PTA-13563.

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC775 SRC, a representative sample seed of the cultivar having been deposited with the ATCC under ATCC Accession No. PTA-13563.

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC775 SRC, a representative sample seed of the cultivar having been deposited with the ATCC under ATCC Accession No. PTA-13563, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC775 SRC, a representative sample seed of the cultivar having been deposited with the ATCC under ATCC Accession No. PTA-13563, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC775 SRC, a representative sample seed of the cultivar having been deposited with the ATCC under ATCC Accession No. PTA-13563, and where the tobacco product is selected from the group consisting of a cigarillo, a non-ventilated recess filter cigarette, a vented recess filter cigarette, a cigar, snuff, and chewing tobacco, and further where the product has a reduced amount of nornicotine and/or N'-nitrosonornicotine (NNN).

In another aspect, the present disclosure includes a seed of tobacco cultivar NC645 SRC, a representative sample seed of the cultivar having been deposited with the ATCC under ATCC Accession No. PTA-13566.

In an aspect, the present disclosure includes a tobacco plant, or part thereof, produced by growing the seed of tobacco cultivar NC645 SRC, a representative sample seed of the cultivar having been deposited with the ATCC under ATCC Accession No. PTA-13566.

In another aspect, the present disclosure includes a harvested leaf, or part thereof, of a tobacco plant, or part thereof, produced by growing the seed of tobacco cultivar NC645 SRC, a representative sample seed of the cultivar having been deposited with the ATCC under ATCC Accession No. PTA-13566.

In an aspect, the present disclosure includes a harvested leaf, or part thereof, of a tobacco plant, produced by growing the seed of tobacco cultivar NC645 SRC, a representative sample seed of the cultivar having been deposited with the ATCC under ATCC Accession No. PTA-13566, where the leaf has a reduced amount of nornicotine and/or N'-nitrosonornicotine (NNN).

In another aspect, the present disclosure includes a harvested leaf, or part thereof, produced by growing the seed of tobacco cultivar NC645 SRC, a representative sample seed of the cultivar having been deposited with the ATCC under ATCC Accession No. PTA-13566, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar NC645 SRC, a representative sample seed of the cultivar having been deposited with the ATCC under ATCC Accession No. PTA-13566, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar NC645 SRC, a representative sample seed of the cultivar having been deposited with the ATCC under ATCC Accession No. PTA-13566, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar NC645 SRC, a representative sample seed of the cultivar having been deposited with the ATCC under ATCC Accession No. PTA-13566, where the product is selected from the group consisting of a cigarillo, a non-ventilated recess filter cigarette, a vented recess filter cigarette, a cigar, snuff, and chewing tobacco where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar NC645 SRC, a representative sample seed of the cultivar having been deposited with the ATCC under ATCC Accession No. PTA-13566, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or second product comprises a reduced amount of nornicotine and/or N'-nitrosonornicotine (NNN).

In an aspect, the present disclosure includes a part of a tobacco plant, produced by growing the seed of tobacco cultivar NC645 SRC, a representative sample seed of the cultivar having been deposited with the ATCC under ATCC Accession No. PTA-13566, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar NC645 SRC, a representative sample seed of the cultivar having been deposited with the ATCC under ATCC Accession No. PTA-13566, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar NC645 SRC, a representative sample seed of the cultivar having been deposited with the ATCC under ATCC Accession No. PTA-13566, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole, where the regenerated plant has all or essentially all of the morphological and physiological characteristics of cultivar NC645 SRC.

In an aspect, the present disclosure includes an $F_1$ progeny plant of tobacco cultivar NC645 SRC, a representative sample seed of the cultivar having been deposited with the ATCC under ATCC Accession No. PTA-13566.

In another aspect, the present disclosure includes an $F_1$ progeny plant of tobacco cultivar NC645 SRC, a representative sample seed of the cultivar having been deposited with the ATCC under ATCC Accession No. PTA-13566, where the $F_1$ plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC645 SRC, a representative sample seed of the cultivar having been deposited with the ATCC under ATCC Accession No. PTA-13566.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC645 SRC, a representative sample seed of the cultivar having been deposited with the ATCC under ATCC Accession No. PTA-13566, where the plant of tobacco cultivar NC645 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC645 SRC, a representative sample seed of the cultivar having been deposited with the ATCC under ATCC Accession No. PTA-13566, where the plant of tobacco cultivar NC645 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC645 SRC, a representative sample seed of the cultivar having been deposited with the ATCC under ATCC Accession No. PTA-13566, where at least one tobacco plant is cytoplasmic male sterile (CMS).

In another aspect, the present disclosure includes an $F_1$ progeny seed produced by crossing two tobacco plants and harvesting the resultant tobacco seed, where at least one tobacco plant is a tobacco plant produced by growing the seed of tobacco cultivar NC645 SRC, a representative sample seed of the cultivar having been deposited with the ATCC under ATCC Accession No. PTA-13566, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar NC645 SRC, a representative sample seed of the cultivar having been deposited with the ATCC under ATCC Accession No. PTA-13566, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar NC645 SRC, a representative sample seed of the cultivar having been deposited with the ATCC under ATCC Accession No. PTA-13566, and where at least one tobacco plant is cytoplasmic male sterile (CMS).

In an aspect, the present disclosure also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar NC645 SRC, a representative sample seed of the cultivar having been deposited with the ATCC under ATCC Accession No. PTA-13566, where at least one tobacco plant is cytoplasmic male sterile (CMS).

In another aspect, the present disclosure further includes a harvested leaf of an $F_1$ progeny plant having a reduced amount of nomicotine and/or N'-nitrosonomicotine (NNN) produced by growing a seed produced by crossing two tobacco plants and harvesting the resultant tobacco seed, where at least one tobacco plant is a tobacco plant produced by growing the seed of tobacco cultivar NC645 SRC, a representative sample seed of the cultivar having been deposited with the ATCC under ATCC Accession No. PTA-13566, where at least one tobacco plant is cytoplasmic male sterile (CMS).

In an aspect, the present disclosure also includes a harvested leaf of an $F_1$ progeny plant having a reduced amount of nomicotine and/or N'-nitrosonomicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar NC645 SRC, a representative sample seed of the cultivar having been deposited with the ATCC under ATCC Accession No. PTA-13566, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar NC645 SRC, a representative sample seed of the cultivar having been deposited with the ATCC under ATCC Accession No. PTA-13566, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar NC645 SRC, a representative sample seed of the cultivar having been deposited with the ATCC under ATCC Accession No. PTA-13566, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar NC645 SRC, a representative sample seed of the cultivar having been deposited with the ATCC under ATCC Accession No. PTA-13566, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco, and further where the product has a reduced amount of nomicotine and/or N'-nitrosonornicotine (NNN).

In another aspect, the present disclosure includes a seed of hybrid tobacco cultivar NC7 SRC (ATCC Accession No. PTA-13564). Seeds of hybrid cultivar NC7 SRC are obtainable by crossing plants of cultivars NC775 SRC and CMS NC775 SRC and collecting the seeds.

In an aspect, the present disclosure includes a tobacco plant, or part thereof, produced by growing a seed of hybrid tobacco cultivar NC7 SRC.

In a further aspect, the present disclosure includes a harvested leaf, or part thereof, of a tobacco plant, or part thereof, produced by growing the seed of hybrid tobacco cultivar NC7 SRC.

In another aspect, the present disclosure includes a harvested leaf, or part thereof, of a tobacco plant, produced by growing the seed of hybrid tobacco cultivar NC7 SRC, where the leaf has a reduced amount of nomicotine and/or N'-nitrosonomicotine (NNN).

In an aspect, the present disclosure includes a harvested leaf, or part thereof, produced by growing the seed of hybrid tobacco cultivar NC7 SRC, where the leaf has a reduced amount of nomicotine and/or N'-nitrosonomicotine (NNN), where the reduced amount of nomicotine and/or N'-nitrosonomicotine (NNN) is reduced in a smoke stream produced from the leaf.

In a further aspect, the present disclosure includes a tobacco product, prepared from a tobacco plant, or part thereof, produced by growing the seed of hybrid tobacco cultivar NC7 SRC, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of hybrid tobacco cultivar NC7 SRC, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of hybrid tobacco cultivar NC7 SRC, where the product is selected from the group consisting of a cigarillo, a non-ventilated recess filter cigarette, a vented recess filter cigarette, a cigar, snuff, and chewing tobacco where the product has a reduced amount of nornicotine and/or N'-nitrosonomicotine (NNN).

In a further aspect, the present disclosure includes a second tobacco product prepared or produced from a first tobacco product prepared from a tobacco plant, or part thereof, produced by growing the seed of hybrid tobacco cultivar NC7 SRC, where the first tobacco product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and/or second product comprises a reduced amount of nornicotine and/or N'-nitrosonornicotine (NNN).

In an aspect, the present disclosure includes a part of a tobacco plant, produced by growing a seed of hybrid tobacco cultivar NC7 SRC, where the part is selected from the group consisting of leaf, pollen, ovule, embryo, cotyledon, hypocotyl, meristematic cell, protoplast, root, root tip, pistil, anther, flower, shoot, stem, pod, and petiole.

In a further aspect, the present disclosure includes a tissue culture produced from a protoplast or cell from a tobacco plant, or part thereof, produced by growing the seed of hybrid tobacco cultivar NC7 SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of hybrid tobacco cultivar NC7 SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole, where the regenerated plant has all or essentially all of the morphological and physiological characteristics of hybrid cultivar NC7 SRC.

In an aspect, the present disclosure includes an $F_1$ progeny plant of hybrid tobacco cultivar NC7 SRC.

In an aspect, the present disclosure includes an $F_1$ progeny plant of hybrid tobacco cultivar NC7 SRC, where the plant of tobacco cultivar NC7 SRC is the female parent.

In another aspect, the present disclosure includes an $F_1$ progeny plant of hybrid tobacco cultivar NC7 SRC where the $F_1$ plant is cytoplasmic male sterile (CMS).

In another aspect, the present disclosure includes a method for producing a tobacco seed of NC7 SRC comprising crossing two tobacco plants and harvesting the resultant tobacco seed, where one tobacco plant is a tobacco plant produced by growing the seed of tobacco cultivar NC775 SRC, a representative sample seed of the cultivar having been deposited with the ATCC under ATCC Accession No. PTA-120312.

In another aspect, the present disclosure includes a method for producing a tobacco seed of NC7 SRC comprising crossing two tobacco plants and harvesting the resultant tobacco seed, where one tobacco plant is a tobacco plant produced by growing the seed of tobacco cultivar CMS NC775 SRC, a representative sample seed of the cultivar having been deposited with the ATCC under ATCC Accession No. PTA-13563.

In another aspect, the present disclosure includes a method for producing a tobacco seed of NC7 SRC comprising crossing two tobacco plants and harvesting the resultant tobacco seed, where one tobacco plant is a tobacco plant produced by growing the seed of tobacco cultivar CMS NC775 SRC, a representative sample seed of the cultivar having been deposited with the ATCC under ATCC Accession No. PTA-13563 and a second tobacco plant is a tobacco plant produced by growing the seed of tobacco cultivar NC775 SRC, a representative sample seed of the cultivar having been deposited with the ATCC under ATCC Accession No. PTA-120312.

In an aspect, the present disclosure includes a method of vegetatively propagating a plant of a tobacco cultivar comprising the steps of (a) collecting tissue capable of being propagated from a plant of a tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, NC645 SRC, a representative sample seed of the cultivar having been deposited with the ATCC under ATCC Accession No. PTA-13566, and hybrid cultivar NC7 SRC; (b) cultivating the tissue to obtain a proliferated shoot; and (c) rooting the proliferated shoots to obtain a rooted plantlet.

In an aspect, the present disclosure includes a method of vegetatively propagating a plant of a tobacco cultivar comprising the steps of (a) collecting tissue capable of being propagated from a plant of a tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, NC645 SRC, a representative sample seed of the cultivar having been deposited with the ATCC under ATCC Accession No. PTA-13566, and hybrid cultivar NC7 SRC; (b) cultivating the tissue to obtain a proliferated shoot; (c) rooting the proliferated shoots to obtain a rooted plantlet; and (d) growing a plant from the rooted plantlet.

In an aspect, the present disclosure includes a method of introducing a desired trait into a tobacco cultivar comprising: (a) crossing a plant of a first tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, and NC645 SRC, a representative sample seed of the cultivar having been deposited with the ATCC under ATCC Accession No. PTA-13566, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of said first tobacco cultivar, NC775 SRC, CMS NC775 SRC, or NC645 SRC, respectively, and (e) repeating steps (c) and (d) three or more times (e.g., 3, 4, 5, 6, 7, 8, 9, 10, and the like) in succession to produce selected fourth or higher backcross progeny that comprise the desired trait. In additional aspects, steps (c) and (d) can be repeated one or more times (e.g., 1, 2, 3, 4, 5, 6, 7, 8, 9, 10, and the like) in succession to produce second or higher backcross progeny comprising the desired trait.

In an aspect, the present disclosure includes a method of introducing a desired trait into a tobacco cultivar comprising: (a) crossing a plant of a first tobacco cultivar selected from the group consisting of NC775 SRC, a representative sample seed of the cultivar having been deposited with the ATCC under ATCC Accession No. PTA-120312 and NC645 SRC, a representative sample seed of the cultivar having been deposited with the ATCC under ATCC Accession No. PTA-13566, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar. NC775 SRC or NC645 SRC, respectively; and (e) repeating steps (c) and (d) three or more times in succession to produce selected fourth or higher backcross progeny that comprise the desired trait, where the trait is cytoplasmic male sterility (CMS). In additional aspects, steps (c) and (d) can be repeated one or more times in succession to produce second or higher backcross progeny comprising the desired trait, where the trait is CMS.

In an aspect, the present disclosure includes a method of introducing a desired trait into a tobacco cultivar comprising: (a) crossing a plant of a first tobacco cultivar selected from the group consisting of NC775 SRC, a representative sample seed of the cultivar having been deposited with the ATCC under ATCC Accession No. PTA-120312 and NC645 SRC, a representative sample seed of the cultivar having been deposited with the ATCC under ATCC Accession No. PTA-13566, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed: (d) growing the $BC_1F_1$ progeny seed and selecting a backcross $BC_1F_1$ progeny plant comprising the desired trait and the physiological and essentially all of morphological characteristics of the first tobacco cultivar NC775 SRC or NC645 SRC, respectively; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens* or *Nicotiana glauca*. In additional aspects, steps (c) and (d) can be repeated one or more times in succession to produce second or higher backcross progeny comprising the desired trait, where the trait is CMS and the CMS trait is obtained from the cytoplasm of *Nicotiana suaveolens* or *Nicotiana glauca*.

In an aspect, the present disclosure includes a method of introducing a desired trait into a tobacco cultivar comprising: (a) crossing a plant of a first tobacco cultivar selected from the group consisting of NC775 SRC, a representative sample seed of the cultivar having been deposited with the ATCC under ATCC Accession No. PTA-120312 and NC645 SRC, a representative sample seed of the cultivar having been deposited with the ATCC under ATCC Accession No. PTA-13566 with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of tobacco cultivar NC775 SRC or NC645 SRC, respectively; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens*, and where the second tobacco plant is CMS NC775 SRC. In additional aspects, steps (c) and (d) can be repeated one or more times in succession to produce second or higher backcross progeny comprising the CMS trait obtained from the cytoplasm of *Nicotiana suaveolens*, and where the second tobacco plant is CMS NC775 SRC.

In an aspect, the present disclosure includes a tobacco plant produced by a method comprising introducing a desired trait into a tobacco cultivar comprising: (a) crossing a plant of a first tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, and NC645 SRC, a representative sample seed of the cultivar having been deposited with the ATCC under ATCC Accession No. PTA-13566, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar NC775 SRC, CMS NC775 SRC, or NC645 SRC, respectively; and (e) repeating steps (c) and (d) three or more times in succession to produce selected fourth or higher backcross progeny that comprise the desired trait. In additional aspects, steps (c) and (d) can be repeated one or more times in succession to produce second or higher backcross progeny comprising the desired trait.

In another aspect, the present disclosure includes a method of introducing a desired trait into a tobacco cultivar comprising: (a) crossing a plant of a first tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, and NC645 SRC, a representative sample seed of the cultivar having been deposited with the ATCC under ATCC Accession No. PTA-13566, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of said first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, NC775 SRC, CMS NC775 SRC, or NC645 SRC, respectively; and (e) repeating steps (c) and (d) one or more times in succession to produce a selected second, third, fourth or higher backcross progeny plant that comprises the desired trait and essentially all of the physiological and morphological characteristics of the first tobacco cultivar, NC775 SRC, CMS NC775 SRC, or NC645 SRC, respectively.

In another aspect, the present disclosure includes a method of introducing a desired trait into a tobacco cultivar comprising: (a) crossing a plant of a first tobacco cultivar selected from the group consisting of NC775 SRC, a representative sample seed of the cultivar having been deposited with the ATCC under ATCC Accession No. PTA- 120312, CMS NC775 SRC, a representative sample seed of the cultivar having been deposited with the ATCC under ATCC Accession No. PTA-13563, and NC645 SRC, a representative sample seed of the cultivar having been deposited with the ATCC under ATCC Accession No. PTA-13566, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of said first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of a tobacco cultivar. NC775 SRC, CMS NC775 SRC, or NC645 SRC, respectively; and (e) repeating steps (c) and (d) one or more times in succession to produce a selected second, third, fourth or higher backcross progeny plant that comprises the desired trait and essentially all of the physiological and morphological characteristics of the first tobacco cultivar, NC775 SRC, CMS NC775 SRC, or NC645 SRC, respectively, where the plant has a desired trait.

In another aspect, the present disclosure includes a method of introducing a desired trait into a tobacco cultivar comprising: (a) crossing a plant of a first tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, and NC645 SRC, a representative sample seed of the cultivar having been deposited with the ATCC under ATCC Accession No. PTA-13566, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait, (c) crossing the selected $F_1$ progeny plant with a plant of said first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, NC775 SRC, CMS NC775 SRC, or NC645 SRC, respectively; and (e) repeating steps (c) and (d) one or more times in succession to produce a selected second, third, fourth or higher backcross progeny plant that comprises the desired trait and essentially all of the physiological and morphological characteristics of a tobacco cultivar, NC775 SRC, CMS NC775 SRC, or NC645 SRC, respectively, where the plant has a desired trait of disease resistance.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof, crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the first tobacco plant is a plant of a tobacco cultivar selected from the group consisting of tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, NC645 SRC, a representative sample seed of the cultivar having been deposited with the ATCC under ATCC Accession No. PTA-13566, and hybrid cultivar NC7 SRC.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the third tobacco plant is a plant of a tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, NC645 SRC, a representative sample seed of the cultivar having been deposited with the ATCC under ATCC Accession No. PTA-13566, and hybrid cultivar NC7 SRC.

In another aspect, the present disclosure includes a method of producing a plant of a tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, and NC645 SRC, a representative sample seed of the cultivar having been deposited with the ATCC under ATCC Accession No. PTA-13566, comprising at least one (e.g., 1, 2, 3, 4, 5, 6, 7, 8, and the like) additional desired trait comprising the steps of: (a) collecting tissue capable of being propagated from a plant of a tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, and NC645 SRC, a representative sample seed of the cultivar having been deposited with the ATCC under ATCC Accession No. PTA-13566; and (b) introducing at least one transgene (nucleic acid construct) conferring at least one desired trait into the tissue.

In another aspect, the present disclosure includes a method of producing an herbicide resistant tobacco plant comprising transforming a tobacco plant, or part thereof, produced by growing a seed of a tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, NC645 SRC, a representative sample seed of the cultivar having been deposited with the ATCC under ATCC Accession No. PTA-13566, and hybrid cultivar NC7 SRC, with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes an herbicide resistant tobacco plant produced by a method comprising transforming a tobacco plant, or part thereof, produced by growing a seed of a tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, NC645 SRC, a representative sample seed of the cultivar having been deposited with the ATCC under ATCC Accession No. PTA-13566, and hybrid cultivar NC7 SRC, with at least one transgene (nucleic acid construct), where the at least one transgene (nucleic acid construct) confers resistance to an herbicide selected from the group consisting of imidazolinone, cyclohexanedione, sulfonylurea glyphosate, glufosinate, phenoxy proprionic acid, L-phosphinothricin, triazine, benzonitrile, and any combination thereof.

In another aspect, the present disclosure includes a method of producing a pest and/or insect resistant tobacco plant where the method comprises transforming a tobacco plant produced by growing a seed of a tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, NC645 SRC, a representative sample seed of the cultivar having been deposited with the ATCC under ATCC Accession No. PTA-13566, and hybrid cultivar NC7 SRC, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of a tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, NC645 SRC, a representative sample seed of the cultivar having been deposited with the ATCC under ATCC Accession No. PTA-13566, and hybrid cultivar NC7 SRC with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of a tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, NC645 SRC, a representative sample seed of the cultivar having been deposited with the ATCC under ATCC Accession No. PTA-13566, and hybrid cultivar NC7 SRC, with at least one transgene (nucleic acid construct) that confers pest and/or insect resistance, where the transgene encodes a *Bacillus thuringiensis* (BT) endotoxin.

In another aspect, the present disclosure includes a method of producing a disease resistant tobacco plant where the method comprises transforming a tobacco plant produced by growing a seed of a tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, NC645 SRC, a representative sample seed of the cultivar having been deposited with the ATCC under ATCC Accession No. PTA-13566, and hybrid cultivar NC7 SRC with at least one transgene (nucleic acid construct) that confers disease resistance.

In a further aspect, the present disclosure includes a disease resistant tobacco plant produced by a method comprising transforming a tobacco plant produced by growing a seed of a tobacco cultivar selected from the group consisting of NC775 SRC, a representative sample seed of the cultivar having been deposited with the ATCC under ATCC Accession No. PTA-120312, CMS NC775 SRC, a representative sample seed of the cultivar having been deposited with the ATCC under ATCC Accession No. PTA-13563, NC645 SRC, a representative sample seed of the cultivar having been deposited with the ATCC under ATCC Accession No. PTA-13566, and hybrid cultivar NC7 SRC, with at least one transgene (nucleic acid construct) that confers disease resistance.

In an aspect, the present disclosure includes a seed of tobacco cultivar NC638 SRC, a representative sample seed of the cultivar having been deposited with the American Type Culture Collection (ATCC) under ATCC Accession No. PTA-120313.

In another aspect, the present disclosure includes a tobacco plant, or part thereof, produced by growing the seed of tobacco cultivar NC638 SRC, a representative sample seed of the cultivar having been deposited with the ATCC under ATCC Accession No. PTA-120313.

In a further aspect, the present disclosure includes a harvested leaf, or part thereof, of a tobacco plant, or part thereof, produced by growing the seed of tobacco cultivar NC638 SRC, a representative sample seed of the cultivar having been deposited with the ATCC under ATCC Accession No. PTA-120313.

In an aspect, the present disclosure includes a harvested leaf, or part thereof, of a tobacco plant, produced by growing the seed of tobacco cultivar NC638 SRC, a representative sample seed of the cultivar having been deposited with the ATCC under ATCC Accession No. PTA-120313, where the leaf has a reduced amount of nomicotine and/or N'-nitrosonornicotine (NNN).

In an aspect, the present disclosure includes a harvested leaf, or part thereof, produced by growing the seed of tobacco cultivar NC638 SRC, a representative sample seed of the cultivar having been deposited with the ATCC under ATCC Accession No. PTA-120313, where the leaf has a reduced amount of nomicotine and/or N'-nitrosonornicotine (NNN), where the reduced amount of nomicotine and/or N'-nitrosonomicotine (NNN) is reduced in a smoke stream produced from the leaf.

In a further aspect, the present disclosure includes a tobacco product, prepared from a tobacco plant, or part thereof, produced by growing the seed of tobacco cultivar NC638 SRC, a representative sample seed of the cultivar having been deposited with the ATCC under ATCC Accession No. PTA-120313, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar NC638 SRC, a representative sample seed of the cultivar having been deposited with the ATCC under ATCC Accession No. PTA-120313, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar NC638 SRC, a representative sample seed of the cultivar having been deposited with the ATCC under ATCC Accession No. PTA-120313, where the product is selected from the group consisting of a cigarillo, a non-ventilated recess filter cigarette, a vented recess filter cigarette, a cigar, snuff, and chewing tobacco, and where the product has a reduced amount of nomicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar NC638 SRC, a representative sample seed of the cultivar having been deposited with the ATCC under ATCC Accession No. PTA-120313, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and second product comprises a reduced amount of nomicotine and/or N'-nitrosonomicotine (NNN).

In an aspect, the present disclosure includes a part of a tobacco plant, produced by growing the seed of tobacco cultivar NC638 SRC, a representative sample seed of the cultivar having been deposited with the ATCC under ATCC Accession No. PTA-120313, where the part is selected from the group consisting of leaf, pollen, ovule, embryo, cotyledon, hypocotyl, meristematic cell, protoplast, root, root tip, pistil, anther, flower, shoot, stem, pod and petiole.

In another aspect, the present disclosure includes a tissue culture produced from a protoplast or cell from a tobacco plant, or part thereof, produced by growing the seed of tobacco cultivar NC638 SRC, a representative sample seed of the cultivar having been deposited with the ATCC under ATCC Accession No. PTA-120313, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar NC638 SRC, a representative sample seed of the cultivar having been deposited with the ATCC under ATCC Accession No. PTA-120313, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole, where the regenerated plant has all, or essentially all of the morphological and physiological characteristics of cultivar NC638 SRC.

In an aspect, the present disclosure includes an $F_1$ progeny plant of tobacco cultivar NC638 SRC, a representative sample seed of the cultivar having been deposited with the ATCC under ATCC Accession No. PTA-120313.

In another aspect, the present disclosure includes an $F_1$ progeny plant of tobacco cultivar NC638 SRC, a representative sample seed of the cultivar having been deposited with the ATCC under ATCC Accession No. PTA-120313, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is a tobacco plant produced by growing the seed of tobacco cultivar NC638 SRC, a representative sample seed of the cultivar having been deposited with the ATCC under ATCC Accession No. PTA-120313, where at least one tobacco plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC638 SRC, a representative sample seed of the cultivar having been deposited with the ATCC under ATCC Accession No. PTA-120313.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC638 SRC, a representative sample seed of the cultivar having been deposited with the ATCC under ATCC Accession No. PTA-120313, where the plant of tobacco cultivar NC638 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC638 SRC, a representative sample seed of the cultivar having been deposited with the ATCC under ATCC Accession No. PTA-120313, where the plant of tobacco cultivar NC638 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar NC638 SRC, a representative sample seed of the cultivar having been deposited with the ATCC under ATCC Accession No. PTA-120313, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar NC638 SRC, a representative sample seed of the cultivar having been deposited with the ATCC under ATCC Accession No. PTA-120313, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar NC638 SRC, a representative sample seed of the cultivar having been deposited with the ATCC under ATCC Accession No. PTA-120313, and where at least one tobacco plant is cytoplasmic male sterile (CMS).

In an aspect, the present disclosure also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar NC638 SRC, a representative sample seed of the cultivar having been deposited with the ATCC under ATCC Accession No. PTA-120313, where at least one tobacco plant is cytoplasmic male sterile (CMS).

In another aspect, the present disclosure further includes a harvested leaf of an $F_1$ progeny plant having a reduced amount of nomicotine and/or N'-nitrosonomicotine (NNN) produced by growing a seed produced by crossing two tobacco plants and harvesting the resultant tobacco seed, where at least one tobacco plant is a tobacco plant produced by growing the seed of tobacco cultivar NC638 SRC, a representative sample seed of the cultivar having been deposited with the ATCC under ATCC Accession No. PTA-120313, where at least one tobacco plant is cytoplasmic male sterile (CMS).

In an aspect, the present disclosure also includes a harvested leaf of an $F_1$ progeny plant having a reduced amount of nomicotine and/or N'-nitrosonomicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar NC638 SRC, a representative sample seed of the cultivar having been deposited with the ATCC under ATCC Accession No. PTA-120313, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar NC638 SRC, a representative sample seed of the cultivar having been deposited with the ATCC under ATCC Accession No. PTA-120313, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar NC638 SRC, a representative sample seed of the cultivar having been deposited with the ATCC under ATCC Accession No. PTA-120313, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar NC638 SRC, a representative sample seed of the cultivar having been deposited with the ATCC under ATCC Accession No. PTA-120313, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco, and further where the product has a reduced amount of nomicotine and/or N'-nitrosonomicotine (NNN).

In another aspect, the present disclosure includes a seed of tobacco cultivar CMS NC638 SRC, a representative sample seed of the cultivar having been deposited with the ATCC under ATCC Accession No. PTA-13568.

In an aspect, the present disclosure includes a tobacco plant, or part thereof, produced by growing the seed of tobacco cultivar CMS NC638 SRC, a representative sample seed of the cultivar having been deposited with the ATCC under ATCC Accession No. PTA-13568.

In another aspect, the present disclosure includes a harvested leaf, or part thereof, of a tobacco plant, or part thereof, produced by growing the seed of tobacco cultivar CMS NC638 SRC, a representative sample seed of the cultivar having been deposited with the ATCC under ATCC Accession No. PTA-13568.

In an aspect, the present disclosure includes a harvested leaf, or part thereof, of a tobacco plant, produced by growing the seed of tobacco cultivar CMS NC638 SRC, a representative sample seed of the cultivar having been deposited with the ATCC under ATCC Accession No. PTA-13568, where the leaf has a reduced amount of nomicotine and/or N'-nitrosonornicotine (NNN).

In another aspect, the present disclosure includes a harvested leaf, or part thereof, produced by growing the seed of tobacco cultivar CMS NC638 SRC, a representative sample seed of the cultivar having been deposited with the ATCC under ATCC Accession No. PTA-13568, where the leaf has a reduced amount of nomicotine and/or N'-nitrosonomicotine (NNN), where the reduced amount of nomicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar CMS NC638 SRC, a representative sample seed of the cultivar having been deposited with the ATCC under ATCC Accession No. PTA-13568, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar CMS NC638 SRC, a representative sample seed of the cultivar having been deposited with the ATCC under ATCC Accession No. PTA-13568, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar CMS NC638 SRC, a representative sample seed of the cultivar having been deposited with the ATCC under ATCC Accession No. PTA-13568, where the product is selected from the group consisting of a cigarillo, a non-ventilated recess filter cigarette, a vented recess filter cigarette, a cigar, snuff, and chewing tobacco where the product has a reduced amount of nomicotine and/or N'-nitrosonomicotine (NNN).

In a further aspect, the present disclosure includes a second tobacco product prepared or produced from a first tobacco product prepared from a tobacco plant, or part thereof, produced by growing the seed of tobacco cultivar CMS NC638 SRC, a representative sample seed of the cultivar having been deposited with the ATCC under ATCC Accession No. PTA-13568, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and second product comprises a reduced amount of nomicotine and/or N'-nitrosonomicotine (NNN).

In an aspect, the present disclosure includes a part of a tobacco plant, produced by growing the seed of tobacco cultivar CMS NC638 SRC, a representative sample seed of the cultivar having been deposited with the ATCC under ATCC Accession No. PTA-13568, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar CMS NC638 SRC, a representative sample seed of the cultivar having been deposited with the ATCC under ATCC Accession No. PTA-13568, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar CMS NC638 SRC, a representative sample seed of the cultivar having been deposited with the ATCC under ATCC Accession No. PTA-13568, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole, where the regenerated plant has all, or essentially all of the morphological and physiological characteristics of cultivar CMS NC638 SRC.

In an aspect, the present disclosure includes an $F_1$ progeny plant of tobacco cultivar CMS NC638 SRC, a representative sample seed of the cultivar having been deposited with the ATCC under ATCC Accession No. PTA-13568.

In another aspect, the present disclosure includes an $F_1$ progeny plant of tobacco cultivar CMS NC638 SRC, a representative sample seed of the cultivar having been deposited with the ATCC under ATCC Accession No. PTA-13568, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is cytoplasmic male sterile (CMS), where the cytoplasmic male sterile plant is a plant of tobacco cultivar CMS NC638 SRC, a representative sample seed of the cultivar having been deposited with the ATCC under ATCC Accession No. PTA-13568.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS NC638 SRC, a representative sample seed of the cultivar having been deposited with the ATCC under ATCC Accession No. PTA-13568.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS NC638 SRC, a representative sample seed of the cultivar having been deposited with the ATCC under ATCC Accession No. PTA-13568, where the plant of tobacco cultivar CMS NC638 SRC is the female parent.

In another aspect, the present disclosure includes a method for producing a tobacco seed comprising crossing two tobacco plants and harvesting the resultant tobacco seed, where at least one tobacco plant is cytoplasmic male sterile (CMS), where the cytoplasmic male sterile plant is a plant of tobacco cultivar CMS NC638 SRC, a representative sample seed of the cultivar having been deposited with the ATCC under ATCC Accession No. PTA-13568.

In an aspect, the present disclosure also includes a container of $F_1$ progeny seeds produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC638 SRC, a representative sample seed of the cultivar having been deposited with the ATCC under ATCC Accession No. PTA-13568.

In an aspect, the present disclosure includes an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC638 SRC, a representative sample seed of the cultivar having been deposited with the ATCC under ATCC Accession No. PTA-13568.

In an aspect, the present disclosure also includes a harvested leaf of an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC638 SRC, a representative sample seed of the cultivar having been deposited with the ATCC under ATCC Accession No. PTA-13568.

In another aspect, the present disclosure further includes a harvested leaf of an $F_1$ progeny plant having a reduced amount of nornicotine and/or N'-nitrosonornicotine (NNN) produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC638 SRC, a representative sample seed of the cultivar having been deposited with the ATCC under ATCC Accession No. PTA-13568.

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC638 SRC, a representative sample seed of the cultivar having been deposited with the ATCC under ATCC Accession No. PTA-13568.

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC638 SRC, a representative sample seed of the cultivar having been deposited with the ATCC under ATCC Accession No. PTA-13568, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC638 SRC, a representative sample seed of the cultivar having been deposited with the ATCC under ATCC Accession No. PTA-13568, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS NC638 SRC, a representative sample seed of the cultivar having been deposited with the ATCC under ATCC Accession No. PTA-13568, and where the tobacco product is selected from the group consisting of a cigarillo, a non-ventilated recess filter cigarette, a vented recess filter cigarette, a cigar, snuff, and chewing tobacco, and further where the product has a reduced amount of nornicotine and/or N'-nitrosonornicotine (NNN).

In an aspect, the present disclosure includes a method for producing a tobacco seed comprising crossing two tobacco plants and harvesting the resultant tobacco seed, where at least one tobacco plant is cytoplasmic male sterile, where the cytoplasmic male sterile plant is a plant of tobacco cultivar CMS NC638 SRC, a representative sample seed of the cultivar having been deposited with the ATCC under ATCC Accession No. PTA-13568.

In another aspect, the present disclosure includes a seed of tobacco cultivar TN86 SRC, a representative sample seed of the cultivar having been deposited with the ATCC under ATCC Accession No. PTA-13565.

In an aspect, the present disclosure includes a tobacco plant, or part thereof, produced by growing the seed of tobacco cultivar TN86 SRC, a representative sample seed of the cultivar having been deposited with the ATCC under ATCC Accession No. PTA-13565.

In another aspect, the present disclosure includes a harvested leaf, or part thereof, of a tobacco plant, or part thereof, produced by growing the seed of tobacco cultivar TN86 SRC, a representative sample seed of the cultivar having been deposited with the ATCC under ATCC Accession No. PTA-13565.

In an aspect, the present disclosure includes a harvested leaf, or part thereof, of a tobacco plant, produced by growing the seed of tobacco cultivar TN86 SRC, a representative sample seed of the cultivar having been deposited with the ATCC under ATCC Accession No. PTA-13565, where the leaf has a reduced amount of nornicotine and/or N'-nitrosonornicotine (NNN).

In another aspect, the present disclosure includes a harvested leaf, or part thereof, produced by growing the seed of tobacco cultivar TN86 SRC, a representative sample seed of the cultivar having been deposited with the ATCC under ATCC Accession No. PTA-13565, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar TN86 SRC, a representative sample seed of the cultivar having been deposited with the ATCC under ATCC Accession No. PTA-13565, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar TN86

SRC, a representative sample seed of the cultivar having been deposited with the ATCC under ATCC Accession No. PTA-13565, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar TN86 SRC, a representative sample seed of the cultivar having been deposited with the ATCC under ATCC Accession No. PTA-13565, where the product is selected from the group consisting of a cigarillo, a non-ventilated recess filter cigarette, a vented recess filter cigarette, a cigar, snuff, and chewing tobacco where the product has a reduced amount of nornicotine and/or N'-nitrosonornicotine (NNN).

In a further aspect, the present disclosure includes a second tobacco product prepared or produced from a first tobacco product prepared from a tobacco plant, or part thereof, produced by growing the seed of tobacco cultivar TN86 SRC, a representative sample seed of the cultivar having been deposited with the ATCC under ATCC Accession No. PTA-13565, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and second product comprises a reduced amount of nornicotine and/or N'-nitrosonornicotine (NNN).

In an aspect, the present disclosure includes a part of a tobacco plant, produced by growing the seed of tobacco cultivar TN86 SRC, a representative sample seed of the cultivar having been deposited with the ATCC under ATCC Accession No. PTA-13565, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar TN86 SRC, a representative sample seed of the cultivar having been deposited with the ATCC under ATCC Accession No. PTA-13565, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar TN86 SRC, a representative sample seed of the cultivar having been deposited with the ATCC under ATCC Accession No. PTA-13565, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole, where the regenerated plant has all, or essentially all of the morphological and physiological characteristics of cultivar TN86 SRC.

In an aspect, the present disclosure includes an $F_1$ progeny plant of tobacco cultivar TN86 SRC, a representative sample seed of the cultivar having been deposited with the ATCC under ATCC Accession No. PTA-13565.

In another aspect, the present disclosure includes an $F_1$ progeny plant of tobacco cultivar TN86 SRC, a representative sample seed of the cultivar having been deposited with the ATCC under ATCC Accession No. PTA-13565, where the $F_1$ plant is cytoplasmic male sterile (CMS).

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar TN86 SRC, a representative sample seed of the cultivar having been deposited with the ATCC under ATCC Accession No. PTA-13565.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar TN86 SRC, a representative sample seed of the cultivar having been deposited with the ATCC under ATCC Accession No. PTA-13565, where the plant of tobacco cultivar TN86 SRC is the male parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar TN86 SRC, a representative sample seed of the cultivar having been deposited with the ATCC under ATCC Accession No. PTA-13565, where the plant of tobacco cultivar TN86 SRC is the female parent.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar TN86 SRC, a representative sample seed of the cultivar having been deposited with the ATCC under ATCC Accession No. PTA-13565, where at least one tobacco plant is cytoplasmic male sterile (CMS).

In another aspect, the present disclosure includes an $F_1$ progeny seed produced by crossing two tobacco plants and harvesting the resultant tobacco seed, where at least one tobacco plant is a tobacco plant produced by growing the seed of tobacco cultivar TN86 SRC, a representative sample seed of the cultivar having been deposited with the ATCC under ATCC Accession No. PTA-13565, where at least one tobacco plant is cytoplasmic male sterile (CMS).

In an aspect, the present disclosure also includes a container of $F_1$ progeny seeds produced by crossing two tobacco plants and harvesting the resultant tobacco seed, where at least one tobacco plant is a tobacco plant produced by growing the seed of tobacco cultivar TN86 SRC, a representative sample seed of the cultivar having been deposited with the ATCC under ATCC Accession No. PTA-13565, where at least one tobacco plant is cytoplasmic male sterile (CMS).

In an aspect, the present disclosure includes an $F_1$ progeny plant produced by growing a seed produced by crossing two tobacco plants and harvesting the resultant tobacco seed, where at least one tobacco plant is a tobacco plant produced by growing the seed of tobacco cultivar TN86 SRC, a representative sample seed of the cultivar having been deposited with the ATCC under ATCC Accession No. PTA-13565, and where at least one tobacco plant is cytoplasmic male sterile (CMS).

In an aspect, the present disclosure also includes a harvested leaf of an $F_1$ progeny plant produced by growing a seed produced by crossing two tobacco plants and harvesting the resultant tobacco seed, where at least one tobacco plant is a tobacco plant produced by growing the seed of tobacco cultivar TN86 SRC, a representative sample seed of the cultivar having been deposited with the ATCC under ATCC Accession No. PTA-13565, where at least one tobacco plant is cytoplasmic male sterile (CMS).

In another aspect, the present disclosure further includes a harvested leaf of an $F_1$ progeny plant having a reduced amount of nornicotine and/or N'-nitrosonornicotine (NNN) produced by growing a seed produced by crossing two tobacco plants and harvesting the resultant tobacco seed, where at least one tobacco plant is a tobacco plant produced by growing the seed of tobacco cultivar TN86 SRC, a representative sample seed of the cultivar having been deposited with the ATCC under ATCC Accession No. PTA-13565, where at least one tobacco plant is cytoplasmic male sterile (CMS).

In an aspect, the present disclosure also includes a harvested leaf of an $F_1$ progeny plant having a reduced amount of nornicotine and/or N'-nitrosonornicotine (NNN) in a smoke stream produced from the leaf, where the plant is produced by growing a seed produced by crossing two tobacco plants and harvesting the resultant tobacco seed, where at least one tobacco plant is a tobacco plant produced by growing the seed of tobacco cultivar TN86 SRC, a representative sample seed of the cultivar having been deposited with the ATCC under ATCC Accession No. PTA-13565, where at least one tobacco plant is cytoplasmic male sterile (CMS).

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar TN86 SRC, a representative sample seed of the cultivar having been deposited with the ATCC under ATCC Accession No. PTA-13565, where at least one tobacco plant is cytoplasmic male sterile, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar TN86 SRC, a representative sample seed of the cultivar having been deposited with the ATCC under ATCC Accession No. PTA-13565, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is produced by growing a seed of tobacco cultivar TN86 SRC, a representative sample seed of the cultivar having been deposited with the ATCC under ATCC Accession No. PTA-13565, where at least one tobacco plant is cytoplasmic male sterile, and where the tobacco product is selected from the group consisting of a cigarillo, a non-ventilated recess filter cigarette, a vented recess filter cigarette, a cigar, snuff, and chewing tobacco, and further where the product has a reduced amount of nornicotine and/or N'-nitrosonornicotine (NNN).

In another aspect, the present disclosure includes a seed of tobacco cultivar CMS TN86 SRC, a representative sample seed of the cultivar having been deposited with the ATCC under ATCC Accession No. PTA-13570.

In an aspect, the present disclosure includes a tobacco plant, or part thereof, produced by growing the seed of tobacco cultivar CMS TN86 SRC, a representative sample seed of the cultivar having been deposited with the ATCC under ATCC Accession No. PTA-13570.

In another aspect, the present disclosure includes a harvested leaf, or part thereof, of a tobacco plant, or part thereof, produced by growing the seed of tobacco cultivar CMS TN86SRC, a representative sample seed of the cultivar having been deposited with the ATCC under ATCC Accession No. PTA-13570.

In an aspect, the present disclosure includes a harvested leaf, or part thereof, of a tobacco plant, produced by growing the seed of tobacco cultivar CMS TN86 SRC, a representative sample seed of the cultivar having been deposited with the ATCC under ATCC Accession No. PTA-13570, where the leaf has a reduced amount of nornicotine and/or N'-nitrosonornicotine (NNN).

In another aspect, the present disclosure includes a harvested leaf, or part thereof, produced by growing the seed of tobacco cultivar CMS TN86 SRC, a representative sample seed of the cultivar having been deposited with the ATCC under ATCC Accession No. PTA-13570, where the leaf has a reduced amount of nornicotine and/or N'-nitrosonornicotine (NNN), where the reduced amount of nornicotine and/or N'-nitrosonornicotine (NNN) is reduced in a smoke stream produced from the leaf.

In a further aspect, the present disclosure includes a tobacco product, prepared from a tobacco plant, or part thereof, produced by growing the seed of tobacco cultivar CMS TN86 SRC, a representative sample seed of the cultivar having been deposited with the ATCC under ATCC Accession No. PTA-13570, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of tobacco cultivar CMS TN86 SRC, a representative sample seed of the cultivar having been deposited with the ATCC under ATCC Accession No. PTA-13570, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of tobacco cultivar CMS TN86 SRC, a representative sample seed of the cultivar having been deposited with the ATCC under ATCC Accession No. PTA-13570, where the product is selected from the group consisting of a cigarillo, a non-ventilated recess filter cigarette, a vented recess filter cigarette, a cigar, snuff, and chewing tobacco where the product has a reduced amount of nomicotine and/or N'-nitrosonomicotine (NNN).

In a further aspect, the present disclosure includes a second tobacco product prepared or produced from a first tobacco product prepared from a tobacco plant, or part thereof, produced by growing the seed of tobacco cultivar CMS TN86 SRC, a representative sample seed of the cultivar having been deposited with the ATCC under ATCC Accession No. PTA-13570, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and second product comprises a reduced amount of nomicotine and/or N'-nitrosonomicotine (NNN).

In an aspect, the present disclosure includes a part of a tobacco plant, produced by growing the seed of tobacco cultivar CMS TN86 SRC, a representative sample seed of the cultivar having been deposited with the ATCC under ATCC Accession No. PTA-13570, where the part is selected from the group consisting of leaf, pollen, ovule, embryo, cotyledon, hypocotyl, meristematic cell, protoplast, root, root tip, pistil, anther, flower, shoot, stem, pod, and petiole.

In another aspect, the present disclosure includes a tissue culture produced from a protoplast or cell from a tobacco plant, or part thereof, produced by growing the seed of tobacco cultivar CMS TN86 SRC, a representative sample seed of the cultivar having been deposited with the ATCC under ATCC Accession No. PTA-13570, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of tobacco cultivar CMS TN86 SRC, a representative sample seed of the cultivar having been deposited with the ATCC under ATCC Accession No. PTA-13570, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole, where the regenerated plant has all, or essentially all of the morphological and physiological characteristics of cultivar CMS TN86SRC.

In an aspect, the present disclosure includes an $F_1$ progeny plant of tobacco cultivar CMS TN86 SRC, a representative sample seed of the cultivar having been deposited with the ATCC under ATCC Accession No. PTA-13570.

In another aspect, the present disclosure includes an $F_1$ progeny plant of tobacco cultivar CMS TN86 SRC, a representative sample seed of the cultivar having been deposited with the ATCC under ATCC Accession No. PTA-13570, where the $F_1$ plant is cytoplasmic male sterile (CMS).

In another aspect, the present disclosure includes an $F_1$ progeny seed produced by crossing two tobacco plants and harvesting the resultant tobacco seed, where at least one tobacco plant is cytoplasmic male sterile (CMS), where the cytoplasmic male sterile plant is a plant of tobacco cultivar CMS TN86 SRC, a representative sample seed of the cultivar having been deposited with the ATCC under ATCC Accession No. PTA-13570.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS TN86 SRC, a representative sample seed of the cultivar having been deposited with the ATCC under ATCC Accession No. PTA-13570.

In another aspect, the present disclosure includes a method for producing a tobacco seed comprising crossing two tobacco plants and harvesting the resultant tobacco seed, where at least one tobacco plant is a tobacco plant produced by growing the seed of tobacco cultivar CMS TN86 SRC, a representative sample seed of the cultivar having been deposited with the ATCC under ATCC Accession No. PTA-13570, where the plant of tobacco cultivar CMS TN86 SRC is the female parent.

In another aspect, the present disclosure includes a method for producing a tobacco seed comprising crossing two tobacco plants and harvesting the resultant tobacco seed, where at least one tobacco plant is cytoplasmic male sterile (CMS), where the cytoplasmic male sterile plant is a plant of tobacco cultivar CMS TN86 SRC, a representative sample seed of the cultivar having been deposited with the ATCC under ATCC Accession No. PTA-13570.

In an aspect, the present disclosure also includes a container of $F_1$ progeny seeds produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN86 SRC, a representative sample seed of the cultivar having been deposited with the ATCC under ATCC Accession No. PTA-13570.

In an aspect, the present disclosure includes an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN86 SRC, a representative sample seed of the cultivar having been deposited with the ATCC under ATCC Accession No. PTA-13570.

In an aspect, the present disclosure also includes a harvested leaf of an $F_1$ progeny plant produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN86 SRC, a representative sample seed of the cultivar having been deposited with the ATCC under ATCC Accession No. PTA-13570.

In another aspect, the present disclosure further includes a harvested leaf of an $F_1$ progeny plant having a reduced amount of nomicotine and/or N'-nitrosonomicotine (NNN) produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN86 SRC, a representative sample seed of the cultivar having been deposited with the ATCC under ATCC Accession No. PTA-13570.

In an aspect, the present disclosure also includes a harvested leaf of an $F_1$ progeny plant having a reduced amount of nomicotine and/or N'-nitrosonomicotine (NNN) in a smoke stream produced from the leaf, where the plant is produced by growing a seed produced by crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN86 SRC, a representative sample seed of the cultivar having been deposited with the ATCC under ATCC Accession No. PTA-13570.

In an aspect, the present disclosure includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN86 SRC, a representative sample seed of the cultivar having been deposited with the ATCC under ATCC Accession No. PTA-13570, and where the tobacco product is selected from the group consisting of pipe tobacco, cigar tobacco, cigarette tobacco, chewing tobacco, leaf tobacco, shredded tobacco, cut tobacco, and any combination thereof.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN86 SRC, a representative sample seed of the cultivar having been deposited with the ATCC under ATCC Accession No. PTA-13570, and where the tobacco product is selected from the group consisting of a cigarillo, a non-ventilated recess filter cigarette, a vented recess filter cigarette, a cigar, snuff, and chewing tobacco.

In an aspect, the present disclosure further includes a tobacco product prepared from an $F_1$ progeny tobacco plant, or part thereof, where the plant or part thereof is produced by growing a $F_1$ progeny seed produced by a method comprising crossing two tobacco plants and harvesting the resultant tobacco seed, where at least one tobacco plant is cytoplasmic male sterile (CMS), where the cytoplasmic male sterile plant is a tobacco plant produced by growing the seed of tobacco cultivar CMS TN86 SRC, a representative sample seed of the cultivar having been deposited with the ATCC under ATCC Accession No. PTA-13570, and where the tobacco product is selected from the group consisting of a cigarillo, a non-ventilated recess filter cigarette, a vented recess filter cigarette, a cigar, snuff, and chewing tobacco, and further where the product has a reduced amount of nomicotine and/or N'-nitrosonomicotine (NNN).

In an aspect, the present disclosure includes a method for producing a tobacco seed comprising crossing two tobacco plants and harvesting the resultant tobacco seed, where at least one tobacco plant is cytoplasmic male sterile, where the cytoplasmic male sterile plant is a plant of tobacco cultivar CMS TN86 SRC, a representative sample seed of the cultivar having been deposited with the ATCC under ATCC Accession No. PTA-13570.

In another aspect, the present disclosure includes a seed of hybrid tobacco cultivar NCBH129 SRC (ATCC Accession No. PTA-13562). Seeds of hybrid cultivar NCBH129 SRC are obtainable by crossing plants of cultivars TN86 SRC and CMS NC638 SRC and collecting the seeds.

In an aspect, the present disclosure includes a tobacco plant, or part thereof, produced by growing a seed of hybrid tobacco cultivar NCBH129 SRC.

In a further aspect, the present disclosure includes a harvested leaf, or part thereof, of a tobacco plant, or part thereof, produced by growing the seed of hybrid tobacco cultivar NCBH129 SRC.

In another aspect, the present disclosure includes a harvested leaf, or part thereof, of a tobacco plant, produced by growing the seed of hybrid tobacco cultivar NCBH129 SRC, where the leaf has a reduced amount of nomicotine and/or N'-nitrosonomicotine (NNN).

In an aspect, the present disclosure includes a harvested leaf, or part thereof, produced by growing the seed of hybrid tobacco cultivar NCBH129 SRC, where the leaf has a reduced amount of nomicotine and/or N'-nitrosonomicotine (NNN), where the reduced amount of nomicotine and/or N'-nitrosonomicotine (NNN) is reduced in a smoke stream produced from the leaf.

In a further aspect, the present disclosure includes a tobacco product, prepared from a tobacco plant, or part thereof, produced by growing the seed of hybrid tobacco cultivar NCBH129 SRC, where the product is selected from the group consisting of pipe tobacco, cigar tobacco, cigarette tobacco, chewing tobacco, leaf tobacco, shredded tobacco, cut tobacco, and any combination thereof.

In an aspect, the present disclosure includes a tobacco product, prepared from a tobacco plant, or part thereof, produced by growing the seed of hybrid tobacco cultivar NCBH129 SRC, where the product is selected from the group consisting of a cigarillo, a non-ventilated recess filter cigarette, a vented recess filter cigarette, a cigar, snuff, and chewing tobacco.

In another aspect, the present disclosure includes a tobacco product, prepared from a tobacco plant, or part thereof, produced by growing the seed of hybrid tobacco cultivar NCBH129 SRC, where the product is selected from the group consisting of a cigarillo, a non-ventilated recess filter cigarette, a vented recess filter cigarette, a cigar, snuff, and chewing tobacco where the product has a reduced amount of nomicotine and/or N'-nitrosonomicotine (NNN).

In a further aspect, the present disclosure includes a second tobacco product prepared or produced from a first tobacco product prepared from a tobacco plant, or part thereof, produced by growing the seed of tobacco cultivar NCBH129 SRC, where first product is selected from the group consisting of pipe tobacco, cigar tobacco, cigarette tobacco, chewing tobacco, leaf tobacco, shredded tobacco, cut tobacco and any combination thereof, and the second tobacco product is selected from the group consisting of a cigarillo, a non-ventilated recess filter cigarette, a vented recess filter cigarette, a cigar, snuff, and chewing tobacco. In some aspects, the first and second product comprises a reduced amount of nomicotine and/or N'-nitrosornicotine (NNN).

In an aspect, the present disclosure includes a part of a tobacco plant, produced by growing a seed of hybrid tobacco cultivar NCBH129 SRC, where the part is selected from the group consisting of leaf, pollen, ovule, embryo, cotyledon, hypocotyl, meristematic cell, protoplast, root, root tip, pistil, anther, flower, shoot, stem, pod, and petiole.

In a further aspect, the present disclosure includes a tissue culture produced from a protoplast or cell from a tobacco plant, or part thereof, produced by growing the seed of hybrid tobacco cultivar NCBH129 SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole.

In an aspect, the present disclosure includes a tobacco plant regenerated from a tissue culture produced from a protoplast or cell from a tobacco plant, or part thereof, produced by growing the seed of hybrid tobacco cultivar NCBH129 SRC, where the cell or protoplast of the tissue culture is produced from a plant part selected from the group consisting of a leaf, pollen, embryo, cotyledon, hypocotyl, meristematic cell, root, root tip, pistil, anther, flower, shoot, stem, pod, and petiole, where the regenerated plant has all, or essentially all of the morphological and physiological characteristics of hybrid cultivar NCBH129 SRC.

In an aspect, the present disclosure includes an $F_1$ progeny plant of hybrid tobacco cultivar NCBH129 SRC.

In an aspect, the present disclosure includes an $F_1$ progeny plant of hybrid tobacco cultivar NCBH129 SRC, where the plant of tobacco cultivar NCBH129 SRC is the female parent.

In another aspect, the present disclosure includes an $F_1$ progeny plant of hybrid tobacco cultivar NCBH129 SRC where the $F_1$ plant is cytoplasmic male sterile (CMS).

In another aspect, the present disclosure includes a method for producing a tobacco seed of NCBH129 SRC comprising crossing two tobacco plants and harvesting the resultant tobacco seed, where one tobacco plant is a tobacco plant produced by growing the seed of tobacco cultivar NC638 SRC, a representative sample seed of the cultivar having been deposited with the ATCC under ATCC Accession No. PTA-120313.

In another aspect, the present disclosure includes a method for producing a tobacco seed of NCBH129 SRC comprising crossing two tobacco plants and harvesting the resultant tobacco seed, where one tobacco plant is a tobacco plant produced by growing the seed of tobacco cultivar CMS NC638 SRC, a representative sample seed of the cultivar having been deposited with the ATCC under ATCC Accession No. PTA-13568 and a second tobacco plant is a tobacco plant produced by growing the seed of tobacco cultivar NC638 SRC, a representative sample seed of the cultivar having been deposited with the ATCC under ATCC Accession No. PTA-120313.

In an aspect, the present disclosure includes a method of vegetatively propagating a plant of a tobacco cultivar comprising the steps of (a) collecting tissue capable of being propagated from a plant of a tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, CMS TN86 SRC, a representative sample seed of the cultivar having been deposited with the ATCC under ATCC Accession No. PTA-13570, and hybrid cultivar NCBH129 SRC; (b) cultivating the tissue to obtain a proliferated shoot; and (c) rooting the proliferated shoots to obtain a rooted plantlet.

In an aspect, the present disclosure includes a method of vegetatively propagating a plant of a tobacco cultivar comprising the steps of (a) collecting tissue capable of being propagated from a plant of a tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568. TN86 SRC, a representative sample seed of the cultivar having been deposited with the ATCC under ATCC Accession No. PTA-13565, CMS TN86 SRC, a representative sample seed of the cultivar having been deposited with the ATCC under ATCC Accession No. PTA-13570, and hybrid cultivar NCBH129 SRC; (b) cultivating the tissue to obtain a proliferated shoot; (c) rooting the proliferated shoots to obtain a rooted plantlet; and (d) growing a plant from the rooted plantlet.

In an aspect, the present disclosure includes a method of introducing a desired trait into a tobacco cultivar comprising: (a) crossing a plant of a first tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, and CMS TN86 SRC, a representative sample seed of the cultivar having been deposited with the ATCC under ATCC Accession No. PTA-13570, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of said first tobacco cultivar. NC638 SRC, CMS NC638 SRC, TN86 SRC, or CMS TN86 SRC, respectively; and (e) repeating steps (c) and (d) three or more times (e.g., 3, 4, 5, 6, 7, 8, 9, 10, and the like) in succession to produce selected fourth or higher backcross progeny that comprise the desired trait. In additional aspects, steps (c) and (d) can be repeated one or more times (e.g., 1, 2, 3, 4, 5, 6, 7, 8, 9, 10, and the like) in succession to produce second or higher backcross progeny comprising the desired trait.

In an aspect, the present disclosure includes a method of introducing a desired trait into a tobacco cultivar comprising: (a) crossing a plant of a first tobacco cultivar selected from the group consisting of NC638 SRC, a representative sample seed of the cultivar having been deposited with the ATCC under ATCC Accession No. PTA-120313, and TN86 SRC, a representative sample seed of the cultivar having been deposited with the ATCC under ATCC Accession No. PTA-13565, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar, NC638 SRC, or TN86 SRC, respectively; and (e) repeating steps (c) and (d) three or more times in succession to produce selected fourth or higher backcross progeny that comprise the desired trait, where the trait is cytoplasmic male sterility (CMS). In additional aspects, steps (c) and (d) can be repeated one or more times in succession to produce second or higher backcross progeny comprising the desired trait, where the trait is CMS.

In an aspect, the present disclosure includes a method of introducing a desired trait into a tobacco cultivar comprising: (a) crossing a plant of a first tobacco cultivar selected from the group consisting of NC638 SRC, a representative sample seed of the cultivar having been deposited with the ATCC under ATCC Accession No. PTA-120313, and TN86 SRC, a representative sample seed of the cultivar having been deposited with the ATCC under ATCC Accession No. PTA-13565, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and the physiological and essentially all of morphological characteristics of the first tobacco cultivar NC638 SRC or TN86 SRC, respectively; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens* or *Nicotiana glauca*. In additional aspects, steps (c) and (d) can be repeated one or more times in succession to produce second or higher backcross progeny comprising the desired trait, where the trait is CMS and the CMS trait is obtained from the cytoplasm of *Nicotiana suaveolens* or *Nicotiana glauca*.

In an aspect, the present disclosure includes a method of introducing a desired trait into a tobacco cultivar comprising: (a) crossing a plant of a first tobacco cultivar selected from the group consisting of NC638 SRC, a representative sample seed of the cultivar having been deposited with the ATCC under ATCC Accession No. PTA-120313, and TN86 SRC, a representative sample seed of the cultivar having been deposited with the ATCC under ATCC Accession No. PTA-13565 with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of tobacco cultivar NC638 SRC or TN86 SRC, respectively; and (e) repeating steps (c) and (d) three or more times in succession to produce selected fourth or higher backcross progeny that comprise the desired trait, where the trait is cytoplasmic male sterility (CMS) and the CMS trait is obtained from the cytoplasm of *Nicotiana suaveolens*, and where the second tobacco plant is selected from the group consisting of CMS NC638 SRC and CMS TN86 SRC. In additional aspects, steps (c) and (d) can be repeated one or more times in succession to produce second or higher backcross progeny comprising the desired trait, where the trait is CMS and the CMS trait is obtained from the cytoplasm of *Nicotiana suaveolens*.

In an aspect, the present disclosure includes a tobacco plant produced by a method comprising introducing a desired trait into a tobacco cultivar comprising: (a) crossing a plant of a first tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, and CMS TN86 SRC, a representative sample seed of the cultivar having been deposited with the ATCC under ATCC Accession No. PTA-13570, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of said first tobacco cultivar to produce a backcross $BC_1F_1$ progeny seed; (d) growing the $BC_1F_1$ progeny seed and selecting a backcross $BC_1F_1$ progeny plant comprising the desired trait and essentially all of the physiological and morphological characteristics of the first tobacco cultivar NC638 SRC, CMS NC638 SRC, TN86 SRC, or CMS TN86 SRC, respectively; and (e) repeating steps (c) and (d) three or more times in succession to produce selected fourth or higher backcross progeny that comprise the desired trait. In additional aspects, steps (c) and (d) can be repeated one or more times in succession to produce second or higher backcross progeny that comprise the desired trait.

In another aspect, the present disclosure includes a method of introducing a desired trait into a tobacco cultivar comprising: (a) crossing a plant of a first tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, and CMS TN86 SRC, a representative sample seed of the cultivar having been deposited with the ATCC under ATCC Accession No. PTA-13570, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of said first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of the first tobacco cultivar, NC638 SRC, CMS NC638 SRC, TN86 SRC, or CMS TN86 SRC, respectively; and (e) repeating steps (c) and (d) one or more times in succession to produce a selected second, third, fourth or higher backcross progeny plant that comprises the desired trait and essentially all of the physiological and morphological characteristics of the first tobacco cultivar, NC638 SRC, CMS NC638 SRC, TN86 SRC or CMS TN86 SRC, respectively.

In another aspect, the present disclosure includes a method of introducing a desired trait into a tobacco cultivar comprising: (a) crossing a plant of a first tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, and CMS TN86 SRC, a representative sample seed of the cultivar having been deposited with the ATCC under ATCC Accession No. PTA-13570, with a plant of a second tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing, small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of said first tobacco cultivar to produce a backcross progeny plant seed; (d) growing the backcross progeny plant seed into a backcross progeny plant and selecting the backcross progeny plant comprising the desired trait and essentially all of the physiological and morphological characteristics of said first tobacco cultivar, NC638 SRC, CMS NC638 SRC, TN86 SRC, or CMS TN86 SRC, respectively; and (e) repeating steps (c) and (d) one or more times in succession to produce a selected second, third, fourth or higher backcross progeny plant that comprises the desired trait and essentially all of the physiological and morphological characteristics of a tobacco cultivar, NC638 SRC, CMS NC638 SRC, TN86 SRC, or CMS TN86 SRC, respectively, where the desired trait is disease resistance.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 1 and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the first tobacco plant is a plant of a tobacco cultivar selected from the group consisting of tobacco cultivar NC638 SRC, a representative sample seed of the cultivar having been deposited with the ATCC under ATCC Accession No. PTA-120313, tobacco cultivar CMS NC638 SRC, a representative sample seed of the cultivar having been deposited with the ATCC under ATCC Accession No. PTA-13568, tobacco cultivar TN86 SRC, a representative sample seed of the cultivar having been deposited with the ATCC under ATCC Accession No. PTA-13565, tobacco cultivar CMS TN86 SRC, a representative sample seed of the cultivar having been deposited with the ATCC under ATCC Accession No. PTA-13570, and hybrid cultivar NCBH129 SRC.

In an aspect, the present disclosure includes a method for producing a tobacco plant having decreased nicotine conversion comprising: identifying a first tobacco plant comprising a nucleotide sequence selected from the group consisting of the nucleotide sequence of SEQ ID NO: 1, SEQ ID NO: 2, SEQ ID NO: 11, and any combination thereof; crossing the first tobacco plant with a second tobacco plant and collecting an $F_1$ seed; crossing a plant grown from the $F_1$ seed to a third tobacco plant and collecting a second tobacco seed; and identifying a second tobacco seed or a plant grown from the second seed that is homozygous for the nucleotide sequence selected from the group consisting of the nucleotide sequence of SEQ ID NO: 1, SEQ ID NO: 2, SEQ ID NO: 11, and any combination thereof, where the third tobacco plant is a plant of a tobacco cultivar selected from the group consisting of the tobacco cultivar NC638 SRC, a representative sample seed of the cultivar having been deposited with the ATCC under ATCC Accession No. PTA-120313, tobacco cultivar CMS NC638 SRC, a representative sample seed of the cultivar having been deposited with the ATCC under ATCC Accession No. PTA-13568, tobacco cultivar TN86 SRC, a representative sample seed of the cultivar having been deposited with the ATCC under ATCC Accession No. PTA-13565, CMS TN86 SRC, a representative sample seed of the cultivar having been deposited with the ATCC under ATCC Accession No. PTA-13570, and hybrid cultivar NCBH129 SRC.

In another aspect, the present disclosure includes a method of producing a plant of a tobacco cultivar selected from the group consisting of tobacco cultivar NC638 SRC, a representative sample seed of the cultivar having been deposited with the ATCC under ATCC Accession No. PTA-120313, tobacco cultivar CMS NC638 SRC, a representative sample seed of the cultivar having been deposited with the ATCC under ATCC Accession No. PTA-13568, tobacco cultivar TN86 SRC, a representative sample seed of the cultivar having been deposited with the ATCC under ATCC Accession No. PTA-13565, tobacco cultivar CMS TN86 SRC, a representative sample seed of the cultivar having been deposited with the ATCC under ATCC Accession No. PTA-13570, and hybrid cultivar NCBH129 SRC comprising at least one (e.g., 1, 2, 3, 4, 5, 6, 7, 8, and the like) additional desired trait comprising the steps of: (a) collecting tissue capable of being propagated from a plant of a tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, CMS TN86 SRC, a representative sample seed of the cultivar having been deposited with the ATCC under ATCC Accession No. PTA-13570, and hybrid cultivar NCBH129 SRC; and (b) introducing at least one transgene (nucleic acid construct) conferring at least one desired trait into the tissue.

In another aspect, the present disclosure includes a method of producing an herbicide resistant tobacco plant comprising transforming a tobacco plant, or part thereof, produced by growing a seed of a tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, CMS TN86 SRC, a representative sample seed of the cultivar having been deposited with the ATCC under ATCC Accession No. PTA-13570, and hybrid cultivar NCBH129 SRC with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes an herbicide resistant tobacco plant produced by a method comprising transforming a tobacco plant, or part thereof, produced by growing a seed of a tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, CMS TN86 SRC, a representative sample seed of the cultivar having been deposited with the ATCC under ATCC Accession No. PTA-13570, and hybrid cultivar NCBH129 SRC, with at least one transgene (nucleic acid construct), where the at least one transgene (nucleic acid construct) confers resistance to an herbicide selected from the group consisting of imidazolinone, cyclohexanedione, sulfonylurea, glyphosate, glufosinate, phenoxy proprionic acid, L-phosphinothricin, triazine, benzonitrile, and any combination thereof.

In another aspect, the present disclosure includes a method of producing a pest and/or insect resistant tobacco plant where the method comprises transforming a tobacco plant produced by growing a seed of a tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, CMS TN86 SRC, a representative sample seed of the cultivar having been deposited with the ATCC under ATCC Accession No. PTA-13570, and hybrid cultivar NCBH129 SRC, with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of a tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, CMS TN86 SRC, a representative sample seed of the cultivar having been deposited with the ATCC under ATCC Accession No. PTA-13570, and hybrid cultivar NCBH129 SRC with at least one transgene (nucleic acid construct) that confers pest and/or insect resistance.

In a further aspect, the present disclosure includes a pest and/or insect resistant tobacco plant produced by a method comprising transforming a tobacco plant produced by growing a seed of a tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, CMS TN86 SRC, a representative sample seed of the cultivar having been deposited with the ATCC under ATCC Accession No. PTA-13570, and hybrid cultivar NCBH129 SRC, with at least one transgene (nucleic acid construct) that confers pest and/or insect resistance, where the transgene encodes a *Bacillus thuringiensis* (BT) endotoxin.

In another aspect, the present disclosure includes a method of producing a disease resistant tobacco plant where the method comprises transforming a tobacco plant produced by growing a seed of a tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, CMS TN86 SRC, a representative sample seed of the cultivar having been deposited with the ATCC under ATCC Accession No. PTA-13570, and hybrid cultivar NCBH129 SRC with at least one transgene (nucleic acid construct) that confers disease resistance.

In a further aspect, the present disclosure includes a disease resistant tobacco plant produced by a method comprising transforming a tobacco plant produced by growing a seed of a tobacco cultivar selected from the group consisting of NC638 SRC, a representative sample seed of the cultivar having been deposited with the ATCC under ATCC Accession No. PTA-120313, CMS NC638 SRC, a representative sample seed of the cultivar having been deposited with the ATCC under ATCC Accession No. PTA-13568, TN86 SRC, a representative sample seed of the cultivar having been deposited with the ATCC under ATCC Accession No. PTA-13565, CMS TN86 SRC, a representative sample seed of the cultivar having been deposited with the ATCC under ATCC Accession No. PTA-13570, and hybrid cultivar NCBH129 SRC with at least one transgene (nucleic acid construct) that confers disease resistance.

BRIEF DESCRIPTION OF THE SEQUENCES

SEQ ID NO: 1 sets forth a cyp82e4 W329Stop nucleotide sequence.

SEQ ID NO: 2 sets forth a cyp82e5v2 W422Stop nucleotide sequence.

SEQ ID NO: 3 sets forth a cyp82e4 W329Stop amino acid sequence.

SEQ ID NO: 4 sets forth a cyp82e5v2 W422Stop amino acid sequence.

SEQ ID NO: 5 sets forth a CYP82E4 wild-type nucleotide sequence.

SEQ ID NO: 6 sets forth a CYP82E5v2 wild-type nucleotide sequence.

SEQ ID NO: 7 sets forth a CYP82E4 wild-type amino acid sequence.

SEQ ID NO: 8 sets forth a CYP82E5v2 wild-type amino acid sequence.

SEQ ID NO: 9 sets forth a CYP82E10 wild-type nucleotide sequence.

SEQ ID NO: 10 sets forth a CYP82E10 wild-type amino acid sequence.

SEQ ID NO: 11 sets forth a CYP82E10 P381S nucleotide sequence.

SEQ ID NO: 12 sets forth a CYP82E10 P381S amino acid sequence.

All three tobacco Nicotine Demethylase genes (CYP82E4, CYP82E5v2, CYP82E10) share a common structure: a 939 bp exon 1 and a 612 bp exon 2 separated by a large intron, whose length varies among the three genes. See Lewis et al., "Three nicotine demethylase genes mediate nomicotine biosynthesis in *Nicotiana tabacum* L.: Functional characterization of the CYP82E10 gene," *Phytochemistry*, 71 (2010), 1988-1998. SEQ ID NOs: 1, 2, 5, 6, 9, and 11 set forth wild-type or mutant versions of coding sequences of CYP82E4, CYP82E5v2, and CYP82E10. It is understood that, used herein, a plant comprising, having, or homozygous for a sequence selected from SEQ ID NOs: 1, 2, 5, 6, 9, and 11 refers to a plant comprising at the CYP82E4, CYP82E5v2, or CYP82E10 endogenous locus a genomic sequence comprising the coding sequence of SEQ ID NO: 1, 2, 5, 6, 9, or 11.

BRIEF DESCRIPTION OF THE DRAWINGS

FIGS. 9A-9B: Evaluations of smoke NNN levels in blended cigarettes made with an Extramural Blend comprising varying amounts of TN90 SRC as the Burley component. Experimental blends with increasing percentages of TN90 SRC (33% Experimental comprising 8% TN90 SRC and 15% TN90 LC, 67% Experimental comprising 15% TN90 SRC and 8% TN90 LC, and 100% Experimental comprising 23% TN90 SRC) are compared to a control blend comprising 23% TN90 LC and no TN90 SRC (0% Experimental). FIG. 9A shows formulations of control and experimental blends. Each component is shown by their percent dry weight. Both the International Organization of Standardization (ISO) smoking method (shown as Smoke ISO on the x-axis) and the Health Canada Intense (HCI) smoking method (shown as Smoke HC Intense on the x-axis) are used. FIG. 9B shows that the inclusion of TN90 SRC filler in an Extramural Blend (even when TN90 SRC only constitutes 33% or 67% of the total Burly component of the blend, e.g., 33% Experimental or 67% Experimental) reduces the level of smoke NNN measured by either the ISO smoking method or the HCI smoking method. Further, blended cigarettes with an Extramural Blend comprising TN90 SRC filler as 100% of the Burley component (100% Experimental; TN90 SRC=23% of overall blend) show a reduction of 38% (ISO method) and 35% (HCI method) in smoke NNN compared to a control blend comprising TN90 LC filler as 100% of the Burley component (0% Experimental; TN90 LC=23% of overall blend). 0% E, 33% E, 67% E, and 100% E shown on the x-axis represents control, 33% Experimental, 67% Experimental, and 100% Experimental blends respectively.

DETAILED DESCRIPTION

Figure 1:
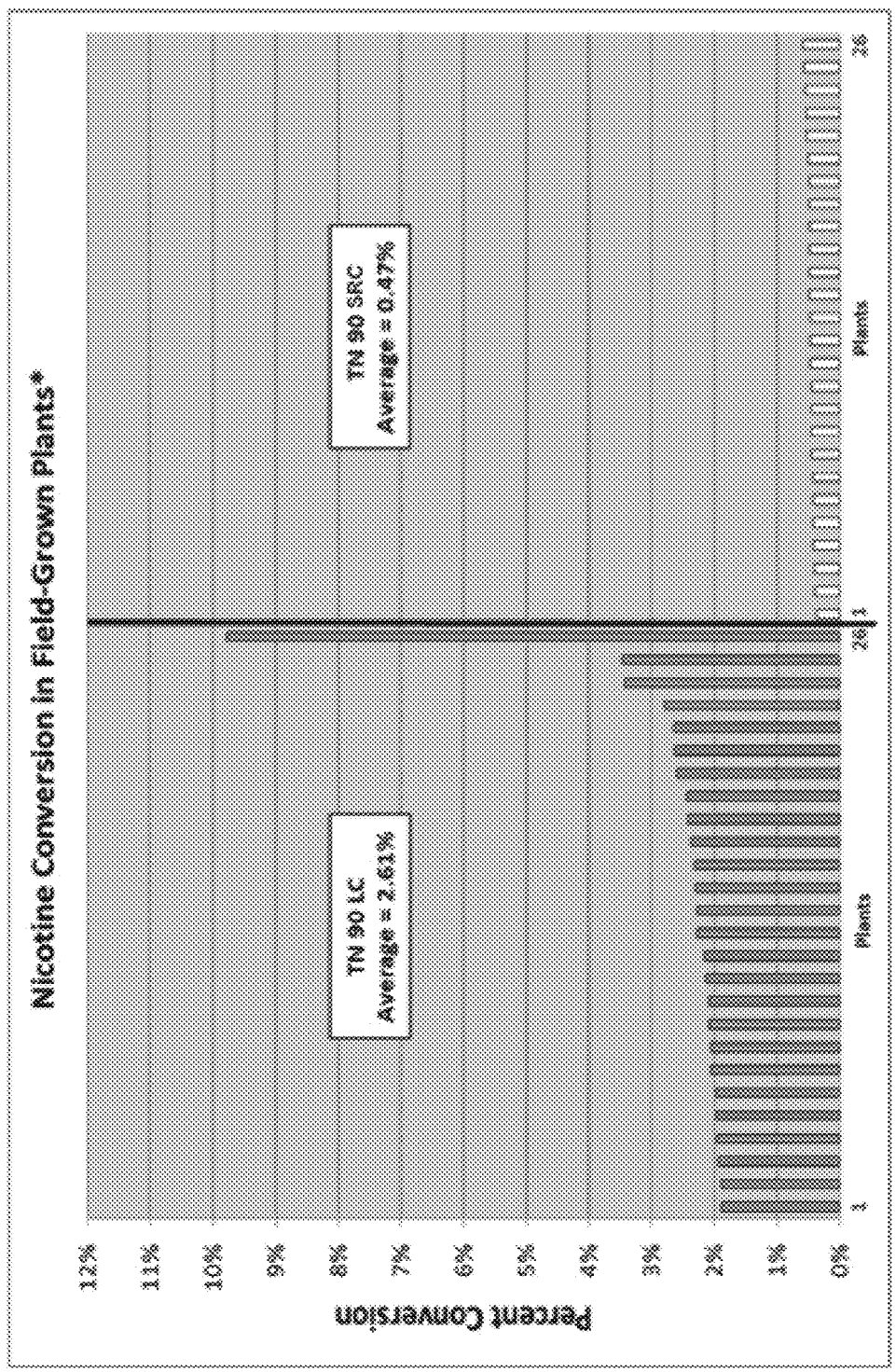
FIG. 1: A comparison between populations of TN90 LC plants and TN90 SRC plants showing a more stable and lower average percent nicotine conversion in TN90 SRC. Leaves from 26 plants of each variety are sampled at the layby stage and ethephon-treated prior to analysis for nicotine and nomicotine levels using gas chromatography equipment.

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed disclosure. Thus, the term "consisting essentially of" when used in a claim of this disclosure is not intended to be interpreted to be equivalent to "comprising."

"Introducing," in the context of a polynucleotide sequence (e.g., a recombinant polynucleotide and/or expression cassette of the disclosure), means presenting a polynucleotide sequence to the plant, plant part, and/or plant cell in such a manner that the polynucleotide sequence gains access to the interior of a cell. Where more than one polynucleotide sequence is to be introduced these polynucleotide sequences can be assembled as part of a single polynucleotide or nucleic acid construct, or as separate polynucleotide or nucleic acid constructs, and can be located on the same or different transformation vectors. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, in some embodiments, a plant cell, plant part or plant of this disclosure can be stably transformed with a recombinant polynucleotide of the disclosure. In other embodiments, a plant cell, plant part or plant of this disclosure can be transiently transformed with a recombinant polynucleotide of the disclosure.

"Tobacco product" is defined as "any product made or derived from tobacco that is intended for human use or consumption, including any component, part, or accessory of a tobacco product (except for raw materials other than tobacco used in manufacturing a component, part, or accessory of a tobacco product)" (section 201 of the FD&C Act; 21 U.S.C. 321). The label and packaging is part of a tobacco product.

Terms "nicotine conversion rate," "percent nicotine conversion." and "percentage nicotine conversion" are used interchangeably. Percent nicotine demethylation in a sample is calculated by dividing the level of nomicotine by the combined level of nicotine and nomicotine as measured in the sample, and multiplying by 100.

TN90 SRC

In some aspects, the present disclosure provides tobacco cultivars, and parts thereof, from TN90 SRC, representative sample seeds of this cultivar having been deposited with the ATCC under ATCC Accession No. PTA-13567. In other aspects, the present disclosure provides a tobacco plant, or part thereof, produced by growing a seed of TN90 SRC. In further aspects, a plant of the present disclosure can include a plant with all, or essentially all, of the morphological and physiological characteristics of cultivar TN90 SRC.

While not being limited by process, TN90 SRC is a result of the introduction of three mutated CYP82E genes in a burley tobacco cultivar TN90. The three genes are a mutated CYP82E4 gene recited as 325-6 #775 in Lewis et al. ("Three nicotine demethylase genes mediate nomicotine biosynthesis in *Nicotiana tabacum* L.: Functional characterization of the CYP82E10 gene," *Phytochemistry*, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13 (SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO: 11, which sets forth a cyp82e10 P381S, hereby incorporated by reference in its entirety). Mutations cyp82e4 W329Stop and cyp82e5v2 W422Stop result in truncated proteins while cyp82E10 P381S results in a non-functional protein. A cyp82e4 W329Stop ("e4"), a cyp82e5v2 W422Stop ("e5"), and a cyp82e10 P381S ("e10") mutation are introduced from a e4e4|e5e5|e10e10 triple mutant from a strong converter burley background, line DH98-325-6, as listed in Table 4 of Lewis et al. (supra) into a burley tobacco cultivar TN90 background.

TN90 SRC is the result of seven backcrosses with burley cultivar TN90 as the recurrent parent, followed by two rounds of selfing with selection for homozygosity for the cyp82e4 W329Stop, the cyp82e5v2 W422Stop, and cyp82e10 P381S mutations to yield $BC_7F_5$ plants (TN90 SRC) in which the wild-type CYP82E4, CYP82E5v2 and CYP82E10 alleles of TN90 are replaced by the mutant alleles (e.g., cyp82e4 W329Stop, cyp82e5v2 W422Stop, and cyp82e10 P381S).

TN90 SRC progeny plants have genetic backgrounds that are at least 95%, at least 97%, at least 98%, or at least 99% similar to TN90. TN90 SRC plants exhibit low nomicotine levels and produce leaves with reduced potential for accumulating derived NNN during curing, storage, and smoking.

CMS TN90 SRC

In some aspects, the present disclosure provides tobacco cultivars, and parts thereof, from CMS TN90 SRC, representative sample seeds of this cultivar having been deposited with the ATCC under ATCC Accession No. PTA-13573. In further aspects, the present disclosure also includes a tobacco plant, or part thereof, produced by growing a seed of CMS TN90 SRC. In still further aspects, a plant of the present disclosure can include a plant with all, or essentially all, of the morphological and physiological characteristics of cultivar CMS TN90 SRC. CMS TN90 SRC is a male-sterile (CMS) version of TN90 SRC (CMS TN90 SRC) produced by crossing a plant of CMS TN90 as a female with pollen of TN90 SRC $BC_6F_1$ to produce male-sterile plants heterozygous for all three mutations. The CMS progeny plants of the CMS TN90×TN90 SRC $BC_6F_1$ cross are male sterile. A plurality of CMS TN90×TN90 SRC $BC_6F_1$×CMS plants (e.g., CMS $F_1$ progeny plants) are screened for the cyp82e4 W329Stop, cyp82e5v2 W422Stop, and cyp82e10 P381S mutations to identify plants heterozygous for all three mutations. A single male-sterile plant resulting from this cross is backcrossed as a female to TN90 SRC to prepare $BC_7F_1$ CMS progeny. $BC_7F_1$ CMS progeny homozygous for the cyp82e4 W329Stop, the cyp82e5v2 W422Stop, and cyp82e10 P381S mutations are identified by genotyping and designated as CMS TN90 SRC. Because the CMS TN90 SRC line is male sterile, it is maintained via pollination with TN90 SRC. TN90 SRC is crossed as the male parent to CMS TN90 SRC to prepare CMS TN90 SRC $F_1$ progeny plants.

CMS TN90 SRC and CMS TN90 SRC $F_1$ progeny plants have genetic backgrounds that are at least 95%, at least 97%, at least 98%, or at least 99% similar to TN90. CMS TN90 SRC and CMS TN90 SRC $F_1$ progeny plants exhibit low nomicotine levels and produce leaves with reduced potential for accumulating derived NNN during curing, storage, and smoking.

KY14 SRC

In one aspect, the present disclosure provides tobacco cultivars, and parts thereof, from KY14 SRC, representative sample seeds of this cultivar having been deposited with the ATCC under ATCC Accession No. PTA-120311. In another aspect, the present disclosure provides a tobacco plant, or part thereof, produced by growing a seed of KY14 SRC. In a further aspect, a plant of the present disclosure can include a plant with all, or essentially all, of the morphological and physiological characteristics of cultivar KY14 SRC.

While not being limited by process, KY14 SRC is a result of the introduction of three mutated CYP82E genes in a burley tobacco cultivar KY14. The three genes are a mutated CYP82E4 gene recited as 325-6 #775 in Lewis et al. ("Three nicotine demethylase genes mediate nornicotine biosynthesis in *Nicotiana tabacum* L.: Functional characterization of the CYP82E10 gene," *Phytochemistry*, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13 (SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO: 11, which sets forth a cyp82e10 P381S, hereby incorporated by reference in its entirety). Mutations cyp82e4 W329Stop and cyp82e5v2 W422Stop result in truncated proteins while cyp82E10 P381S results in a non-functional protein. A cyp82e4 W329Stop ("e4"), a cyp82e5v2 W422Stop ("e5"), and a cyp82e10 P381S ("e10") mutation are introduced from a e4e4|e5e5|e10e10 triple mutant from a strong converter burley background, line DH98-325-6, as listed in Table 4 of Lewis et al. (supra) into a burley tobacco cultivar KY14 background.

KY14 SRC is the result of seven backcrosses with burley cultivar KY14 as the recurrent parent, followed by two rounds of selfing with selection for homozygosity for the cyp82e4 W329Stop, the cyp82e5v2 W422Stop, and cyp82e10 P381S mutations to yield $BC_7F_3$ plants (KY14 SRC) in which the wild-type CYP82E4, CYP82E5v2 and CYP82E10 alleles of KY14 are replaced by the mutant (e.g., cyp82e4 W329Stop, cyp82e5v2 W422Stop, and cyp82e10 P381S) alleles.

KY14 SRC progeny plants have genetic backgrounds that are at least 95%, at least 97%, at least 98%, or at least 99% similar to KY14. KY14 SRC plants exhibit low nomicotine levels and produce leaves with reduced potential for accumulating derived NNN during curing, storage, and smoking.

CMS KY14 SRC

In other aspects, the present disclosure also provides tobacco cultivars, and parts thereof, from CMS KY14 SRC, representative sample seeds of this cultivar having been deposited with the ATCC under ATCC Accession No. PTA-13571. In further aspects, the present disclosure provides a tobacco plant, or part thereof, produced by growing a seed of CMS KY14 SRC. In still further aspects, the plant of the present disclosure can include a plant with all, or essentially all, of the morphological and physiological characteristics of cultivar CMS KY14 SRC. CMS KY14 SRC is a male-sterile (CMS) version of KY14 SRC (CMS KY14 SRC) produced by crossing a plant of CMS KY14 as a female with pollen of KY14 SRC $BC_6F_1$ to produce male-sterile plants heterozygous for all three mutations. The CMS progeny plants of the CMS KY14×KY14 SRC $BC_6F$ cross are male sterile. A plurality of CMS KY14×KY14 SRC $BC_6F_1$×CMS plants (e.g., CMS $F_1$ progeny plants) are screened for the cyp82e4 W329Stop, cyp82e5v2 W422Stop, and cyp82e10 P381S mutations to identify plants heterozygous for all three mutations. A single male-sterile plant resulting from this cross is backcrossed as a female to KY14 SRC to prepare $BC_7F_1$ CMS progeny. $BC_7F_1$ CMS progeny homozygous for the cyp82e4 W329Stop, the cyp82e5v2 W422Stop, and cyp82e10 P381S mutations are identified by genotyping and designated as CMS KY14 SRC. Because the CMS KY14 SRC line is male sterile, it is maintained via pollination with KY14 SRC. KY14 SRC is crossed as the male parent to CMS KY14 SRC to prepare CMS KY14 SRC $F_1$ progeny plants.

CMS KY14 SRC and CMS KY14 SRC $F_1$ progeny plants have genetic backgrounds that are at least 95%, at least 97%, at least 98%, or at least 99% similar to KY14. CMS KY14 SRC and CMS KY14 SRC $F_1$ progeny plants exhibit low nomicotine levels and produce leaves with reduced potential for accumulating derived NNN during curing, storage, and smoking.

L8 SRC

In some aspects, the present disclosure provides tobacco cultivars, and parts thereof, from L8 SRC, where representative sample seeds of this cultivar have been deposited with the ATCC under ATCC Accession No. PTA-13572. In other aspects, the present disclosure provides a tobacco plant, or part thereof, produced by growing a seed of L8 SRC. In still further aspects, a plant of the present disclosure can include a plant with all, or essentially all, of the morphological and physiological characteristics of cultivar L8 SRC. While not being limited by process, L8 SRC is a result of introducing the cyp82e4 W329Stop, cyp82e5v2 W422Stop, and cyp82e10 P381S mutations from DH98-325-6. $F_1$ individuals originating from a cross between L8 and DH98-325-6 and heterozygous for each mutation are then backcrossed seven times to L8 to produce $BC_7F_1$ progeny. $BC_7F_1$ individuals heterozygous for all three mutations are self-pollinated to produce $BC_7F_2$ seed and individuals homozygous for all three mutations identified. A single $BC_7F_2$ plant is self-pollinated to produce $BC_7F_3$(L8 SRC) in which the wild-type CYP82E4, CYP82E5v2 and CYP82E10 alleles of L8 are replaced by the mutant (e.g., cyp82e4 W329Stop, cyp82e5v2 W422Stop, and cyp82e10 P381S).

L8 SRC has a genetic background that is at least 95%, at least 97%, at least 98%, or at least 99% similar to L8. L8 SRC exhibits low nomicotine levels and produce leaves with reduced potential for accumulating derived NNN during curing, storage, and smoking.

KY14×L8 SRC

In other aspects, the present disclosure provides tobacco cultivars, and parts thereof, from KY14×L8 SRC. In another aspect, the present disclosure provides a tobacco plant, or part thereof, produced by growing the seed of KY14×L8 SRC. In a further aspect, a plant of the present disclosure can include a plant with all, or essentially all, of the morphological and physiological characteristics of cultivar KY14×L8 SRC.

While not being limited by process, KY14×L8 SRC is produced by pollinating plants of CMS KY14 SRC with pollen of L8 SRC. Again, not limited by any particular scientific theory, cyp82e4 W329Stop, cyp82e5v2 W422Stop, and cyp82e10 P381S mutations all encode for proteins with reduced or eliminated ability to convert nicotine to nornicotine. KY14×L8 SRC has a genetic background that is at least 95%, at least 97%, at least 98%, or at least 99% similar to burley tobacco cultivar KY14×L8, a hybrid generated by pollinating plants of a male-sterile breeding line CMS KY14 with pollen produced by fertile breeding line L8. KY14×L8 SRC exhibits low nomicotine and is not subject to conversion to high nornicotine.

NC775 SRC

In one aspect, the present disclosure provides tobacco cultivars, and parts thereof, from NC775 SRC, representative sample seeds of this cultivar having been deposited with the ATCC under ATCC Accession No. PTA-120312. In another aspect, the present disclosure additionally provides a tobacco plant, or part thereof, produced by growing a seed of NC775 SRC. In a further aspect, a plant of the present disclosure can include a plant with all or essentially all of the morphological and physiological characteristics of cultivar NC775 SRC.

While not being limited by process, NC775 SRC is a result of the introduction of three mutated CYP82E genes in a burley tobacco cultivar NC775. The three genes are a mutated CYP82E4 gene recited as 325-6 #775 in Lewis et al. ("Three nicotine demethylase genes mediate nornicotine biosynthesis in *Nicotiana tabacum* L.: Functional characterization of the CYP82E10 gene," *Phytochemistry*, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13 (SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO:11, which sets forth a cyp82e10 P381S, hereby incorporated by reference in its entirety). Mutations cyp82e4 W329Stop and cyp82e5v2 W422Stop result in truncated proteins while cyp82E10 P381S results in a nonfunctional protein. A cyp82e4 W329Stop ("e4"), a cyp82e5v2 W422Stop ("e5"), and a cyp82e10 P381S ("e10") mutation are introduced from a e4e4|e5e5|e10e10 triple mutant from a strong converter burley background, line DH98-325-6, as listed in Table 4 of Lewis et al. (supra) into a burley tobacco cultivar NC775 background.

NC775 SRC is the result of seven backcrosses with burley cultivar NC775 as the recurrent parent, followed by two rounds of selfing with selection for homozygosity for the cyp82e4 W329Stop, the cyp82e5v2 W422Stop, and cyp82e10 P381S mutations to yield $BC_7F_3$ plants (NC775 SRC) in which the wild-type CYP82E4, CYP82E5v2, and CYP82E10 alleles of NC775 are replaced by the mutant (e.g., cyp82e4 W329Stop, cyp82e5v2 W422Stop, and cyp82e10 P381 S) alleles.

NC775 SRC progeny plants have genetic backgrounds that are at least 95%, at least 97%, at least 98%, or at least 99% similar to NC775. NC775 SRC plants exhibit low nomicotine levels and produce leaves with reduced potential for accumulating derived NNN during curing, storage, and smoking.

CMS NC775 SRC

In some aspects, the present disclosure provides tobacco cultivars, and parts thereof, from CMS NC775 SRC, representative sample seeds of this cultivar having been deposited with the ATCC under ATCC Accession No. PTA-13563. In further aspects, the present disclosure additionally provides a tobacco plant, or part thereof, produced by growing a seed of CMS NC775 SRC. In still further aspects, a plant of the present disclosure can include a plant with all or essentially all, of the morphological and physiological characteristics of cultivar CMS NC775 SRC. CMS NC775 SRC is a male-sterile (CMS) version of NC775 SRC (CMS NC775 SRC) produced by crossing a plant of CMS NC775 as a female with pollen of NC775 SRC $BC_6F_1$ to produce male-sterile plants heterozygous for all three mutations. The CMS progeny plants of the CMS NC775×NC775 SRC $BC_6F_1$ cross are male sterile. A plurality of CMS NC775×NC775 SRC $BC_6F_1$×CMS plants (e.g., CMS $F_1$ progeny plants) are screened for the cyp82e4 W329Stop, cyp82e5v2 W422Stop, and cyp82e10 P381S mutations to identify plants heterozygous for all three mutations. A single male-sterile plant resulting from this cross is backcrossed as a female to NC775 SRC to prepare $BC_7F_1$ CMS progeny. $BC_7F_1$ CMS progeny homozygous for the cyp82e4 W329Stop, the cyp82e5v2 W422Stop, and cyp82e10 P381S mutations are identified by genotyping and designated as CMS NC775 SRC. Because the CMS NC775 SRC line is male sterile, it is maintained via pollination with NC775 SRC. NC775 SRC is crossed as the male parent to CMS NC775 SRC to prepare CMS NC775 SRC $F_1$ progeny plants.

CMS NC775 SRC and CMS NC775 SRC $F_1$ progeny plants have genetic backgrounds that are at least 95%, at least 97%, at least 98%, or at least 99% similar to NC775. CMS NC775 SRC and CMS NC775 SRC $F_1$ progeny plants exhibit low nomicotine levels and produce leaves with reduced potential for accumulating derived NNN during curing, storage, and smoking.

NC645 SRC

In some aspects, the present disclosure provides tobacco cultivars, and parts thereof, from NC645 SRC, where representative sample seeds of this cultivar have been deposited with the ATCC under ATCC Accession No. PTA-13566. In further aspects, the present disclosure additionally provides a tobacco plant, or part thereof, produced by growing a seed of NC645 SRC. In still further aspects, a plant of the present disclosure can include a plant with all or essentially all of the morphological and physiological characteristics of cultivar NC645 SRC. While not being limited by process, NC645 SRC is a result of introducing the cyp82e4 W329Stop, cyp82e5v2 W422Stop, and cyp82e10 P381S mutations from DH98-325-6. $F_1$ individuals originating from a cross between NC645 and DH98-325-6 and heterozygous for each mutation are then backcrossed seven times to NC645 to produce $BC_7F_1$ progeny. $BC_7F_1$ individuals heterozygous for all three mutations are self-pollinated to produce $BC_7F_2$ seed and individuals homozygous for all three mutations identified. A single BC₇F₂ plant is self-pollinated to produce BC₇F₃ (NC645 SRC) in which the wild-type CYP82E4, CYP82E5v2 and CYP82E10 alleles of NC645 are replaced by the mutant (e.g., cyp82e4 W329Stop, cyp82e5v2 W422Stop, and cyp82e10 P381S).

NC645 SRC has a genetic background that is at least 95%, at least 97%, at least 98%, or at least 99% similar to NC645. NC645 SRC exhibits low nomicotine levels and produce leaves with reduced potential for accumulating derived NNN during curing, storage, and smoking.

NC7 SRC

In some aspects, the present disclosure provides tobacco cultivars, and parts thereof, from NC7 SRC. In another aspect, the present disclosure provides a tobacco plant, or part thereof, produced by growing the seed of NC7 SRC. In still further aspects, a plant of the present disclosure can include a plant with all or essentially all of the morphological and physiological characteristics of cultivar NC7 SRC.

While not being limited by process, NC7 SRC is produced by pollinating plants of CMS NC775 SRC with pollen of NC645 SRC. Again, not limited by any particular scientific theory, cyp82e4 W329Stop, cyp82e5v2 W422Stop, and cyp82e10 P381S mutations all encode for proteins with reduced or eliminated ability to convert nicotine or nomicotine. NC7 SRC has a genetic background that is at least 95%, at least 97%, at least 98%, or at least 99% similar to burley tobacco cultivar NC7, a hybrid generated by pollinating plants of a male-sterile breeding line NC775 with pollen produced by fertile breeding line NC645. NC7 SRC exhibits low nomicotine and is not subject to conversion to high nomicotine.

NC638 SRC

In one aspect, the present disclosure provides tobacco cultivars, and parts thereof, from NC638 SRC, representative sample seeds of this cultivar having been deposited with the ATCC under ATCC Accession No. PTA-120313. In another aspect, the present disclosure provides a tobacco plant, or part thereof, produced by growing a seed of NC638 SRC. In a further aspect, a plant of the present disclosure can further include a plant with all, or essentially all of the morphological and physiological characteristics of cultivar NC638 SRC.

While not being limited by process, NC638 SRC is a result of the introduction of three mutated CYP82E genes in a burley tobacco cultivar NC638. The three genes are a mutated CYP82E4 gene recited as 325-6 #775 in Lewis et al. ("Three nicotine demethylase genes mediate nomicotine biosynthesis in *Nicotiana tabacum* L.: Functional characterization of the CYP82E10 gene," *Phytochemistry*, 71 (2010), 1988-1998 (SEQ ID NO: 1, which sets forth a cyp82e4 W329Stop, hereby incorporated by reference in its entirety)), a mutated CYP82E5v2 recited in Lewis et al. (supra) as 325-6 #1-13 (SEQ ID NO: 2, which sets forth a cyp82e5v2 W422Stop, hereby incorporated by reference in its entirety), and a mutated CYP82E10 recited in Lewis et al. (supra) as 325-6 #1041 (SEQ ID NO: 11, which sets forth a cyp82e10 P381S, hereby incorporated by reference in its entirety). Mutations cyp82e4 W329Stop and cyp82e5v2 W422Stop result in truncated proteins while cyp82E10 P381S results in a nonfunctional protein. A cyp82e4 W329Stop ("e4"), a cyp82e5v2 W422Stop ("e5"), and a cyp82e10 P381S ("e10") mutation are introduced from a e4e4|e5e5|e10e10 triple mutant from a strong converter burley background, line DH98-325-6, as listed in Table 4 of Lewis et al. (supra) into a burley tobacco cultivar NC638 background.

NC638 SRC is the result of seven backcrosses with burley cultivar NC638 as the recurrent parent, followed by two rounds of selfing with selection for homozygosity for the cyp82e4 W329Stop, the cyp82e5v2 W422Stop, and cyp82e10 P381S mutations to yield BC₇F₃ plants (NC638 SRC) in which the wild-type CYP82E4, CYP82E5v2 and CYP82E10 alleles of NC638 are replaced by the mutant (e.g., cyp82e4 W329Stop, cyp82e5v2 W422Stop, and cyp82e10 P381S) alleles.

NC638 SRC progeny plants have genetic backgrounds that are at least 95%, at least 97%, at least 98%, or at least 99% similar to NC638. NC638 SRC plants exhibit low nomicotine levels and produce leaves with reduced potential for accumulating derived NNN during curing, storage, and smoking.

CMS NC638 SRC

In some aspects, the present disclosure also provides tobacco cultivars, and parts thereof, from CMS NC638 SRC, representative sample seeds of this cultivar having been deposited with the ATCC under ATCC Accession No. PTA-13568. In further aspects, the present disclosure also includes a tobacco plant, or part thereof, produced by growing a seed of CMS NC638 SRC. In still further aspects, a plant of the present disclosure can further include a plant with all, or essentially all, of the morphological and physiological characteristics of cultivar CMS NC638 SRC. CMS NC638 SRC is a male-sterile (CMS) version of NC638 SRC (CMS NC638 SRC) produced by crossing a plant of CMS NC638 as a female with pollen of NC638 SRC BC₆F₁ to produce male-sterile plants heterozygous for all three mutations. The CMS progeny plants of the CMS NC638×NC638 SRC BC₆F₁ cross are male sterile. A plurality of CMS NC638×NC638 SRC BC₆F₁×CMS plants (e.g., CMS F₁ progeny plants) are screened for the cyp82e4 W329Stop, cyp82e5v2 W422Stop, and cyp82e10 P381S mutations to identify plants heterozygous for all three mutations. A single male-sterile plant resulting from this cross is backcrossed as a female to NC638 SRC to prepare BC₇F₁ CMS progeny. BC₇F₁ CMS progeny homozygous for the cyp82e4 W329Stop, the cyp82e5v2 W422Stop, and cyp82e10 P381S mutations are identified by genotyping and designated as CMS NC638 SRC. Because the CMS NC638 SRC line is male sterile, it is maintained via pollination with NC638 SRC. NC638 SRC is crossed as the male parent to CMS NC638 SRC to prepare CMS NC638 SRC F₁ progeny plants.

CMS NC638 SRC and CMS NC638 SRC F₁ progeny plants have genetic backgrounds that are at least 95%, at least 97%, at least 98%, or at least 99% similar to NC638. CMS NC638 SRC and CMS NC638 SRC F₁ progeny plants exhibit low nomicotine levels and produce leaves with reduced potential for accumulating derived NNN during curing, storage, and smoking.

TN86 SRC

In some aspects, the present disclosure also provides tobacco cultivars, and parts thereof, from TN86 SRC, where representative sample seeds of this cultivar have been deposited with the ATCC under ATCC Accession No. PTA-13565. In further aspects, the present disclosure also includes a tobacco plant, or part thereof, produced by growing a seed of TN86 SRC. In still further aspects, plant of the present disclosure can include a plant with all, or essentially all, of the morphological and physiological characteristics of cultivar TN86 SRC. While not being limited by process, TN86 SRC is a result of introducing the cyp82e4 W329Stop, cyp82e5v2 W422Stop, and cyp82e10 P381S mutations from DH98-325-6. F₁ individuals originating from a cross between TN86 and DH98-325-6 and heterozygous for each mutation are then backcrossed seven times to TN86 to produce $BC_7F_1$ progeny. $BC_7F_1$ individuals heterozygous for all three mutations are self-pollinated to produce $BC_7F_2$ seed and individuals homozygous for all three mutations identified. A single $BC_7F_2$ plant is self-pollinated to produce $BC_7F_3$ (TN86 SRC) in which the wild-type CYP82E4, CYP82E5v2 and CYP82E10 alleles of TN86 are replaced by the mutant (e.g., cyp82e4 W329Stop, cyp82e5v2 W422Stop, and cyp82e10 P381S).

TN86 SRC has a genetic background that is at least 95%, at least 97%, at least 98%, or at least 99% similar to TN86. TN86 SRC exhibits low nomicotine levels and produce leaves with reduced potential for accumulating derived NNN during curing, storage, and smoking.

CMS TN86 SRC

In some aspects, the present disclosure also provides tobacco cultivars, and parts thereof, from CMS TN86 SRC, representative sample seeds of this cultivar having been deposited with the ATCC under ATCC Accession No. PTA-13570. In other aspects, the present disclosure also includes a tobacco plant, or part thereof, produced by growing a seed of CMS TN86 SRC. In still other aspects, the plant of the present disclosure can further include a plant with all, or essentially all, of the morphological and physiological characteristics of cultivar CMS TN86 SRC. CMS TN86 SRC is a male-sterile (CMS) version of TN86 SRC (CMS TN86 SRC) produced by crossing a plant of CMS TN86 as a female with pollen of TN86 SRC $BC_6F_1$ to produce male-sterile plants heterozygous for all three mutations. The CMS progeny plants of the CMS TN86×TN86 SRC $BC_6F_1$ cross are male sterile. A plurality of CMS TN86×TN86 SRC $BC_6F_1$×CMS plants (e.g., CMS $F_1$ progeny plants) are screened for the cyp82e4 W329Stop, cyp82e5v2 W422Stop, and cyp82e10 P381S mutations to identify plants heterozygous for all three mutations. A single male-sterile plant resulting from this cross is backcrossed as a female to TN86 SRC to prepare $BC_7F_1$ CMS progeny. $BC_7F_1$ CMS progeny homozygous for the cyp82e4 W329Stop, the cyp82e5v2 W422Stop, and cyp82e10 P381S mutations are identified by genotyping and designated as CMS TN86 SRC. Because the CMS TN86 SRC line is male sterile, it is maintained via pollination with TN86 SRC. TN86 SRC is crossed as the male parent to CMS TN86 SRC to prepare CMS TN86 SRC $F_1$ progeny plants.

CMS TN86 SRC and CMS TN86 SRC $F_1$ progeny plants have genetic backgrounds that are at least 95%, at least 97%, at least 98%, or at least 99% similar to TN86, CMS TN86 SRC and CMS TN86 SRC $F_1$ progeny plants exhibit low nomicotine levels and produce leaves with reduced potential for accumulating derived NNN during curing, storage, and smoking.

NCBH129 SRC

In some aspects, the present disclosure includes tobacco cultivars, and parts thereof, from NCBH129 SRC. In another aspect, the present disclosure includes a tobacco plant, or part thereof, produced by growing the seed of NCBH129 SRC. In other aspects, the plant of the present disclosure can include a plant with all, or essentially all, of the morphological and physiological characteristics of cultivar NCBH129 SRC.

While not being limited by process, NCBH129 SRC is produced by pollinating plants of CMS NC638 SRC with pollen of TN86 SRC. Again, not limited by any particular scientific theory, cyp82e4 W329Stop, cyp82e5v2 W422Stop, and cyp82e10 P381S mutations all encode for proteins with reduced or eliminated ability to convert nicotine or nomicotine. NCBH129 SRC has a genetic background that is at least 95%, at least 97%, at least 98%, or at least 99% similar to burley tobacco cultivar NCBH129, a hybrid generated by pollinating plants of a male-sterile breeding line NC638 with pollen produced by fertile breeding line TN86. NCBH129 SRC exhibits low nomicotine and is not subject to conversion to high nomicotine.

Other Plants

The present disclosure includes a tobacco seed produced by crossing two parent tobacco plants and harvesting the resultant tobacco seed, where at least one parent tobacco plant is TN90 SRC. In one aspect, the TN90 SRC is the male parent plant. In another aspect, the CMS TN90 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than about 75%, 80%, 85%, 90%, 95%, 98%, or 99% similar to TN90 or CMS TN90. In one aspect, approximately or greater than about 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 99% similar to TN90 or CMS TN90. In another aspect, a plant of the present disclosure exhibits low nomicotine and is not subject to conversion to high nomicotine. In one aspect, a plant of the present disclosure is the progeny plant of a female or male parent plant that is *Fusarium* wilt resistant. In another aspect, a plant of TN90 SRC has low resistance to black shank and moderate resistance to bacterial wilt.

In some aspects, the present disclosure provides a tobacco seed produced by crossing two parent tobacco plants and harvesting the resultant tobacco seed, where at least one parent tobacco plant is KY14 SRC. In one aspect, the KY14 SRC is the male parent plant. In another aspect, the CMS KY14 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than about 75%, 80%, 85%, 90%, 95%, 98%, or 99% similar to KY14 or CMS KY14. In one aspect, approximately or greater than about 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 99% similar to KY14 or CMS KY14. In another aspect, a plant of the present disclosure exhibits low nomicotine and is not subject to conversion to high nomicotine. In one aspect, a plant of the present disclosure is the progeny plant of a female or male parent plant that is *Fusarium* wilt resistant. In another aspect, a plant of KY14 SRC has low resistance to black shank and moderate resistance to bacterial wilt.

The present disclosure includes a tobacco seed produced by crossing two parent tobacco plants and harvesting the resultant tobacco seed, where at least one parent tobacco plant is KY14 SRC. In one aspect, the KY14 SRC is the male parent plant. In another aspect, the CMS KY14 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than about 75%, 80%, 85%, 90%, 95%, 98%, or 99% similar to KY14 or CMS KY14. In one aspect, approximately or greater than about 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 99% similar to KY14 SRC and CMS KY14 SRC. In another aspect, a plant of the present disclosure exhibits low nomicotine and is not subject to conversion to high nomicotine. In one aspect, a plant of the present disclosure is the progeny plant of a female or male parent plant that is *Fusarium* wilt resistant. In another aspect, a plant of KY14× L8 SRC has moderate resistance to black shank and moderate resistance to bacterial wilt.

In some aspects, the present disclosure includes a tobacco seed produced by crossing two parent tobacco plants and harvesting the resultant tobacco seed, where at least one parent tobacco plant is NC775 SRC. In one aspect, the NC775 SRC is the male parent plant. In another aspect, the CMS NC775 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than 75%, 80%, 85%, 90%, 95%, 98%, or 99% similar to NC775 or CMS NC775. In one aspect, approximately or greater than 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 990/o similar to NC775 or CMS NC775. In another aspect, a plant of the present disclosure exhibits low nomicotine and is not subject to conversion to high nornicotine. In one aspect, a plant of the present disclosure is the progeny plant of a female or male parent plant that is *Fusarium* wilt resistant. In another aspect, a plant of NC775 SRC has low resistance to black shank and moderate resistance to bacterial wilt.

The present disclosure includes a tobacco seed produced by crossing two parent tobacco plants and harvesting the resultant tobacco seed, where at least one parent tobacco plant is NC775 SRC. In one aspect, the NC775 SRC is the male parent plant. In another aspect, the CMS NC775 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than 75%, 80%, 85%, 90%, 95%, 98%, or 99% similar to NC775 or CMS NC775. In one aspect, approximately or greater than 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 99% similar to NC775 SRC and CMS NC775 SRC. In another aspect, a plant of the present disclosure exhibits low nomicotine and is not subject to conversion to high nomicotine. In one aspect, a plant of the present disclosure is the progeny plant of a female or male parent plant that is *Fusarium* wilt resistant. In another aspect, a plant of NC7 SRC has moderate resistance to black shank and moderate resistance to bacterial wilt.

The present disclosure includes a tobacco seed produced by crossing two parent tobacco plants and harvesting the resultant tobacco seed, where at least one parent tobacco plant is NC638 SRC. In one aspect, the NC638 SRC is the male parent plant. In another aspect, the CMS NC638 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than about 75%, 80%, 85%, 90%, 95%, 98%, or 99% similar to NC638 or CMS NC638. In one aspect, approximately or greater than about 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 99% similar to NC638 or CMS NC638. In another aspect, a plant of the present disclosure exhibits low nomicotine and is not subject to conversion to high NNN's. In one aspect, a plant of the present disclosure is the progeny plant of a female or male parent plant that is *Fusarium* wilt resistant. In another aspect, a plant of NC638 SRC has low resistance to black shank and moderate resistance to bacterial wilt.

The present disclosure includes a tobacco seed produced by crossing two parent tobacco plants and harvesting the resultant tobacco seed, where at least one parent tobacco plant is NC638 SRC. In one aspect, the NC638 SRC is the male parent plant. In another aspect, the CMS NC638 SRC is the female parent plant. One aspect of the present disclosure provides tobacco plants that are homozygous at the cyp82e4, cyp82e5v2, and cyp82E10 loci for SEQ ID NO: 1, SEQ ID NO: 2, and SEQ ID NO: 11, respectively, and which share a genetic background that is greater than about 75%, 80%, 85%, 90%, 95%, 98%, or 99% similar to NC638 or CMS NC638. In one aspect, approximately or greater than about 50%, 75%, or 100% of a progeny's genetics is provided by a plant of the present disclosure that is homozygous at the cyp82e4, cyp82e5v2, and cyp82E10 loci for SEQ ID NO: 1, SEQ ID NO: 2, and SEQ ID NO: 11, respectively. In one aspect, a plant of the present disclosure has a genetic background that is at least 95%, at least 97%, at least 98%, or at least 99% similar to NC638 SRC and CMS NC638 SRC. In another aspect, a plant of the present disclosure exhibits low nomicotine and is not subject to conversion to high nomicotine. In one aspect, a plant of the present disclosure is the progeny plant of a female or male parent plant that is *Fusarium* wilt resistant. In another aspect, a plant of NC638 SRC has moderate resistance to black shank and moderate resistance to bacterial wilt.

In one aspect, a plant of the present disclosure is a medium-late maturing variety with moderately high yield potential. In another aspect, a plant of the present disclosure offers a broad range of important agronomic characteristics. In a further aspect, a plant of the present disclosure has one, two, three, four or more of the traits including moderate resistance to black shank, some tolerance to blue mold, black root rot resistance, and resistance to common virus diseases. In another aspect, a plant of the present disclosure has blue mold tolerance and level 4 resistance to both races of black shank and high root rot resistance. In one aspect, a plant of the present disclosure, such as TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and/or NCBH129 SRC, lacks *Fusarium* wilt resistance. In another aspect, a plant of the present disclosure is *Fusarium* wilt resistant. In another aspect, a plant of the present disclosure has low resistance to black shank and moderate resistance to bacterial wilt.

In an aspect, the plants of the present disclosure have reduced or eliminated ability to convert nicotine to nornicotine. In an aspect, the percentage nicotine conversion can be less than about 75%, 70%, 60%, 50%, or 25% of that found in a cultivar selected from the group consisting of TN90, KY14, L8, NC775, NC645, NC638, TN86, KY14× L8, NC7, and NCBH129. In other aspects, the nicotine conversion in plants of the present disclosure, including but not limited to TN90 SRC, CMS TN90 SRC. KY14 SRC, CMS KY14 SRC, L8 SRC. NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC, can be less than about 4%, about 3.5%, about 3%, about 2.5%, about 2%, about 1.5%, about 1%, or any range therein. In still other aspects, the nicotine conversion in plants of the present disclosure, including but not limited to TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and/or NCBH129 SRC, can be in a range from about 3% to about 1%, about 3% to about 0.5%, or about 2% to about 0.5%. In a preferred aspect, the percentage nicotine conversion is less than about 25%, 10%, 5%, or 2% of that found in a cultivar selected from the group consisting of TN90, KY14, L8, NC775, NC645, NC638, TN86, KY14×L8, NC7, and NCBH129 without the cyp82e4 W329Stop, the cyp82e5v2 W422Stop, and cyp82e10 P381S mutations. In an aspect, the tobacco plants of the present disclosure can have a nicotine conversion rate of about 3.5, 3.25, 3.0 or 2.75% or less. In another aspect, the nicotine conversion rate of tobacco plants of the present disclosure can be about 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5% or less or any range therein. In another aspect, the nicotine conversion rate of tobacco plants of the present disclosure can be about 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6% or less or any range therein. In another aspect, the nicotine conversion rates can be in a range from about 0.5% to about 0.9%, about 0.5% to about 1.5%, about 0.5% to about 2.0%, about 0.5% to about 2.5%, about 0.5% to about 2.75%, and about 0.5% to about 3.0%. In another aspect, the nicotine conversion rates can be in a range from about 1.0% to about 1.5%, about 1.0% to about 1.75%, about 1.0% to about 2.0%, about 1.0% to about 2.5%, about 1.0% to about 2.75%, or about 1.0% to about 3.0%. In another aspect, the nicotine conversion rate in a plant of the present disclosure can be less than about 2.9, 2.75, 2.5, 2.25, 2.0, 1.9, 1.8, 1.7, 1.6, 1.5, 1.4, 1.3, 1.2, 1.1 or 1.0% or any range therein.

In another aspect, the tobacco plants of the present disclosure typically have a reduced amount of nornicotine of less than about 0.10% dry weight. For example, the nomicotine content in such plants can be about 1.2, 1.0, 0.7, 0.5, 0.4, 0.2, 0.1, 0.09, 0.085, 0.08, 0.075, 0.07, 0.065, 0.06, 0.055, 0.05, 0.045, 0.04, 0.035, 0.025, 0.01, 0.009, 0.0075, 0.005, 0.0025, 0.001, 0.0009, 0.00075, 0.0005, 0.00025, or 0.0001% dry weight, or undetectable, or any range therein. In another aspect, the nomicotine content can be less than about 1.2, 1.0, 0.9, 0.8, 0.7, 0.5, 0.4, 0.2, 0.1, 0.075, 0.05, 0.025, 0.01, 0.009, 0.0075, 0.005, 0.0025, 0.001, 0.0009, 0.00075, 0.0005, 0.00025, or 0.0001% dry weight, or any range therein. In another aspect, the nomicotine content in such plants can be in a range from about 1.2% to about 1.0%, about 0.7% to about 0.5%, about 0.4% to about 0.2%, about 0.1% to about 0.075%, about 0.05% to about 0.025%, about 0.01% to about 0.0075%, about 0.005% to about 0.0025%, about 0.001% to about 0.00075%, about 0.0005% to about 0.00025%, or about 0.0005% to about 0.0001% dry weight. In some aspects, in a plant of the present disclosure, the nomicotine is a relatively small percentage of total alkaloids in the plant compared to a commercial seedlot of a cultivar selected from the group consisting of TN90, KY14, L8, NC775, NC645, NC638, TN86, KY14×L8, NC7, and NCBH129. In some aspects, the nomicotine in a plant of the present disclosure can be about 2% to about 1%, less than 3%, about 2%, about 1.5%, about 1%, or 0.756 of total alkaloids. Tobacco products having a reduced amount of nitrosamine content can be manufactured using tobacco plant material from plants and plant parts of the present disclosure. Thus, in some embodiments, a tobacco product manufactured using tobacco plant material from plants and plant parts of the present disclosure can comprise a reduced amount of nornicotine of less than about 3 mg/g. For example, the nomicotine content in such a product can be 3.0 mg/g, 2.5 mg/g, 2.0 mg/g, 1.5 mg/g, 1.0 mg/g, 750 µg/g, 500 µg/g, 250 µg/g, 100 µg/g, 75 µg/g, 50 µg/g, 25 µg/g, 10 µg/g, 5 µg/g, 1 µg/g, 750 ng/g, 500 ng/g, 250 ng/g, 100 ng/g, 75 ng/g, 50 ng/g, 25 ng/g, 10 ng/g, 5 ng/g, 1 ng/g, 750 pg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, and the like, or undetectable, or any range therein. The tobacco product typically has a reduced amount of NNN of less than about 10 pg/g. For example, the NNN content in such a product can be about 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, and the like, or undetectable, or any range therein. The percentage of secondary alkaloids relative to total alkaloid content contained in a plant of the present disclosure may not be statistically different than from a commercial seedlot of a cultivar selected from the group consisting of TN90, KY14, L8, NC775, NC645, NC638, TN86, KY14×L8, NC7, and NCBH129.

Differences between two inbred tobacco varieties or two hybrid tobacco varieties can be evaluated using statistical approaches. Statistical analysis includes the calculation of mean values, determination of the statistical significance of the sources of variation, and the calculation of the appropriate variance components. Methods for determining statistical significance are known in the art. Statistical software is available, for example, the PROC GLM function of SAS. Significance is generally presented as a "p-value." A statistically significant p-value is less than 0.10. In a preferred aspect, the p-value is less than or equal to 0.05. In another aspect, the p-value is 0.04 or less, 0.03 or less, or 0.02 or less. In yet another aspect, a statistically significant value is less than 0.01. In yet another aspect, it can be less than 0.009, less than 0.008, less than 0.007, less than 0.006, less than 0.005, less than 0.004, less than 0.003, less than 0.002, or less than 0.001.

Tobacco plants of the present disclosure that are homozygous for the cyp82e4 W329Stop, the cyp82e5v2 W422Stop, and cyp82e10 P381S alleles have a reversion rate that is statistically significantly lower than corresponding control low-converter plants having wild type nicotine demethylase CYP82E4. E5, and E10 genes. In addition, homozygous CYP82E4, CYP82E5, and CYP82E10 triple mutant tobacco plants have a percent conversion to nomicotine of less than about 2.0%, e.g., undetectable to about 2.0%, 1.9%, 1.8%, 1.7%, 1.6%, 1.5%, 1.4%, 1.3%, 1.2%, 1.1%, 1.0%, 0.9%, 0.8%, or any range therein. In some aspects, the triple mutant tobacco plants have a percent conversion to nomicotine in a range from, for example, about 1.0% to 2.0%, 0.8% to 1.8%, 0.8% to 2.0%, or 1.0% to 2.0%.

Nicotine and nomicotine can be measured in ethylene-treated leaves using methods known in the art (e.g., gas chromatography). Percent nicotine demethylation in a sample is calculated by dividing the level of nomicotine by the combined level of nicotine and nomicotine as measured in the sample, and multiplying by 100. Percent nicotine demethylation in a sample from a plant of the present disclosure is about 50, 40, 30, 20, or 10 percent of a sample from an individual plant grown from a commercial seedlot of a cultivar selected from the group consisting of TN90, KY14, L8, NC775, NC645, NC638, TN86, KY14×L8, NC7, and NCBH129.

In an aspect, the tobacco plants of the present disclosure have a USDA quality index of about 73, about 72, about 71, about 70, about 69, about 68, about 67 or about 66 or any range therein. In an aspect, the tobacco plants of the present disclosure have a USDA quality index of about 65. In another aspect, the quality index may be at least about 55, 60, 62.5 or greater, or any range therein. In another aspect, tobacco plants of the present disclosure can have a quality index in the range of about 60 to about 65, about 60 to about 70, about 62.5 to about 65, about 62.5 to about 70, or about 65 to about 70.

A plant of the present disclosure, including TN90 SRC, CMS TN90 SRC. KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, or NCBH129 SRC, can have any yield potential, including high (e.g., over 3000 lbs/A), moderately high (e.g., 2200-3000 lbs/A), and moderate (e.g., less than 2000 lbs/A) yield potential.

In another aspect, the present disclosure also provides for a plant grown from the seed of a TN90 SRC or CMS TN90 SRC plant in which alkaloids obtained from tobacco plants grown for the seed have decreased nomicotine, as well as plant parts and tissue cultures from such plants, representative sample seeds of these cultivars having been deposited with the ATCC, for example, under ATCC Accession No. PTA-13567 for TN90 SRC and ATCC Accession No. PTA-13573 for CMS TN90 SRC.

In another aspect, the present disclosure also provides for a plant grown from the seed of a KY14 SRC, CMS KY14 SRC. L8 SRC, or a hybrid KY14×L8 SRC plant in which alkaloids obtained from tobacco plants grown for the seed have decreased nomicotine, as well as plant parts and tissue cultures from such plants, representative sample seeds of these cultivars having been deposited with the ATCC, for example, under ATCC Accession No. PTA-120311 for KY14 SRC, ATCC Accession No. PTA-13571 for CMS KY14 SRC, ATCC Accession No. PTA-13572 for L8 SRC. Seeds of hybrid cultivar KY14×L8 SRC are obtainable by crossing plants of cultivars L8 SRC and CMS KY14 SRC and collecting seeds.

In another aspect, the present disclosure also provides for a plant grown from the seed of a NC775 SRC, CMS NC775 SRC, NC645 SRC, or a hybrid NC7 SRC plant in which alkaloids obtained from tobacco plants grown for the seed have decreased nomicotine, as well as plant parts and tissue cultures from such plants, representative sample seeds of these cultivars having been deposited with the ATCC, for example, under ATCC Accession No. PTA-120312 for NC775 SRC, ATCC Accession No. PTA-13563 for CMS NC775 SRC, ATCC Accession No. PTA-13566 for NC645 SRC. Seeds of hybrid cultivar NC7 SRC are obtainable by crossing plants of cultivars NC645 SRC and CMS NC775 SRC and collecting seeds.

In another aspect, the present disclosure also provides for a plant grown from the seed of a NC638 SRC, CMS NC638 SRC, TN86 SRC, CMS TN86 SRC, or a hybrid NCBH129 SRC plant in which alkaloids obtained from tobacco plants grown for the seed have decreased nomicotine, as well as plant parts and tissue cultures from such plants, representative sample seeds of these cultivars having been deposited with the ATCC, for example, under ATCC Accession No. PTA-120313 for NC638 SRC. ATCC Accession No. PTA-13568 for CMS NC638 SRC, ATCC Accession No. PTA-13565 for TN86 SRC, and ATCC Accession No. PTA-13570 for CMS TN86 SRC. Seeds of hybrid cultivar NCBH129 SRC are obtainable by crossing plants of cultivars TN86 SRC and CMS NC638 SRC and collecting seeds.

An aspect of the present disclosure provides for parts of a cultivar selected from the group consisting of TN90 SRC, CMS TN90 SRC. KY14 SRC, CMS KY14 SRC, L8 SRC, NC775 SRC, CMS NC775 SRC, NC645 SRC. NC638 SRC, CMS NC638 SRC, TN86 SRC, CMS TN86 SRC, KY14×L8 SRC, NC7 SRC, and NCBH129 SRC. A part of a cultivar can comprise any plant part and includes, but is not limited to, leaves, pollen, embryos, cotyledons, hypocotyls, roots, root tips, anthers, flowers, ovules, shoots, stems, stalks, pith and capsules, tissue culture comprising tissue, callus, cells or protoplasts. In another aspect, the present disclosure provides for parts from hybrids derived from a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC. In yet another aspect, the present disclosure provides for parts from genetically modified (e.g., by conventional breeding or genetic engineering techniques) forms of the foregoing plants and tissue culture.

Additional aspects of the present disclosure provide products comprising tobacco from the plants of the present disclosure, and parts thereof. Other aspects of the disclosure provide cured plant parts, which include, but are not limited to, a leaf, pollen, ovule, embryo, cotyledon, hypocotyl, meristematic cell, protoplast, root, root tip, pistil, anther, flower, shoot, stem, pod, petiole, and the like, and combinations thereof.

Thus, in some aspects, the present disclosure provides a cured tobacco comprising the leaves of the tobacco plant designated TN90 SRC, a representative sample seed of said cultivar having been deposited with the ATCC under ATCC Accession No. PTA-13567. In another aspect, the present disclosure provides a cured tobacco comprising the leaves of the tobacco plant designated CMS TN90 SRC, a representative sample seed of said cultivar having been deposited with the ATCC under ATCC Accession No. PTA-13573.

In an aspect, the present disclosure provides a cured tobacco comprising the stems of the tobacco plant designated TN90 SRC, a representative sample seed of said cultivar having been deposited with the ATCC under ATCC Accession No. PTA-13567. In another aspect, the present disclosure provides a cured tobacco comprising the stems of the tobacco plant designated CMS TN90 SRC, a representative sample seed of said cultivar having been deposited with the ATCC under ATCC Accession No. PTA-13573.

In an aspect, the present disclosure provides a cured tobacco comprising the leaves and stems of the tobacco plants designated TN90 SRC, a representative sample seed of said cultivar having been deposited with the ATCC under ATCC Accession No. PTA-13567. In another aspect, the present disclosure provides a cured tobacco comprising the leaves and stems of the tobacco plants designated CMS TN90 SRC, a representative sample seed of said cultivar having been deposited with the ATCC under ATCC Accession No. PTA-13573.

The present disclosure also provides a container of TN90 SRC or CMS TN90 SRC seeds or other seeds of the present disclosure in which alkaloids obtained from tobacco plants grown from greater than about 50% of the seeds have decreased nomicotine. In another aspect, alkaloids obtained from TN90 SRC or CMS TN90 SRC plants or other plants of the present disclosure grown from greater than about 55%, 60%, 65%, 70%, 75%, 80%, 85%, 90%, or 95% of the seeds in the container have decreased nomicotine, representative samples of seeds of these cultivars having been deposited with the ATCC, for example, under ATCC Accession No. PTA-13567 for TN90 SRC and/or ATCC Accession No. PTA-13573 for CMS TN90 SRC.

The container of TN90 SRC or CMS TN90 SRC seeds or other seeds of the present disclosure may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Representative samples of seeds of these cultivars having been deposited with the ATCC, for example, under ATCC Accession No. PTA-13567 for TN90 SRC and/or ATCC Accession No. PTA-13573 for CMS TN90 SRC.

Containers of TN90 SRC or CMS TN90 SRC seeds or other seeds of the present disclosure may be any container available in the art. By way of a non-limiting example, a container may be a box, a bag, a packet, a pouch, a tape roll, a pail, a foil, or a tube. Representative samples of seeds of these cultivars having been deposited with the ATCC, for example, under ATCC Accession No. PTA-13567 for TN90 SRC and/or ATCC Accession No. PTA-13573 for CMS TN90 SRC.

In another aspect, the present disclosure also provides a container of TN90 SRC or CMS TN90 SRC seeds in which greater than about 50% of TN90 SRC or CMS TN90 SRC seeds or other seeds of the present disclosure have decreased nomicotine. Representative samples of seeds of these cultivars having been deposited with the ATCC, for example under ATCC Accession No. PTA-13567 for TN90 SRC and/or ATCC Accession No. PTA-13573 for CMS TN90 SRC.

In one aspect, the present disclosure provides a seed of a TN90 SRC or CMS TN90 SRC plant or other plant of the present disclosure in which a plant grown from said seed is male sterile. Representative samples of seeds of these cultivars having been deposited with the ATCC, for example, under ATCC Accession No. PTA-13567 for TN90 SRC and/or ATCC Accession No. PTA-13573 for CMS TN90 SRC.

In some aspects, the present disclosure provides a cured tobacco comprising the leaves of the tobacco plant designated KY14 SRC, a representative sample seed of said cultivar having been deposited with the ATCC under ATCC Accession No. PTA-120311. In another aspect, the present disclosure provides a cured tobacco comprising the leaves of the tobacco plant designated CMS KY14 SRC, a representative sample seed of said cultivar having been deposited with the ATCC under ATCC Accession No. PTA-13571. In another aspect, the present disclosure provides a cured tobacco comprising the leaves of the tobacco plant designated L8 SRC, a representative sample seed of said cultivar having been deposited with the ATCC under ATCC Accession No. PTA-13572. In yet another aspect, the present disclosure provides a cured tobacco comprising the leaves of the hybrid tobacco plant designated KY14×L8 SRC. Seeds of hybrid cultivar KY14×L8 SRC are obtainable by crossing plants of cultivars L8 SRC and CMS KY14 SRC and collecting seeds.

In an aspect, the present disclosure provides a cured tobacco comprising the stems of the tobacco plant designated KY14 SRC, a representative sample seed of said cultivar having been deposited with the ATCC under ATCC Accession No. PTA-120311. In another aspect, the present disclosure provides a cured tobacco comprising the stems of the tobacco plant designated CMS KY14 SRC, a representative sample seed of said cultivar having been deposited with the ATCC under ATCC Accession No. PTA-13571. In an aspect, the present disclosure provides a cured tobacco comprising the stems of the tobacco plant designated L8 SRC, a representative sample seed of said cultivar having been deposited with the ATCC under ATCC Accession No. PTA-13572. In yet another aspect, the present disclosure provides a cured tobacco comprising the stems of the hybrid tobacco plant designated KY14×L8 SRC. Seeds of hybrid cultivar KY14×L8 SRC are obtainable by crossing plants of cultivars L8 SRC and CMS KY14 SRC and collecting seeds.

In an aspect, the present disclosure provides a cured tobacco comprising the leaves and stems of the tobacco plants designated KY14 SRC, a representative sample seed of said cultivar having been deposited with the ATCC under ATCC Accession No. PTA-120311. In another aspect, the present disclosure provides a cured tobacco comprising the leaves and stems of the tobacco plants designated CMS KY14 SRC, a representative sample seed of said cultivar having been deposited with the ATCC under ATCC Accession No. PTA-13571. In an aspect, the present disclosure provides a cured tobacco comprising the leaves and stems of the tobacco plants designated L8 SRC, a representative sample seed of said cultivar having been deposited with the ATCC under ATCC Accession No. PTA-13572. In yet another aspect, the present disclosure provides a cured tobacco comprising the leaves and stems of the hybrid tobacco plants designated KY14×L8 SRC. Seeds of hybrid cultivar KY14×L8 SRC are obtainable by crossing plants of cultivars L8 SRC and CMS KY14 SRC and collecting seeds.

The present disclosure also provides a container of KY14 SRC, CMS KY14 SRC, L8 SRC, or hybrid KY14×L8 SRC seeds or other seeds of the present disclosure in which alkaloids obtained from tobacco plants grown from greater than about 50% of the seeds have decreased nornicotine. In another aspect, alkaloids obtained from KY14 SRC, CMS KY14 SRC, L8 SRC, or hybrid KY14×L8 SRC plants or other plants of the present disclosure grown from greater than about 55%, 60%, 65%, 70%, 75%, 80%, 85%, 90%, or 95% of the seeds in the container have decreased nomicotine, representative samples of seeds of these cultivars having been deposited with the ATCC, for example, under ATCC Accession No. PTA-120311 for KY14 SRC, ATCC Accession No. PTA-13571 for CMS KY14 SRC, and/or ATCC Accession No. PTA-13572 for L8 SRC. Seeds of hybrid cultivar KY14×L8 SRC are obtainable by crossing plants of cultivars L8 SRC and CMS KY14 SRC and collecting seeds.

The container of KY14 SRC, CMS KY14 SRC, L8 SRC, or hybrid KY14×L8 SRC seeds or other seeds of the present disclosure may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Representative samples of seeds of these cultivars having been deposited with the ATCC, for example, under ATCC Accession No. PTA-120311 for KY14 SRC, ATCC Accession No. PTA-13571 for CMS KY14 SRC, or ATCC Accession No. PTA-13572 for L8 SRC. Seeds of hybrid cultivar KY14×L8 SRC are obtainable by crossing plants of cultivars L8 SRC and CMS KY14 SRC and collecting seeds.

Containers of KY14 SRC, CMS KY14 SRC, L8 SRC or hybrid KY14×L8 SRC seeds or other seeds of the present disclosure may be any container available in the art. By way of a non-limiting example, a container may be a box, a bag, a packet, a pouch, a tape roll, a pail, a foil, or a tube. Representative samples of seeds of these cultivars having been deposited with the ATCC, for example, under ATCC Accession No. PTA-120311 for KY14 SRC, ATCC Accession No. PTA-13571 for CMS KY14 SRC, and/or ATCC Accession No. PTA-13572 for L8 SRC. Seeds of hybrid cultivar KY14×L8 SRC are obtainable by crossing plants of cultivars L8 SRC and CMS KY14 SRC and collecting seeds.

In another aspect, the present disclosure also provides a container of KY14 SRC, CMS KY14 SRC, L8 SRC, or hybrid cultivar KY14×L8 SRC seeds in which greater than about 50% of KY14 SRC, CMS KY14 SRC, L8 SRC, or hybrid KY14×L8 SRC seeds or other seeds of the present disclosure have decreased nomicotine. Representative samples of seeds of these cultivars having been deposited with the ATCC, for example under ATCC Accession No. PTA-120311 for KY14 SRC, ATCC Accession No. PTA-13571 for CMS KY14 SRC, and/or ATCC Accession No. PTA-13572 for L8 SRC. Seeds of hybrid cultivar KY14×L8 SRC are obtainable by crossing plants of cultivars L8 SRC and CMS KY14 SRC and collecting seeds.

In one aspect, the present disclosure provides a seed of a KY14 SRC, CMS KY14 SRC, L8 SRC, or hybrid KY14×L8 SRC plant or other plant of the present disclosure in which a plant grown from a seed is male sterile. Representative samples of seeds of these cultivars having been deposited with the ATCC, for example, under ATCC Accession No. PTA-120311 for KY14 SRC, ATCC Accession No. PTA-13571 for CMS KY14 SRC, ATCC Accession No. PTA-13572 for L8 SRC. Seeds of hybrid cultivar KY14×L8 SRC are obtainable by crossing plants of cultivars L8 SRC and CMS KY14 SRC and collecting seeds.

In some aspects, the present disclosure provides a cured tobacco comprising the leaves of the tobacco plant designated NC775 SRC, a representative sample seed of said cultivar having been deposited with the ATCC under ATCC Accession No. PTA-120312. In another aspect, the present disclosure provides a cured tobacco comprising the leaves of the tobacco plant designated CMS NC775 SRC, a representative sample seed of said cultivar having been deposited with the ATCC under ATCC Accession No. PTA-13563. In another aspect, the present disclosure provides a cured tobacco comprising the leaves of the tobacco plant designated NC645 SRC, a representative sample seed of said cultivar having been deposited with the ATCC under ATCC Accession No. PTA-13566. In yet another aspect, the present disclosure provides a cured tobacco comprising the leaves of the hybrid tobacco plant designated NC7 SRC. Seeds of hybrid cultivar NC7 SRC are obtainable by crossing plants of cultivars NC645 SRC and CMS NC775 SRC and collecting seeds.

In an aspect, the present disclosure provides a cured tobacco comprising the stems of the tobacco plant designated NC775 SRC, a representative sample seed of said cultivar having been deposited with the ATCC under ATCC Accession No. PTA-120312. In another aspect, the present disclosure provides a cured tobacco comprising the stems of the tobacco plant designated CMS NC775 SRC, a representative sample seed of said cultivar having been deposited with the ATCC under ATCC Accession No. PTA-13563. In an aspect, the present disclosure provides a cured tobacco comprising the stems of the tobacco plant designated NC645 SRC, a representative sample seed of said cultivar having been deposited with the ATCC under ATCC Accession No. PTA-13566. In yet another aspect, the present disclosure provides a cured tobacco comprising the stems of the hybrid tobacco plant designated NC7 SRC. Seeds of hybrid cultivar NC7 SRC are obtainable by crossing plants of cultivars NC645 SRC and CMS NC775 SRC and collecting seeds.

In an aspect, the present disclosure provides a cured tobacco comprising the leaves and stems of the tobacco plants designated NC775 SRC, a representative sample seed of said cultivar having been deposited with the ATCC under ATCC Accession No. PTA-120312. In another aspect, the present disclosure provides a cured tobacco comprising the leaves and stems of the tobacco plants designated CMS NC775 SRC, a representative sample seed of said cultivar having been deposited with the ATCC under ATCC Accession No. PTA-13563. In an aspect, the present disclosure provides a cured tobacco comprising the leaves and stems of the tobacco plants designated NC645 SRC, a representative sample seed of said cultivar having been deposited with the ATCC under ATCC Accession No. PTA-13566. In yet another aspect, the present disclosure provides a cured tobacco comprising the leaves and stems of the hybrid tobacco plants designated NC7 SRC. Seeds of hybrid cultivar NC7 SRC are obtainable by crossing plants of cultivars NC645 SRC and CMS NC775 SRC and collecting seeds.

The present disclosure also provides a container of NC775 SRC, CMS NC775 SRC, NC645 SRC, or hybrid NC7 SRC seeds or other seeds of the present disclosure in which alkaloids obtained from tobacco plants grown from greater than about 50% of the seeds have decreased nomicotine. In another aspect, alkaloids obtained from NC775 SRC, CMS NC775 SRC, NC645 SRC, or hybrid NC7 SRC plants or other plants of the present disclosure grown from greater than about 55%, 60%, 65%, 70%, 75%, 80%, 85%, 90%, or 95% of the seeds in the container have decreased nornicotine, representative samples of seeds of these cultivars having been deposited with the ATCC, for example, under ATCC Accession No. PTA-120312 for NC775 SRC, ATCC Accession No. PTA-13563 for CMS NC775 SRC, ATCC Accession No. PTA-13566 for NC645 SRC. Seeds of hybrid cultivar NC7 SRC are obtainable by crossing plants of cultivars NC645 SRC and CMS NC775 SRC and collecting seeds.

The container of NC775 SRC, CMS NC775 SRC, NC645 SRC, or hybrid NC7 SRC seeds or other seeds of the present disclosure may contain any number, weight, or volume of seeds. For example, a container can contain at least, or greater than, about 100, 200, 300, 400, 500, 600, 700, 800, 900, 1000, 1500, 2000, 2500, 3000, 3500, 4000, or more seeds. Alternatively, the container can contain at least, or greater than, about 1 ounce, 5 ounces, 10 ounces, 1 pound, 2 pounds, 3 pounds, 4 pounds, 5 pounds, or more seeds. Representative samples of seeds of these cultivars having been deposited with the ATCC, for example, under ATCC Accession No. PTA-120312 for NC775 SRC, ATCC Accession No. PTA-13563 for CMS NC775 SRC, ATCC Accession No. PTA-13566 for NC645 SRC. Seeds of hybrid cultivar NC7 SRC are obtainable by crossing plants of cultivars NC645 SRC and CMS NC775 SRC and collecting seeds.

Containers of NC775 SRC, CMS NC775 SRC, NC645 SRC or hybrid NC7 SRC seeds or other seeds of the present disclosure may be any container available in the art. By way of a non-limiting example, a container may be a box, a bag, a packet, a pouch, a tape roll, a pail, a foil, or a tube. Representative samples of seeds of these cultivars having been deposited with the ATCC, for example, under ATCC Accession No. PTA-120312 for NC775 SRC, ATCC Accession No. PTA-13563 for CMS NC775 SRC, ATCC Accession No. PTA-13566 for NC645 SRC. Seeds of hybrid cultivar NC7 SRC are obtainable by crossing plants of cultivars NC645 SRC and CMS NC775 SRC and collecting seeds.

In another aspect, the present disclosure also provides a container of NC775 SRC, CMS NC775 SRC, NC645 SRC, or hybrid cultivar NC7 SRC in which greater than 50% of NC775 SRC, CMS NC775 SRC, NC645 SRC, or hybrid NC7 SRC seeds or other seeds of the present disclosure have decreased nomicotine. Representative samples of seeds of these cultivars having been deposited with the ATCC, for example under ATCC Accession No. PTA-120312 for NC775 SRC. ATCC Accession No. PTA-13563 for CMS NC775 SRC. ATCC Accession No. PTA-13566 for NC645 SRC. Seeds of hybrid cultivar NC7 SRC are obtainable by crossing plants of cultivars NC645 SRC and CMS NC775 SRC and collecting seeds.

In one aspect, the present disclosure provides a seed of a NC775 SRC, CMS NC775 SRC, NC645 SRC, or hybrid NC7 SRC plant or other plant of the present disclosure in which a plant grown from a seed is male sterile. Representative samples of seeds of these cultivars having been deposited with the ATCC, for example, under ATCC Accession No. PTA-120312 for NC775 SRC. ATCC Accession No. PTA-13563 for CMS NC775 SRC, ATCC Accession No. PTA-13566 for NC645 SRC. Seeds of hybrid cultivar NC7 SRC are obtainable by crossing plants of cultivars NC645 SRC and CMS NC775 SRC and collecting seeds.

In some aspects, the present disclosure provides a cured tobacco comprising the leaves of the tobacco plant designated NC638 SRC, a representative sample seed of said cultivar having been deposited with the ATCC under ATCC Accession No. PTA-120313. In another aspect, the present disclosure provides a cured tobacco comprising the leaves of the tobacco plant designated CMS NC638 SRC, a representative sample seed of said cultivar having been deposited with the ATCC under ATCC Accession No. PTA-13568. In another aspect, the present disclosure provides a cured tobacco comprising the leaves of the tobacco plant designated TN86 SRC, a representative sample seed of said cultivar having been deposited with the ATCC under ATCC Accession No. PTA-13565. In further aspect, the present disclosure provides a cured tobacco comprising the leaves of the tobacco plant designated CMS TN86 SRC, a representative sample seed of said cultivar having been deposited with the ATCC under ATCC Accession No. PTA-13570. In yet another aspect, the present disclosure provides a cured tobacco comprising the leaves of the hybrid tobacco plant designated NCBH129 SRC. Seeds of hybrid cultivar NCBH129 SRC are obtainable by crossing plants of cultivars TN86 SRC and CMS NC638 SRC and collecting seeds.

In an aspect, the present disclosure provides a cured tobacco comprising the stems of the tobacco plant designated NC638 SRC, a representative sample seed of said cultivar having been deposited with the ATCC under ATCC Accession No. PTA-120313. In another aspect, the present disclosure provides a cured tobacco comprising the stems of the tobacco plant designated CMS NC638 SRC, a representative sample seed of said cultivar having been deposited with the ATCC under ATCC Accession No. PTA-13568. In an aspect, the present disclosure provides a cured tobacco comprising the stems of the tobacco plant designated TN86 SRC, a representative sample seed of said cultivar having been deposited with the ATCC under ATCC Accession No. PTA-13565. In further aspect, the present disclosure provides a cured tobacco comprising the stems of the tobacco plant designated CMS TN86 SRC, a representative sample seed of said cultivar having been deposited with the ATCC under ATCC Accession No. PTA-13570. In yet another aspect, the present disclosure provides a cured tobacco comprising the stems of the hybrid tobacco plant designated NCBH129 SRC. Seeds of hybrid cultivar NCBH129 SRC are obtainable by crossing plants of cultivars TN86 SRC and CMS NC638 SRC and collecting seeds.

In an aspect, the present disclosure provides a cured tobacco comprising the leaves and stems of the tobacco plants designated NC638 SRC, a representative sample seed of said cultivar having been deposited with the ATCC under ATCC Accession No. PTA-120313. In another aspect, the present disclosure provides a cured tobacco comprising the leaves and stems of the tobacco plants designated CMS NC638 SRC, a representative sample seed of said cultivar having been deposited with the ATCC under ATCC Accession No. PTA-13568. In an aspect, the present disclosure provides a cured tobacco comprising the leaves and stems of the tobacco plants designated TN86 SRC, a representative sample seed of said cultivar having been deposited with the ATCC under ATCC Accession No. PTA-13565. In further aspect, the present disclosure provides a cured tobacco comprising the leaves and stems of the tobacco plant designated CMS TN86 SRC, a representative sample seed of said cultivar having been deposited with the ATCC under ATCC Accession No. PTA-13570. In yet another aspect, the present disclosure provides a cured tobacco comprising the leaves and stems of the hybrid tobacco plants designated NCBH129 SRC. Seeds of hybrid cultivar NCBH129 SRC are obtainable by crossing plants of cultivars TN86 SRC and CMS NC638 SRC and collecting seeds.

The present disclosure also provides a container of NC638 SRC, CMS NC638 SRC, TN86 SRC, CMS TN86 SRC, or hybrid NCBH129 SRC seeds or other seeds of the present disclosure in which alkaloids obtained from tobacco plants grown from greater than 50% of the seeds have decreased nomicotine. In another aspect, alkaloids obtained from NC638 SRC, CMS NC638 SRC, TN86 SRC, CMS TN86 SRC, or hybrid NCBH129 SRC plants or other plants of the present disclosure grown from greater than about 55%, 60%, 65%, 70%, 75%, 80%, 85%, 90%, or 95% of the seeds in the container have decreased nomicotine, representative samples of seeds of these cultivars having been deposited with the ATCC, for example, under ATCC Accession No. PTA-120313 for NC638 SRC, ATCC Accession No. PTA-13568 for CMS NC638 SRC, ATCC Accession No. PTA-13565 for TN86 SRC, and/or ATCC Accession No. PTA-13570 for CMS TN86 SRC. Seeds of hybrid cultivar NCBH129 SRC are obtainable by crossing plants of cultivars TN86 SRC and CMS NC638 SRC and collecting seeds.

The container of NC638 SRC, CMS NC638 SRC, TN86 SRC, CMS TN86 SRC, or hybrid NCBH129 SRC seeds or other seeds of the present disclosure may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Representative samples of seeds of these cultivars having been deposited with the ATCC, for example, under ATCC Accession No. PTA-120313 for NC638 SRC, ATCC Accession No. PTA-13568 for CMS NC638 SRC, ATCC Accession No. PTA-13565 for TN86 SRC, and/or ATCC Accession No. PTA-13570 for CMS TN86 SRC. Seeds of hybrid cultivar NCBH129 SRC are obtainable by crossing plants of cultivars TN86 SRC and CMS NC638 SRC and collecting seeds.

Containers of NC638 SRC, CMS NC638 SRC, TN86 SRC, CMS TN86 SRC, or hybrid NCBH129 SRC seeds or other seeds of the present disclosure may be any container available in the art. By way of a non-limiting example, a container may be a box, a bag, a packet, a pouch, a tape roll, a pail, a foil, or a tube. Representative samples of seeds of these cultivars having been deposited with the ATCC, for example, under ATCC Accession No. PTA-120313 for NC638 SRC. ATCC Accession No. PTA-13568 for CMS NC638 SRC. ATCC Accession No. PTA-13565 for TN86 SRC, and/or ATCC Accession No. PTA-13570 for CMS TN86 SRC. Seeds of hybrid cultivar NCBH129 SRC are obtainable by crossing plants of cultivars TN86 SRC and CMS NC638 SRC and collecting seeds.

In another aspect, the present disclosure also provides a container of NC638 SRC, CMS NC638 SRC, TN86 SRC, CMS TN86 SRC, or hybrid cultivar NCBH129 SRC seeds in which greater than about 50% of NC638 SRC, CMS NC638 SRC, TN86 SRC, CMS TN86 SRC, or hybrid NCBH129 SRC seeds or other seeds of the present disclosure have decreased nomicotine. Representative samples of seeds of these cultivars having been deposited with the ATCC, for example under ATCC Accession No. PTA-120313 for NC638 SRC, ATCC Accession No. PTA-13568 for CMS NC638 SRC, ATCC Accession No. PTA-13565 for TN86 SRC and/or ATCC Accession No. PTA-13570 for CMS TN86 SRC. Seeds of hybrid cultivar NCBH129 SRC are obtainable by crossing plants of cultivars TN86 SRC and CMS NC638 SRC and collecting seeds.

In one aspect, the present disclosure provides a seed of a NC638 SRC, CMS NC638 SRC, TN86 SRC, CMS TN86 SRC, or hybrid NCBH129 SRC plant or other plant of the present disclosure in which a plant grown from a seed is male sterile. Representative samples of seeds of these cultivars having been deposited with the ATCC, for example, under ATCC Accession No. PTA-120313 for NC638 SRC, ATCC Accession No. PTA-13568 for CMS NC638 SRC, ATCC Accession No. PTA-13565 for TN86 SRC and/or ATCC Accession No. PTA-13570 for CMS TN86 SRC. Seeds of hybrid cultivar NCBH129 SRC are obtainable by crossing plants of cultivars TN86 SRC and CMS NC638 SRC and collecting seeds.

Tobacco material obtained from the tobacco lines, varieties or hybrids of the present disclosure can be used to make tobacco products including, without limitation, cigarette products (e.g., cigarettes and bidi cigarettes), cigar products (e.g., cigar wrapping tobacco and cigarillos), pipe tobacco products, smokeless cigarette products, smokeless tobacco products (e.g., moist snuff, dry snuff, and chewing tobacco), films, chewables, tabs, shaped parts, gels, consumable units, insoluble matrices, hollow shapes and the like. See, e.g., U.S. Patent Publication No. US 2006/0191548, which is herein incorporated by reference in its entirety.

Tobacco products derived from plants of the present disclosure also include cigarettes and other smoking articles, particularly those smoking articles including filter elements, wherein the rod of smokeable material includes cured tobacco within a tobacco blend. In an aspect, a tobacco product can include but is not limited to pipe tobacco, cigar tobacco, cigarette tobacco, chewing tobacco, leaf tobacco, shredded tobacco, and/or cut tobacco or any combination thereof.

In an aspect, a tobacco product of the instant disclosure is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the instant disclosure is a smokeless tobacco product. In a further aspect, a tobacco product of the instant disclosure is selected from the group consisting of loose leaf chewing tobacco, plug chewing tobacco, moist snuff, and nasal snuff. In yet another aspect, a tobacco product of the instant disclosure is selected from the group consisting of an electronically heated cigarette, an e-cigarette, an electronic vaporing device.

In an aspect, the tobacco product of the present disclosure can be a blended tobacco product. In other aspects of the disclosure, the tobacco product of the present disclosure can be a reduced nicotine tobacco product. In still other aspects, the tobacco product of the present disclosure can be a blended tobacco product with reduced nicotine content. Thus, the tobacco product of the present disclosure can be a blended reduced nicotine tobacco product. Tobacco product material comprises a blend of tobacco materials from the present disclosure, wherein the blend comprises at least about 5, 10, 20, 30, 40, 50, 60, 70, 80, 90, or 95 percent by weight of a cured tobacco, or any range therein, based on the dry weight of the tobacco material. US 2008/0245377 is herein incorporated by reference for blend mixtures in its entirety.

In an aspect, tobacco products having a reduced amount of nitrosamine content can be manufactured using tobacco plant material from plants and plant parts of the present disclosure. Thus, in some aspects, a tobacco product manufactured using tobacco plant material from plants and plant parts of the present disclosure can comprise a reduced amount of nomicotine of less than about 3 mg/g. For example, the nomicotine content in such a product can be 3.0 mg/g, 2.5 mg/g, 2.0 mg/g, 1.5 mg/g, 1.0 mg/g, 750 µg/g, 500 µg/g, 250 µg/g, 100 µg/g, 75 µg/g, 50 µg/g, 25 µg/g, 10 µg/g, 5 µg/g, 1 µg/g, 750 ng/g, 500 ng/g, 250 ng/g, 100 ng/g, 75 ng/g, 50 ng/g, 25 ng/g, 10 ng/g, 5 ng/g, 1 ng/g, 750 pg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable, or any range therein. The tobacco product typically has a reduced amount of NNN of less than about 10 pg/g. For example, the NNN content in such a product can be about 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable, or any range therein. The percentage of secondary alkaloids relative to total alkaloid content contained in a plant of the present disclosure may not be statistically different than from a commercial seedlot of a cultivar selected from the group consisting of TN90, KY14, L8, NC775, NC645, NC638, TN86, KY14×L8, NC7, and NCBH129.

The instant disclosure further provides a method of manufacturing a tobacco product, where the method comprising conditioning aged tobacco material made from an tobacco plant disclosed herein to increase its moisture content from between about 12.5% and about 13.5% to about 21%, blending the conditioned tobacco material to produce a desirable blend. In one aspect, the method of manufacturing a tobacco product disclosed herein uses tobacco material from a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC. In another aspect, the method of manufacturing a tobacco product disclosed herein further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

A tobacco plant of the present disclosure designated TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC carrying the cyp82e4 W329Stop, the cyp82e5v2 W422Stop, and cyp82e10 P381S alleles can be used in a plant breeding program to create useful lines, cultivars, varieties, progeny, inbreds, and hybrids. Thus, in some aspects, an $F_1$, $F_2$, $F_1$ or later generation tobacco plant containing the cyp82e4 W329Stop, the cyp82e5v2 W422Stop, and cyp82e10 P381S alleles is crossed with a second *Nicotiana* plant, and progeny of the cross are identified in which the cyp82e4 W329Stop, the cyp82e5v2 W422Stop, and cyp82e10 P381S alleles are present. It will be appreciated that the second *Nicotiana* plant can be TN90, KY14, L8, NC775, NC645, NC638, TN86, or any other *Nicotiana* species or line, optionally with an additional desirable trait, such as herbicide resistance.

In still other aspects, methods of the present disclosure further include self-pollinating or pollinating a male sterile pollen acceptor with a pollen donor capable of being used in production of a progeny plant of the present disclosure, such as a male sterile hybrid of the present disclosure. Either the male sterile pollen acceptor plant or the pollen donor plant has at least one mutant allele, two, or even three mutant alleles at a nicotine demethylase locus, such as the cyp82e4 W329Stop allele, the cyp82e5v2 W422Stop allele, and/or the cyp82e10 P381S allele. In an aspect, all three alleles at each nicotine demethylase locus are mutant alleles, making the plant homozygous for cyp82e4 W329Stop, cyp82e5v2 W422Stop, and cyp82e10 P381S.

Breeding can be carried out via any known procedures. DNA fingerprinting. SNP or similar technologies may be used in a marker-assisted selection (MAS) breeding program to transfer or breed mutant alleles of a nicotine demethylase gene into other tobaccos. For example, a breeder can create segregating populations from hybridizations of a genotype containing cyp82e4 W329Stop, cyp82e5v2 W422Stop, and cyp82e10 P381S alleles with an agronomically desirable genotype. Plants in the $F_2$ or backcross generations can be screened using a marker developed from cyp82e4 W329Stop, cyp82e5v2 W422Stop, or cyp82e10 P381S alleles or a fragment thereof, using one of the techniques known in the art or disclosed herein. Plants identified as possessing one or more cyp82e4 W329Stop, cyp82e5v2 W422Stop, and cyp82e10 P381 S alleles can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered. A recurrent parent in the present disclosure can be a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC. Other breeding techniques can be found, for example, in Wernsman, E. A., and Rufty, R. C., 1987. Chapter Seventeen. Tobacco, pages 669-698 In: Cultivar Development. Crop Species. W. H. Fehr (ed.), MacMillan Publishing Go., Inc., New York, N.Y., incorporated herein by reference in their entireties.

*Nicotiana* species which exhibit breeding compatibility with *Nicotiana tabacum* include *Nicotiana amplexicaulis*, PI 271989; *Nicotiana benthamiana* PI 555478; *Nicotiana bigelovii* PI 555485; *Nicotiana debneyi*; *Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica*; *Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572. See also, Compendium of Tobacco Diseases published by American Phytopathology Society, or The Genus *Nicotiana* Illustrated, published by Japan Tobacco Inc, hereby incorporated by reference in their entireties.

The result of a plant breeding program using the mutant tobacco plants described herein includes useful lines, cultivars, varieties, progeny, inbreds, and hybrids. As used herein, the term "cultivar" or "variety" refers to a population of plants that share constant characteristics which separate them from other plants of the same species. A cultivar or variety is often, although not always, sold commercially. While possessing one or more distinctive traits, a cultivar or variety is further characterized by a very small overall variation between individuals within that cultivar or variety. A "pure line" variety may be created by several generations of self-pollination and selection, or vegetative propagation from a single parent using tissue or cell culture techniques. A cultivar or variety can be essentially derived from another cultivar, line, or variety. As defined by the International Convention for the Protection of New Varieties of Plants (Dec. 2, 1961, as revised at Geneva on Nov. 10, 1972, on Oct. 23, 1978, and on Mar. 19, 1991), a cultivar or variety is "essentially derived" from an initial cultivar or variety if: a) it is predominantly derived from the initial cultivar or variety, or from a cultivar or variety that is predominantly derived from the initial cultivar or variety, while retaining the expression of the essential characteristics that result from the genotype or combination of genotypes of the initial cultivar or variety; b) it is clearly distinguishable from the initial cultivar or variety; and c) except for the differences which result from the act of derivation, it conforms to the initial cultivar or variety in the expression of the essential characteristics that result from the genotype or combination of genotypes of the initial cultivar or variety. Essentially derived varieties can be obtained, for example, by the selection of a natural or induced mutant, a somaclonal variant, a variant individual from plants of the initial cultivar or variety, backcrossing, or transformation. A "line" as distinguished from a cultivar or variety most often denotes a group of plants used non-commercially, for example in plant research. A line typically displays little overall variation between individuals for one or more traits of interest, although there may be some variation between individuals for other traits.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In aspects in which the female parent plants are CMS, pollen may be harvested from male fertile plants and applied manually to the stigmas of CMS female parent plants, and the resulting $F_1$ seed is harvested.

Plants can be used to form single-cross tobacco $F_1$ hybrids. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

Successful crosses yield $F_1$ plants that are fertile, have cyp82e4 W329Stop, cyp82e5v2 W422Stop, and cyp82e10 P381S alleles, and can be backcrossed with one of the parents, such as a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC, if desired. In some aspects, a plant population in the $F_2$ generation is screened for cyp82e4 W329Stop, the cyp82e5v2 W422Stop, and cyp82e10 P381S alleles. Selected plants can be crossed with one of the parents and the first backcross (BC1) generation plants are self-pollinated to produce a BC1 $F_2$ population that is again screened for variant nicotine demethylase gene expression (e.g., the null version of the nicotine demethylase gene). The process of backcrossing, self-pollination, and screening is repeated, for example, at least four times, until the final screening produces a plant that is fertile and reasonably similar to the recurrent parent. This plant, if desired, is self-pollinated and the progeny are subsequently screened again to confirm that the plant exhibits the same low nicotine conversion phenotype as a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC. Breeder's seed of the selected plant is produced using standard methods including, for example, field testing, confirmation of the null condition for nicotine demethylase, chemical analyses of cured leaf to determine the level of alkaloids and/or chemical analyses of cured leaf to determine the ratio of nomicotine to nicotine+nornicotine.

In one aspect, a $F_1$ progeny is the result of a cross between TN90 SRC and CMS TN90 SRC to generate $F_1$ progeny that are male sterile. In one aspect, a $F_1$ progeny is the result of a cross between KY14 SRC and CMS KY14 SRC to generate $F_1$ progeny that are male sterile. In another aspect, a $F_1$ progeny is the result of a cross between L8 SRC and CMS KY14 SRC to generate $F_1$ progeny that are male sterile. In one aspect, a $F_1$ progeny is the result of a cross between NC775 SRC and CMS NC775 SRC to generate $F_1$ progeny that are male sterile. In another aspect, a $F_1$ progeny is the result of a cross between NC645 SRC and CMS NC775 SRC to generate $F_1$ progeny that are male sterile. In one aspect, a $F_1$ progeny is the result of a cross between NC638 SRC and CMS NC638 SRC to generate $F_1$ progeny that are male sterile. In another aspect, a $F_1$ progeny is the result of a cross between TN86 SRC and CMS TN86 SRC to generate $F_1$ progeny that are male sterile. Male sterile tobacco plants may be produced by any method known in the art. Methods of producing male sterile tobacco are described in Wemsman, E. A., and Rufty, R. C., 1987. Chapter Seventeen. Tobacco, pages 669-698 In: Cultivar Development. Crop Species. W. H. Fehr (ed.), MacMillan Publishing Go., Inc., New York. N.Y. 761 pp.

The present disclosure further provides methods of producing a tobacco plant by crossing a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC with itself or a different tobacco line. The disclosure further relates to methods for producing other tobacco cultivars or breeding lines derived from a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC by crossing a plant of a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC with a second tobacco plant and growing the progeny seed to yield a tobacco plant derived from TN90 SRC, CMS TN90 SRC, KY14 SRC, CMS KY14 SRC. L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, or NCBH129 SRC. An additional aspect of the present disclosure provides a method for producing a tobacco plant that contains in its genetic material one or more transgenes, comprising crossing cultivars of the present disclosure with a second cultivar containing one or more transgenes wherein progeny are produced, so that the genetic material of the progeny that result from the cross comprise the transgene(s) optionally operably linked to one or more regulatory elements. In one aspect, the second cultivar may be a plant derived from a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC, transformed with one or more transgenes.

The disclosure further provides for the vegetative propagation of a plant, hybrids and progeny thereof, of a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC. In one aspect, the disclosure provides for a method of vegetatively propagating a plant of a tobacco cultivar comprising collecting tissue capable of being propagated from a plant of a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC, cultivating the tissue to obtain a proliferated shoot and rooting the proliferated shoots to obtain a rooted plantlet. In another aspect, the plant tissue may be collected from an $F_1$ hybrid of a plant of a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC. In an aspect, the plant tissue may be collected from an $F_2$, $F_3$, $F_4$ or later progeny plant obtained by breeding a plant of a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC.

A plant comprising a mutation in a nicotine demethylase gene can be identified by selecting or screening the mutagenized plant material, or progeny thereof. Such screening and selection methodologies are known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

It is understood that a tobacco plant of the present disclosure, including, but not limited to, TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC, can be transformed by a genetic construct (nucleic acid construct) or transgene using any technique known in the art. Without limitation, an example of a desired trait can include herbicide resistance, pest resistance, disease resistance, high yield, high grade index, curability, curing quality, mechanical harvestability, holding ability, leaf quality, height, plant maturation (e.g., early maturing, early to medium maturing, medium maturing, medium to late maturing, or late maturing), stalk size (e.g., small, medium, or large stalk), or leaf number per plant (e.g., small (e.g., 5-10 leaves), medium (e.g., 11-15 leaves), or large (e.g., 16-21) number of leaves), or any combination. Any plant of the present disclosure can be used as a basis for tissue culture, regeneration, transformed, or a combination of any of these. In an aspect, a plant of the present disclosure derived by tissue culture, transformation, or both has all, or essentially all, of the morphological and physiological characteristics of a cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC.

Having now generally described the disclosure, the same will be more readily understood through reference to the following examples that are provided by way of illustration, and are not intended to be limiting of the present disclosure, unless specified.

EXAMPLES

Example 1

Breeding of Homozygous cyp82e4 W329Stop, the cyp82e5v2 W422Stop, and cyp82e10 P381S Mutant Plants into the TN90 Burley Tobacco Cultivar TN90 SRC is a backcross-derived version of burley tobacco cultivar TN90 carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry*, 71 (2010), 1988-1998). The introduced mutations in CYP82E4 cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nomicotine (Id.). When in homozygous condition, the three mutations result in tobacco plants with (1) reduced genetic capacity to demethylate nicotine to form nomicotine, and (2) a corresponding diminished potential to accumulate N-nitrosonomicotine (NNN), a potent carcinogen found in many tobacco products. The mutation in CYP82E4 (cyp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nomicotine accumulation in burley tobacco: appendix A—the LC protocol. *Rec. Adv. Tob. Sci.* 33: 58-79).

The original tobacco cultivar TN90 is a fertile inbred line. CMS TN90 is a cytoplasmic male-sterile version of TN90. To develop TN90 SRC, an individual plant of TN90 is pollinated with a plant of the genetic background DH98-325-6 carrying mutations in each of the three nicotine demethylase genes. $F_1$ individuals originating from this cross and heterozygous for each mutation are backcrossed to the recurrent parent, TN90, to produce $BC_1F_1$ progeny. $BC_1F_1$ progeny are screened using genotyping methodologies to identify individuals heterozygous for all three mutations. A single triple heterozygous $BC_1F_1$ plant is backcrossed to TN90 to produce $BC_2F_1$ progeny. The process of backcrossing and identification of individuals heterozygous for all three mutations is repeated through the $BC_3F_1$, BC$_4$F$_1$, BC$_5$F$_1$, BC$_6$F$_1$, and BC$_7$F$_1$ stages. At the BC$_7$F$_1$ stage, individuals heterozygous for all three mutations from each pedigree are self-pollinated to produce BC$_7$F$_2$ seed. A large number of BC$_7$F$_2$ progeny from each pedigree are genotyped to identify individuals homozygous for all three mutations. A single BC$_7$F$_2$ plant homozygous for all three mutations is self-pollinated to produce a BC$_7$F$_3$ family (TN90 SRC) in which the wild-type CYP82E4, CYP82E5v2, and CYP82E10 alleles of TN90 were replaced by the mutant alleles (cyp82e4 W329Stop, cyp82e5v2 W422Stop, and cyp82e10 P381S).

The male-sterile (CMS) version of TN90 SRC (CMS TN90 SRC) is produced by crossing a plant of CMS TN90 as a female with pollen of TN90 SRC to produce male-sterile plants heterozygous for all three mutations. A single male-sterile plant resulting from this cross is then subsequently backcrossed as a female to TN90 SRC to produce progeny that are segregating for individuals homozygous for all three mutations. Triple homozygous individuals are identified by DNA genotyping to produce the CMS TN90 SRC line. Because the line is male-sterile, it is maintained via pollination with TN90 SRC.

Commercial TN90 SRC is produced by pollinating plants of CMS TN90 SRC with pollen of TN90 SRC.

Testing of TN90 SRC

TN90 SRC is evaluated for cured leaf chemistry, yield, and physical quality at three North Carolina field research locations during 2012 (Laurel Springs, Reidsville, Waynesville). TN90 is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nomicotine, anatabine, anabasine, and percent nicotine conversion using gas chromatography equipment.

Comparisons using the least significant difference (LSD) test indicates that TN90 SRC has significantly (P<0.05) lower levels of nomicotine and percent nicotine conversion relative to TN90 (Table 1). TN90 and TN90 SRC are not significantly different from each other for percent nicotine, yield, or cured leaf quality indices.

TN90 SRC is further evaluated for percent nicotine conversion in a field at Blackstone, Va. during 2013. A commercial TN90 LC variety is included for comparison. Leaves are sampled at the layby stage and ethephon-treated prior to analysis for nicotine and nomicotine levels using gas chromatography equipment. Random sampling of 26 plants indicates that TN90 LC has an average percent nicotine conversion of 2.61%, whereas TN90 SRC has an average percent nicotine conversion of 0.47% (FIG. 1). The low percent nicotine conversion in TN90 SRC is also more stable compared to TN90 LC.

Analysis of NNN Levels in TN90 SRC Tobacco Filler and Cigarette Smoke

Figure 2:
FIG. 2: Tobacco plants grown in the field treated with different amounts of nitrogen fertilizers.

TN90 SRC is also evaluated for NNN levels in both tobacco filler and cigarette smoke at two Virginia field research locations during 2013 (Glade Spring and Blackstone). A commercial TN90 LC variety is included for comparison. Various levels of nitrogen fertilizer (0, 224, and 448 kg/ha) are tested to evaluate the impact of nitrate levels on NNN levels in tobacco filler and smoke (FIG. 2).

Figure 3:
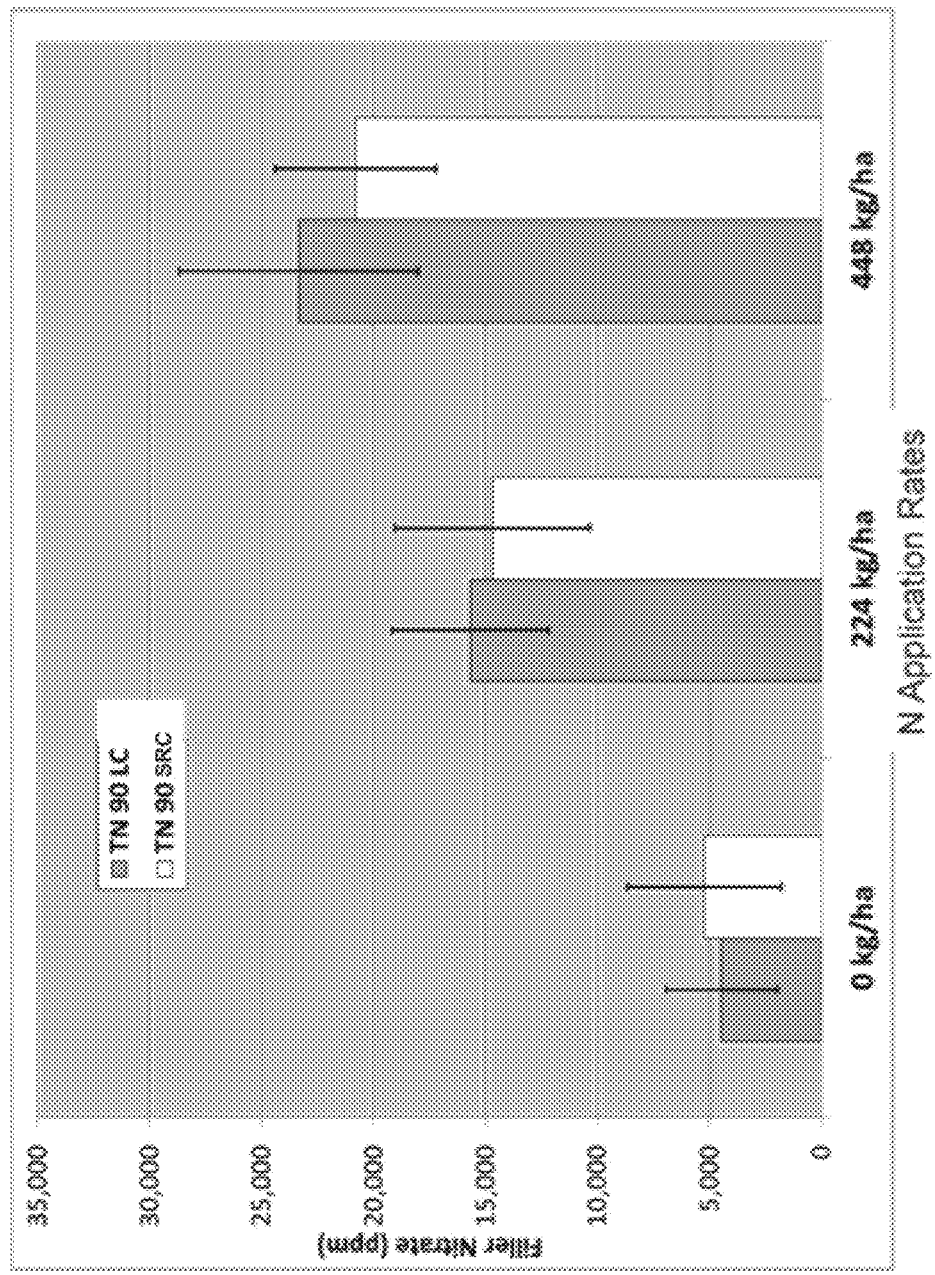
FIG. 3: Comparable nitrate levels in tobacco filler from TN90 LC and TN90 SRC grown under a same nitrogen fertilizer level. No statistical difference is observed for nitrate concentrations between TN90 SRC and TN90 LC tobacco filler grown under a same nitrogen fertilizer level.
Figure 4:
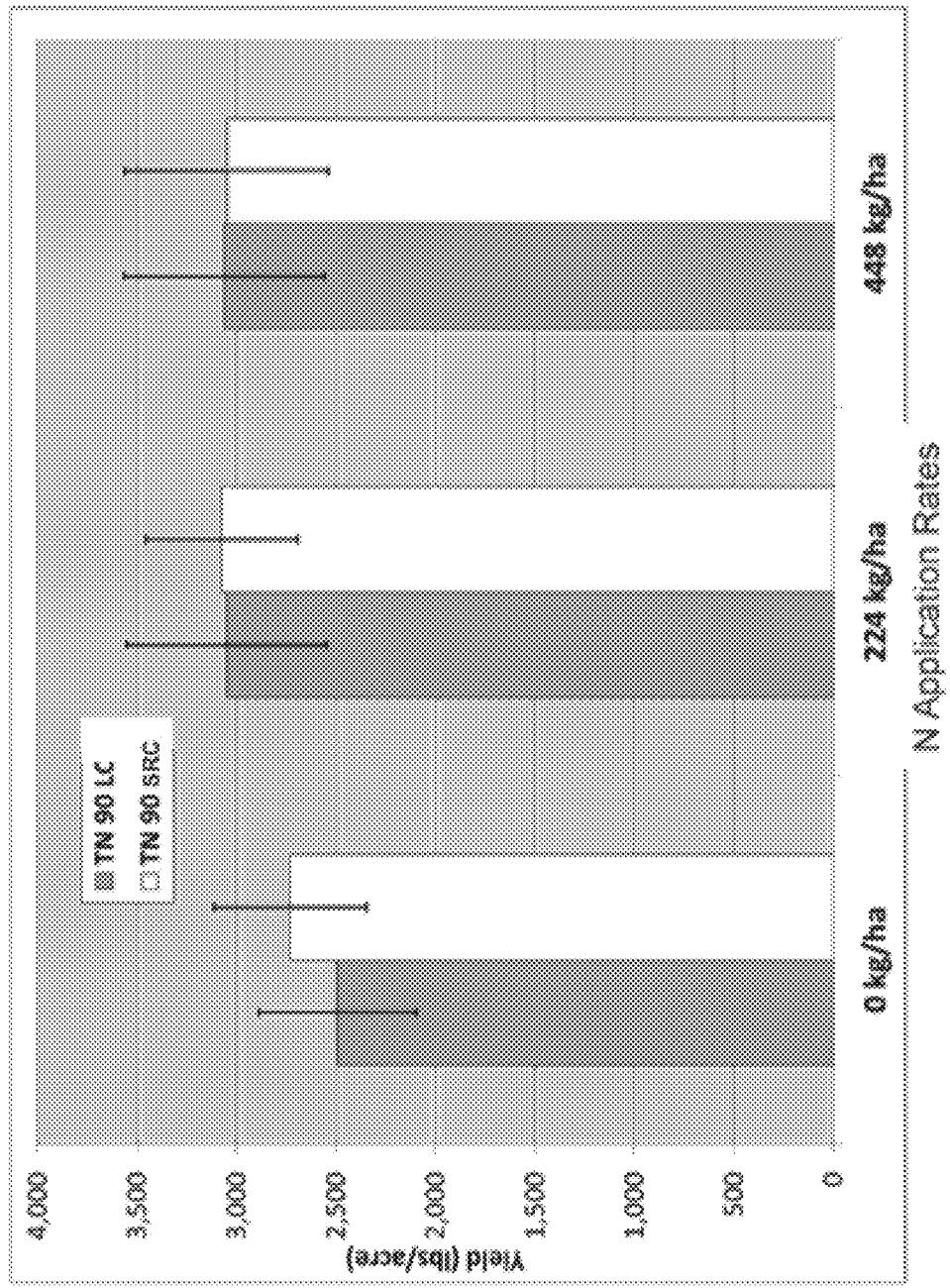
FIG. 4: Comparable tobacco yields from TN90 LC and TN90 SRC grown under a same nitrogen fertilizer level. No statistical difference is observed for tobacco yields between TN90 SRC and TN90 LC tobacco filler grown under a same nitrogen fertilizer level.
Figure 5:
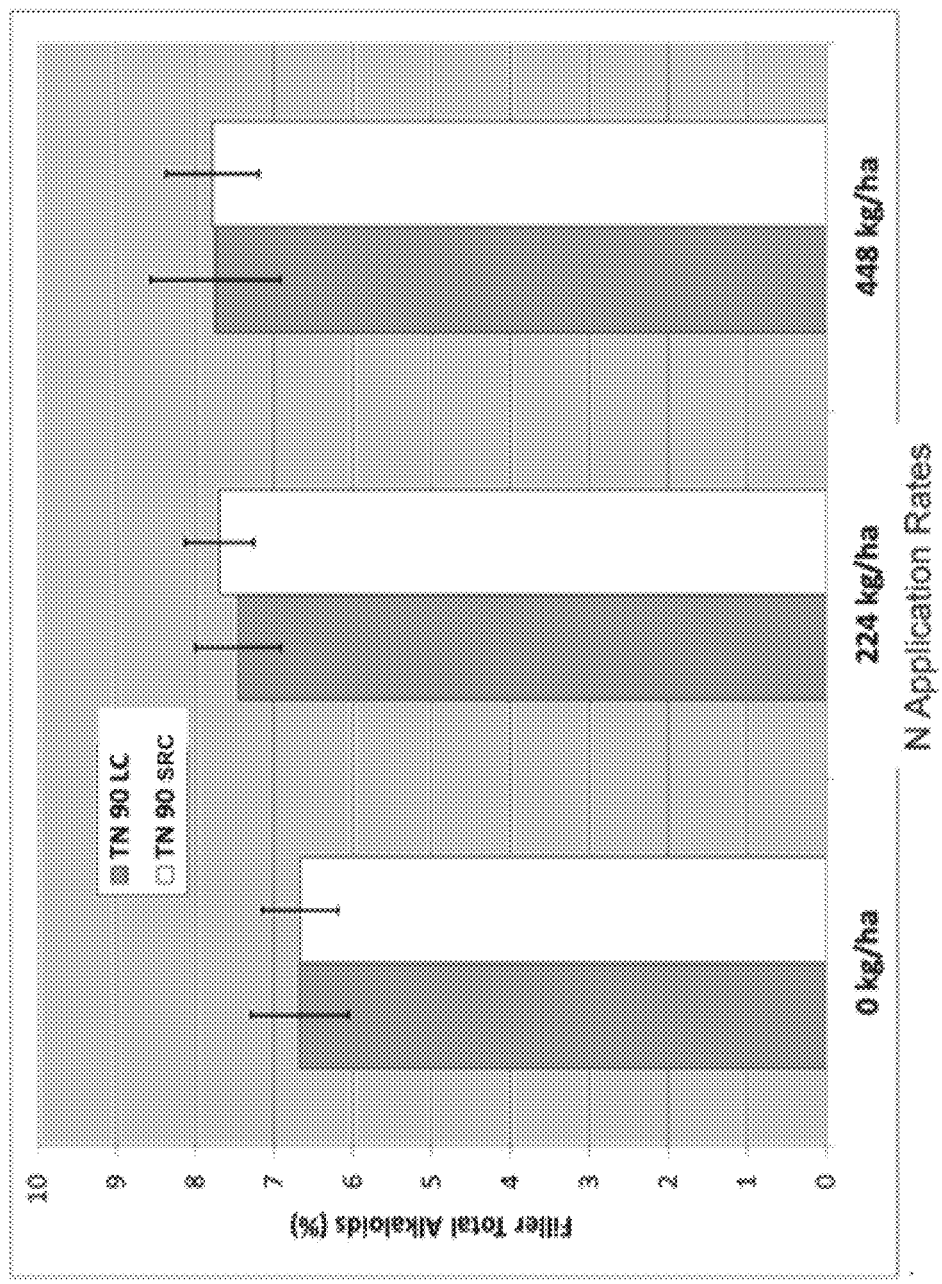
FIG. 5: Comparable levels of total alkaloids from TN90 LC and TN90 SRC grown under a same nitrogen fertilizer level. No statistical difference is observed for total alkaloids levels between TN90 SRC and TN90 LC tobacco filler grown under a same nitrogen fertilizer level.

Both TN90 SRC and TN90 LC contains increasing levels of nitrate in tobacco filler as the level of nitrogen fertilizer increases from 0, to 224, and to 448 kg/ha. No statistical difference is observed for nitrate concentrations between TN90 SRC and TN90 LC tobacco filler grown under a same nitrogen fertilizer level (FIG. 3). Further, no statistical difference is observed for tobacco yields between TN90 SRC and TN90 LC grown under a same nitrogen fertilizer level (FIG. 4). Neither is a statistical difference observed for the total level of alkaloids between TN90 SRC and TN90 LC tobacco filler grown under a same nitrogen fertilizer level (FIG. 5).

Figure 6:
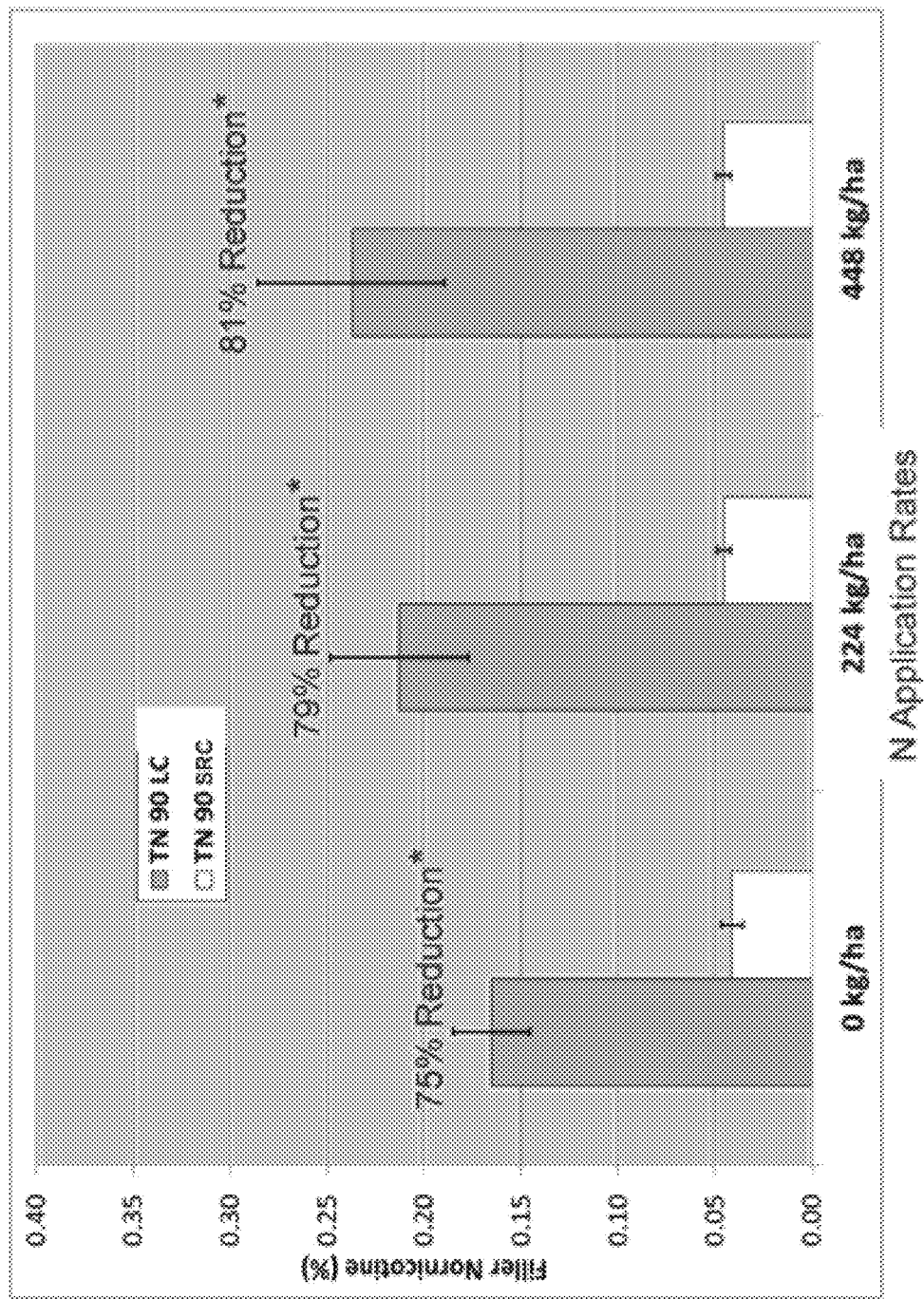
FIG. 6: TN90 SRC contains a significantly reduced level of nomicotine in tobacco filler compared to TN90 LC when grown under a same nitrogen fertilizer level. Asterisks (*) indicate significant differences for filler nomicotine based on Tukey-Kramer HSD ($P<0.05$).

TN90 SRC contains a significantly reduced level of nornicotine in tobacco filler compared to TN90 LC when grown under a same nitrogen fertilizer level (FIG. 6). Specifically, a 75% reduction of nomicotine is observed in TN90 SRC filler compared to TN90 LC filler when both are grown with 0 kg/ha nitrogen fertilizer. Reductions of 79% and 81% are observed for nomicotine levels in TN90 SRC filler compared to TN90 LC filler when both are grown with 224 and 448 kg/ha nitrogen fertilizers, respectively. Notably, the level of nomicotine increases in TN90 LC filler as the level of nitrogen fertilizer increases. However, TN90 SRC filler contains a relatively constant level of nomicotine across different levels of nitrogen fertilizer treatments (FIG. 6).

Figure 7:
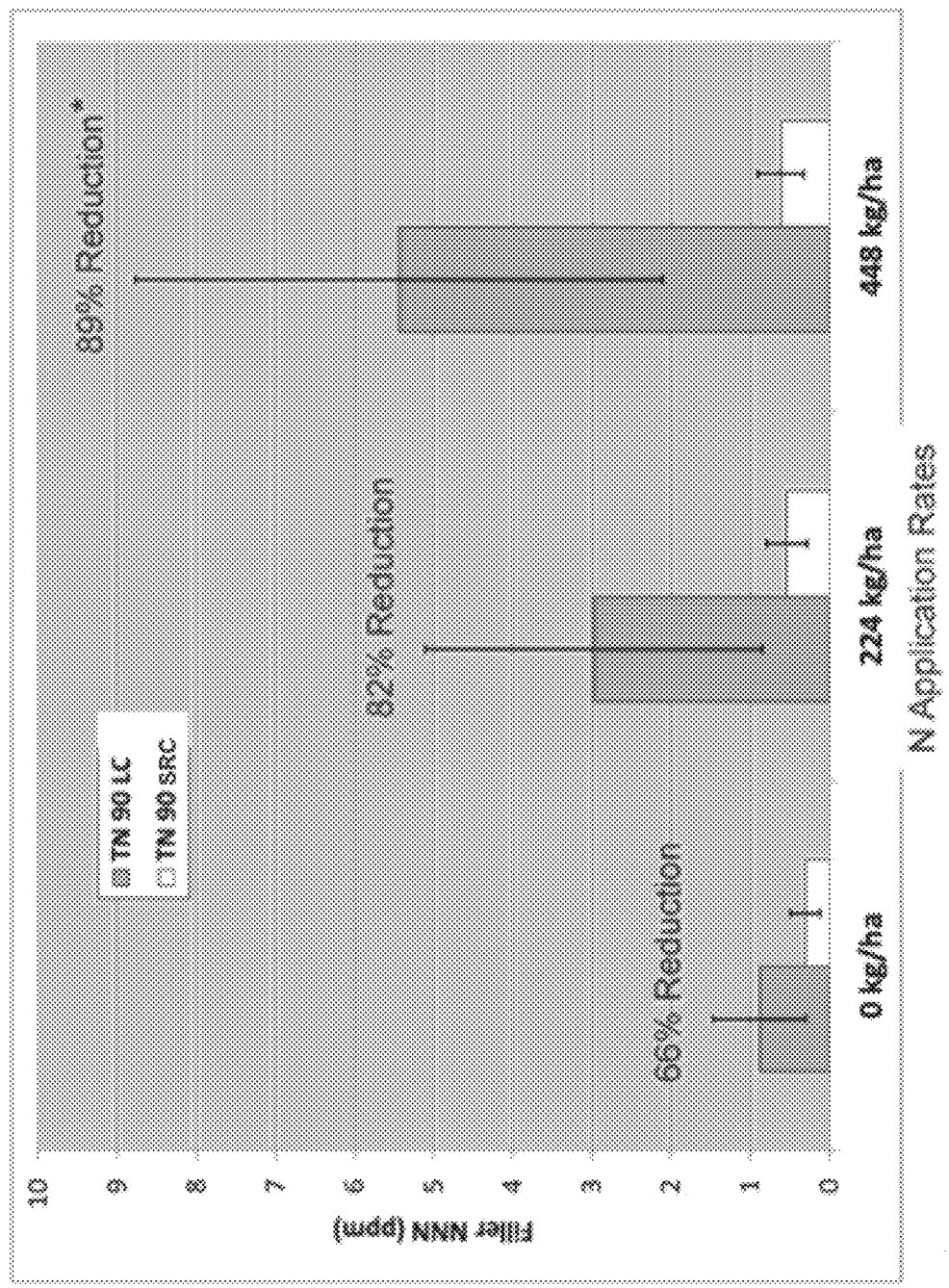
FIG. 7: TN90 SRC contains a significantly reduced level of NNN in tobacco filler compared to TN90 LC when grown under a high nitrogen fertilizer level (448 kg/ha). The asterisk (*) indicates a significant difference for NNN levels in tobacco filler based on Tukey-Kramer HSD ($P<0.05$).

TN90 SRC also contains a significantly reduced level of NNN in tobacco filler compared to TN90 LC when grown under a same nitrogen fertilizer level (FIG. 7). Specifically, a 66% reduction of NNN is observed in TN90 SRC filler compared to TN90 LC filler when both are grown with 0 kg/ha nitrogen fertilizer. Reductions of 82% and 89% are observed for NNN levels in TN90 SRC filler compared to TN90 LC filler when both are grown with 224 and 448 kg/ha nitrogen fertilizers, respectively.

Figure 8:
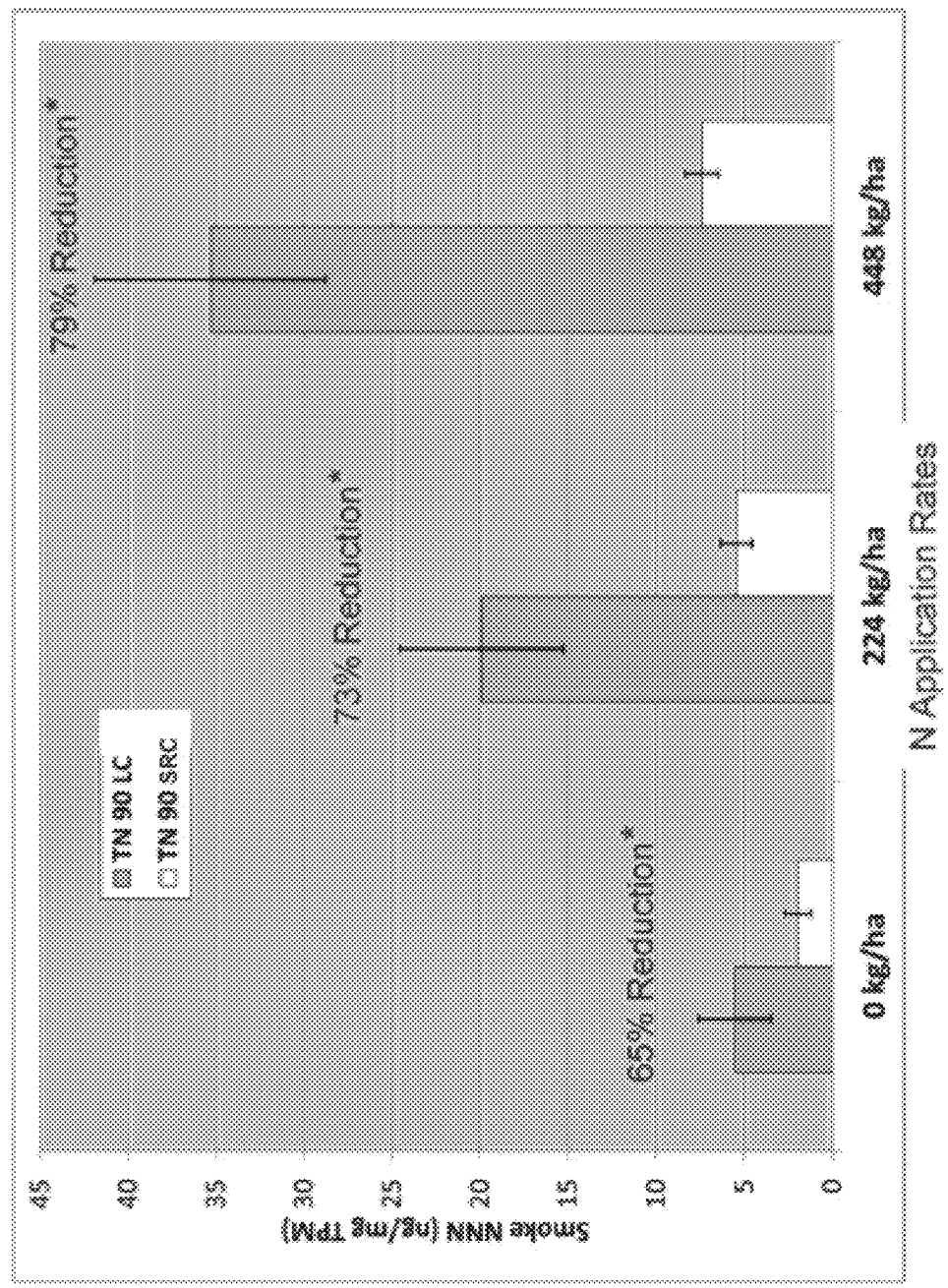
FIG. 8: Comparisons of NNN levels in cigarette smoke from cigarettes comprising 100% TN90 SRC or 100% TN90 LC. TN90 SRC cigarette smoke contains a significantly reduced level of NNN compared to TN90 LC cigarette smoke when both varieties are grown under a same nitrogen fertilizer level. Asterisks (*) indicate significant differences for NNN levels in tobacco filler based on Tukey-Kramer HSD ($P<0.05$).

The level of NNN is further tested in cigarette smoke from cigarettes comprising 100% TN90 SRC or 100% TN90 LC. TN90 SRC cigarette smoke contains a significantly reduced level of NNN compared to TN90 LC cigarette smoke when both varieties are grown under a same nitrogen fertilizer level (FIG. 8). Specifically, a 65% reduction of NNN is observed in TN90 SRC cigarette smoke compared to TN90 LC cigarette smoke when both are grown with 0 kg/ha nitrogen fertilizer. Reductions of 73% and 79% are observed for NNN levels in TN90 SRC cigarette smoke compared to TN90 LC cigarette smoke when both are grown with 224 and 448 kg/ha nitrogen fertilizers, respectively.

Analysis of Smoke NNN Levels in Blended Cigarettes Comprising TN90 SRC

NNN levels are further evaluated in cigarette smoke from blended cigarettes made with an Extramural Blend comprising varying amounts of TN90 SRC as the Burley component. An Extramural Blend comprise a blend formulation of about 23% Burley tobacco, 35% Bright tobacco (also known as flue-cured tobacco), 15% Oriental tobacco, and 27% reconstitute leaves (RL). Experimental blends with increasing percentages of TN90 SRC (33% Experimental comprising 8% TN90 SRC and 15% TN90 LC, 67% Experimental comprising 15% TN90 SRC and 8% TN90 LC, and 100% Experimental comprising 23% TN90 SRC) are compared to a control blend comprising 23% TN90 LC and no TN90 SRC (FIG. 9A). Both the International Organization of Standardization (ISO) smoking method (35 cm$^3$ puff volume, 2 second duration, 60 second frequency, 0% vent blocking, see Routine analytical cigarette-smoking machine—Definitions and standard conditions (ISO 3308: 2012) and the Health Canada Intense (HCI) smoking method (55 cm$^3$ puff volume, 2 second duration, 30 second frequency, 100% vent blocking; see Health Canada Test Method T-115. Determination of Tar, Water, Nicotine and Carbon Monoxide in Mainstream Tobacco Smoke, 1999 Dec. 31) are used to assess smoke NNN levels.

Figure 9B:
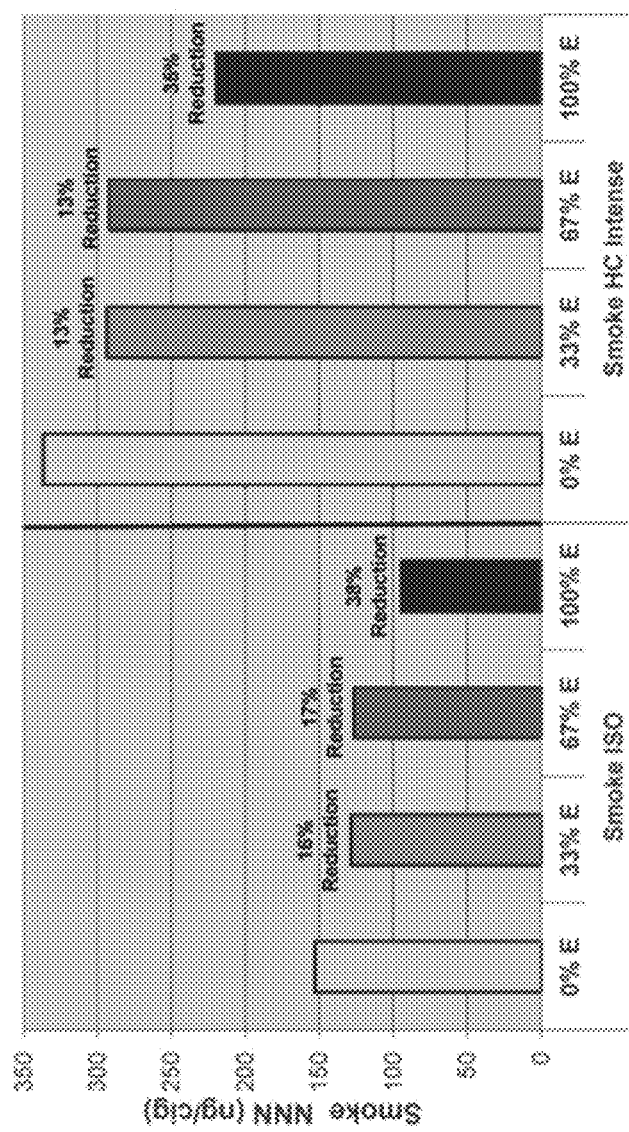

The inclusion of TN90 SRC filler in an Extramural Blend (even when TN90 SRC only constitutes 33% or 67% of the total Burly component of the blend, e.g., 33% Experimental or 67% Experimental) reduces the level of smoke NNN measured by either the ISO smoking method or the HCI smoking method. Specifically, blended cigarettes with an Extramural Blend comprising TN90 SRC filler as 100% of the Burley component (100% Experimental; TN90 SRC=23% of overall blend) show a reduction of 38% (ISO method) and 35% (HCI method) in smoke NNN compared to a control blend comprising TN90 LC filler as 100% of the Burley component (0% Experimental; TN90 LC=23% of overall blend) (FIG. 9B).

(cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Lewis et al. 2010). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cyp82e4 W329Stop (SEQ ID NO: 1)) also provides phenotypic stability for the "nico-

TABLE 1

Means for experiment EX13-132 entries evaluated in three 2012 NC environments.

| Genotype | Yield (lbs/A) | Grade Index | Nic (%) | Nor (%) | Anab (%) | Anat (%) | % Total Alkaloids | % Conversion |
|---|---|---|---|---|---|---|---|---|
| TN86 LC | 2780 | 74.0 | 3.067 | 0.127 | 0.023 | 0.283 | 3.500 | 4.108 |
| TN86 SRC | 2870 | 73.2 | 3.023 | 0.011 | 0.021 | 0.282 | 3.337 | 0.391 |
| TN90 LC | 2773 | 70.5 | 3.572 | 0.108 | 0.025 | 0.307 | 4.011 | 3.066 |
| TN90 SRC | 2852 | 75.5 | 3.864 | 0.017 | 0.025 | 0.304 | 4.209 | 0.448 |
| VA509 | 2685 | 74.1 | 3.498 | 0.207 | 0.024 | 0.272 | 4.001 | 5.509 |
| KY 14 LC | 3029 | 72.9 | 2.940 | 0.055 | 0.021 | 0.249 | 3.265 | 1.941 |
| LSD 0.05 (GXE) | 269 | 4.4 | 0.432 | 0.037 | 0.003 | 0.045 | 0.458 | 0.930 |
| CV % (GXE) | 12 | 7.3 | 15.023 | 157.440 | 14.275 | 18.991 | 14.544 | 134.014 |

Nic = nicotine;
nor = nornicotine;
anab = anabasine;
anat = anatabine

TABLE 2

Means for experiment EX13-131 entries evaluated in three 2012 NC environments.

| Genotype | Yield (lbs/A) | Grade Index | NIC (%) | Nor (%) | Anab (%) | Anat (%) | % Total Alkaloids | % Conversion |
|---|---|---|---|---|---|---|---|---|
| NC 638 | 2767 | 77.0 | 3.438 | 0.049 | 0.020 | 0.191 | 3.697 | 1.489 |
| NC 638 SRC | 2679 | 78.6 | 3.968 | 0.012 | 0.020 | 0.204 | 4.204 | 0.373 |
| NC645 | 2829 | 81.9 | 3.546 | 0.124 | 0.022 | 0.268 | 3.959 | 3.293 |
| NC645 SRC | 2773 | 78.3 | 3.950 | 0.017 | 0.023 | 0.273 | 4.263 | 0.492 |
| NC775 | 2849 | 77.5 | 3.086 | 0.204 | 0.022 | 0.277 | 3.589 | 6.101 |
| NC775 SRC | 2847 | 76.6 | 3.426 | 0.014 | 0.019 | 0.223 | 3.682 | 0.476 |
| NC 7 LC | 2999 | 76.2 | 3.164 | 0.121 | 0.020 | 0.261 | 3.567 | 3.705 |
| NC 7 SRC | 3023 | 79.2 | 3.597 | 0.014 | 0.021 | 0.257 | 3.890 | 0.453 |
| KY14 x L8 LC | 2877 | 79.4 | 3.548 | 0.138 | 0.025 | 0.291 | 4.003 | 3.408 |
| KY14 x L8 SRC | 3087 | 77.9 | 3.891 | 0.013 | 0.022 | 0.239 | 4.165 | 0.381 |
| NCBH 129 LC | 3098 | 77.0 | 3.285 | 0.079 | 0.021 | 0.234 | 3.619 | 2.281 |
| NCBH 129 SRC | 3230 | 79.8 | 3.811 | 0.013 | 0.022 | 0.237 | 4.083 | 0.404 |
| KY 14 LC | 3112 | 76.5 | 3.030 | 0.059 | 0.021 | 0.253 | 3.363 | 1.935 |
| CMS KY 14 SRC | 3129 | 79.6 | 3.842 | 0.013 | 0.025 | 0.249 | 4.128 | 0.410 |
| VA509 | 2903 | 78.7 | 3.393 | 0.240 | 0.023 | 0.268 | 3.923 | 6.543 |
| LSD 0.05 (GXE) | 313 | 3.0 | 0.438 | 0.066 | 0.003 | 0.050 | 0.479 | 1.262 |
| CV % (GXE) | 13 | 4.6 | 14.606 | 156.671 | 18.726 | 24.900 | 14.696 | 105.809 |

Example 2

Breeding of Homozygous cyp82e4 W329Stop, the cyp82e5v2 W422Stop, and cyp82e10 P381S Mutant Plants into the KY14 Burley Tobacco Cultivar KY14 SRC is a backcross-derived version of burley tobacco cultivar KY14 carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., 2010). The introduced mutations in CYP82E4 tine conversion" trait and eliminates the requirement to utilize the cumbersome "LC" method for reducing levels of nornicotine in tobacco cultivars.

The original tobacco cultivar KY14 is a fertile inbred line. CMS KY14 is a cytoplasmic male-sterile version of KY14. To develop KY14 SRC, an individual plant of KY14 is pollinated with a plant of the genetic background DH98-325-6 carrying mutations in each of the three nicotine demethylase genes. $F_1$ individuals originating from this cross and heterozygous for each mutation are backcrossed to the recurrent parent, KY14, to produce $BC_1F_1$ progeny. $BC_1F_1$ progeny are screened using genotyping methodologies to identify individuals heterozygous for all three mutations. A single triple heterozygous $BC_1F_1$ plant is backcrossed to KY14 to produce $BC_2F_1$ progeny. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. A single $BC_7F_2$ plant homozygous for all three mutations is self-pollinated to produce a $BC_7F_3$ family (KY14 SRC) in which the wild-type CYP82E4, CYP82E5v2, and CYP82E10 alleles of KY14 were replaced by the mutant alleles (cyp82e4 W329Stop, cyp82e5v2 W422Stop, and cyp82e10 P381S).

The male-sterile (CMS) version of KY14 SRC (CMS KY14 SRC) is produced by crossing a plant of CMS KY14 as a female with pollen of KY14 SRC to produce male-sterile plants heterozygous for all three mutations. A single male-sterile plant resulting from this cross is then subsequently backcrossed as a female to KY14 SRC to produce progeny that are segregating for individuals homozygous for all three mutations. Triple homozygous individuals are identified by DNA genotyping to produce the CMS KY14 SRC line. Because the line is male-sterile, it is maintained via pollination with KY14 SRC.

Commercial KY14 SRC is produced by pollinating plants of CMS KY14 SRC with pollen of KY14 SRC.

Testing of KY14 SRC

KY14 SRC is evaluated for cured leaf chemistry, yield, and physical quality at three North Carolina field research locations during 2012 (Laurel Springs, Reidsville, Waynesville). KY14 is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicates that KY14 SRC has significantly (P<0.05) lower levels of nornicotine and percent nicotine conversion relative to KY14 (Table 2). KY14 and KY14 SRC are not significantly different from each other for percent nicotine, yield, or cured leaf quality indices.

Example 3

Breeding of Homozygous cyp82e4 W329Stop, the cyp82e5v2 W422Stop, and cyp82e10 P381S Mutant Plants into the L8 Burley Tobacco Cultivar L8 SRC is a backcross-derived version of burley tobacco cultivar L8 carrying introduced null mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry*, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cyp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

The original tobacco cultivar L8 is a fertile inbred line. To develop L8 SRC, an individual plant of L8 is initially pollinated with a plant of the genetic background DH98-325-6 carrying mutations in each of the three nicotine demethylase genes. $F_1$ individuals originating from this cross and heterozygous for each mutation are backcrossed to the recurrent parent, L8, to produce $BC_1F_1$ progeny. $BC_1F_1$ progeny are screened using genotyping methodologies to identify individuals heterozygous for all three mutations. A single triple heterozygous $BC_1F_1$ plant is backcrossed to L8 to produce $BC_2F_1$ progeny. The process of backcrossing and identification of individuals heterozygous for all three mutations is repeated through the $BC_3F_1$, $BC_4F_1$, $BC_5F_1$, $BC_6F_1$ and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. A single $BC_7F_2$ plant homozygous for all three mutations is self-pollinated to produce a $BC_7F_3$ family (L8 SRC) in which the wild-type CYP82E4, CYP82E5v2, and CYP82E10 alleles of L8 were replaced by the mutant alleles (cyp82e4 W329Stop, cyp82e5v2 W422Stop, and cyp82e10 P381S).

Testing of L8 SRC

L8 SRC is evaluated for cured leaf chemistry, yield, and physical quality at three North Carolina field research locations during 2012 (Laurel Springs, Reidsville, Waynesville). L8 is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicated that L8 SRC has significantly (P<0.05) lower levels of nornicotine and percent nicotine conversion relative to L8 (Table 2). L8 and L8 SRC are not significantly different from each other for percent nicotine, yield, or cured leaf quality indices.

Example 4

Breeding of Homozygous cyp82e4 W329Stop, the cyp82e5v2 W422Stop, and cyp82e10 P381S Mutant Plants into the KY14×L8 Burley Tobacco Cultivar The original tobacco cultivar KY14×L8 LC is a hybrid generated by pollinating plants of a male-sterile breeding line CMS KY14 with pollen produced by fertile breeding line L8. Hybrid cultivar KY14×L8 SRC is a hybrid generated by pollinating plants of a male-sterile breeding line CMS KY14 SRC with pollen produced by fertile breeding line L8 SRC with each breeding line carrying introduced deleterious mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., Phytochemistry, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cyp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nornicotine accumulation in burley tobacco: appendix A—the LC protocol. Rec. Adv. Tob. Sci. 33: 58-79).

The original tobacco cultivar KY14×L8 LC is a hybrid generated by pollinating plants of a male-sterile breeding line CMS KY14 with pollen produced by fertile breeding line L8. To develop hybrid cultivar KY14×L8 SRC, individual plants of fertile KY14 are first pollinated with a plant of the genetic background DH98-325-6 carrying mutations in each of the three nicotine demethylase genes. $F_1$ individuals originating from each cross and heterozygous for each mutation are backcrossed to the recurrent parent (KY14) to produce $BC_1F_1$ progenies.

$BC_1F_1$ progenies are screened using genotyping methodologies to identify individuals heterozygous for all three mutations. A single $BC_1F_1$ plant from each pedigree is backcrossed to KY14, to produce $BC_2F_1$ progenies. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. $BC_7F_2$ plants homozygous for all three mutations are self-pollinated to produce $BC_7F_3$ families (KY14 SRC) in which the wild-type CYP82E4, CYP82E5v2, and CYP82E10 alleles of KY14 are replaced by the mutant alleles (cyp82e4 W329Stop, cyp82e5v2 W422Stop, and cyp82e10 P381S).

The female parental line of KY14, CMS KY14, is cytoplasmic male sterile which causes pollen to not be produced. To develop CMS KY14 SRC, a plant of CMS KY14 is crossed with KY14 SRC to produce male-sterile plants heterozygous for all three mutations. A single male-sterile plant resulting from this cross is backcrossed as a female to KY14 SRC to produce progeny that are segregating for individuals homozygous for all three mutations. Triple homozygous individuals are identified by DNA genotyping to produce the CMS KY14 SRC line. Because the line is male-sterile, it is maintained via pollination with KY14 SRC (see above).

Hybrid cultivar KY14×L8 SRC is produced by pollinating plants of CMS KY14 SRC with pollen of L8 SRC.

Testing of Hybrid Cultivar KY14×L8 SRC

Hybrid cultivar KY14×L8 SRC is evaluated for cured leaf chemistry, yield, and physical quality at three North Carolina field research locations during 2012 (Laurel Springs, Reidsville, Waynesville). Hybrid cultivar KY14×L8 LC is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicates that hybrid cultivar KY14×L8 SRC has significantly (P<0.05) lower levels of nornicotine and percent nicotine conversion relative to KY14×L8 LC (Table 2). KY14×L8 LC and hybrid cultivar KY14×L8 SRC are not significantly different from each other for percent nicotine, yield, or cured leaf quality indices.

Example 5

Breeding of Homozygous cyp82e4 W329Stop, the cyp82e5v2 W422Stop, and cyp82e10 P381S Mutant Plants into the NC775 Burley Tobacco Cultivar NC775 SRC is a backcross-derived version of burley tobacco cultivar NC775 carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., Phytochemistry, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nornicotine accumulation in burley tobacco: appendix A—the LC protocol. Rec. Adv. Tob. Sci. 33: 58-79).

The original tobacco cultivar NC775 is a fertile inbred line. CMS NC775 is a cytoplasmic male-sterile version of NC775. To develop NC775 SRC, an individual plant of NC775 is pollinated with a plant of the genetic background DH98-325-6 carrying mutations in each of the three nicotine demethylase genes. $F_1$ individuals originating from this cross and heterozygous for each mutation are backcrossed to the recurrent parent, NC775, to produce $BC_1F_1$ progeny. $BC_1F_1$ progeny are screened using genotyping methodologies to identify individuals heterozygous for all three mutations. A single triple heterozygous $BC_1F_1$ plant is backcrossed to NC775 to produce $BC_2F_1$ progeny. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. A single $BC_7F_2$ plant homozygous for all three mutations is self-pollinated to produce a $BC_7F_3$ family (NC775 SRC) in which the wild-type CYP82E4, CYP82E5v2, and CYP82E10 alleles of NC775 were replaced by the mutant alleles (cyp82e4 W329Stop, cyp82e5v2 W422Stop, and cyp82e10 P381S).

The male-sterile (CMS) version of NC775 SRC (CMS NC775 SRC) is produced by crossing a plant of CMS NC775 as a female with pollen of NC775 SRC to produce male-sterile plants heterozygous for all three mutations. A single male-sterile plant resulting from this cross is then subsequently backcrossed as a female to NC775 SRC to produce progeny that are segregating for individuals homozygous for all three mutations. Triple homozygous individuals are identified by DNA genotyping to produce the CMS NC775 SRC line. Because the line is male-sterile, it is maintained via pollination with NC775 SRC.

Commercial NC775 SRC is produced by pollinating plants of CMS NC775 SRC with pollen of NC775 SRC (see below).

Testing of NC775 SRC

NC775 SRC is evaluated for cured leaf chemistry, yield, and physical quality at three North Carolina field research locations during 2012 (Laurel Springs, Reidsville, Waynesville). NC775 is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicates that NC775 SRC has significantly ($P<0.05$) lower levels of nornicotine and percent nicotine conversion relative to NC775 (Table 2). NC775 and NC775 SRC are not significantly different from each other for percent nicotine, yield, or cured leaf quality indices.

Example 6

Breeding of Homozygous cyp82e4 W329Stop, the cyp82e5v2 W422Stop, and cyp82e10 P381S Mutant Plants into the NC645 Burley Tobacco Cultivar NC645 SRC is a backcross-derived version of burley tobacco cultivar NC645 carrying introduced null mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry*, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381 S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cyp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

The original tobacco cultivar NC645 is a fertile inbred line. To develop NC645 SRC, an individual plant of NC645 is initially pollinated with a plant of the genetic background DH98-325-6 carrying mutations in each of the three nicotine demethylase genes. $F_1$ individuals originating from this cross and heterozygous for each mutation are backcrossed to the recurrent parent, NC645, to produce $BC_1F_1$ progeny. $BC_1F_1$ progeny are screened using genotyping methodologies to identify individuals heterozygous for all three mutations. A single triple heterozygous $BC_1F_1$ plant is backcrossed to NC645 to produce $BC_2F_1$ progeny. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. A single $BC_7F_2$ plant homozygous for all three mutations is self-pollinated to produce a $BC_7F_3$ family (NC645 SRC) in which the wild-type CYP82E4, CYP82E5v2, and CYP82E10 alleles of NC645 were replaced by the mutant alleles (cyp82e4 W329Stop, cyp82e5v2 W422Stop, and cyp82e10 P381S).

Testing of NC645 SRC

NC645 SRC is evaluated for cured leaf chemistry, yield, and physical quality at three North Carolina field research locations during 2012 (Laurel Springs, Reidsville, Waynesville). NC645 is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicated that NC645 SRC has significantly ($P<0.05$) lower levels of nornicotine and percent nicotine conversion relative to NC645 (Table 2). NC645 and NC645 SRC are not significantly different from each other for percent nicotine, yield, or cured leaf quality indices.

Example 7

Breeding of Homozygous cyp82e4 W329Stop, the cyp82e5v2 W422Stop, and cyp82e10 P381S Mutant Plants into the NC7 Hybrid Burley Tobacco Cultivar The original tobacco cultivar NC7 is a hybrid generated by pollinating plants of a male-sterile breeding line CMS NC775 with pollen produced by fertile breeding line NC645. Hybrid cultivar NC7 SRC is a hybrid generated by pollinating plants of a male-sterile breeding line CMS NC775 SRC with pollen produced by fertile breeding line NC645 SRC with each breeding line carrying introduced deleterious mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry*, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cyp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

The original tobacco cultivar NC7 is a hybrid generated by pollinating plants of a male-sterile breeding line CMS NC775 with pollen produced by fertile breeding line NC645. To develop hybrid cultivar NC7 SRC, individual plants of fertile NC775 are first pollinated with a plant of the genetic background DH98-325-6 carrying mutations in each of the three nicotine demethylase genes. $F_1$ individuals originating from each cross and heterozygous for each mutation are backcrossed to the recurrent parent (NC775) to produce $BC_1F_1$ progenies.

$BC_1F_1$ progenies are screened using genotyping methodologies to identify individuals heterozygous for all three mutations. A single $BC_1F_1$ plant from each pedigree is backcrossed to NC775, to produce $BC_2F_1$ progenies. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. $BC_7F_2$ plants homozygous for all three mutations are self-pollinated to produce $BC_7F_3$ families (NC775 SRC) in which the wild-type CYP82E4, CYP82E5v2, and CYP82E10 alleles of NC775 are replaced by the mutant alleles (cyp82e4 W329Stop, cyp82e5v2 W422Stop, and cyp82e10 P381 S).

The female parental line of NC7, CMS NC775, is cytoplasmic male sterile which causes pollen to not be produced. To develop CMS NC775 SRC, a plant of CMS NC775 is crossed with NC775 SRC to produce male-sterile plants heterozygous for all three mutations. A single male-sterile plant resulting from this cross is backcrossed as a female to NC775 SRC to produce progeny that are segregating for individuals homozygous for all three mutations. Triple homozygous individuals are identified by DNA genotyping to produce the CMS NC775 SRC line. Because the line is male-sterile, it is maintained via pollination with NC775 SRC (see above).

Hybrid cultivar NC7 SRC is produced by pollinating plants of CMS NC775 SRC with pollen of NC645 SRC.

Testing of Hybrid Cultivar NC7 SRC

Hybrid cultivar NC7 SRC is evaluated for cured leaf chemistry, yield, and physical quality at three North Carolina field research locations during 2012 (Laurel Springs, Reidsville, Waynesville). Hybrid cultivar NC7 LC is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicates that hybrid cultivar NC7 SRC has significantly ($P<0.05$) lower levels of nornicotine and percent nicotine conversion relative to NC7 LC (Table 2). NC7 LC and hybrid cultivar NC7 SRC are not significantly different from each other for percent nicotine, yield, or cured leaf quality indices.

Example 8

Breeding of Homozygous cyp82e4 W329Stop, the cyp82e5v2 W422Stop, and cyp82e10 P381S Mutant Plants into the NC638 Burley Tobacco Cultivar NC638 SRC is a backcross-derived version of burley tobacco cultivar NC638 carrying introduced mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry*, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381 S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cyp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

The original tobacco cultivar NC638 is a fertile inbred line. CMS NC638 is a cytoplasmic male-sterile version of NC638. To develop NC638 SRC, an individual plant of NC638 is pollinated with a plant of the genetic background DH98-325-6 carrying mutations in each of the three nicotine demethylase genes. $F_1$ individuals originating from this cross and heterozygous for each mutation are backcrossed to the recurrent parent, NC638, to produce $BC_1F_1$ progeny. $BC_1F_1$ progeny are screened using genotyping methodologies to identify individuals heterozygous for all three mutations. A single triple heterozygous $BC_1F_1$ plant is backcrossed to NC638 to produce $BC_2F_1$ progeny. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. A single $BC_7F_2$ plant homozygous for all three mutations is self-pollinated to produce a $BC_7F_3$ family (NC638 SRC) in which the wild-type CYP82E4, CYP82E5v2, and CYP82E10 alleles of NC638 were replaced by the mutant alleles (cyp82e4 W329Stop, cyp82e5v2 W422Stop, and cyp82e10 P381S).

The male-sterile (CMS) version of NC638 SRC (CMS NC638 SRC) is produced by crossing a plant of CMS NC638 as a female with pollen of NC638 SRC to produce male-sterile plants heterozygous for all three mutations. A single male-sterile plant resulting from this cross is then subsequently backcrossed as a female to NC638 SRC to produce progeny that are segregating for individuals homozygous for all three mutations. Triple homozygous individuals are identified by DNA genotyping to produce the CMS NC638 SRC line. Because the line is male-sterile, it is maintained via pollination with NC638 SRC.

Commercial NC638 SRC is produced by pollinating plants of CMS NC638 SRC with pollen of TN86 SRC (see below).

Testing of NC638 SRC

NC638 SRC is evaluated for cured leaf chemistry, yield, and physical quality at three North Carolina field research locations during 2012 (Laurel Springs, Reidsville, Waynesville). NC638 is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicates that NC638 SRC has significantly ($P<0.05$) lower levels of nornicotine and percent nicotine conversion relative to NC638 (Table 2). NC638 and NC638 SRC are not significantly different from each other for percent nicotine, yield, or cured leaf quality indices.

Example 9

Breeding of Homozygous cyp82e4 W329Stop, the cyp82e5v2 W422Stop, and cyp82e10 P381S Mutant Plants into the TN86 Burley Tobacco Cultivar TN86 SRC is a backcross-derived version of burley tobacco cultivar TN86 carrying introduced null mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry,* 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381 S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cyp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

The original tobacco cultivar TN86 is a fertile inbred line. To develop TN86 SRC, an individual plant of TN86 is initially pollinated with a plant of the genetic background DH98-325-6 carrying mutations in each of the three nicotine demethylase genes. $F_1$ individuals originating from this cross and heterozygous for each mutation are backcrossed to the recurrent parent, TN86, to produce $BC_1F_1$ progeny. $BC_1F_1$ progeny are screened using genotyping methodologies to identify individuals heterozygous for all three mutations. A single triple heterozygous $BC_1F_1$ plant is backcrossed to TN86 to produce $BC_2F_1$ progeny. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F_1$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. A single $BC_7F_2$ plant homozygous for all three mutations is self-pollinated to produce a $BC_7F_3$ family (TN86 SRC) in which the wild-type CYP82E4, CYP82E5v2, and CYP82E10 alleles of TN86 were replaced by the mutant alleles (cyp82e4 W329Stop, cyp82e5v2 W422Stop, and cyp82e10 P381S).

The male-sterile (CMS) version of TN86 SRC (CMS TN86 SRC) is produced by crossing a plant of CMS TN86 as a female with pollen of TN86 SRC to produce male-sterile plants heterozygous for all three mutations. A single male-sterile plant resulting from this cross is then subsequently backcrossed as a female to TN86 SRC to produce progeny that are segregating for individuals homozygous for all three mutations. Triple homozygous individuals are identified by DNA genotyping to produce the CMS TN86 SRC line. Because the line is male-sterile, it is maintained via pollination with TN86 SRC.

Commercial TN86 SRC is produced by pollinating plants of CMS TN86 SRC with pollen of TN86 SRC.

Testing of TN86 SRC

TN86 SRC is evaluated for cured leaf chemistry, yield, and physical quality at three North Carolina field research locations during 2012 (Laurel Springs, Reidsville, Waynesville). TN86 is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicated that TN86 SRC has significantly ($P<0.05$) lower levels of nornicotine and percent nicotine conversion relative to TN86 (Table 1). TN86 and TN86 SRC are not significantly different from each other for percent nicotine, yield, or cured leaf quality indices.

Example 10

Breeding of Homozygous cyp82e4 W329Stop, the cyp82e5v2 W422Stop, and cyp82e10 P381S Mutant Plants into the NCBH129 Burley Tobacco Hybrid Cultivar The original tobacco cultivar NCBH129 is a hybrid generated by pollinating plants of a male-sterile breeding line CMS NC638 with pollen produced by fertile breeding line TN86. Hybrid cultivar NCBH129 SRC is a hybrid generated by pollinating plants of a male-sterile breeding line CMS NC638 SRC with pollen produced by fertile breeding line TN86 SRC with each breeding line carrying introduced deleterious mutations in three genes (CYP82E4 (SEQ ID NO: 5), CYP82E5 (SEQ ID NO: 8), and CYP82E10 (SEQ ID NO: 9)) previously documented to encode for nicotine demethylase enzymes (Lewis et al., *Phytochemistry*, 71 (2010), 1988-1998). The introduced mutations in CYP82E4 (cyp82e4 W329Stop (SEQ ID NO: 1)) and CYP82E5 (cyp82e5v2 W422Stop (SEQ ID NO: 2)) encode for premature stop codons which render the genes non-functional. The introduced mutation in CYP82E10 (cyp82e10 P381S (SEQ ID NO: 11)) does not encode for a premature stop codon, but does render the gene product non-functional for converting nicotine to nornicotine (Id.). When in homozygous condition, the three mutations result in tobacco plants with (1) reduced genetic capacity to demethylate nicotine to form nornicotine, and (2) a corresponding diminished potential to accumulate N-nitrosonornicotine (NNN), a potent carcinogen found in many tobacco products. The mutation in CYP82E4 (cyp82e4 W329Stop (SEQ ID NO: 1)) also provides phenotypic stability for the "nicotine conversion" trait and eliminates the requirement to utilize the cumbersome "LC" method for reducing levels of nornicotine in tobacco cultivars (see e.g., Jack et al. 2007. Implications of reducing nornicotine accumulation in burley tobacco: appendix A—the LC protocol. *Rec. Adv. Tob. Sci.* 33: 58-79).

The original tobacco cultivar NCBH129 is a hybrid generated by pollinating plants of a male-sterile breeding line CMS NC638 with pollen produced by fertile breeding line TN86. To develop hybrid cultivar NCBH1129 SRC, individual plants of fertile NC638 and TN86 are first pollinated with a plant of the genetic background DH98-325-6 carrying mutations in each of the three nicotine demethylase genes. $F_1$ individuals originating from each cross and heterozygous for each mutation are backcrossed to the recurrent parent (NC638 or TN86, respectively) to produce $BC_1F_1$ progenies.

$BC_1F_1$ progenies are screened using genotyping methodologies to identify individuals heterozygous for all three mutations. A single $BC_1F_1$ plant from each pedigree is backcrossed to either NC638 or TN86, respectively, to produce $BC_2F_1$ progenies. The process of backcrossing and identification of individuals heterozygous for all three mutations is repeated through the $BC_3F_1$, $BC_4F_1$, $BC_5F_1$, $BC_6F_1$, and $BC_7F_1$ stages. At the $BC_7F$ stage, individuals heterozygous for all three mutations from each pedigree are self-pollinated to produce $BC_7F_2$ seed. A large number of $BC_7F_2$ progeny from each pedigree are genotyped to identify individuals homozygous for all three mutations. $BC_7F_2$ plants homozygous for all three mutations are self-pollinated to produce $BC_7F_3$ families (NC638 SRC and TN86 SRC) in which the wild-type CYP82E4, CYP82E5v2, and CYP82E10 alleles of NC638 and TN86 are replaced by the mutant alleles (cyp82e4 W329Stop, cyp82e5v2 W422Stop, and cyp82e10 P381S).

The female parental line of NCBH129, CMS NC638, is cytoplasmic male sterile which causes pollen to not be produced. To develop CMS NC638 SRC, a plant of CMS NC638 is crossed with NC638 SRC to produce male-sterile plants heterozygous for all three mutations. A single male-sterile plant resulting from this cross is backcrossed as a female to NC638 SRC to produce progeny that are segregating for individuals homozygous for all three mutations. Triple homozygous individuals are identified by DNA genotyping to produce the CMS NC638 SRC line. Because the line is male-sterile, it is maintained via pollination with NC638 SRC (see above).

Hybrid cultivar NCBH129 SRC is produced by pollinating plants of CMS NC638 SRC with pollen of TN86 SRC.

Testing of Hybrid Cultivar NCBH129 SRC

Hybrid cultivar NCBH129 SRC is evaluated for cured leaf chemistry, yield, and physical quality at three North Carolina field research locations during 2012 (Laurel Springs, Reidsville, Waynesville). Hybrid cultivar NCBH129 LC is included for comparison. The experimental design at each location is a randomized complete block design with four replications. Experimental units are single 20-plant plots. Plots are harvested and air-cured. Plot weights are used to determine per acre yields. Cured leaf is evaluated by a former USDA tobacco grader. Fifty gram composite leaf samples are collected from each plot and analyzed for percent nicotine, nornicotine, anatabine, anabasine, and percent nicotine conversion using gas chromatography equipment.

Comparisons using the least significant difference (LSD) test indicates that hybrid cultivar NCBH129 SRC has significantly ($P<0.05$) lower levels of nornicotine and percent nicotine conversion relative to NCBH129 (Table 2). NCBH129 LC and hybrid cultivar NCBH129 SRC are not significantly different from each other for percent nicotine, yield, or cured leaf quality indices.

Deposit Information

A deposit of the proprietary inbred and hybrid plant lines disclosed above and recited in the appended claims have been made with American Type Culture Collection (ATCC), 10801 University Boulevard, Manassas, Va. 20110. The date of deposit for TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC was Feb. 26, 2013. The deposits of 2500 seeds for each variety was taken from the same deposits maintained since prior to the filing date of this application. Upon issuance of a patent, all restrictions upon the deposits will be removed, and the deposits are intended to meet all of the requirements of 37 C.F.R. § 1.801-1.809. The ATCC has issued the following accession numbers: ATCC Accession No. PTA-13567 for TN90 SRC, ATCC Accession No. PTA-13573 for CMS TN90 SRC, ATCC Accession No. PTA-120311 for KY14 SRC, ATCC Accession No. PTA-13571 for CMS KY14 SRC, ATCC Accession No. PTA-13572 for L8 SRC, ATCC Accession No. PTA-13569 for hybrid cultivar KY14×L8 SRC, ATCC Accession No. PTA-120312 for NC775 SRC, ATCC Accession No. PTA-13563 for CMS NC775 SRC, ATCC Accession No. PTA-13566 for NC645 SRC, ATCC Accession No. PTA-13564 for hybrid cultivar NC7 SRC, ATCC Accession No. PTA-120313 for NC638 SRC, ATCC Accession No. PTA-13568 for CMS NC638 SRC, ATCC Accession No. PTA-13565 for TN86 SRC, ATCC Accession No. PTA-13570 for CMS TN86 SRC, and ATCC Accession No. PTA-13562 for hybrid cultivar NCBH129 SRC. These deposits will be maintained in the depository for a period of 30 years, or 5 years after the last request, or for the effective life of the patent, whichever is longer, and will be replaced as necessary during that period. Applicants do not waive any infringement of their rights granted under this patent or under the Plant Variety Protection Act (7 U.S.C. 2321 et seq.).

What is claimed is:

1. A method of producing an F1 progeny tobacco seed comprising:
   a. crossing a first tobacco plant with a second tobacco plant, wherein said first tobacco plant is a tobacco plant produced by growing the seed of a tobacco cultivar elected from the group consisting of TN90 SRC, CMS TN90 SRC, KY14SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC; wherein a representative sample seed of said TN90 SRC, CMS TN90 SRC, KY14 SRC, CMS KY14 SRC, L8 SRC, NC775SRC, CMS NC775 SRC, NC645 SRC, NC638 SRC, CMS NC638 SRC, TN86SRC, CMS TN86 SRC, KY14×L8 SRC, NC7 SRC, and NCBH129 SRC has been deposited at the ATCC with the following ATCC Accession Nos.: ATCC Accession No. PTA-13567 for TN90 SRC, ATCC Accession No. PTA-13573 for CMS TN90 SRC, ATCC Accession No. PTA-120311 for KY14 SRC, ATCC Accession No. PTA-13571 for CMS KY14 SRC, ATCC Accession No. PTA-13572 for L8 SRC, ATCC Accession No. PTA-13569 for hybrid cultivar KY14×L8 SRC, ATCC Accession No. PTA-120312 for NC775 SRC, ATCC Accession No. PTA-13563 for CMS NC775 SRC, ATCC Accession No. PTA-13566 for NC645 SRC, ATCC Accession No. PTA-13564 for hybrid cultivar NC7 SRC, ATCC Accession No. PTA-120313 for NC638 SRC, ATCC Accession No. PTA-13568 for CMS NC638 SRC, ATCC Accession No. PTA-13565 for TN86 SRC, ATCC Accession No. PTA-13570 for CMS TN86 SRC, and ATCC Accession No. PTA-13562 for hybrid cultivar NCBH129 SRC; and
   b. harvesting the resultant tobacco seed.

2. The method of producing a tobacco seed of claim 1, wherein said first tobacco plant is the male parent.

3. The method of producing a tobacco seed of claim 1, wherein said first tobacco plant is the female parent.

4. The method of producing a tobacco seed of claim 1, wherein at least one said tobacco plant is a cytoplasmic male sterile (CMS).

5. A container of F1 progeny seeds of claim 1.

6. The container of F1 progeny seeds of claim 5, wherein said container is a box, a bag, a packet, a pouch, a tape roll, a pail, a foil, or a tube.

7. The, container of F1 progeny seeds of claim 5, wherein greater than about 50% of plants grown from said F1 progeny seeds have decreased nornicotine.

8. The container of F1 progeny seeds of claim 7, wherein greater than 55%, 60%, 65%, 70%, 75%, 80%, 85%, 90%, or 95% of plants grown from said F1progeny seeds have decreased nornicotine.

9. The container of F1 progeny seeds of claim 5, wherein alkaloids obtained from tobacco plants grown from greater than about 50% of said F1progeny seeds have decreased nornicotine.

10. A harvested leaf of an F1 progeny plant, wherein said F1 progeny plant is of a tobacco cultivar selected from the group consisting of TN90 SRC, CMS TN90 SRC, KY14 SRC, CMS KY14 SRC, L8 SRC, NC775SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC; wherein a representative sample seed of said TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC has been deposited at the ATCC with the following ATCC Accession Nos.: ATCC Accession No. PTA-13567 for TN90 SRC, ATCC Accession No. PTA-13573 for CMS TN90 SRC, ATCC Accession No. PTA-120311 for KY14 SRC, ATCC Accession No. PTA-13571 for CMS KY14 SRC, ATCC Accession No. PTA-13572 for L8 SRC, ATCC Accession No. PTA-13569 for hybrid cultivar KY14×L8SRC, ATCC Accession No. PTA-120312 for NC775 SRC, ATCC Accession No. PTA-13563 for CMS NC775 SRC, ATCC Accession No. PTA-13566 for NC645SRC, ATCC Accession No. PTA-13564 for hybrid cultivar NC7 SRC, ATCC Accession No. PTA-120313 for NC638 SRC, ATCC Accession No. PTA-13568 for CMS NC638 SRC, ATCC Accession No. PTA-13565 for TN86 SRC, ATCC Accession No. PTA-13570 for CMS TN86 SRC, and ATCC Accession No. PTA-13562 for hybrid cultivar NCBH129 SRC, wherein said harvested leaf has a reduced amount of nornicotine and/or N'-nitrosonornicotine (NNN) compared to a control leaf having a similar genetic background without any of the cyp82e4 W329Stop, cyp82e5v2 W422Stop, and cyp82e10 P381S alleles.

11. The harvested leaf of claim 10, wherein said reduced amount of nornicotine and/or N-nitrosonornicotine (NNN) is reduced in a smoke stream produced from said leaf compared to a control leaf having a similar genetic background without any of the cyp82e4 W329Stop, cyp82e5v2 W422Stop, and cyp82e10 P381S alleles.

12. A tobacco product prepared from an F1 progeny tobacco plant, or part thereof, wherein said F1 progeny plant is of a tobacco cultivar selected from the group consisting of TN90 SRC, CMS TN90 SRC, KY14 SRC, CMS KY14 SRC, L8 SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC; wherein a representative sample seed of said TN90 SRC, CMS TN90 SRC, KY14 SRC, CMS KY14 SRC, L8SRC, NC775 SRC, CMS NC775 SRC, NC645 SRC, NC638 SRC, CMS NC638 SRC, TN86 SRC, CMS TN86 SRC, KY14×L8 SRC, NC7 SRC, and NCBH129 SRC has been deposited at the ATCC with the following ATCC Accession Nos.: ATCC Accession No. PTA-13567 for TN90 SRC, ATCC Accession No. PTA-13573 for CMS TN90 SRC, ATCC Accession No. PTA-120311 for KY14 SRC, ATCC Accession No. PTA-13571for CMS KY14 SRC, ATCC Accession No. PTA-13572 for L8 SRC, ATCC Accession No. PTA-13569 for hybrid cultivar KY14×L8 SRC, ATCC Accession No. PTA-120312for NC775 SRC, ATCC Accession No. PTA-13563 for CMS NC775 SRC, ATCC Accession No. PTA-13566 for NC645 SRC, ATCC Accession No. PTA-13564 for hybrid cultivar NC7 SRC, ATCC Accession No. PTA-120313 for NC638 SRC, ATCC Accession No. PTA-13568 for CMS NC638 SRC, ATCC Accession No. PTA-13565 for TN86 SRC, ATCC Accession No. PTA-13570 for CMS TN86 SRC, and ATCC Accession No. PTA-13562 for hybrid cultivar NCBH129 SRC.

13. The F1 progeny plant of claim 12, wherein said F1 plant is male sterile.

14. The tobacco product of claim 12, wherein said tobacco product has an amount of nornicotine of less than about 3 mg/g.

* * * * *

UNITED STATES PATENT AND TRADEMARK OFFICE
CERTIFICATE OF CORRECTION

PATENT NO. : 10,091,963 B2  
APPLICATION NO. : 15/420799  
DATED : October 9, 2018  
INVENTOR(S) : Lewis et al.

Page 1 of 13

It is certified that error appears in the above-identified patent and that said Letters Patent is hereby corrected as shown below:

On the Title Page

Item (56) References Cited, U.S. PATENT DOCUMENTS, Column 2, Line 6:  
Please correct "5,231,019 A 4/1994 Q" to read -- 5,231,019 A 7/1993 Paskowski et al. --

Item (56) References Cited, U.S. PATENT DOCUMENTS, Page 2, Column 1, Line 32:  
Please correct "2007/0199097 A1 8/2007 Xu" to read -- 2007/0199097 A1 8/2007 Xu et al. --

Item (56) References Cited, U.S. PATENT DOCUMENTS, Page 2, Column 1, Line 35:  
Please correct "2008/0202541 A1 8/2008 Dewey" to read -- 2008/0202541 A1 8/2008 Dewey et al. --

Item (56) References Cited, OTHER PUBLICATIONS, Page 2, Column 2, Lines 11-12, Allen cite:  
Please correct "Biotecn-nology" to read -- Biotechnology --

Item (56) References Cited, OTHER PUBLICATIONS, Page 2, Column 2, Line 33, Bartoszewski cite: Please correct "124(4)" to read -- 127(4) --

Item (56) References Cited, OTHER PUBLICATIONS, Page 2, Column 2, Line 37, Batard cite:  
Please correct "P4500-Reductase" to read -- P450-Reductase --

Item (56) References Cited, OTHER PUBLICATIONS, Page 2, Column 2, Line 40, Baulcombe cite:  
Please correct "Test Forward" to read -- Fast Forward --

Item (56) References Cited, OTHER PUBLICATIONS, Page 2, Column 2, Line 44, Bolitno cite:  
Please correct "Bolitno" to read -- Bolitho --

Item (56) References Cited, OTHER PUBLICATIONS, Page 2, Column 2, Line 44, Bolitno cite:  
Please correct "applc" to read -- apple --

Signed and Sealed this  
Twenty-third Day of July, 2019

Andrei Iancu  
*Director of the United States Patent and Trademark Office*

CERTIFICATE OF CORRECTION (continued)
U.S. Pat. No. 10,091,963 B2

Item (56) References Cited, OTHER PUBLICATIONS, Page 3, Column 1, Line 30, 2nd Chakrabarti cite: Please correct "CYP62E2" to read -- CYP82E2 --

Item (56) References Cited, OTHER PUBLICATIONS, Page 3, Column 2, Line 10, D'Souze cite: Please correct "D'Souze" to read -- D'Souza --

Item (56) References Cited, OTHER PUBLICATIONS, Page 3, Column 2, Line 32, Elkind cite: Please correct "piant" to read -- plant --

Item (56) References Cited, OTHER PUBLICATIONS, Page 4, Column 1, Line 24, 6th GenBank Accession No. cite: Please correct "GenBank33" to read -- GenBank --

Item (56) References Cited, OTHER PUBLICATIONS, Page 4, Column 2, Line 40, 2nd Hao cite: Please correct "Cuitures" to read -- Cultures --

Item (56) References Cited, OTHER PUBLICATIONS, Page 4, Column 2, Line 41, Hoe cite: Please correct "Hoe" to read -- Hao --

Item (56) References Cited, OTHER PUBLICATIONS, Page 5, Column 1, Line 15, Huang cite: Please correct "Huang et et al., "Insights into Reguiation" to read -- Huang et al., "Insights into Regulation --

Item (56) References Cited, OTHER PUBLICATIONS, Page 5, Column 1, Line 21, Inglebrecht cite: Please correct "10509" to read -- 10506 --

Item (56) References Cited, OTHER PUBLICATIONS, Page 5, Column 2, Line 1, Kim cite: Please correct "CYP35A2" to read -- CYP85A2 --

Item (56) References Cited, OTHER PUBLICATIONS, Page 5, Column 2, Line 2, Kim cite: Please correct "Brassinoilde" to read -- Brassinolide --

Item (56) References Cited, OTHER PUBLICATIONS, Page 6, Column 1, Line 30, 1st Notification cite: Please correct "PCT/US20112/026864" to read -- PCT/US2012/026864 --

Item (56) References Cited, OTHER PUBLICATIONS, Page 6, Column 1, Line 52, Odell cite: Please correct "810-612" to read -- 810-812 --

Item (56) References Cited, OTHER PUBLICATIONS, Page 6, Column 2, Line 62, Siminszky cite: Please correct "nomicotine" to read -- nornicotine --

Item (56) References Cited, OTHER PUBLICATIONS, Page 6, Column 2, Line 65, Sinvany-Vilialcbo cite: Please correct "Sinvany-Vilialcbo" to read -- Sinvany-Villalobo --

Item (56) References Cited, OTHER PUBLICATIONS, Page 6, Column 2, Line 68, Skarnes cite: Please correct "Mammailan" to read -- Mammalian --

CERTIFICATE OF CORRECTION (continued)
U.S. Pat. No. 10,091,963 B2

Item (56) References Cited, OTHER PUBLICATIONS, Page 7, Column 1, Line 10, Spradling cite: Please correct "compnent" to read -- component --

Item (56) References Cited, OTHER PUBLICATIONS, Page 7, Column 1, Line 15, Sunclaresan cite: Please correct "Sunclaresan" to read -- Sundaresan --

Item (56) References Cited, OTHER PUBLICATIONS, Page 7, Column 1, Line 63, 2nd U.S. Appl. cite: Please correct "14/636,576" to read -- 14/636,876 --

Item (56) References Cited, OTHER PUBLICATIONS, Page 7, Column 2, Line 15, 1st Van der Krol cite: Please correct "(1968)" to read -- (1988) --

Item (56) References Cited, OTHER PUBLICATIONS, Page 7, Column 2, Line 33, 1st Wang cite: Please correct "silcencing" to read -- silencing --

Item (56) References Cited, OTHER PUBLICATIONS, Page 7, Column 2, Line 49, Werck-Reichart cite: Please correct "Werck-Reichart" to read -- Werck-Reichhart --

Item (56) References Cited, OTHER PUBLICATIONS, Page 7, Column 2, Line 49, Werck-Reichart cite: Please correct "dry" to read -- story --

Item (56) References Cited, OTHER PUBLICATIONS, Page 7, Column 2, Line 64, Whitbread cite: Please correct "Whitbread" to read -- Whitbred --

In the Specification

Column 1, Line 53: Please correct "nomicotine" to read -- nornicotine --

Column 1, Line 54: Please correct "N-Nitrosonomicotine" to read -- N-Nitrosonornicotine --

Column 1, Lines 59-60: Please correct "nomicotine" to read -- nornicotine --

Column 1, Line 60: Please correct "Nomicotine" to read -- Nornicotine --

Column 1, Line 62: Please correct "Nomicotine" to read -- Nornicotine --

Column 1, Line 65: Please correct "nomicotine" to read -- nornicotine --

Column 1, Line 67: Please correct "nomicotine" to read -- nornicotine --

Column 2, Line 2: Please correct "nomicotine" to read -- nornicotine --

Column 2, Line 3: Please correct "Wemsman" to read -- Wernsman --

Column 2, Line 8: Please correct "nomicotine" to read -- nornicotine --

CERTIFICATE OF CORRECTION (continued)
U.S. Pat. No. 10,091,963 B2

Column 2, Line 57: Please correct "nomicotine" to read -- nornicotine --

Column 2, Line 64: Please correct "nomicotine and/or N'-nitrosonomicotine" to read -- nornicotine and/or N'-nitrosonornicotine --

Column 2, Lines 65-66: Please correct "nomicotine and/or N'-nitrosonomicotine" to read -- nornicotine and/or N'-nitrosonornicotine --

Column 3, Line 28: Please correct "nomicotine and/or N'-nitrosonomicotine" to read -- nornicotine and/or N'-nitrosonornicotine --

Column 3, Line 43: Please correct "N'-nitrosonomicotine" to read -- N'-nitrosonornicotine --

Column 5, Line 24: Please correct "nomicotine and/or N'-nitrosonomicotine" to read -- nornicotine and/or N'-nitrosonornicotine --

Column 5, Line 35: Please correct "nomicotine and/or N'-nitrosonomicotine" to read -- nornicotine and/or N'-nitrosonornicotine --

Column 6, Lines 26-27: Please correct "nomicotine and/or N'-nitrosonomicotine" to read -- nornicotine and/or N'-nitrosonornicotine --

Column 6, Lines 33-34: Please correct "N'-nitrosonomicotine" to read -- N'-nitrosonornicotine --

Column 6, Lines 34-35: Please correct "nomicotine and/or N'-nitrosonomicotine" to read -- nornicotine and/or N'-nitrosonornicotine --

Column 6, Line 64: Please correct "nomicotine and/or N'-nitrosonomicotine" to read -- nornicotine and/or N'-nitrosonornicotine --

Column 8, Line 52: Please correct "nomicotine and/or N'-nitrosonomicotine" to read -- nornicotine and/or N'-nitrosonornicotine --

Column 8, Line 63: Please correct "nomicotine and/or N'-nitrosonomicotine" to read -- nornicotine and/or N'-nitrosonornicotine --

Column 9, Lines 49-50: Please correct "nomicotine and/or N'-nitrosonomicotine" to read -- nornicotine and/or N'-nitrosonornicotine --

Column 17, Lines 39-40: Please correct "nomicotine and/or N'-nitrosonomicotine" to read -- nornicotine and/or N'-nitrosonornicotine --

Column 17, Line 46: Please correct "nomicotine and/or N'-nitrosonomicotine" to read -- nornicotine and/or N'-nitrosonornicotine --

Column 17, Line 48: Please correct "N'-nitrosonomicotine" to read -- N'-nitrosonornicotine --

Column 18, Line 11: Please correct "nomicotine and/or N'-nitrosonomicotine" to read -- nornicotine and/or N'-nitrosonornicotine --

Column 18, Line 26: Please correct "nomicotine" to read -- nornicotine --

Column 20, Line 7: Please correct "nomicotine and/or N'-nitrosonomicotine" to read -- nornicotine and/or N'-nitrosonornicotine --

Column 20, Line 18: Please correct "nomicotine and/or N'-nitrosonomicotine" to read -- nornicotine and/or N'-nitrosonornicotine --

Column 21, Line 3: Please correct "nomicotine" to read -- nornicotine --

Column 21, Line 25: Please correct "nomicotine" to read -- nornicotine --

Column 21, Lines 32-33: Please correct "N'-nitrosonomicotine" to read -- N'-nitrosonornicotine --

Column 21, Line 33: Please correct "nomicotine" to read -- nornicotine --

Column 21, Line 63: Please correct "nomicotine and/or N'-nitrosonomicotine" to read -- nornicotine and/or N'-nitrosonornicotine --

Column 22, Lines 11-12: Please correct "nomicotine and/or N'-nitrosonomicotine" to read -- nornicotine and/or N'-nitrosonornicotine --

Column 23, Line 51: Please correct "nomicotine and/or N'-nitrosonomicotine" to read -- nornicotine and/or N'-nitrosonornicotine --

Column 23, Line 62: Please correct "nomicotine and/or N'-nitrosonomicotine" to read -- nornicotine and/or N'-nitrosonornicotine --

Column 25, Lines 10-11: Please correct "nomicotine and/or N'-nitrosonomicotine" to read -- nornicotine and/or N'-nitrosonornicotine --

Column 25, Line 17: Please correct "nomicotine and/or N'-nitrosonomicotine" to read -- nornicotine and/or N'-nitrosonornicotine --

Column 25, Lines 18-19: Please correct "nomicotine and/or N'-nitrosonomicotine" to read -- nornicotine and/or N'-nitrosonornicotine --

Column 25, Line 48: Please correct "nomicotine and/or N'-nitrosonomicotine" to read -- nornicotine and/or N'-nitrosonornicotine --

Column 25, Line 63: Please correct "nomicotine" to read -- nornicotine --

CERTIFICATE OF CORRECTION (continued)

Column 27, Line 43: Please correct "nomicotine and/or N'-nitrosonomicotine" to read -- nornicotine and/or N'-nitrosonornicotine --

Column 27, Line 54: Please correct "nomicotine and/or N'-nitrosonomicotine" to read -- nornicotine and/or N'-nitrosonornicotine --

Column 28, Line 39: Please correct "nomicotine" to read -- nornicotine --

Column 28, Lines 56-57: Please correct "nomicotine and/or N'-nitrosonomicotine" to read -- nornicotine and/or N'-nitrosonornicotine --

Column 28, Line 61: Please correct "nomicotine" to read -- nornicotine --

Column 28, Line 63: Please correct "N'-nitrosonomicotine" to read -- N'-nitrosonornicotine --

Column 29, Line 19: Please correct "nomicotine and/or N'-nitrosonomicotine" to read -- nornicotine and/or N'-nitrosonornicotine --

Column 29, Lines 32-33: Please correct "nomicotine and/or N'-nitrosonomicotine" to read -- nornicotine and/or N'-nitrosonornicotine --

Column 37, Lines 9-10: Please correct "nomicotine and/or N'-nitrosonomicotine" to read -- nornicotine and/or N'-nitrosonornicotine --

Column 37, Line 16: Please correct "nomicotine and/or N'-nitrosonomicotine" to read -- nornicotine and/or N'-nitrosonornicotine --

Column 37, Lines 17-18: Please correct "nomicotine and/or N'-nitrosonomicotine" to read -- nornicotine and/or N'-nitrosonornicotine --

Column 37, Line 47: Please correct "nomicotine and/or N'-nitrosonomicotine" to read -- nornicotine and/or N'-nitrosonornicotine --

Column 37, Line 62: Please correct "nomicotine and/or N'-nitrosonomicotine" to read -- nornicotine and/or N'-nitrosonornicotine --

Column 39, Line 42: Please correct "nomicotine and/or N'-nitrosonomicotine" to read -- nornicotine and/or N'-nitrosonornicotine --

Column 39, Line 53: Please correct "nomicotine and/or N'-nitrosonomicotine" to read -- nornicotine and/or N'-nitrosonornicotine --

Column 40, Line 38: Please correct "nomicotine" to read -- nornicotine --

Column 40, Lines 60-61: Please correct "N'-nitrosonomicotine" to read -- N'-nitrosonornicotine --

CERTIFICATE OF CORRECTION (continued)
U.S. Pat. No. 10,091,963 B2

Column 40, Line 67 - Column 41, Line 1: Please correct "nomicotine and/or N'-nitrosonomicotine" to read -- nornicotine and/or N'-nitrosonornicotine --

Column 41, Lines 1-2: Please correct "nomicotine and/or N'-nitrosonomicotine" to read -- nornicotine and/or N'-nitrosonornicotine --

Column 41, Line 31: Please correct "nomicotine and/or N'-nitrosonomicotine" to read -- nornicotine and/or N'-nitrosonornicotine --

Column 41, Line 46: Please correct "nomicotine" to read -- nornicotine --

Column 43, Line 18: Please correct "nomicotine and/or N'-nitrosonomicotine" to read -- nornicotine and/or N'-nitrosonornicotine --

Column 43, Line 29: Please correct "nomicotine and/or N'-nitrosonomicotine" to read -- nornicotine and/or N'-nitrosonornicotine --

Column 44, Line 16: Please correct "nomicotine and/or N'-nitrosonomicotine" to read -- nornicotine and/or N'-nitrosonornicotine --

Column 44, Line 37: Please correct "nomicotine" to read -- nornicotine --

Column 44, Line 44: Please correct "nomicotine and/or N'-nitrosonomicotine" to read -- nornicotine and/or N'-nitrosonornicotine --

Column 45, Line 8: Please correct "nomicotine and/or N'-nitrosonomicotine" to read -- nornicotine and/or N'-nitrosonornicotine --

Column 47, Line 3: Please correct "nomicotine and/or N'-nitrosonomicotine" to read -- nornicotine and/or N'-nitrosonornicotine --

Column 47, Line 14: Please correct "nomicotine and/or N'-nitrosonomicotine" to read -- nornicotine and/or N'-nitrosonornicotine --

Column 47, Line 66: Please correct "nomicotine" to read -- nornicotine --

Column 48, Lines 17-18: Please correct "nomicotine and/or N'-nitrosonomicotine" to read -- nornicotine and/or N'-nitrosonornicotine --

Column 48, Line 22: Please correct "nomicotine and/or N'-nitrosonomicotine" to read -- nornicotine and/or N'-nitrosonornicotine --

Column 48, Lines 23-24: Please correct "nomicotine and/or N'-nitrosonomicotine" to read -- nornicotine and/or N'-nitrosonornicotine --

Column 48, Line 47: Please correct "N'-nitrosonomicotine" to read -- N'-nitrosonornicotine --

CERTIFICATE OF CORRECTION (continued)
U.S. Pat. No. 10,091,963 B2

Column 57, Lines 9-10: Please correct "nomicotine and/or N'-nitrosonomicotine" to read
-- nornicotine and/or N'-nitrosonornicotine --

Column 57, Line 16: Please correct "nomicotine" to read -- nornicotine --

Column 57, Lines 17-18: Please correct "nomicotine and/or N'-nitrosonomicotine" to read
-- nornicotine and/or N'-nitrosonornicotine --

Column 57, Line 47: Please correct "nomicotine" to read -- nornicotine --

Column 57, Line 62: Please correct "nomicotine and/or N'-nitrosonomicotine" to read -- nornicotine
and/or N'-nitrosonornicotine --

Column 59, Line 42: Please correct "nomicotine and/or N'-nitrosonomicotine" to read -- nornicotine
and/or N'-nitrosonornicotine --

Column 59, Line 53: Please correct "nomicotine and/or N'-nitrosonomicotine" to read -- nornicotine
and/or N'-nitrosonornicotine --

Column 60, Lines 38-39: Please correct "nomicotine and/or N'-nitrosonomicotine" to read
-- nornicotine and/or N'-nitrosonornicotine --

Column 60, Line 60: Please correct "nomicotine" to read -- nornicotine --

Column 60, Line 67 - Column 61, Line 1: Please correct "nomicotine and/or N'-nitrosonomicotine" to
read -- nornicotine and/or N'-nitrosonornicotine --

Column 61, Line 1: Please correct "nomicotine" to read -- nornicotine --

Column 61, Line 31: Please correct "nomicotine and/or N'-nitrosonomicotine" to read -- nornicotine
and/or N'-nitrosonornicotine --

Column 61, Lines 46-47: Please correct "nomicotine and/or N'-nitrosonomicotine" to read
-- nornicotine and/or N'-nitrosonornicotine --

Column 63, Line 18: Please correct "nomicotine and/or N'-nitrosonomicotine" to read -- nornicotine
and/or N'-nitrosonornicotine --

Column 63, Line 29: Please correct "nomicotine and/or N'-nitrosonomicotine" to read -- nornicotine
and/or N'-nitrosonornicotine --

Column 64, Line 16: Please correct "nomicotine and/or N'-nitrosonomicotine" to read -- nornicotine
and/or N'-nitrosonornicotine --

Column 64, Lines 45-46: Please correct "nomicotine and/or N'-nitrosonomicotine" to read
-- nornicotine and/or N'-nitrosonornicotine --

CERTIFICATE OF CORRECTION (continued)
U.S. Pat. No. 10,091,963 B2

Column 64, Line 52: Please correct "N'-nitrosonomicotine" to read -- N'-nitrosonornicotine --

Column 64, Lines 53-54: Please correct "nomicotine and/or N'-nitrosonomicotine" to read -- nornicotine and/or N'-nitrosonornicotine --

Column 65, Line 16: Please correct "nomicotine and/or N'-nitrosonomicotine" to read -- nornicotine and/or N'-nitrosonornicotine --

Column 65, Line 31: Please correct "nomicotine and/or N'-nitrosonomicotine" to read -- nornicotine and/or N'-nitrosonornicotine --

Column 67, Line 12: Please correct "nomicotine and/or N'-nitrosonomicotine" to read -- nornicotine and/or N'-nitrosonornicotine --

Column 67, Line 23: Please correct "nomicotine and/or N'-nitrosonomicotine" to read -- nornicotine and/or N'-nitrosonornicotine --

Column 68, Line 8: Please correct "nomicotine and/or N'-nitrosonomicotine" to read -- nornicotine and/or N'-nitrosonornicotine --

Column 68, Line 31: Please correct "nomicotine" to read -- nornicotine --

Column 68, Lines 38-39: Please correct "nomicotine and/or N'-nitrosonomicotine" to read -- nornicotine and/or N'-nitrosonornicotine --

Column 68, Lines 39-40: Please correct "nomicotine and/or N'-nitrosonomicotine" to read -- nornicotine and/or N'-nitrosonornicotine --

Column 69, Line 2: Please correct "nomicotine and/or N'-nitrosonomicotine" to read -- nornicotine and/or N'-nitrosonornicotine --

Column 69, Lines 17-18: Please correct "nomicotine and/or N'-nitrosonomicotine" to read -- nornicotine and/or N'-nitrosonornicotine --

Column 70, Line 56: Please correct "nomicotine and/or N'-nitrosonomicotine" to read -- nornicotine and/or N'-nitrosonornicotine --

Column 70, Line 67: Please correct "nomicotine and/or N'-nitrosonomicotine" to read -- nornicotine and/or N'-nitrosonornicotine --

Column 71, Line 54: Please correct "nomicotine and/or N'-nitrosonomicotine" to read -- nornicotine and/or N'-nitrosonornicotine --

Column 72, Lines 11-12: Please correct "nomicotine and/or N'-nitrosonomicotine" to read -- nornicotine and/or N'-nitrosonornicotine --

Column 72, Line 16: Please correct "nomicotine and/or N'-nitrosonomicotine" to read -- nornicotine and/or N'-nitrosonornicotine --

Column 72, Lines 17-18: Please correct "nomicotine and/or N'-nitrosonomicotine" to read -- nornicotine and/or N'-nitrosonornicotine --

Column 72, Line 41: Please correct "nomicotine and/or N'-nitrosonomicotine" to read -- nornicotine and/or N'-nitrosonornicotine --

Column 72, Line 54: Please correct "nomicotine" to read -- nornicotine --

Column 81, Line 31: Please correct "nomicotine" to read -- nornicotine --

Column 87, Line 28: Please correct "nomicotine" to read -- nornicotine --

Column 89, Line 32: Please correct "nomicotine" to read -- nornicotine --

Column 92, Line 1: Please correct "nomicotine" to read -- nornicotine --

Column 92, Line 7: Please correct "nomicotine" to read -- nornicotine --

Column 92, Line 55: Please correct "nomicotine" to read -- nornicotine --

Column 92, Line 56: Please correct "nomicotine" to read -- nornicotine --

Column 93, Line 14: Please correct "nomicotine" to read -- nornicotine --

Column 93, Line 15: Please correct "nomicotine" to read -- nornicotine --

Column 93, Line 38: Please correct "990/o" to read -- 99% --

Column 93, Line 40: Please correct "nomicotine" to read -- nornicotine --

Column 93, Lines 65-66: Please correct "nomicotine" to read -- nornicotine --

Column 93, Line 66: Please correct "nomicotine" to read -- nornicotine --

Column 94, Lines 24-25: Please correct "nomicotine" to read -- nornicotine --

Column 94, Line 51: Please correct "nomicotine" to read -- nornicotine --

Column 94, Line 52: Please correct "nomicotine" to read -- nornicotine --

Column 95, Line 62: Please correct "nomicotine" to read -- nornicotine --

Column 95, Lines 63-64: Please correct "nomicotine" to read -- nornicotine --

Column 96, Line 2: Please correct "nomicotine" to read -- nornicotine --

Column 96, Line 6: Please correct "nomicotine" to read -- nornicotine --

Column 96, Line 14: Please correct "nomicotine" to read -- nornicotine --

Column 96, Line 18: Please correct "nomicotine" to read -- nornicotine --

Column 96, Line 28: Please correct "nomicotine" to read -- nornicotine --

Column 97, Line 5: Please correct "nomicotine" to read -- nornicotine --

Column 97, Line 12: Please correct "nomicotine" to read -- nornicotine --

Column 97, Line 15: Please correct "nomicotine" to read -- nornicotine --

Column 97, Line 16: Please correct "nomicotine" to read -- nornicotine --

Column 97, Line 56: Please correct "nomicotine" to read -- nornicotine --

Column 98, Line 2: Please correct "nomicotine" to read -- nornicotine --

Column 98, Line 15: Please correct "nomicotine" to read -- nornicotine --

Column 99, Line 18: Please correct "nomicotine" to read -- nornicotine --

Column 99, Line 22: Please correct "nomicotine" to read -- nornicotine --

Column 99, Line 53: Please correct "nomicotine" to read -- nornicotine --

Column 100, Lines 64-65: Please correct "nomicotine" to read -- nornicotine --

Column 101, Line 39: Please correct "nomicotine" to read -- nornicotine --

Column 102, Lines 51-52: Please correct "nomicotine" to read -- nornicotine --

Column 103, Line 33: Please correct "nomicotine" to read -- nornicotine --

Column 104, Line 60: Please correct "nomicotine" to read -- nornicotine --

Column 104, Line 65: Please correct "nomicotine" to read -- nornicotine --

Column 105, Line 46: Please correct "nomicotine" to read -- nornicotine --

Column 106, Line 56: Please correct "nomicotine" to read -- nornicotine --

Column 106, Line 57: Please correct "nomicotine" to read -- nornicotine --

Column 107, Line 40: Please correct "$F_1, F_2, F_1$" to read -- $F_1, F_2, F_3$ --

Column 110, Line 11: Please correct "nomicotine" to read -- nornicotine --

Column 112, Line 34: Please correct "CYP82E4 cyp82e4" to read -- CYP82E4 (cyp82e4 --

Column 112, Lines 40-41: Please correct "nomicotine" to read -- nornicotine --

Column 112, Line 43: Please correct "nomicotine" to read -- nornicotine --

Column 112, Lines 44-45: Please correct "N-nitrosonomicotine" to read -- N-nitrosonornicotine --

Column 112, Line 51: Please correct "nomicotine" to read -- nornicotine --

Column 113, Line 36: Please correct "nomicotine" to read -- nornicotine --

Column 113, Line 49: Please correct "nomicotine" to read -- nornicotine --

Column 114, Line 13: Please correct "nomicotine" to read -- nornicotine --

Column 114, Line 16: Please correct "nomicotine" to read -- nornicotine --

Column 114, Line 19: Please correct "nomicotine" to read -- nornicotine --

Column 114, Line 21: Please correct "nomicotine" to read -- nornicotine --

Column 126, Line 20: Please correct "$BC_LF_J$" to read -- $BC_1F_1$ --

Column 127, Line 60: Please correct "$BC_7F$" to read -- $BC_7F_1$ --

In the Claims

Column 153, Claim 1, Line 37: Please correct "KY14SRC" to read -- KY14 SRC --

Column 153, Claim 1, Line 43: Please correct "NC775SRC" to read -- NC775 SRC --

Column 153, Claim 1, Line 44: Please correct "TN86SRC" to read -- TN86 SRC --

Column 154, Claim 10, Line 53: Please correct "NC775SRC" to read -- NC775 SRC --

Column 155, Claim 10, Line 3: Please correct "NC645SRC" to read -- NC645 SRC --

CERTIFICATE OF CORRECTION (continued)
U.S. Pat. No. 10,091,963 B2

Column 156, Claim 12, Line 2: Please correct "L8SRC" to read -- L8 SRC --

Column 156, Claim 12, Line 13: Please correct "PTA-120312for" to read -- PTA-120312 for --

```
                              SEQUENCE LISTING

<160> NUMBER OF SEQ ID NOS: 12

<210> SEQ ID NO 1
<211> LENGTH: 1554
<212> TYPE: DNA
<213> ORGANISM: Nicotiana tabacum
<220> FEATURE:
<221> NAME/KEY: Mutation
<222> LOCATION: (986)..(986)
<223> OTHER INFORMATION: G to A

<400> SEQUENCE: 1
atgctttctc ccatagaagc cattgtagga ctagtaacct tcacatttct cttcttcttc         60
ctatggacaa aaaatctca aaaccttca aaaccttac caccgaaaat ccccggagga          120
tggccggtaa tcggccatct tttccacttc aatgacgacg cgacgaccg tccattagct         180 cgaaaactcg gagacttagc tgacaaatac ggccccgttt tcacttttcg gctaggcctt        240
ccccttgtct tagttgtaag cagttacgaa gctgtaaaag actgtttctc tacaaatgac        300 gccattttt ccaatcgtcc agcttttctt tacggcgatt accttggcta caataatgcc         360
atgctatttt tggccaatta cggaccttac tggcgaaaaa atcgaaaatt agttattcag        420
gaagttctct ccgctagtcg tctcgaaaaa ttcaaacacg tgagatttgc aagaattcaa        480
gcgagcatta agaatttata tactcgaatt gatggaaatt cgagtacgat aaatttaact        540
gattggttag aagaattgaa ttttggtctg atcgtgaaga tgatcgctgg aaaaaattat       600
gaatccggta aaggagatga acaagtggag agatttaaga aagcgtttaa ggattttatg       660
attttatcaa tggagtttgt gttatgggat gcatttccaa ttccattatt taaatgggtg       720
gattttcaag gcatgttaa ggctatgaaa aggacttta aagatataga ttctgttttt        780
cagaattggt tagaggaaca tattaataaa agagaaaaaa tggaggttaa tgcagaaggg       840
aatgaacaag atttcattga tgtggtgctt tcaaaaatga gtaatgaata tcttggtgaa       900
ggttactctc gtgatactgt cattaaagca acggtgttta gtttggtctt ggatgcagca       960
gacacagttg ctcttcacat aaattaggga atggcattat tgataaacaa tcaaaaggcc      1020
ttgacgaaag cacaagaaga gatagacaca aaagttggta aggacagatg ggtagaagag      1080
agtgatatta aggatttggt atacctccaa gctattgtta aagaagtgtt acgattatat      1140
ccaccaggac ctttgttagt accacacgaa aatgtagaag attgtgttgt tagtggatat      1200
cacattccta aagggacaag attattcgca aacgtcatga aactgcaacg tgatcctaaa      1260
ctctggtctg atcctgatac tttcgatcca gagagattca ttgctactga tattgacttt      1320
cgtggtcagt actataagta tatcccgttt ggttctggaa gacgatcttg tccagggatg      1380
acttatgcat tgcaagtgga acacttaaca atggcacatt tgatccaagg tttcaattac      1440
agaactccaa atgacgagcc cttggatatg aaggaaggtg caggcataac tatacgtaag      1500
gtaaatcctg tggaactgat aatagcgcct cgcctggcac ctgagcttta ttaa            1554

<210> SEQ ID NO 2
<211> LENGTH: 1554
<212> TYPE: DNA
<213> ORGANISM: Nicotiana tabacum
```

```
<220> FEATURE:
<221> NAME/KEY: Mutation
<222> LOCATION: (1266)..(1266)
<223> OTHER INFORMATION: G to A

<400> SEQUENCE: 2
atggtttctc ccgtagaagc cattgtagga ctagtaaccc ttacacttct cttctacttc      60
ctatggccca aaaatttca aataccttca aaaccattac caccgaaaat tcccggaggg     120
tggccggtaa tcggccatct tttctacttc gatgatgacg gcgacgaccg tccattagct     180
cgaaaactcg gagacttagc tgacaaatac ggcccggttt tcactttccg gctaggcctt     240
ccgcttgtgt tagttgtaag cagttacgaa gctgtaaaag actgcttctc tacaaatgac     300
gccatttttct ccaatcgtcc agcttttctt tacggtgaat accttggcta cagtaatgcc     360
atgctatttt tgacaaaata cggaccttat tggcgaaaaa atagaaaatt agtcattcag     420
gaagttctct ctgctagtcg tctcgaaaaa ttgaagcacg tgagatttgg taaaattcaa     480
acgagcatta agagtttata cactcgaatt gatggaaatt cgagtacgat aaatctaact     540
gattggttag aagaattgaa ttttggtctg atcgtgaaaa tgatcgctgg gaaaaattat     600
gaatccggta aggagatgaa acaagtggag agatttagga aagcgtttaa ggatttttata    660
attttatcaa tggagtttgt gttatgggat gcttttccaa ttccattgtt caaatgggtg     720
gattttcaag gccatgttaa ggccatgaaa aggacattta aggatataga ttctgttttt     780
cagaattggt tagaggaaca tgtcaagaaa agagaaaaaa tggaggttaa tgcacaaggg     840
aatgaacaag atttcattga tgtggtgctt tcaaaaatga gtaatgaata tcttgatgaa     900
ggttactctc gtgatactgt cataaaagca acagtgttta gtttggtctt ggatgctgcg     960
gacacagttg ctcttcacat gaattgggga atggcattac tgataaacaa tcaacatgcc    1020
ttgaagaaag cacaagaaga gatcgataaa aaagttggta aggaaagatg ggtagaagag    1080
agtgatatta aggatttggt ctacctccaa gctattgtta agaaagtgtt acgattatat    1140
ccaccaggac ctttattagt acctcatgaa aatgtagagg attgtgttgt tagtggatat    1200
cacattccta aagggactag actattcgcg aacgttatga aattgcagcg cgatcctaaa    1260
ctctgatcaa atcctgataa gtttgatcca gagagattct tcgctgatga tattgactac    1320
cgtggtcagc actatgagtt tatcccattt ggttctggaa gacgatcttg tccggggatg    1380
acttatgcat tacaagtgga acacctaaca atagcacatt tgatccaggg tttcaattac    1440
aaaactccaa atgacgagcc cttggatatg aaggaaggtg caggattaac tatacgtaaa    1500
gtaaatcctg tagaagtgac aattacggct cgcctggcac tgagctttta ttaa          1554

<210> SEQ ID NO 3
<211> LENGTH: 328
<212> TYPE: PRT
<213> ORGANISM: Nicotiana tabacum

<400> SEQUENCE: 3

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60
```

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Ile Asn
                325

<210> SEQ ID NO 4
<211> LENGTH: 421
<212> TYPE: PRT
<213> ORGANISM: Nicotiana tabacum

<400> SEQUENCE: 4

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
         115                 120                 125

Pro Tyr Trp Arg Lys Asn Arg Lys Leu Val Ile Gln Glu Val Leu Ser
130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu
            420

<210> SEQ ID NO 5
<211> LENGTH: 1554
<212> TYPE: DNA
<213> ORGANISM: Nicotiana tabacum

<400> SEQUENCE: 5
atgctttctc ccatagaagc cattgtagga ctagtaacct tcacatttct cttcttcttc    60
ctatggacaa aaaatctca aaaccttca aaacccttac accgaaaat ccccggagga      120 tggccggtaa tcggccatct tttccacttc aatgacgacg gcgacgaccg tccattagct    180
cgaaaactcg gagacttagc tgacaaatac ggccccgttt tcacttttcg gctaggcctt    240 cccccttgtct tagttgtaag cagttacgaa gctgtaaaag actgtttctc tacaaatgac    300

```
gccattttttt ccaatcgtcc agcttttctt tacggcgatt accttggcta caataatgcc    360
atgctatttt tggccaatta cggaccttac tggcgaaaaa atcgaaaatt agttattcag    420
gaagttctct ccgctagtcg tctcgaaaaa ttcaaacacg tgagatttgc aagaattcaa    480
gcgagcatta agaatttata tactcgaatt gatggaaatt cgagtacgat aaatttaact    540
gattggttag aagaattgaa ttttggtctg atcgtgaaga tgatcgctgg aaaaaattat    600
gaatccggta aggagatgaa acaagtggag agatttaaga aagcgtttaa ggattttatg    660
attttatcaa tggagtttgt gttatgggat gcatttccaa ttccattatt taaatgggtg    720
gattttcaag ggcatgttaa ggctatgaaa aggacttttaa aagatataga ttctgttttt    780
cagaattggt tagaggaaca tattaataaa agagaaaaaa tggaggttaa tgcagaaggg    840
aatgaacaag atttcattga tgtggtgctt tcaaaaatga gtaatgaata tcttggtgaa    900
ggttactctc gtgatactgt cattaaagca acggtgttta gtttggtctt ggatgcagca    960
gacacagttg ctcttcacat aaattgggga atggcattat tgataaacaa tcaaaaggcc   1020
ttgacgaaag cacaagaaga gatagacaca aaagttggta aggacagatg ggtagaagag   1080
agtgatatta aggatttggt atacctccaa gctattgtta agaagtgtt acgattatat   1140 ccaccaggac ctttgttagt accacacgaa aatgtagaag attgtgttgt tagtggatat   1200
cacattccta aagggacaag attattcgca aacgtcatga aactgcaacg tgatcctaaa   1260
ctctggtctg atcctgatac tttcgatcca gagagattca ttgctactga tattgacttt   1320
cgtggtcagt actataagta tcccgtttt ggttctggaa gacgatcttg tccagggatg   1380
acttatgcat tgcaagtgga acacttaaca atggcacatt tgatccaagg tttcaattac   1440
agaactccaa atgacgagcc cttggatatg aaggaaggtg caggcataac tatacgtaag   1500
gtaaatcctg tggaactgat aatagcgcct cgcctggcac ctgagcttta ttaa         1554

<210> SEQ ID NO 6
<211> LENGTH: 1554
<212> TYPE: DNA
<213> ORGANISM: Nicotiana tabacum

<400> SEQUENCE: 6
atggtttctc ccgtagaagc cattgtagga ctagtaaccc ttacacttct cttctacttc     60
ctatggccca aaaatttca aataccttca aaaccattac caccgaaaat tcccggaggg    120
tggccggtaa tcggccatct tttctacttc gatgatgacg gcgacgaccg tccattagct    180
cgaaaactcg gagacttagc tgacaaatac ggcccggttt tcactttccg gctaggcctt    240
ccgcttgtgt tagttgtaag cagttacgaa gctgtaaaag actgcttctc tacaaatgac    300 gccatttttct ccaatcgtcc agcttttctt tacggtgaat accttggcta cagtaatgcc    360
atgctatttt tgacaaaata cggaccttat tggcgaaaaa atagaaaatt agtcattcag    420
gaagttctct ctgctagtcg tctcgaaaaa ttgaagcacg tgagatttgg taaaattcaa    480
acgagcatta agagtttata cactcgaatt gatggaaatt cgagtacgat aaatctaact    540
gattggttag aagaattgaa ttttggtctg atcgtgaaaa tgatcgctgg gaaaaattat    600
gaatccggta aggagatgaa acaagtggag agatttagga aagcgtttaa ggattttata    660
attttatcaa tggagtttgt gttatgggat gctttttccaa ttccattgtt caaatgggtg    720
gattttcaag gccatgttaa ggccatgaaa aggacattta aggatataga ttctgttttt    780
cagaattggt tagaggaaca tgtcaagaaa agagaaaaaa tggaggttaa tgcacaaggg    840
aatgaacaag atttcattga tgtggtgctt tcaaaaatga gtaatgaata tcttgatgaa    900
```

```
ggttactctc gtgatactgt cataaaagca acagtgttta gtttggtctt ggatgctgcg    960
gacacagttg ctcttcacat gaattgggga atggcattac tgataaacaa tcaacatgcc   1020
ttgaagaaag cacaagaaga gatcgataaa aaagttggta aggaaagatg ggtagaagag   1080
agtgatatta aggatttggt ctacctccaa gctattgtta agaagtgtt acgattatat    1140 ccaccaggac ctttattagt acctcatgaa aatgtagagg attgtgttgt tagtggatat   1200
cacattccta aagggactag actattcgcg aacgttatga aattgcagcg cgatcctaaa   1260
ctctggtcaa atcctgataa gtttgatcca gagagattct tcgctgatga tattgactac   1320
cgtggtcagc actatgagtt tatcccattt ggttctggaa gacgatcttg tccggggatg   1380
acttatgcat tacaagtgga acacctaaca atagcacatt tgatccaggg tttcaattac   1440
aaaactccaa atgacgagcc cttggatatg aaggaaggtg caggattaac tatacgtaaa   1500
gtaaatcctg tagaagtgac aattacggct cgcctggcac ctgagcttta ttaa         1554
```

<210> SEQ ID NO 7
<211> LENGTH: 517
<212> TYPE: PRT
<213> ORGANISM: Nicotiana tabacum

<400> SEQUENCE: 7

```
Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255
```

-continued

```
Asp Ser Val Phe Gln Asn Trp Leu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 8
<211> LENGTH: 517
<212> TYPE: PRT
<213> ORGANISM: Nicotiana tabacum

<400> SEQUENCE: 8

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110
```

```
Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515
```

<210> SEQ ID NO 9
<211> LENGTH: 1554
<212> TYPE: DNA
<213> ORGANISM: Nicotiana tabacum

<400> SEQUENCE: 9

```
atggtttctc ccgtagaagc catcgtagga ctagtaactc ttacacttct cttctacttc      60
atacggacca aaaatctcca aaaccttca aaccattac caccgaaaat ccccggaggg       120
tggccggtaa tcggccatct tttctatttc gatgacgaca gcgacgaccg tccattagca     180
cgaaaactcg gagacttagc tgacaaatac ggcccggttt tcacttttcg gctaggcctt     240
ccgcttgtgt tagttgtaag cagttacgaa gctataaaag actgcttctc tacaaatgat     300
gccatttttct ccaatcgtcc agcttttctt tatggcgaat accttggcta caataatgcc    360
atgctatttt tgacaaaata cggacctac tggcgaaaaa atagaaaatt agtcattcag      420
gaagttctct gtgctagtcg tctcgaaaaa ttgaagcacg tgagatttgg tgaaattcag    480
acgagcatta agaatttata cactcgaatt gatggaaatt cgagtacgat aaatctaacc    540
gattggttag aagaattgaa ttttggtctg atcgtgaaaa tgatcgctgg gaaaaattat    600
gaatccggta aggagatga acaagtggag agatttagga aagcgtttaa ggatttttata   660
attttatcaa tggagtttgt gttatgggat gcttttccaa ttccattgtt caatgggtg    720
gattttcaag gccatgttaa ggccatgaaa aggacattta aggatataga ttctgttttt   780
cagaattggt tagaggaaca tgtcaagaaa aagaaaaaa tggaggttaa tgcagaagga    840
aatgaacaag atttcattga tgtggtgctt tcaaaaatga gtaatgaata tcttgatgaa    900
ggctactctc gtgatactgt cataaaagca acagtgttta gtttagtctt ggatgctgcg    960
gacacagttg ctcttcacat gaattgggga atggcattat tgataaacaa tcaacatgcc  1020
ttgaagaaag cgcaagaaga gatagataaa aagttggta aggatagatg ggtagaagag    1080
agtgatatta aggatttggt atacctccaa actattgtta agaagtgtt acgattatat    1140
ccaccgggac ctttattagt accccatgaa aatgtagagg attgtgttgt tagtggatat    1200
cacattccta aagggactag actattcgcg aacgttatga aattacagcg cgatcctaaa   1260
ctctggtcaa atcctgataa gttcgatcca gagagatttt tcgctgctga tattgacttt   1320
cgtggtcaac actatgagtt tatcccatttt ggttctggaa gacgatcttg tccggggatg  1380
acttatgcaa tgcaagtgga acacctaaca atcgcacact tgatccaggg tttcaattac   1440
aaaactccaa atgacgagcc cttggatatg aaggaaggtg caggattaac tatacgtaag   1500
gtaaatccta tagaagtggt aattacgcct cgcctgacac ctgagcttta ttaa          1554
```

<210> SEQ ID NO 10
<211> LENGTH: 517
<212> TYPE: PRT
<213> ORGANISM: Nicotiana tabacum

<400> SEQUENCE: 10

```
Met Val Ser Pro Val Glu Ala Ile Val Gly Leu Val Thr Leu Thr Leu
1               5                  10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Ser Asp Asp Arg Pro Leu Ala Arg Lys Leu Gly
    50                  55                  60
```

```
Asp Leu Ala Asp Lys Tyr Gly Pro Val Phe Thr Phe Arg Leu Gly Leu
 65                  70                  75                  80

Pro Leu Val Leu Val Ser Ser Tyr Glu Ala Ile Lys Asp Cys Phe
             85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Cys
            130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Val Lys Lys Lys Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Asp Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
            325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
            355                 360                 365

Leu Gln Thr Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
            435                 440                 445

Pro Phe Gly Ser Gly Arg Arg Ser Cys Pro Gly Met Thr Tyr Ala Met
            450                 455                 460

Gln Val Glu His Leu Thr Ile Ala His Leu Ile Gln Gly Phe Asn Tyr
465                 470                 475                 480
```

```
Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
        500                 505                 510

Thr Pro Glu Leu Tyr
        515

<210> SEQ ID NO 11
<211> LENGTH: 1554
<212> TYPE: DNA
<213> ORGANISM: Nicotiana tabacum
<220> FEATURE:
<221> NAME/KEY: Mutation
<222> LOCATION: (1141)..(1141)
<223> OTHER INFORMATION: C to T

<400> SEQUENCE: 11
atggtttctc ccgtagaagc catcgtagga ctagtaactc ttacacttct cttctacttc      60
atacggacca aaaatctcaa aaaccttca  aaaccattac caccgaaaat ccccggaggg     120
tggccggtaa tcggccatct tttctatttc gatgacgaca gcgacgaccg tccattagca    180
cgaaaactcg gagacttagc tgacaaatac ggcccggttt tcacttttcg gctaggcctt    240
ccgcttgtgt tagttgtaag cagttacgaa gctataaaag actgcttctc tacaaatgat    300
gccatttttct ccaatcgtcc agcttttctt tatggcgaat accttggcta caataatgcc   360
atgctatttt tgacaaaata cggaccttac tggcgaaaaa atagaaaatt agtcattcag    420
gaagttctct gtgctagtcg tctcgaaaaa ttgaagcacg tgagatttgg tgaaattcag    480
acgagcatta agaatttata cactcgaatt gatgaaaatt cgagtacgat aaatctaacc    540
gattggttag aagaattgaa ttttggtctg atcgtgaaaa tgatcgctgg gaaaaattat    600
gaatccggta aggagatga  acaagtggag agatttagga aagcgtttaa ggattttata    660
atttatatcaa tggagtttgt gttatgggat gcttttccaa ttccattgtt caaatgggtg   720
gattttcaag gccatgttaa ggccatgaaa aggacattta aggatataga ttctgttttt    780
cagaattggt tagaggaaca tgtcaagaaa aagaaaaaa  tggaggttaa tgcagaagga    840
aatgaacaag atttcattga tgtggtgctt tcaaaaatga gtaatgaata tcttgatgaa    900
ggctactctc gtgatactgt cataaaagca acagtgttta gtttagtctt ggatgctgcg    960
gacacagttg ctcttcacat gaattgggga atggcattat tgataaacaa tcaacatgcc   1020
ttgaagaaag cgcaagaaga gatagataaa aaagttggta aggatagatg ggtagaagag   1080
agtgatatta aggatttggt ataccctcca actattgtta agaagtgtt  acgattatat   1140
tcaccgggac ctttattagt accccatgaa aatgtagagg attgtgttgt tagtggatat   1200
cacattccta aagggactag actattcgcg aacgttatga aattacagcg cgatcctaaa   1260
ctctggtcaa atcctgataa gttcgatcca gagagatttt tcgctgctga tattgacttt   1320
cgtggtcaac actatgagtt tatcccattt ggttctggaa gacgatcttg tccggggatg   1380
acttatgcaa tgcaagtgga acacctaaca atcgcacact tgatccaggg tttcaattac   1440
aaaactccaa atgacgagcc cttggatatg aaggaaggtg caggattaac tatacgtaag   1500
gtaaatccta tagaagtggt aattacgcct cgcctgacac ctgagcttta ttaa         1554

<210> SEQ ID NO 12
<211> LENGTH: 571
<212> TYPE: PRT
<213> ORGANISM: Nicotiana tabacum
```

```
<400> SEQUENCE: 12

Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Ser Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125

Pro Tyr Trp Arg Lys Asn Arg Lys Leu Val Ile Gln Glu Val Leu Cys
    130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
        355                 360                 365

Leu Gln Thr Ile Val Lys Glu Val Leu Arg Leu Tyr Ser Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415
```

-continued

```
Arg Asp Pro Lys Leu Trp Ser Asn Pro Asp Lys Phe Asp Pro Glu Arg
            420             425             430
Phe Phe Ala Ala Asp Ile Asp Phe Arg Gly Gln His Tyr Glu Phe Ile
        435             440             445
Pro Phe Gly Ser Gly Arg Arg Ser Cys Pro Gly Met Thr Tyr Ala Met
    450             455             460
Gln Val Glu His Leu Thr Ile Ala His Leu Ile Gln Gly Phe Asn Tyr
465             470             475             480
Lys Thr Pro Asn Asp Glu Pro Leu Asp Met Lys Glu Gly Ala Gly Leu
            485             490             495
Thr Ile Arg Lys Val Asn Pro Ile Glu Val Val Ile Thr Pro Arg Leu
        500             505             510
Thr Pro Glu Leu Tyr Gly Thr Ala Ala Ala Thr Cys Cys Thr Ala Thr
        515             520             525
Ala Gly Ala Ala Gly Thr Gly Gly Thr Ala Ala Thr Thr Ala Cys Gly
        530             535             540
Cys Cys Thr Cys Gly Cys Cys Thr Gly Ala Cys Ala Cys Cys Thr Gly
545             550             555             560
Ala Gly Cys Thr Thr Thr Ala Thr Thr Ala Ala
                565             570
```